(12) United States Patent
Priepke et al.

US008951999B2

(10) Patent No.: US 8,951,999 B2
(45) Date of Patent: Feb. 10, 2015

(54) COMPOUNDS

(75) Inventors: Henning Priepke, Warthausen (DE);
Henri Doods, Warthausen (DE);
Raimund Kuelzer, Mittlelbiberach (DE); Roland Pfau, Biberach (DE);
Dirk Stenkamp, Biberach (DE); Robert Roenn, Uppsala (SE); Benjamin Pelcman, Uppsala (SE)

(73) Assignee: Orexo AB, Stockholm (SE)

( * ) Notice: Subject to any disclaimer, the term of this patent is extended or adjusted under 35 U.S.C. 154(b) by 299 days.

(21) Appl. No.: 12/908,172

(22) Filed: Oct. 20, 2010

(65) Prior Publication Data

US 2011/0263556 A1    Oct. 27, 2011

(30) Foreign Application Priority Data

Oct. 23, 2009   (EP) ..................... 09173872

(51) Int. Cl.
| | | |
|---|---|---|
| *A61K 31/445* | (2006.01) | |
| *C07D 211/32* | (2006.01) | |
| *C07C 311/14* | (2006.01) | |
| *C07D 213/82* | (2006.01) | |
| *C07C 237/42* | (2006.01) | |
| *C07C 237/44* | (2006.01) | |
| *C07C 255/23* | (2006.01) | |
| *C07C 255/60* | (2006.01) | |
| *C07D 205/04* | (2006.01) | |
| *C07D 207/10* | (2006.01) | |
| *C07D 207/22* | (2006.01) | |

(Continued)

(52) U.S. Cl.
CPC ............ *C07D 213/82* (2013.01); *C07C 237/42* (2013.01); *C07C 237/44* (2013.01); *C07C 255/23* (2013.01); *C07C 255/60* (2013.01); *C07C 311/14* (2013.01); *C07D 205/04* (2013.01); *C07D 207/10* (2013.01); *C07D 207/22* (2013.01); *C07D 207/34* (2013.01); *C07D 209/08* (2013.01); *C07D 211/14* (2013.01); *C07D 211/16* (2013.01); *C07D 211/18* (2013.01); *C07D 211/38* (2013.01); *C07D 213/40* (2013.01); *C07D 213/75* (2013.01); *C07D 213/81* (2013.01); *C07D 215/42* (2013.01); *C07D 237/30* (2013.01); *C07D 277/46* (2013.01); *C07D 277/56* (2013.01); *C07D 277/60* (2013.01); *C07D 277/82* (2013.01); *C07D 295/15* (2013.01); *C07D 295/155* (2013.01); *C07D 307/20* (2013.01); *C07D 307/24* (2013.01); *C07D 309/12* (2013.01); *C07D 309/14* (2013.01); *C07D 333/38* (2013.01); *C07D 335/02* (2013.01); *C07D 417/04* (2013.01); *C07C 2101/02* (2013.01); *C07C 2101/04* (2013.01); *C07C 2101/08* (2013.01); *C07C 2101/14* (2013.01)
USPC ...... 514/210.01; 514/256; 514/313; 514/331; 514/349; 514/352; 514/355; 514/357; 514/365; 514/367; 514/423; 514/428; 514/432; 514/448; 514/459; 514/601; 544/329; 546/169; 546/234; 546/297; 546/309; 546/323; 548/163; 548/188; 548/469; 548/537; 548/577; 549/72; 549/424; 549/426; 549/475; 549/496; 564/80; 564/153

(58) Field of Classification Search
USPC ............ 514/210.01, 256, 313, 331, 349, 352, 514/355, 357, 365, 367, 370, 371, 419, 423, 514/428, 432, 448, 459, 471, 601; 544/329; 546/160, 234, 297, 309, 323; 548/163, 548/188, 194, 195, 469, 487, 537, 569, 577, 548/950; 549/28, 72, 424, 426, 475, 487, 549/496; 564/80, 153
See application file for complete search history.

(56) References Cited

U.S. PATENT DOCUMENTS

| 5,039,805 A | * | 8/1991 | Alig et al. ..................... 546/224 |
| 6,187,285 B1 | * | 2/2001 | Meyer et al. ................. 424/1.65 |
| 6,444,849 B1 | * | 9/2002 | Ando et al. .................... 564/155 |

FOREIGN PATENT DOCUMENTS

WO    WO2006070878    *    7/2006

OTHER PUBLICATIONS

Exhibit 1 p. 1 (2013).*
Federal Regisdtry v.76(27) p. 7162-7175 (2011).*
Delaet et al. "Preparation of pyridinylcarboxamide . . . " CA146:521686 (2007).*
Supplemental Examination Guideline, Improper Markush, p. 1, 64-67 (2011).*
Ishihara et al. "Preparation of carboxylic . . . " CA145:124613 (2006).*
Patani et al. "Bioisostersim: a Rational . . . " Chem. Rev. 96 p. 3147-3176 (1996).*

(Continued)

*Primary Examiner* — Celia Chang

(57) ABSTRACT

This invention relates to compounds of formula I,

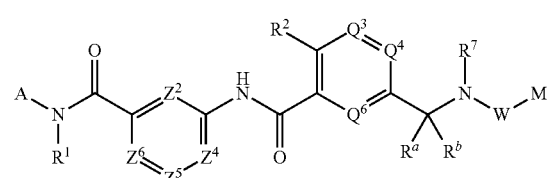

their use as inhibitors of the microsomal prostaglandin $E_2$ synthase-1 (mPGES-1), pharmaceutical compositions containing them, and their use as medicaments for the treatment and/or prevention of inflammatory diseases and associated conditions such as inflammatory/nociceptive pain.
A, M, $R^1$, $R^2$, $R^7$, $R^a$, $R^b$, $Q^3$, $Q^4$, $Q^6$, $Z^2$, $Z^4$, $Z^5$, $Z^6$ and W have meanings given in the description.

2 Claims, No Drawings

(51) Int. Cl.

| | |
|---|---|
| *C07D 207/34* | (2006.01) |
| *C07D 209/08* | (2006.01) |
| *C07D 211/14* | (2006.01) |
| *C07D 211/16* | (2006.01) |
| *C07D 211/18* | (2006.01) |
| *C07D 211/38* | (2006.01) |
| *C07D 213/40* | (2006.01) |
| *C07D 213/75* | (2006.01) |
| *C07D 213/81* | (2006.01) |
| *C07D 215/42* | (2006.01) |
| *C07D 237/30* | (2006.01) |
| *C07D 277/46* | (2006.01) |
| *C07D 277/56* | (2006.01) |
| *C07D 277/60* | (2006.01) |
| *C07D 277/82* | (2006.01) |
| *C07D 295/15* | (2006.01) |
| *C07D 295/155* | (2006.01) |
| *C07D 307/20* | (2006.01) |
| *C07D 307/24* | (2006.01) |
| *C07D 309/12* | (2006.01) |
| *C07D 309/14* | (2006.01) |
| *C07D 333/38* | (2006.01) |
| *C07D 335/02* | (2006.01) |
| *C07D 417/04* | (2006.01) |

(56) References Cited

OTHER PUBLICATIONS

RN 1062311-29-8 (2008).*
Waltenberger et al. "Pharmacophore . . . " J. Med. Chem. 54 p. 3163-3174 (2011).*
Dorwald "Side reactions in organic synthesis" p. ix (2005).*
Alig. et al. "Preparation of N-amidobenzoyl . . . " CA115:92947 (1991).*

* cited by examiner

COMPOUNDS

FIELD OF THE INVENTION

This invention relates to novel compounds, which are inhibitors of the microsomal prostaglandin $E_2$ synthase-1 (mPGES-1), pharmaceutical compositions containing them, and their use as medicaments for the treatment and/or prevention of inflammatory diseases and associated conditions such as inflammatory/nociceptive pain.

BACKGROUND OF THE INVENTION

There are many acute and chronic diseases/disorders that are inflammatory in their nature including but not limited to rheumatoid diseases e.g. rheumatoid arthritis, osteoarthritis, diseases of the visceral system e.g. inflammatory bowel syndrome, autoimmune diseases, e.g. lupus erythematodes, lung diseases like asthma and COPD. Current treatment with non-steroidal anti-inflammatory drugs (NSAIDs) and cyclooxygenase (COX)-2 inhibitors are efficacious, but show a prevalence for gastrointestinal and cardiovascular side effects. There is a high need for new treatment options showing equivalent efficacy with an improved side effect profile.

mPGES inhibitors may show such an improved side effect profile because they block the generation of $PGE_2$ in a more specific manner as described below.

NSAIDs and COX-2 inhibitors reduce inflammation and pain through inhibition of one or both isoformes of COX enzymes. The cyclooxygenase (COX) enzyme exists in two forms, one that is constitutively expressed in many cells and tissues (COX-1), and one that in most cells and tissues is induced by pro-inflammatory stimuli, such as cytokines, during an inflammatory response (COX-2). COXs metabolise arachidonic acid to the unstable intermediate prostaglandin $H_2$ ($PGH_2$). $PGH_2$ is further metabolized to other prostaglandins including $PGE_2$, $PGF_{2\alpha}$, $PGD_2$, prostacyclin and thromboxane $A_2$. These arachidonic acid metabolites are known to have pronounced physiological and pathophysiological activity including pro-inflammatory effects. $PGE_2$ in particular is known to be a strong pro-inflammatory mediator, and is also known to induce fever, inflammation and pain. Consequently, numerous drugs were developed with a view to inhibiting the formation of $PGE_2$, including "NSAIDs" (non-steroidal antiinflammatory drugs) and "coxibs" (selective COX-2 inhibitors). These drugs act predominantly by inhibition of COX-1 and/or COX-2, thereby reducing the formation of $PGE_2$. However, the inhibition of COXs has the disadvantage that it results in the reduction of the formation of all metabolites downstream of $PGH_2$, some of which are known to have beneficial properties. In view of this, drugs which act by inhibition of COXs are therefore known/suspected to cause adverse biological effects.

For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

An alternative treatment of inflammatory diseases that does not give rise to the above-mentioned side effects would thus be of real benefit in the clinic. In particular, a drug that preferably inhibits the transformation of $PGH_2$ to the pro-inflammatory mediator $PGE_2$ selectively might be expected to reduce the inflammatory response in the absence of a corresponding reduction of the formation of other, beneficial arachidonic acid metabolites. Such inhibition would accordingly be expected to alleviate the undesirable side-effects mentioned above.

$PGH_2$ may be transformed to $PGE_2$ by prostaglandin E synthases (PGES). Two microsomal prostaglandin E synthases (mPGES-1 and mPGES-2), and one cytosolic prostaglandin E synthase (cPGES) have been described. mPGES-1 is proposed to be closely linked to COX-2 and both enzyme's are upregulated during e.g. inflammation. Thus agents that are capable of inhibiting the action of mPGES-1 and thereby reducing the formation of $PGE_2$ are likely to be of benefit for the treatment of inflammation and more general acute and chronic pain conditions

DETAILED DESCRIPTION OF THE INVENTION

The present invention provides a compound of formula I,

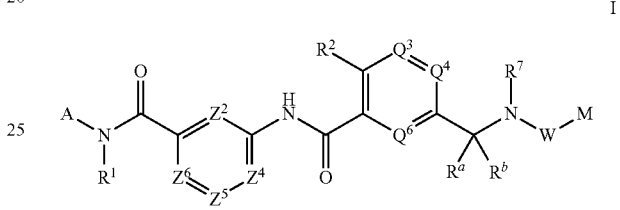

I in which
$Z^2$, $Z^4$, $Z^5$ and $Z^6$ respectively represent —$C(R^{Z2})$=, —$C(R^{Z4})$=; —$C(R^{Z5})$=; —$C(R^{Z6})$=;
or
$Z^2$ and $Z^4$ respectively represent —$C(R^{Z2})$= and —$C(R^{Z4})$=, and
any one or two of $Z^5$ or $Z^6$ represent —N=;
$Q^3$, $Q^4$ and $Q^6$ respectively represent —$C(R^3)$=, —$C(R^4)$= and —$C(R^6)$=;
$R^1$ represents hydrogen or $C_{1-3}$ alkyl which is optionally substituted by one or more fluorine atoms;
$R^2$ represents halo, CN, —$N(R^{y1})R^{y2}$, —$OR^{y10}$;
$C_{1-7}$ alkyl, $C_{2-7}$ alkenyl, $C_{2-7}$ alkynyl, $C_{3-8}$ cycloalkyl-$C_{0-2}$ alkyl-, $C_{3-8}$ heterocycloalkyl-$C_{0-2}$ alkyl- [which latter five groups are optionally substituted by one or more substituents independently selected from $R^{alkyl}$];
$R^3$, $R^4$ and $R^6$:
independently represent hydrogen, halo, —CN, —$N(R^{y1})R^{y2}$, —$OR^{y10}$;
$C_{1-7}$ alkyl, $C_{2-7}$ alkenyl, $C_{2-7}$ alkynyl, $C_{3-8}$ cycloalkyl-$C_{0-2}$ alkyl-, $C_{3-8}$ heterocycloalkyl-$C_{0-2}$ alkyl- [which latter five groups are optionally substituted by one or more substituents independently selected from $R^{alkyl}$];
or any adjacent pair of $R^2$, $R^3$ and $R^4$ (i.e. $R^2$ and $R^3$ or $R^3$ and $R^4$) may be linked together to form, along with the essential carbon atoms of the $Q^3$-containing ring to which they are necessarily attached, a further 5- to 7-membered ring, optionally containing one to three heteroatoms, which ring may contain one or two further unsaturations and which is optionally substituted by one or more $C_{1-3}$ alkyl and/or =O substituents;
each $R^{Z2}$, $R^{Z4}$ and $R^{Z5}$
independently represents hydrogen, halo, —$N(R^{y1})R^{y2}$, —$OR^{y10}$, $C_{1-7}$ alkyl, $C_{2-7}$ alkenyl, $C_{2-7}$ alkynyl, $C_{3-8}$ cycloalkyl-$C_{0-2}$ alkyl-, $C_{3-8}$ heterocycloalkyl-$C_{0-2}$ alkyl- [which latter five groups are optionally substituted by one or more substituents independently selected from $R^{alkyl}$];

aryl-$C_{0-2}$ alkyl- or heteroaryl-$C_{0-2}$ alkyl- [which latter two aromatic groups are optionally substituted by one or more substituents selected from $R^{aryl}$];

$R^{Z6}$ represents hydrogen, halo, —N($R^{y1}$)$R^{y2}$, —OH, —O—$C_{1-6}$ alkyl, —O—$C_{2-6}$ alkenyl, —O—$C_{3-6}$ alkynyl, —O—$C_{3-8}$ cycloalkyl, —O—$C_{4-8}$ heterocycloalkyl, $C_{1-7}$ alkyl, $C_{2-7}$ alkenyl, $C_{2-7}$ alkynyl, $C_{3-8}$ cycloalkyl, $C_{4-8}$ heterocycloalkyl [which latter ten groups are optionally substituted by one or more substituents selected from fluoro, —CN, =O, —N($R^{y1}$)$R^{y2}$, —O$R^{y10}$, —N($R^{y3}$)—C(O)—$R^{y4}$, —N($R^{y5}$)—S(O)$_2$—$R^{y6}$, —C(O)O$R^{y7}$, —C(O)N($R^{y8}$)$R^{y9}$, —S(O)$_{0-2}$—$R^{y11}$, —S(O)$_2$O—$R^{y12}$, —S(O)$_2$N($R^{y13}$)$R^{y14}$, —C(O)$R^{y15}$, $C_{1-7}$ alkyl, $C_{2-7}$ alkenyl, $C_{2-7}$ alkynyl, $C_{3-6}$ cycloalkyl, $C_{4-6}$ heterocycloalkyl (which latter five groups are optionally substituted by one or more substituents selected from $R^{alkyl}$), aryl and heteroaryl (which latter two aromatic groups are optionally substituted by one or more substituents independently selected from $R^{aryl}$)]; or aryl or heteroaryl, O-aryl, O-heteroaryl, —N($R^{y1}$)aryl, —N($R^{y1}$)hetaryl (which latter six aromatic groups are optionally substituted by one or more substituents independently selected from $R^{aryl}$);

A represents $C_{3-10}$ heterocycloalkyl-$C_{0-3}$ alkyl-, $C_{3-10}$ cycloalkyl-$C_{0-3}$ alkyl-, $C_{1-12}$ alkyl, $C_{3-12}$ alkenyl or $C_{3-12}$ alkynyl, which latter five groups are optionally substituted by one or more substituents selected from $R^8$;

or aryl-$C_{0-3}$ alkyl- or heteroaryl-$C_{0-3}$ alkyl-, which latter two groups are optionally substituted in the aryl fragment by one or more substituents selected from $R^9$;

$R^a$ and $R^b$ independently represent hydrogen, $C_{1-3}$ alkyl which is optionally substituted by one or more fluorine atoms;

or $R^a$ and $R^b$ together with the carbon atom to which they are attached, may be linked together to form a 3-6 membered cycloalkylene ring, wherein a methylene group may be oxidised to a —C(=O)-group and which ring is optionally substituted by one or more $C_{1-3}$ alkyl substituents or fluorine atoms W represents —C(=O)—, —S(=O)— or —S(=O)$_2$—, M represents $C_{1-9}$ alkyl, $C_{2-9}$ alkenyl, $C_{2-9}$ alkynyl, $C_{3-10}$ cycloalkyl, $C_{3-10}$ heterocycloalkyl all of which groups are optionally substituted by one or more groups selected from fluoro, =O, —O$R^{y10}$, —CN, —N($R^{y1}$)$R^{y2}$, aryl, heteroaryl [which latter two aromatic groups are optionally substituted by one or more substituents independently selected from $R^{aryl}$], $C_{1-7}$ alkyl, $C_{2-7}$ alkynyl, $C_{3-7}$ cycloalkyl-$C_{0-2}$ alkyl-, $C_{3-7}$ heterocycloalkyl-$C_{0-2}$ alkyl- [which latter four groups are optionally substituted by one or more substituents independently selected from $R^{alkyl}$];

or aryl, heteroaryl, both of which groups are optionally substituted by one or more substituents independently selected from halo, —O$R^{y10}$, —CN, —N($R^{y1}$)$R^{y2}$, aryl, heteroaryl, O-phenyl, O-benzyl [which latter four aromatic groups are optionally substituted by one or more substituents independently selected from $R^{aryl}$], $C_{1-7}$ alkyl, $C_{2-7}$ alkynyl, $C_{3-7}$ cycloalkyl-$C_{0-2}$ alkyl-, $C_{3-7}$ heterocycloalkyl-$C_{0-2}$ alkyl [which latter four groups are optionally substituted by one or more substituents independently selected from $R^{alkyl}$];

$R^{alkyl}$ represents fluoro, —CN, =O, —N($R^{y1}$)$R^{y2}$, —OH, —O$C_{1-3}$ alkyl, $C_{1-3}$ alkyl (which latter two groups are optionally substituted by one or more fluorine atoms)

$R^{aryl}$ represents halo, CN, —N($R^{y1}$)$R^{y2}$, OH, —O$C_{1-3}$ alkyl, $C_{1-3}$ alkyl (which latter two groups are optionally substituted by one or more fluorine atoms)

$R^7$ represents hydrogen or $C_{1-3}$ alkyl which is optionally substituted by one or more fluorine atoms;

$R^8$ represents fluoro, =O, —CN, —N($R^{y1}$)$R^{y2}$, —N($R^{y3}$)—C(O)—$R^{y4}$, —N($R^{y5}$)—S(O)$_2$—$R^{y6}$, —C(O)O$R^{y7}$, —C(O)N($R^{y8}$)$R^{y9}$, —O$R^{y10}$, —S(O)$_{0-2}$—$R^{y11}$, —S(O)$_2$N($R^{y13}$)$R^{y14}$ and —C(O)$R^{y15}$;

$C_{1-7}$ alkyl, $C_{2-7}$ alkenyl, $C_{2-7}$ alkynyl, $C_{3-6}$ cycloalkyl-$C_{0-2}$ alkyl-, $C_{3-6}$ heterocycloalkyl-$C_{0-2}$ alkyl- [which latter five groups are optionally substituted by one or more substituents selected from $R^{alkyl}$];

or aryl or heteroaryl [which latter two groups are optionally substituted by one or more substituents independently selected from halo, —CN, —O$R^{y10}$, $C_{1-7}$ alkyl, $C_{2-7}$ alkenyl, $C_{2-7}$ alkynyl, $C_{3-6}$ cycloalkyl-$C_{0-2}$ alkyl-, $C_{3-6}$ heterocycloalkyl-$C_{0-2}$ alkyl-, (which latter five groups are optionally substituted by one or more substituents independently selected from fluoro and —O$R^{y10}$)];

or any two $R^8$ substituents:

when attached to adjacent atoms of the non-aromatic group or in the case where the $R^8$ substituents are attached to the same carbon atom, may be linked together to form, together with the essential atom or atoms of the non-aromatic group to which these $R^8$ substituents are necessarily attached, a further 3- to 8-membered ring, optionally containing a further one or two heteroatoms, and which further ring optionally contains one or two unsaturations and which is optionally substituted by one or more $C_{1-3}$ alkyl and/or =O substituents;

$R^9$ represents halo, —CN, —N($R^{y1}$)$R^{y2}$, —N($R^{y3}$)—C(O)—$R^{y4}$, —N($R^{y5}$)—S(O)$_2$—$R^{y6}$, —C(O)O$R^{y7}$, —C(O)N($R^{y8}$)$R^{y9}$, —O$R^{y10}$, —S(O)$_{0-2}$—$R^{y11}$, —S(O)$_2$O—$R^{y12}$, —S(O)$_2$N($R^{y13}$)$R^{y14}$ and —C(O)$R^{y15}$;

$C_{1-7}$ alkyl, $C_{2-7}$ alkenyl, $C_{2-7}$ alkynyl, $C_{3-6}$ cycloalkyl-$C_{0-2}$ alkyl-, $C_{3-6}$ heterocycloalkyl-$C_{0-2}$ alkyl- [which latter five groups are optionally substituted by one or more substituents selected from fluoro, =O, —CN, —N($R^{y1}$)$R^{y2}$, —N($R^{y3}$)—C(O)—$R^{y4}$, —C(O)O$R^{y7}$, —C(O)N($R^{y8}$)$R^{y9}$, —O$R^{y10}$ and —C(O)$R^{y15}$]; or aryl or heteroaryl [which latter two groups are optionally substituted by one or more substituents selected from halo, —CN, $C_{1-7}$ alkyl, $C_{2-7}$ alkenyl, $C_{2-7}$ alkynyl, $C_{3-6}$ cycloalkyl-$C_{0-2}$ alkyl-, $C_{3-6}$ heterocycloalkyl-$C_{0-2}$ alkyl- (which latter five groups are optionally substituted by one or more substituents selected from fluoro and —O$R^{y10}$), —O—$C_{1-7}$ alkyl, —O—$C_{2-7}$ alkenyl, alkynyl, —O—$C_{0-2}$ alkyl-$C_{3-6}$ cycloalkyl, —O—$C_{0-2}$ alkyl-$C_{3-6}$ heterocycloalkyl (which latter five groups are optionally substituted by one or more fluorine atoms)];

or any two $R^9$ substituents:

when attached to the adjacent atoms of the aryl or hetaryl group may be linked together to form, together with the essential atoms of the aryl group to which the relevant $R^9$ substituents are necessarily attached, a further 5- to 8-membered ring, optionally containing a further one or two heteroatoms, and which further ring optionally contains one or two unsaturations and which is optionally substituted by one or more $C_{1-3}$ alkyl and/or =O substituents;

each $R^{y4}$, $R^{y6}$, $R^{y11}$ and $R^{y15}$:

independently represent $C_{1-7}$ alkyl, $C_{2-7}$ alkenyl, $C_{2-7}$ alkynyl, $C_{3-6}$ cycloalkyl, which latter four groups are optionally substituted by one or more fluorine atoms;

each $R^{y1}$, $R^{y2}$, $R^{y3}$, $R^{y5}$, $R^{y6}$, $R^{y8}$, $R^{y9}$, $R^{y10}$, $R^{y13}$ and $R^{y14}$:

independently represent hydrogen or $C_{1-7}$ alkyl, $C_{2-7}$ alkenyl, $C_{3-7}$ alkynyl, $C_{4-6}$ cycloalkyl, $C_{4-6}$ heterocycloalkyl, which latter five groups are optionally substituted one or more substituents selected from fluoro, —$C_{1-3}$ alkyl and —$OC_{1-3}$ alkyl, which latter two groups are optionally substituted by one or more fluorine atoms;

or any two groups, when attached to the same nitrogen atom (i.e. $R^{y1}$ and $R^{y2}$), may, together with that nitrogen atom to which they are necessarily attached, be linked together to form a 3- to 8-membered ring, optionally containing one or two further heteroatoms and which ring optionally contains one or two unsaturations and is optionally substituted by one or more $C_{1-3}$ alkyl and/or =O substituents or one or more fluorine atoms, or a pharmaceutically acceptable salt thereof.

GENERAL DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

Stereochemistry/Solvates/Hydrates:

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminotetraacetic acid, formic acid, fumaric acid, galacaric acid, gentisic acid, D-glucoheptonic acid, D-gluconic acid, D-glucuronic acid, glutamic acid, glutantic acid, glutaric acid, 2-oxo-glutaric acid, glycerophosphoric acid, glycine, glycolic acid, hexanoic acid, hippuric acid, hydrobromic acid, hydrochloric acid isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

Halogen:

The term halogen generally denotes fluorine, chlorine, bromine and iodine.

Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—

CH₂—CH₂—CH(CH₃)—, H₃C—CH₂—CH(CH₃)—CH₂—, H₃C—CH(CH₃)—CH₂—CH₂—, H₃C—CH₂—C(CH₃)₂—, H₃C—C(CH₃)₂—CH₂—, H₃C—CH(CH₃)—CH(CH₃)— and H₃C—CH₂—CH(CH₂CH₃)—.

Alkenyl:

The term "$C_{2-n}$-alkenyl", is used for a group as defined in the definition for "$C_{1-n}$-alkyl" with at least two carbon atoms, if at least two of those carbon atoms of said group are bound to each other by a double bond. Alkenyl groups may exist as E (entgegen) and Z (zusammen) geometric isomers about each individual double bond. All such isomers and mixtures thereof are included within the scope of the invention. Examples of alkenyl groups include ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, etc.

Alkynyl:

The term "$C_{2-n}$-alkynyl", is used for a group as defined in the definition for "$C_{1-n}$-alkyl" with at least two carbon atoms, if at least two of those carbon atoms of said group are bound to each other by a triple bond.

Examples of alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc.

Cycloalkyl:

The term "$C_{3-n}$-cycloalkyl", wherein n is an integer 3 to n, either alone or in combination with another radical denotes a cyclic hydrocarbon radical with 3 to n C atoms. The term "cycloalkyl" also includes bi-, tri- or tetra-cyclic ring structures consisting only of carbon and containing between one and four rings wherein such rings may be attached together in a pendent manner or may be fused. The term "cycloalkyl" additionally encompasses spiro systems, and bridged systems. The term cyclic hydrocarbon radical may also be fused to an phenyl ring.

Thus, the term "cycloalkyl" includes the following exemplary structures which are not depicted as radicals as each form may be attached through a covalent bond to any atom of the cycloalkyl ring fragment as long as appropriate valencies are maintained:

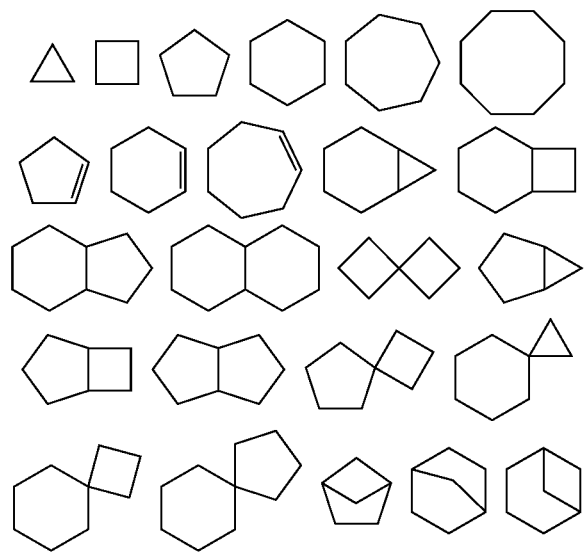
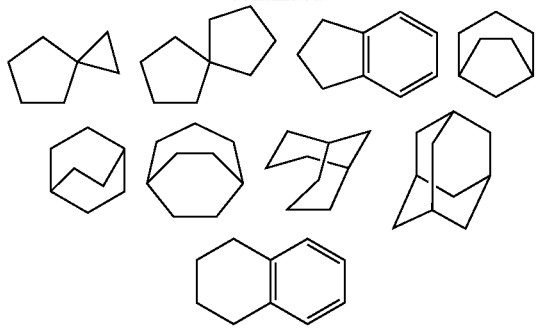

Heterocycloalkyl:

The term "$C_{3-n}$-heterocycloalkyl", wherein n is an integer >3, either alone or in combination with another radical denotes a cyclic non-aromatic mono-, bi-, tri- or spirocyclic radical with 3 to n ring atoms wherein at least one ring atom is selected from nitrogen, oxygen or sulphur and wherein n is the upper limit of ring atoms. In the heterocycloalkyl ring structures one or two carbon atoms and the nitrogen and sulphur atoms can be oxidised to the corresponding —C(═O), N-oxide, —S(═O)— or S(═O)₂-groups.

Further, heterocycloalkyl groups with five or more ring atoms may contain one or two double bonds, forming for example a $C_{5-q}$ heterocycloalkenyl group (where q is the upper limit of the range) e.g. a 3-pyrrolinyl group.

In addition, an aromatic or heteroaromatic ring system can be fused to the heterocycloalkyl radical.

Substituents on heterocycloalkyl groups may, where appropriate, be located on any atom in the ring system including a heteroatom.

The point of attachment of heterocycloalkyl radicals may be via any atom in the non-aromatic ring system including (where appropriate) a heteroatom (such as a nitrogen atom) and also including an atom on any fused non-aromatic carbocyclic ring fragment that may be present as part of the ring system.

Thus, the term "heterocycloalkyl" includes the following exemplary structures which are not depicted as radicals as each form may be attached through a covalent bond to any atom as long as appropriate valencies are maintained:

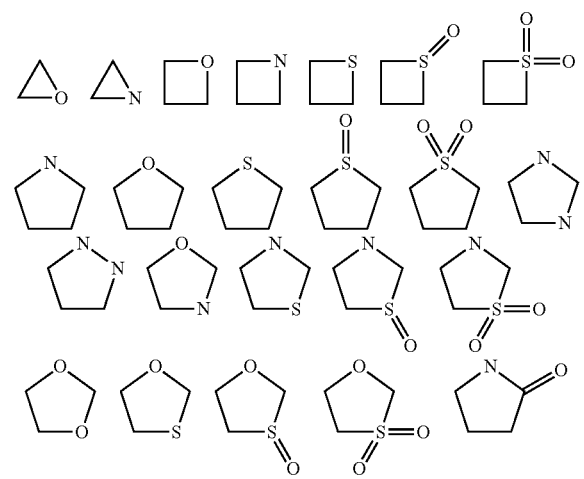

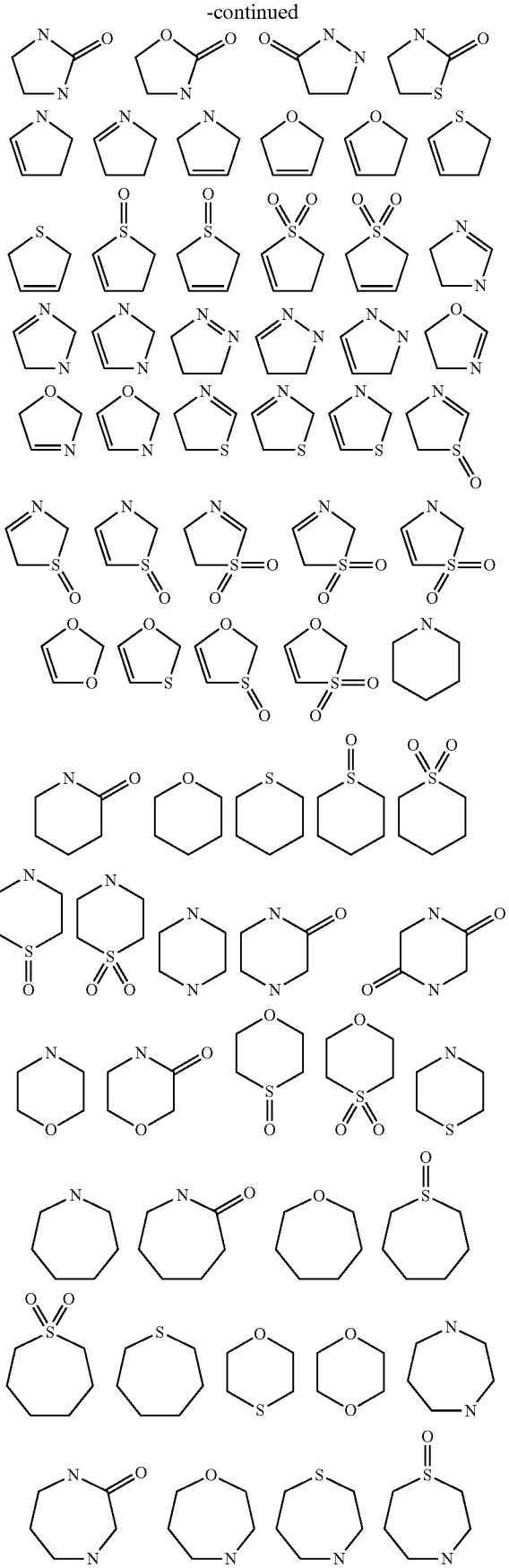
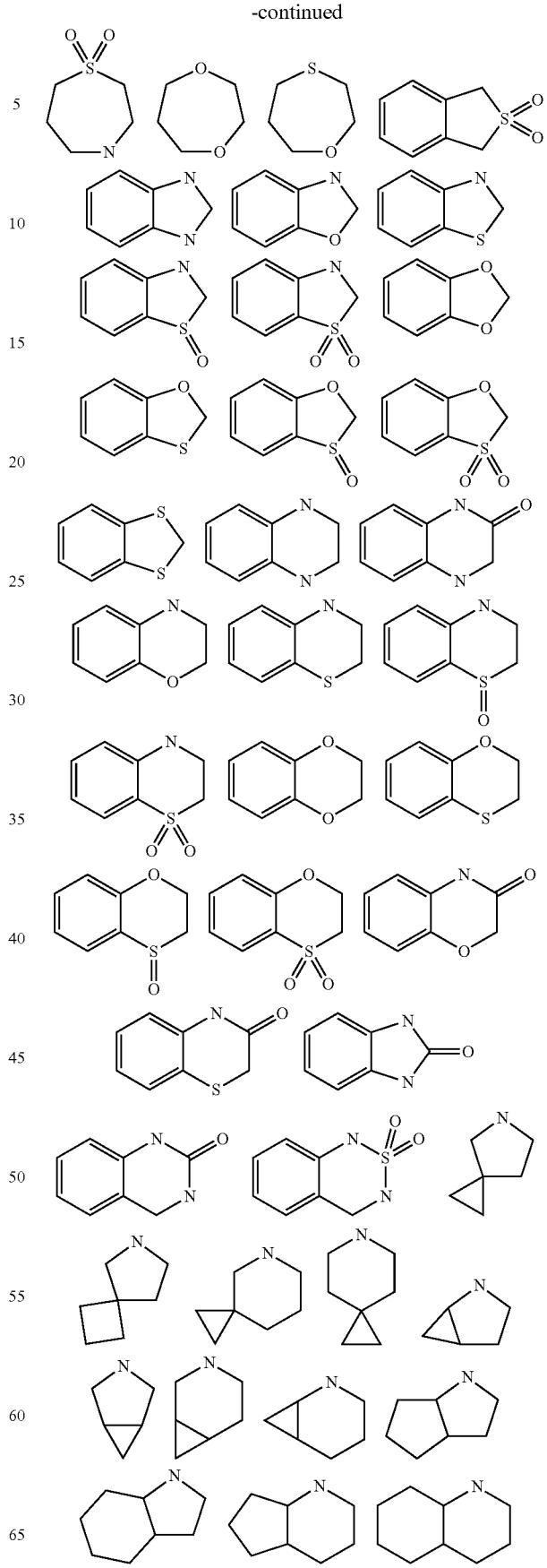

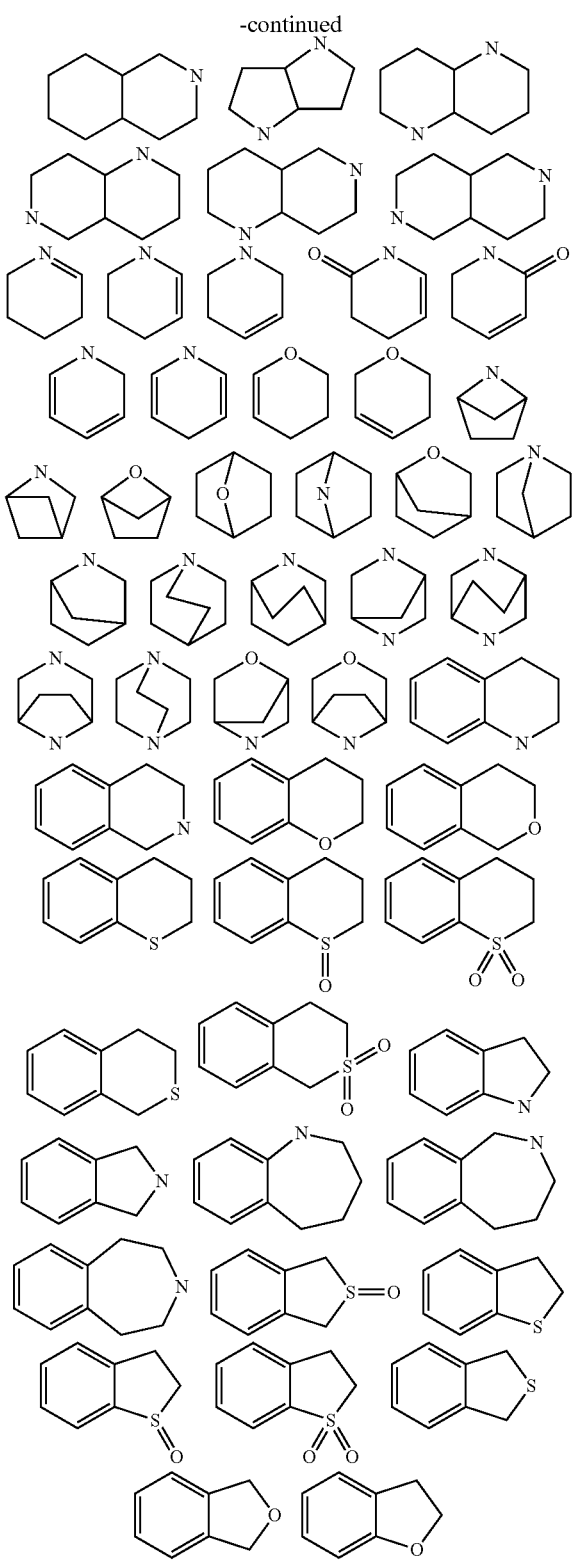

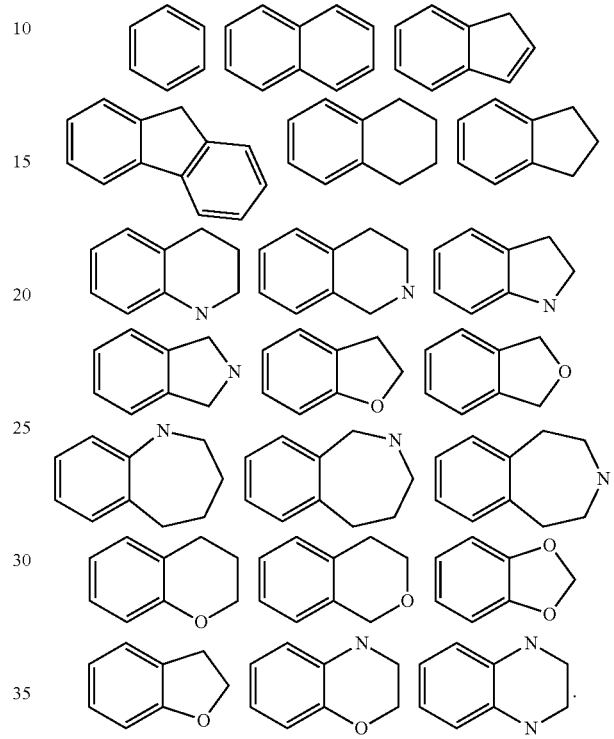

nyl, indenyl, fluorenyl, naphthyl, anthracenyl, phenanthrenyl, tetrahydronaphthyl and dihydronaphthyl.

Thus, the term "aryl" includes the following exemplary structures which are not depicted as radicals as each form may be attached through a covalent bond to any atom of the aromatic ring as long as appropriate valencies are maintained:

Aryl:

The term "aryl" as used herein, either alone or in combination with another radical, denotes a carbocyclic aromatic monocyclic group containing 6 carbon atoms which may be further fused to a second or third 5- or 6-membered carbo- or heterocyclic group which may be aromatic, saturated or unsaturated. Aryl includes, but is not limited to, phenyl, inda- Heteroaryl:

The term "heteroaryl" as used herein, either alone or in combination with another radical, denotes an aromatic monocyclic group containing 5 or 6 atoms wherein at least one ring atom is selected from nitrogen, oxygen or sulphur. This ring system may be further fused to a second and third 5- to 7-membered carbo- or heterocyclic group which may be aromatic, saturated or unsaturated to generate a bi- or tricyclic ring system with not more than 14 ring atoms. The term "heteroaryl" is intended to include all the possible isomeric forms. The nitrogen or sulphur atoms of the ring system may also be oxidised to the N-oxide, —S(=O)— or —S(O)2- group.

Thus, the term "heteroaryl" includes the following exemplary structures which are not depicted as radicals as each form may be attached through a covalent bond to any atom of the mono-, bi- or tricyclic aromatic ring system as long as appropriate valencies are maintained (this explicitly includes also attachment via a carbon atom of the benzo-part of a bi- or tricycle):

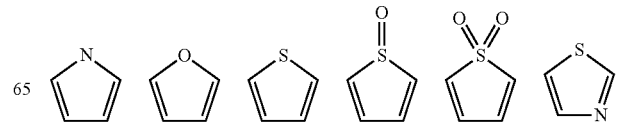

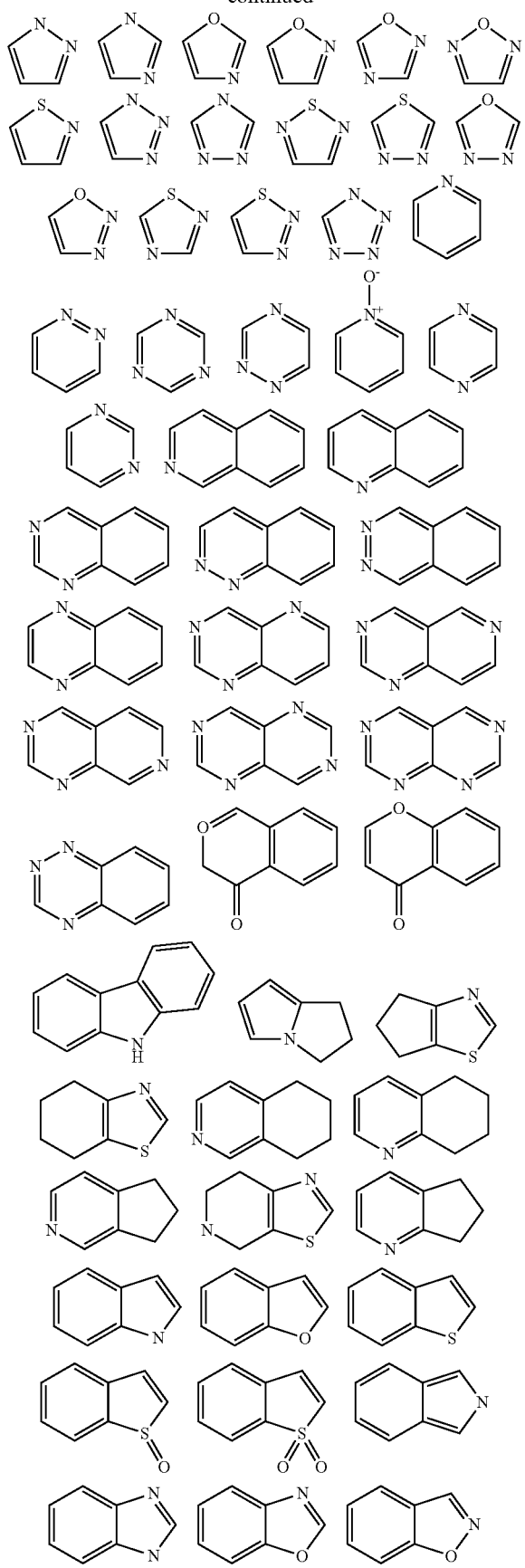
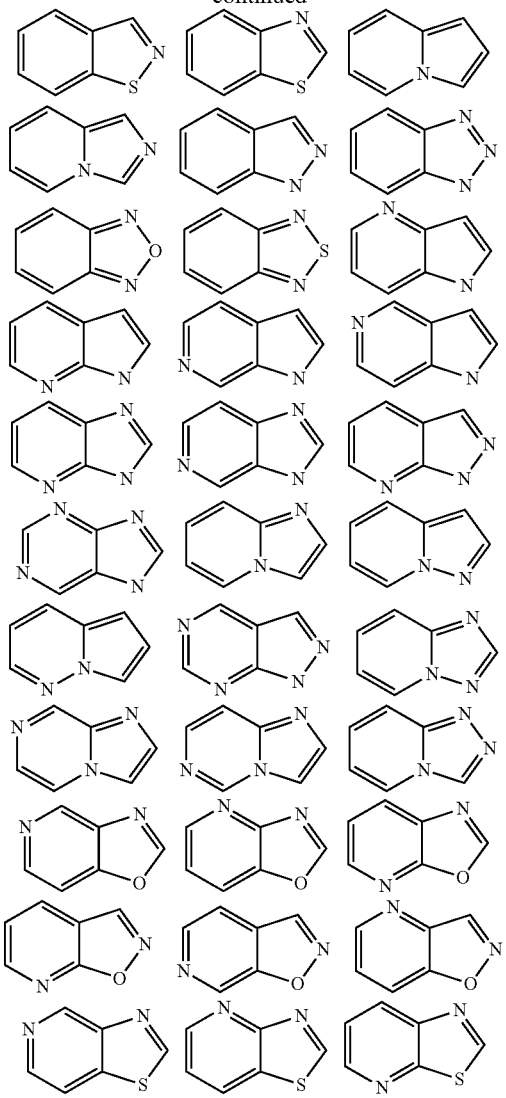

Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused aromatic ring that may be present as part of the ring system.

For the avoidance of doubt, in cases in which the identity of two or more substituents in a compound of formula I may be the same, the actual identities of the respective substituents are not in any way interdependent. Similarly, when groups are substituted by more than one substituent as defined herein, the identities of those individual substituents are not to be regarded as being interdependent. For example, when an A group is substituted by two $R^9$ substituents, in which, in both cases, $R^9$ represents $C_{1-7}$ alkyl substituted by —N($R^{y1}$)$R^{y2}$, then the identities of the two —N($R^{y1}$)$R^{y2}$ groups are not to be regarded as being interdependent, i.e. the two —N($R^{y1}$)$R^{y2}$ moieties may be the same or different, i.e. at each occurrence, $R^{y1}$ and $R^{y2}$ may also be the same or different.

The skilled person will appreciate that compounds of formula I that are the subject of this invention include those that are stable. That is, compounds of the invention include those that are sufficiently robust to survive isolation from e.g. a reaction mixture to a useful degree of purity.

In one embodiment, the invention provides compounds of formula I

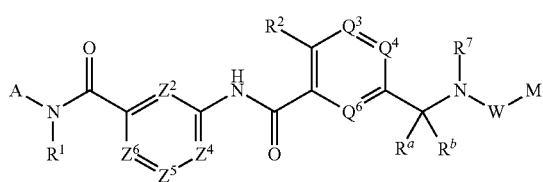

I in which
$Z^2$, $Z^4$, $Z^5$ and $Z^6$ respectively represent —$C(R^{Z2})$=, —$C(R^{Z4})$=; —$C(R^{Z5})$=; —$C(R^{Z6})$=;
or
$Z^2$ and $Z^4$ respectively represent —$C(R^{Z2})$= and —$C(R^{X4})$=, and
any one or two of $Z^5$ or $Z^6$ represent —N=;
$Q^3$, $Q^4$ and $Q^6$ respectively represent —$C(R^3)$=, —$C(R^4)$= and —$C(R^6)$=;
$R^1$ represents hydrogen or $C_{1-3}$ alkyl which is optionally substituted by one or more fluorine atoms;
$R^2$ represents halo, CN, —$N(R^{y1})R^{y2}$, —$OR^{y10}$;
  $C_{1-7}$ alkyl, $C_{2-7}$ alkenyl, $C_{2-7}$ alkynyl, $C_{3-8}$ cycloalkyl-$C_{0-2}$ alkyl-, $C_{3-8}$ heterocycloalkyl-$C_{0-2}$ alkyl- [which latter five groups are optionally substituted by one or more substituents independently selected from $R^{alkyl}$];
$R^3$, $R^4$ and $R^6$:
  independently represent hydrogen, halo, —CN, —$N(R^{y1})R^{y2}$, —$OR^{y10}$;
  $C_{1-7}$ alkyl, $C_{2-7}$ alkenyl, $C_{2-7}$ alkynyl, $C_{3-8}$ cycloalkyl-$C_{0-2}$ alkyl-, $C_{3-8}$ heterocycloalkyl-$C_{0-2}$ alkyl- [which latter five groups are optionally substituted by one or more substituents independently selected from $R^{alkyl}$];
or any adjacent pair of $R^2$, $R^3$ and $R^4$ (i.e. $R^2$ and $R^3$ or $R^3$ and $R^4$) may be linked together to form, along with the essential carbon atoms of the $Q^3$-containing ring to which they are necessarily attached, a further 5- to 7-membered ring, optionally containing one to three heteroatoms, which ring may contain one or two further unsaturations and which is optionally substituted by one or more $C_{1-3}$ alkyl and/or =O substituents;
each $R^{Z2}$, $R^{Z4}$ and $R^{Z5}$
  independently represents hydrogen, halo, —$N(R^{y1})R^{y2}$, —$OR^{y10}$, $C_{1-7}$ alkyl, $C_{2-7}$ alkenyl, $C_{2-7}$ alkynyl, $C_{3-8}$ cycloalkyl-$C_{0-2}$ alkyl-, $C_{3-8}$ heterocycloalkyl-$C_{0-2}$ alkyl- [which latter five groups are optionally substituted by one or more substituents independently selected from $R^{alkyl}$];
  aryl-$C_{0-2}$ alkyl- or heteroaryl-$C_{0-2}$ alkyl- [which latter two aromatic groups are optionally substituted by one or more substituents selected from $R^{aryl}$],
$R^{Z6}$ represents hydrogen, halo, —$N(R^{y1})R^{y2}$, —OH, —O—$C_{1-6}$ alkyl, —O—$C_{2-6}$ alkenyl, —O—$C_{3-6}$ alkynyl, cycloalkyl, —O—$C_{4-8}$ heterocycloalkyl, $C_{1-7}$ alkyl, $C_{2-7}$ alkenyl, $C_{2-7}$ alkynyl, $C_{3-8}$ cycloalkyl, $C_{4-8}$ heterocycloalkyl [which latter ten groups are optionally substituted by one or more substituents selected from fluoro, —CN, =O, —$N(R^{y1})R^{y2}$, —$OR^{y10}$, —$N(R^{y3})$—C(O)—$R^{y4}$, —$N(R^{y5})$—$S(O)_2$—$R^{y6}$, —$C(O)OR^{y7}$, —$C(O)N(R^{y8})R^{y9}$, —$S(O)_{0-2}$—$R^{y11}$, —$S(O)_2O$—$R^{y12}$, —$S(O)_2N(R^{y13})R^{y14}$, —$C(O)R^{y15}$, $C_{1-7}$ alkyl, $C_{2-7}$ alkenyl, $C_{2-7}$ alkynyl, $C_{3-6}$ cycloalkyl, $C_{4-6}$ heterocycloalkyl (which latter five groups are optionally substituted by one or more substituents selected from $R^{alkyl}$), aryl and heteroaryl (which latter two aromatic groups are optionally substituted by one or more substituents independently selected from $R^{aryl}$)], or
  aryl or heteroaryl, O-aryl, O-heteroaryl, —$N(R^{y1})$aryl, —$N(R^{y1})$hetaryl (which latter six aromatic groups are optionally substituted by one or more substituents independently selected from $R^{aryl}$);
A represents $C_{3-10}$ heterocycloalkyl-$C_{0-3}$ alkyl-, $C_{3-10}$ cycloalkyl-$C_{0-3}$ alkyl-, $C_{1-12}$ alkyl, $C_{3-12}$ alkenyl or $C_{3-12}$ alkynyl, which latter five groups are optionally substituted by one or more substituents selected from $R^8$;
or
  aryl-$C_{0-3}$ alkyl- or heteroaryl-$C_{0-3}$ alkyl-, which latter two groups are optionally substituted in the aryl fragment by one or more substituents selected from $R^9$;
$R^a$ and $R^b$ independently represent hydrogen, $C_{1-3}$ alkyl which is optionally substituted by one or more fluorine atoms;
or $R^a$ and $R^b$ together with the carbon atom to which they are attached, may be linked together to form a 3-6 membered cycloalkylene ring, wherein a methylene group may be oxidised to a —C(=O)-group and which ring is optionally substituted by one or more $C_{1-3}$ alkyl substituents or fluorine atoms
W represents —C(=O)—, —S(=O)— or —$S(=O)_2$—,
M represents $C_{1-9}$ alkyl, $C_{2-9}$ alkenyl, $C_{2-9}$ alkynyl, $C_{3-10}$ cycloalkyl, $C_{3-10}$ heterocycloalkyl all of which groups are optionally substituted by one or more groups selected from fluoro, =O, —$OR^{y10}$, —CN, —$N(R^{y1})R^{y2}$, aryl, heteroaryl [which latter two aromatic groups are optionally substituted by one or more substituents independently selected from $R^{aryl}$], $C_{1-7}$ alkyl, $C_{2-7}$ alkynyl, $C_{3-7}$ cycloalkyl-$C_{0-2}$ alkyl-, $C_{3-7}$ heterocycloalkyl-$C_{0-2}$ alkyl- [which latter four groups are optionally substituted by one or more substituents independently selected from $R^{alkyl}$];
or
  aryl, heteroaryl, both of which groups are optionally substituted by one or more substituents independently selected from halo, —$OR^{y10}$, —CN, —$N(R^{y1})R^{y2}$, aryl, heteroaryl, O-phenyl, O-benzyl [which latter four aromatic groups are optionally substituted by one or more substituents independently selected from $R^{aryl}$], $C_{1-7}$ alkyl, $C_{2-7}$ alkynyl, $C_{3-7}$ cycloalkyl-$C_{0-2}$ alkyl, $C_{3-7}$ heterocycloalkyl-$C_{0-2}$ alkyl [which latter four groups are optionally substituted by one or more substituents independently selected from $R^{alkyl}$];
$R^{alkyl}$ represents fluoro, —CN, =O, —$N(R^{y1})R^{y2}$, —OH, —$OC_{1-3}$ alkyl, $C_{1-3}$ alkyl (which latter two groups are optionally substituted by one or more fluorine atoms)
$R^{aryl}$ represents halo, CN, —$N(R^{y1})R^{y2}$, OH, —$OC_{1-3}$ alkyl, $C_{1-3}$ alkyl (which latter two groups are optionally substituted by one or more fluorine atoms)
$R^7$ represents hydrogen or $C_{1-3}$ alkyl which is optionally substituted by one or more fluorine atoms;
$R^8$ represents fluoro, =O, —CN, —$N(R^{y1})R^{y2}$, —$N(R^{y3})$—C(O)—$R^{y4}$, —$N(R^{y5})$—$S(O)_2$—$R^{y6}$, —$C(O)OR^{y7}$, —$C(O)N(R^{y8})R^{y9}$, —$OR^{y10}$, —$S(O)_{0-2}$—$R^{y11}$, —$S(O)_2N(R^{y13})R^{y14}$ and —$C(O)R^{y15}$;
  $C_{1-7}$ alkyl, $C_{2-7}$ alkenyl, $C_{2-7}$ alkynyl, $C_{3-6}$ cycloalkyl-$C_{0-2}$ alkyl-, $C_{3-6}$ heterocycloalkyl-$C_{0-2}$ alkyl- [which latter five groups are optionally substituted by one or more substituents selected from $R^{alkyl}$];
or
  aryl or heteroaryl [which latter two groups are optionally substituted by one or more substituents independently selected from halo, —CN, —OR$^{y10}$, C$_{1-7}$ alkyl, C$_{2-7}$ alkenyl, C$_{2-7}$ alkynyl, C$_{3-6}$ cycloalkyl-C$_{0-2}$ alkyl-, C$_{3-6}$ heterocycloalkyl-C$_{0-2}$ alkyl-, (which latter five groups are optionally substituted by one or more substituents independently selected from fluoro and —OR$^{y10}$)]; or any two R$^8$ substituents:
when attached to adjacent atoms of the non-aromatic group or in the case where the R$^8$ substituents are attached to the same carbon atom,
may be linked together to form, together with the essential atom or atoms of the non-aromatic group to which these R$^8$ substituents are necessarily attached, a further 3- to 8-membered ring, optionally containing a further one or two heteroatoms, and which further ring optionally contains one or two unsaturations and which is optionally substituted by one or more C$_{1-3}$ alkyl and/or =O substituents;

R$^9$ represents halo, —CN, —N(R$^{y1}$)R$^{y2}$, —N(R$^{y3}$)—C(O)—R$^{y4}$, —N(R$^{y5}$)—S(O)$_2$—R$^{y6}$, —C(O)OR$^{y7}$, —C(O)N(R$^{y8}$)R$^{y9}$, —OR$^{y10}$, —S(O)$_{0-2}$—R$^{y11}$, —S(O)$_2$O—R$^{y12}$, —S(O)$_2$N(R$^{y13}$)R$^{y14}$ and —C(O)R$^{y15}$;

C$_{1-7}$ alkyl, C$_{2-7}$ alkenyl, C$_{2-7}$ alkynyl, C$_{3-6}$ cycloalkyl-C$_{0-2}$ alkyl-, C$_{3-6}$ heterocycloalkyl-C$_{0-2}$ alkyl- [which latter five groups are optionally substituted by one or more substituents selected from fluoro, =O, —CN, —N(R$^{y1}$)R$^{y2}$, —N(R$^{y3}$)—C(O)—R$^{y4}$, —C(O)OR$^{y7}$, —C(O)N(R$^{y8}$)R$^{y9}$, —OR$^{y10}$ and —C(O)R$^{y15}$]; or aryl or heteroaryl [which latter two groups are optionally substituted by one or more substituents selected from halo, —CN, C$_{1-7}$ alkyl, C$_{2-7}$ alkenyl, C$_{2-7}$ alkynyl, C$_{3-6}$ cycloalkyl-C$_{0-2}$ alkyl-, C$_{3-6}$ heterocycloalkyl-C$_{0-2}$ alkyl- (which latter five groups are optionally substituted by one or more substituents selected from fluoro and —OR$^{y10}$), —O—C$_{1-7}$ alkyl, —O—C$_{2-7}$ alkenyl, alkynyl, —O—C$_{0-2}$ alkyl-C$_{3-6}$ cycloalkyl, —O—C$_{0-2}$ alkyl-C$_{3-6}$ heterocycloalkyl (which latter five groups are optionally substituted by one or more fluorine atoms)]; or any two R$^9$ substituents:
when attached to the adjacent atoms of the aryl or hetaryl group may be linked together to form, together with the essential atoms of the aryl group to which the relevant R$^9$ substituents are necessarily attached, a further 5- to 8-membered ring, optionally containing a further one or two heteroatoms, and which further ring optionally contains one or two unsaturations and which is optionally substituted by one or more C$_{1-3}$ alkyl and/or =O substituents;

each R$^{y4}$, R$^{y6}$, R$^{y11}$ and R$^{y15}$:
independently represent C$_{1-7}$ alkyl, C$_{2-7}$ alkenyl, C$_{2-7}$ alkynyl, C$_{3-6}$ cycloalkyl, which latter four groups are optionally substituted by one or more fluorine atoms;

each R$^{y1}$, R$^{y2}$, R$^{y3}$, R$^{y5}$, R$^{y7}$, R$^{y8}$, R$^{y9}$, R$^{y10}$, R$^{y12}$, R$^{y13}$ and R$^{y14}$:
independently represent hydrogen or C$_{1-7}$ alkyl, C$_{2-7}$ alkenyl, C$_{3-7}$ alkynyl, C$_{4-6}$ cycloalkyl, C$_{4-6}$ heterocycloalkyl, which latter five groups are optionally substituted one or more selected from fluoro and —OC$_{1-3}$ alkyl; or any two groups, when attached to the same nitrogen atom (i.e. R$^{y1}$ and R$^{y2}$), may, together with that nitrogen atom to which they are necessarily attached, be linked together to form a 3- to 8-membered ring, optionally containing one or two further heteroatoms and which ring optionally contains one or two unsaturations and is optionally substituted by one or more C$_{1-3}$ alkyl and/or =O substituents or one or more fluorine atoms, or a pharmaceutically acceptable salt thereof.

In one embodiment, the invention provides compounds of formula I as described above and in which
Z$^2$, Z$^4$ and Z$^6$ respectively represent —C(R$^{Z2}$)=, —C(R$^{Z4}$)= and —C(R$^{Z6}$)=, and
Z$^5$ represents —N=.

In another embodiment, the invention provides compounds of formula I according to any of the preceding embodiments and
in which
Z$^2$, Z$^4$ and Z$^5$ respectively represent —C(R$^{Z2}$)=, —C(R$^{Z4}$)= and —C(R$^{Z5}$)=, and
Z$^6$ represents —N=.

In another embodiment, the invention provides compounds of formula I according to any of the preceding embodiments and
in which
R$^{Z6}$ represents halo, —N(R$^{y1}$)R$^{y2}$, —OH;
—O—C$_{1-6}$ alkyl, —O—C$_{3-6}$ alkynyl, cycloalkyl, heterocycloalkyl, C$_{1-7}$ alkyl, C$_{2-7}$ alkynyl, C$_{3-8}$ cycloalkyl, C$_{4-8}$ heterocycloalkyl [which latter eight groups are optionally substituted by one or more substituents selected from fluoro, —CN, =O, —N(R$^{y1}$)R$^{y2}$, —OR$^{y10}$, —N(R$^{y3}$)—C(O)—R$^{y4}$, —C(O)N(R$^{y8}$)R$^{y9}$, —C(O)R$^{y15}$, C$_{1-7}$ alkyl, C$_{2-7}$ alkynyl, C$_{3-6}$ cycloalkyl, C$_{4-6}$ heterocycloalkyl (which latter four groups are optionally substituted by one or more substituents independently selected from R$^{alkyl}$), aryl and heteroaryl (which latter two aromatic groups are optionally substituted by one or more substituents selected from R$^{aryl}$)]; or
aryl or heteroaryl, O-aryl, O-heteroaryl, —N(R$^{y1}$)aryl, —N(R$^{y1}$)hetaryl (which latter six aromatic groups are optionally substituted by one or more substituents selected from R$^{aryl}$.

In another embodiment, the invention provides compounds of formula I according to any of the preceding embodiments and
in which
R$^2$ represents halo, CN, —O—C$_{1-6}$ alkyl and C$_{1-6}$ alkyl [which latter two groups are optionally substituted by one or more fluorine atoms].

In another embodiment, the invention provides compounds of formula I according to any of the preceding embodiments and
in which
R$^2$ represents fluoro, chloro, bromo, CN, —O—C$_{1-3}$ alkyl and C$_{1-3}$ alkyl [which latter two groups are optionally substituted by one or more fluorine atoms].

In another embodiment, the invention provides compounds of formula I according to any of the preceding embodiments and
in which
R$^1$ and/or R$^7$ represent hydrogen.

In another embodiment, the invention provides compounds of formula I according to any of the preceding embodiments and
in which
R$^3$, R$^4$ and R$^6$
independently represent hydrogen, halo, —CN, —O—C$_{1-6}$ alkyl and C$_{1-6}$ alkyl [which latter two groups are optionally substituted by one or more fluorine atoms].

In another embodiment, the invention provides compounds of formula I according to any of the preceding embodiments and
in which
$R^3$, $R^4$ and $R^6$
independently represent hydrogen, fluoro, chloro, bromo, CN, —O—$C_{1-3}$ alkyl and $C_{1-3}$ alkyl [which latter two groups are optionally substituted by one or more fluorine atoms].

In another embodiment, the invention provides compounds of formula I according to any of the preceding embodiments and
in which
$R^{Z2}$, $R^{Z4}$ and $R^{Z5}$
independently represent hydrogen, halo, —CN, —O—$C_{1-6}$ alkyl and $C_{1-6}$ alkyl [which latter two groups are optionally substituted by one or more fluorine atoms].

In another embodiment, the invention provides compounds of formula I according to any of the preceding embodiments and
in which
$R^{Z2}$, $R^{Z4}$ and $R^{Z5}$
independently represent hydrogen, fluoro, chloro, bromo, CN, —O—$C_{1-3}$ alkyl and $C_{1-3}$ alkyl [which latter two groups are optionally substituted by one or more fluorine atoms].

In another embodiment, the invention provides compounds of formula I according to any of the preceding embodiments and
in which
$R^a$ and $R^b$ independently represent hydrogen or $CH_3$.

In another embodiment, the invention provides compounds of formula I according to any of the preceding embodiments and
in which
M represents $C_{1-9}$ alkyl, $C_{3-9}$ alkynyl, or
$C_{3-8}$ cycloalkyl selected from:

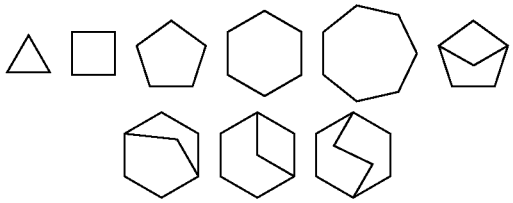

or one of the following $C_{4-6}$ heterocycloalkyl groups which are all bound via a carbon atom to the corresponding W-group:

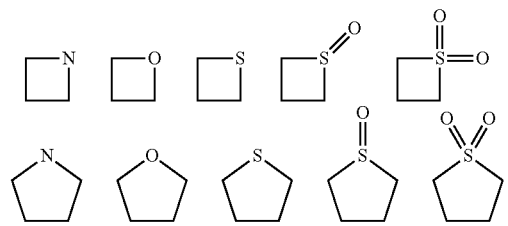

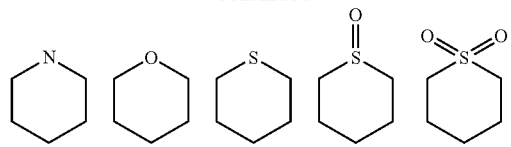

which latter $C_{1-9}$ alkyl, $C_{3-9}$ alkynyl, $C_{3-8}$ cycloalkyl or $C_{4-6}$ heterocycloalkyl groups are optionally substituted by one or more groups selected from fluoro, —$OR^{y10}$, —CN, —$N(R^{y1})R^{y2}$, phenyl, pyridyl, thienyl, thiazolyl, oxazolyl, isoxazolyl [which latter six aromatic groups are optionally substituted by one or more substituents selected from CN, halo, $C_{1-3}$ alkyl, —$OC_{1-3}$ alkyl (which latter two groups are optionally substituted by one or more fluorine atoms)], $C_{1-5}$ alkyl, $C_{2-5}$ alkynyl, $C_{3-5}$ cycloalkyl-$C_{0-2}$ alkyl-, $C_{4-5}$ heterocycloalkyl-$C_{0-2}$ alkyl-, [which latter four groups are optionally substituted by one or more substituents selected from fluoro or $C_{1-3}$ alkyl optionally substituted by one or more fluorine atoms];

or aryl selected from

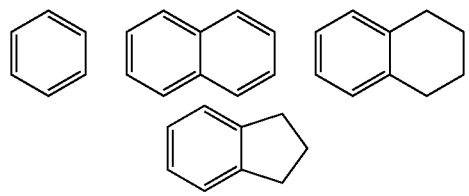

or heteroaryl selected from

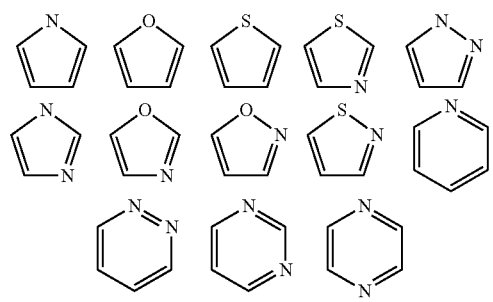

which latter aryl or heteroaryl groups are optionally substituted by one or more substituents selected from halo, —$OR^{y10}$, —CN, —$N(R^{y1})R^{y2}$, phenyl, O-phenyl, O-benzyl, pyridyl, thienyl, thiazolyl, oxazolyl, isoxazolyl [which latter eight aromatic groups are optionally substituted by one or more substituents independently selected from CN, halo, $C_{1-3}$ alkyl, —$OC_{1-3}$ alkyl (which latter two groups are optionally substituted by one or more fluorine atoms)]; or $C_{1-5}$ alkyl, $C_{3-5}$ cycloalkyl-$C_{0-2}$ alkyl, [which latter two groups are optionally substituted by one or more fluorine atoms].

In another embodiment, the invention provides compounds of formula I according to any of the preceding embodiments and
in which
$R^{Z6}$ represents halo, —N(R$^{y1}$)R$^{y2}$, —OH,
—O—C$_{1-4}$ alkyl, —O—C$_{3-6}$ alkynyl, —O—C$_{3-6}$ cycloalkyl, —O—C$_{4-6}$ heterocycloalkyl, C$_{1-4}$ alkyl, C$_{2-4}$ alkynyl, C$_{3-6}$ cycloalkyl, C$_{4-6}$ heterocycloalkyl [which latter eight groups are optionally substituted by one or more substituents selected from fluoro, —CN, =O, —NH(C$_{1-3}$ alkyl), —N(C$_{1-3}$ alkyl)$_2$, —O—C$_{1-3}$ alkyl, C$_{1-3}$ alkyl, C$_{3-5}$ cycloalkyl, C$_{4-6}$ heterocycloalkyl (which latter six groups are optionally substituted by one or more fluorine atoms), phenyl, pyridyl, thienyl, thiazolyl, oxazolyl, isoxazolyl [which latter six aromatic groups are optionally substituted by one or more substituents selected from CN, halo, —O—C$_{1-3}$ alkyl, C$_{1-3}$ alkyl, which latter two groups are optionally substituted by one or more fluorine atoms)];
or
phenyl, pyridyl, thienyl, thiazolyl, oxazolyl, isoxazolyl, —O-phenyl, —O-pyridyl, —N(R$^{y1}$)phenyl, —N(R$^{y1}$)pyridyl, —N(R$^{y1}$)thienyl, —N(R$^{y1}$)thiazolyl, —N(R$^{y1}$)oxazolyl, —N(R$^{y1}$)isoxazolyl, [which latter fourteen aromatic groups are optionally substituted by one or more substituents selected from CN, halo, —O—C$_{1-3}$ alkyl, C$_{1-3}$ alkyl, which latter two groups are optionally substituted by one or more fluorine atoms)].

In another embodiment, the invention provides compounds of formula Ia or Ib

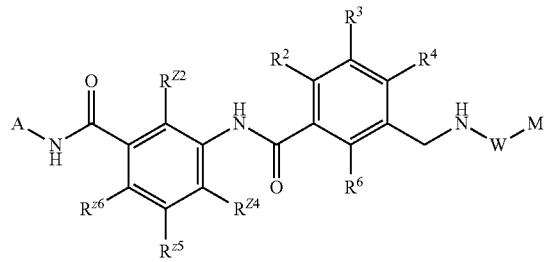

Ia

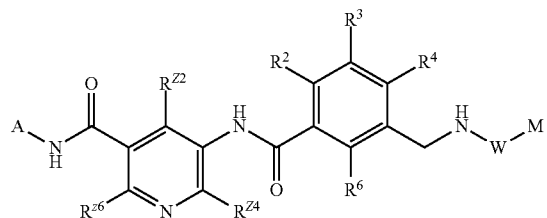

Ib in which:
$R^2$ represents fluoro, chloro, bromo, CN, —O—C$_{1-3}$ alkyl and C$_{1-3}$ alkyl [which latter two groups are optionally substituted by one or more fluorine atoms];
$R^3$, $R^4$ and $R^6$:
independently represent hydrogen, fluoro, chloro, bromo, CN, —O—C$_{1-3}$ alkyl and C$_{1-3}$ alkyl [which latter two groups are optionally substituted by one or more fluorine atoms];
$R^{Z2}$, $R^{Z4}$ and $R^{Z5}$
independently represent hydrogen, fluoro, chloro, bromo, CN, —O—C$_{1-3}$ alkyl and C$_{1-3}$ alkyl [which latter two groups are optionally substituted by one or more fluorine atoms];

$R^{Z6}$ represents fluoro, chloro, bromo, —OH,
C$_{1-4}$ alkyl, C$_{2-4}$ alkynyl, C$_{3-6}$ cycloalkyl, —O—C$_{1-4}$ alkyl, —O—C$_{3-6}$ cycloalkyl, —O-oxetan-3-yl, —O-tetrahydrofuran-3-yl, —O-pyrrolidin-3-yl, —NH(C$_{1-3}$ alkyl), —N(C$_{1-3}$ alkyl)$_2$, piperidinyl, pyrrolidinyl [which latter twelve groups are optionally substituted by one or more substituents selected from fluoro or C$_{1-3}$ alkyl, which latter alkyl group is optionally substituted by one or more fluorine atoms];
W represents —C(=O)—, —(S=O)— or —S(=O)$_2$—,
M represents C$_{1-6}$ alkyl, C$_{3-6}$ alkynyl, or
C$_{3-7}$ cycloalkyl selected from:

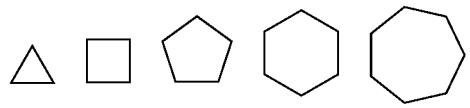

or one of the following C$_{4-6}$ heterocycloalkyl groups which are all bound via a carbon atom to the corresponding W-group:

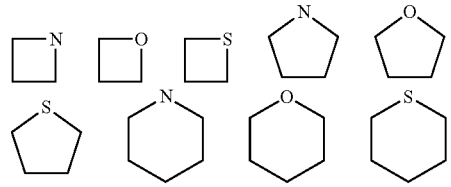

which latter C$_{1-6}$ alkyl, C$_{3-6}$ alkynyl, C$_{3-7}$ cycloalkyl or C$_{4-6}$ heterocycloalkyl groups are optionally substituted by one or more groups selected from
fluoro, C$_{1-3}$ alkyl optionally substituted by one or more fluorine atoms, —OH, —O—C$_{1-3}$ alkyl, —CN, —NH$_2$, —NH(C$_{1-3}$ alkyl), —N(C$_{1-3}$ alkyl)$_2$, pyrrolidinyl, thiazolyl, phenyl optionally substituted by one or more substituents selected from CN, halo, C$_{1-3}$ alkyl, —OC$_{1-3}$ alkyl (which latter two groups are optionally substituted by one or more fluorine atoms);
or
phenyl or heteroaryl selected from

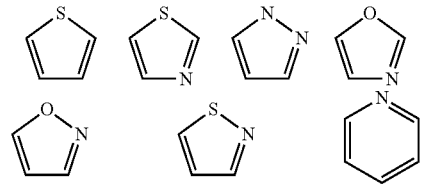

which latter aryl or heteroaryl groups are optionally substituted by one or more substituents selected from halo, —OH, —O—C$_{1-3}$ alkyl, —CN, C$_{1-3}$ alkyl optionally substituted by one or more fluorine atoms;
A represents C$_{3-7}$ cycloalkyl-C$_{0-2}$ alkyl-, C$_{1-8}$ alkyl or C$_{3-6}$ alkynyl, which latter three groups are optionally substituted by one or more substituents selected from fluoro, —CN, =O, —OH, —NH$_2$, —NH(C$_{1-3}$ alkyl), —N(C$_{1-3}$ alkyl)$_2$, —OC$_{1-3}$ alkyl, C$_{1-3}$ alkyl, (which latter four groups are optionally substituted by one or more fluorine atoms), or aryl-$C_{0-3}$ alkyl- or heteroaryl-$C_{0-3}$ alkyl-, in which latter two groups the aryl groups are optionally substituted by one or more substituents selected from halo, —CN, —OH, —NH$_2$, —NH($C_{1-3}$ alkyl), —N($C_{1-3}$ alkyl)$_2$, —O$C_{1-3}$ alkyl, $C_{1-3}$ alkyl, (which latter four groups are optionally substituted by one or more fluorine atoms).

In another embodiment, the invention provides compounds of formula Ia or Ib

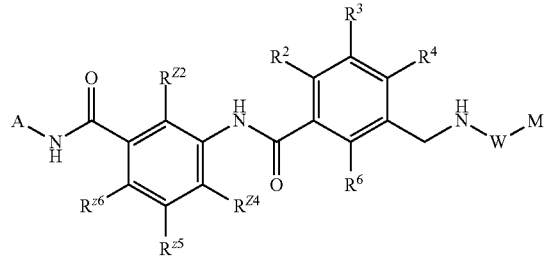

Ia

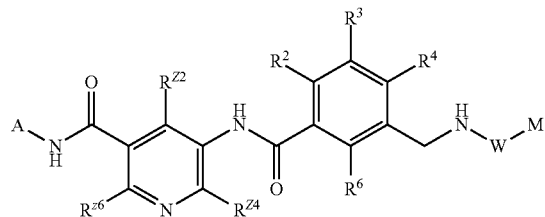

Ib in which
R$^2$ represents fluoro, chloro, bromo, CN, —O—$C_{1-3}$ alkyl and $C_{1-3}$ alkyl [which latter two groups are optionally substituted by one or more fluorine atoms];
R$^3$, R$^4$ and R$^6$:
  independently represent hydrogen, fluoro, chloro, bromo, CN, —O—$C_{1-3}$ alkyl and $C_{1-3}$ alkyl [which latter two groups are optionally substituted by one or more fluorine atoms];
R$^{Z2}$, R$^{Z4}$ and R$^{Z5}$
  independently represent hydrogen, fluoro, chloro, bromo, CN, —O—$C_{1-3}$ alkyl and $C_{1-3}$ alkyl [which latter two groups are optionally substituted by one or more fluorine atoms];
R$^{Z6}$ represents fluoro, chloro, bromo, —OH,
  $C_{1-4}$ alkyl, $C_{2-4}$ alkynyl, $C_{3-6}$ cycloalkyl, —O—$C_{1-4}$ alkyl, —O—$C_{3-6}$ cycloalkyl, —O-oxetan-3-yl, —O-tetrahydrofuran-3-yl, —O-pyrrolidin-3-yl, —NH($C_{1-3}$ alkyl), —N($C_{1-3}$ alkyl)$_2$, piperidinyl, pyrrolidinyl [which latter twelve groups are optionally substituted by one or more substituents selected from fluoro or $C_{1-3}$ alkyl];
W represents —C(=O)—, —(S=O)— or —S(=O)$_2$—,
M represents $C_{1-6}$ alkyl, $C_{3-6}$ alkynyl, or
  $C_{3-7}$ cycloalkyl selected from:

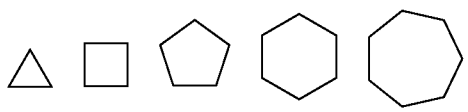

or one of the following $C_{4-6}$ heterocycloalkyl groups which are all bound via a carbon atom to the corresponding W-group:

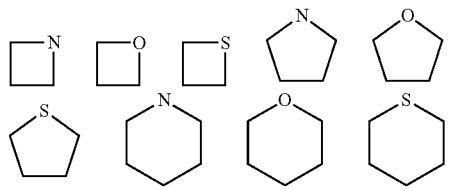

which latter $C_{1-6}$ alkyl, $C_{3-6}$ alkynyl, $C_{3-7}$ cycloalkyl or $C_{4-6}$ heterocycloalkyl groups are optionally substituted by one or more groups selected from
  fluoro, $C_{1-3}$ alkyl optionally substituted by one or more fluorine atoms, —OH, —O—$C_{1-3}$ alkyl, —CN, —NH$_2$, —NH($C_{1-3}$ alkyl), —N($C_{1-3}$ alkyl)$_2$, phenyl optionally substituted by one or more substituents selected from CN, halo, $C_{1-3}$ alkyl, —O$C_{1-3}$ alkyl (which latter two groups are optionally substituted by one or more fluorine atoms);
or
phenyl or heteroaryl selected from

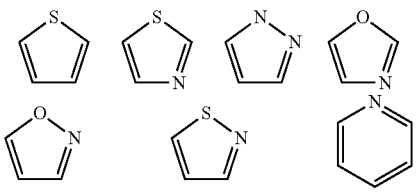

which latter aryl or heteroaryl groups are optionally substituted by one or more substituents selected from halo, —OH, —O—$C_{1-3}$ alkyl, —CN, $C_{1-3}$ alkyl optionally substituted by one or more fluorine atoms;
A represents $C_{3-7}$ cycloalkyl-$C_{0-2}$ alkyl-, $C_{1-8}$ alkyl or $C_{3-6}$ alkynyl, which latter three groups are optionally substituted by one or more substituents selected from fluoro, —CN, =O, —OH, —NH$_2$, —NH($C_{1-3}$ alkyl), —N($C_{1-3}$ alkyl)$_2$, —O$C_{1-3}$ alkyl, $C_{1-3}$ alkyl, (which latter four groups are optionally substituted by one or more fluorine atoms), or
aryl-$C_{0-3}$ alkyl- or heteroaryl-$C_{0-3}$ alkyl-, in which latter two groups the aryl groups are optionally substituted by one or more substituents selected from halo, —CN, —OH, —NH$_2$, —NH($C_{1-3}$ alkyl), —N($C_{1-3}$ alkyl)$_2$, —O$C_{1-3}$ alkyl, $C_{1-3}$ alkyl, (which latter four groups are optionally substituted by one or more fluorine atoms).

In another embodiment, the invention provides compounds of formula Ic

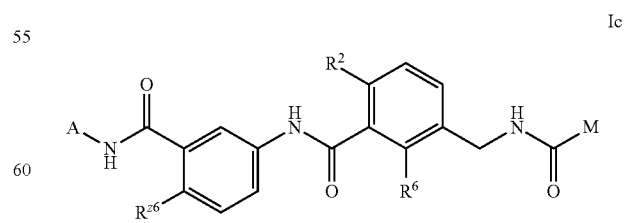

Ic in which
R$^2$ represents fluoro, chloro, bromo and $C_{1-3}$ alkyl, which latter alkyl group is optionally substituted by one or more fluorine atoms];

$R^6$ represents fluoro, chloro, bromo and $C_{1-3}$ alkyl, which latter alkyl group is optionally substituted by one or more fluorine atoms];

$R^{Z6}$ represents fluoro, chloro,
$C_{1-4}$ alkyl, —O—$C_{1-4}$ alkyl, —O—$C_{3-6}$ cycloalkyl, —O-oxetan-3-yl, —O-tetrahydrofuran-3-yl, —NH($C_{1-3}$ alkyl), —N($C_{1-3}$ alkyl)$_2$, piperidinyl, pyrrolidinyl [which latter twelve groups are optionally substituted by one or more substituents selected from fluoro or $C_{1-3}$ alkyl, which latter alkyl group is optionally substituted by one or more fluorine atoms];

M represents $C_{1-6}$ alkyl or $C_{3-7}$ cycloalkyl selected from:

or one of the following $C_{4-6}$ heterocycloalkyl groups which are all bound via a carbon atom to the corresponding W-group:

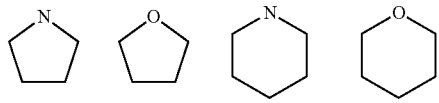

which latter $C_{1-6}$ alkyl, $C_{3-7}$ cycloalkyl or $C_{4-6}$ heterocycloalkyl groups are optionally substituted by one or more groups selected from fluoro, $C_{1-3}$ alkyl optionally substituted by one or more fluorine atoms, —OH, —O—$C_{1-3}$ alkyl, —CN, —NH$_2$, —NH($C_{1-3}$ alkyl), —N($C_{1-3}$ alkyl)$_2$, pyrrolidinyl, thiazolyl, phenyl optionally substituted by one or more substituents selected from CN, halo, $C_{1-3}$ alkyl, —O$C_{1-3}$ alkyl (which latter two groups are optionally substituted by one or more fluorine atoms);

or phenyl or heteroaryl selected from

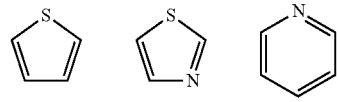

which latter aryl or heteroaryl groups are optionally substituted by one or more substituents selected from halo, —O—$C_{1-3}$ alkyl, $C_{1-3}$ alkyl optionally substituted by one or more fluorine atoms;

A represents $C_{3-7}$ cycloalkyl-$C_{0-2}$ alkyl-, $C_{1-6}$ alkyl or 1-phenyl-propin-3-yl, which latter three groups are optionally substituted by one or more substituents selected from fluoro, —OH, —O$C_{1-3}$ alkyl or $C_{1-3}$ alkyl (which latter two alkyl-groups are optionally substituted by one or more fluorine atoms), or phenyl-$C_{0-1}$ alkyl- or

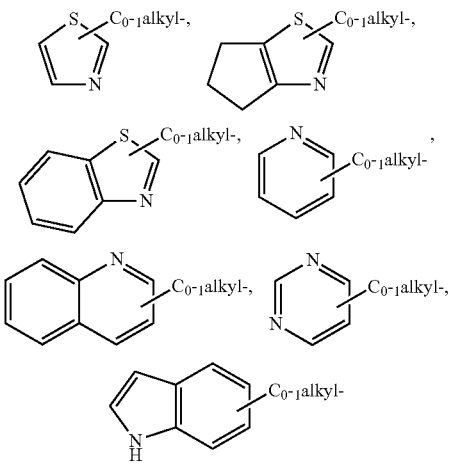

in which latter seven groups the phenyl and heteroaryl groups are optionally substituted by one or more substituents selected from fluoro, chloro, bromo, —CN, —OH, —O$C_{1-2}$ alkyl, $C_{1-2}$ alkyl (which latter two alkyl groups are optionally substituted by one or more fluorine atoms).

In a further embodiment, the invention provides compounds namely those of the examples described hereinafter.

Methods of Preparation

Compounds of the present invention can be prepared in accordance with techniques that are well known to those skilled in the art, for example as described hereinafter and in the experimental section. According to a further aspect of the invention there is provided a process for the preparation of a compound of formula I, which process can be performed for example according to the following schemes a-c.

Schemes a-c ($L^1$, $L^2$, $L^3$ can all represent either OH or Cl or O$C_{1-2}$ alkyl, all other variable groups are as defined in the first embodiment)

a)

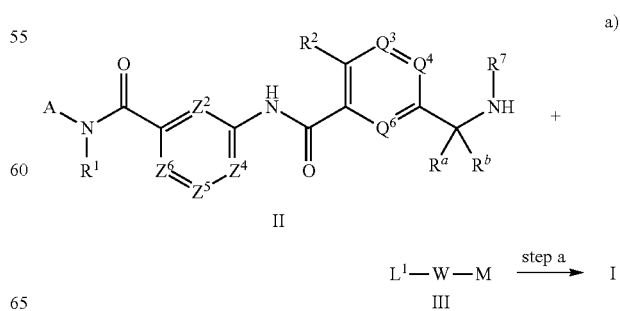

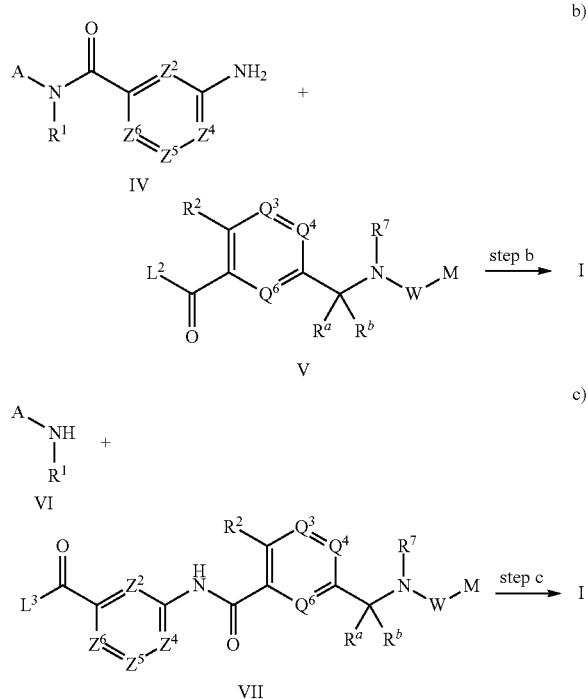

wherein L² or L³ in the acyl building blocks III, V and VII respectively represent OH or Cl or O—C₁₋₂alkyl and wherein II, IV and VI are the corresponding amine coupling partners. When L¹, L², L³ represent OH the reaction steps a, b or c are preferably run in presence of a suitable coupling reagent, for example 1,1'-carbonyldiimidazole, N,N'-dicyclohexylcarbodiimide, N,N-diisopropylcarbodiimide, 1-(3-dimethylamino-propyl)-3-ethylcarbodiimide (or salt, e.g. hydrochloride thereof), N,N'-disuccinimidyl carbonate, benzotriazol-1-yloxytris(dimethylamino) phosphonium hexafluorophosphate, 2-(1H-benzotriazol-1-yl)-1,1,3,3-tetramethyluronium hexafluorophosphate, benzotriazol-1-yloxytrispyrrolidino-phosphonium hexafluorophosphate, bromo-tris-pyrrolidinophosphonium hexafluorophosphate, 2-(1H-benzotriazol-1-yl)-1,1,3,3-tetramethyluronium tetrafluorocarbonate, 1-cyclohexyl-carbodiimide-3-propyloxymethyl polystyrene, O-(7-azabenzotriazol-1-yl)-N,N,N',N'-tetra-methyluronium hexafluorophosphate, O-pentafluorophenyl-N,N,N',N'-tetra-methyluronium hexafluorophosphate, O-(benzotriazol-1-yl)-N,N,N',N'-tetra-methyluronium tetrafluoroborate, 1-chloro-N,N,2-trimethylpropenylamine, propanephosphonic acid cycloanhydride or mixtures thereof around room temperature or above (e.g. up to 40-180° C.), optionally in the presence of a suitable base (e.g. sodium hydride, sodium bicarbonate, potassium carbonate, pyrrolidinopyridine, pyridine, triethylamine, tributylamine, trimethylamine, dimethylaminopyridine, diisopropylamine, diisopropylethylamine, 1,8-diazabicyclo[5.4.0]undec-7-ene, sodium hydroxide, N-ethyldiisopropylamine, N-(methylpolystyrene)-4-(methylamino)pyridine, potassium bis(trimethylsilyl)amide, sodium bis(trimethylsilyl)amide, potassium tert-butoxide, lithium diisopropylamide, lithium 2,2,6,6-tetramethylpiperidine or mixtures thereof) and in an appropriate solvent (e.g. tetrahydrofuran, pyridine, toluene, dichloromethane, chloroform, acetonitrile, dimethylformamide, dimethylsulfoxide, trifluoromethylbenzene, dioxane, triethylamine, water or mixtures thereof);

or alternatively, b) compounds III, V, VII wherein L¹, L², L³ represents OH may first be activated by treatment with a suitable reagent (e.g. oxalyl chloride, thionyl chloride, phosphorous pentachloride, phosphorous oxychloride, 1-chloro-N,N,2-trimethyl-propenylamine or the like, or mixtures thereof) optionally in the presence of an appropriate solvent (e.g. dichloromethane, THF, acetonitrile, dimethylformamide, dimethylsulfoxide, toluene or benzene) and a suitable catalyst (e.g. DMF), resulting in the formation of an activated acyl group in situ which may then be reacted with the corresponding amine II, IV or VI under standard conditions, such as those described above.

Alternatively, when L¹, L², L³ in III, V and VII represent chloro the following reaction conditions known to those skilled in the art can be used for step a, b or c: the reaction may be performed at around room temperature or above (e.g. up to 40-180° C.), optionally in the presence of a suitable base (e.g. sodium hydride, sodium bicarbonate, potassium carbonate, pyrrolidinopyridine, pyridine, triethylamine, tributylamine, trimethylamine, dimethylaminopyridine, diisopropylamine, diisopropylethylamine, 1,8-diazabicyclo[5.4.0]undec-7-ene, sodium hydroxide, N-ethyldiisopropylamine, N-(methylpolystyrene)-4-(methylamino)pyridine, potassium bis(trimethylsilyl)amide, sodium bis(trimethylsilyl)amide, potassium tert-butoxide, lithium diisopropylamide, lithium 2,2,6,6-tetramethylpiperidine or mixtures thereof) and an appropriate solvent (e.g. tetrahydrofuran, pyridine, toluene, dichloromethane, chloroform, acetonitrile, dimethylformamide, dimethylsulfoxide, trifluoromethylbenzene, dioxane, triethylamine, water or mixtures thereof).

Alternatively, when L¹, L², L³ in III, V and VII represent O—C₁₋₂alkyl step a, b and c can be performed in the presence of, e.g. trimethylaluminium, optionally in the presence of a suitable solvent (e.g. dichloromethane or tetrahydrofuran) under an inert atmosphere.

Precursor II can be prepared according to a reaction sequence depicted in scheme d) wherein $L^{2a}$ in VIII represents OH or chloro and $PG^{amino}$ in compound VIII and IX represents an amino-protecting group [e.g. a tert.-butyloxy carbonyl group, a benzyloxycarbonyl group, an allyloxycarbonyl group, a fluorenylmethyloxycarbonyl group, a trifluoracetyl group or other amino protecting groups which are known to those skilled in the art, for example mentioned in "*Protective Groups in Organic Synthesis*", 3ʳᵈ edition, T. W. Greene & P. G. M. Wutz, Wiley-Interscience (1999).]:

Scheme d ($L^{2a}$ in VIII represents OH or chloro or OC₁₋₂ alkyl and $PG^{amino}$ in compound VIII and IX represents an amino-protecting group, all other groups are as defined in claim 1)

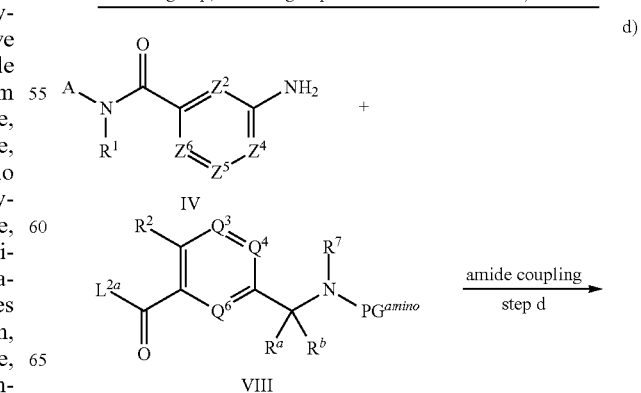

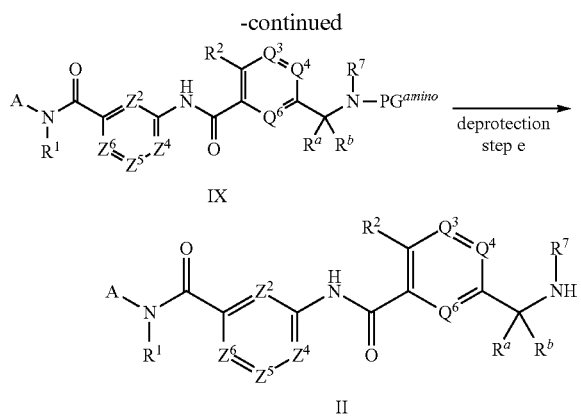

In step d the compounds IV and VIII are coupled under amide coupling conditions as described above to furnish IX.

In step e the protecting group is removed according to standard conditions for example under acidic conditions (e.g. with HCl, $H_2SO_4$, trifluoro acetic acid etc.), under hydrogenolytic conditions with a suitable catalyst (e.g. Pd on charcoal, Pd black etc.), under basic conditions with a suitable base (e.g. NaOH, $Ba(OH)_2$, piperidine, diisopropylethylamine etc.) or under thermal conditions (e.g at 150° C.) in a suitable solvent (e.g. methanol, ethanol, dichloromethane, THF, acetonitrile, dimethylformamide, dimethylsulfoxide, toluene, benzene or xylene) or under conditions which are mentioned in "*Protective Groups in Organic Synthesis*", $3^{rd}$ edition, T. W. Greene & P. G. M. Wutz, Wiley-Interscience (1999).

Precursor VIIa ($L^4$=OH) or VIIb ($L^5$=Cl) can be prepared according to reaction sequence depicted in scheme e) wherein $L^2$ in V is as defined above (for example OH or chloro or $OC_{1-2}$ alkyl) and $R^{ester}O$ in ester X and XI represents the alcohol fragment of ester X wherein $R^{ester}$ represents preferably a $C_{1-6}$ alkyl- (e.g. a $CH_3$—, $CH_3CH_2$—, $CH_3CH_2CH_2$—, $(CH_3)_2CH$— or a $(CH_3)_3C$-group), an allyl- or benzyl-group:

Scheme e ($L^4$ in VIIa represents OH, $L^5$ in VIIb represents chloro, and $R^{ester}$ represents preferably a $C_{1-6}$ alkyl-group (e.g. a $CH_3$—, $CH_3CH_2$—, $CH_3CH_2CH_2$—, $(CH_3)_2CH$— or a $(CH_3)_3C$- group), an allyl- or benzyl-group, L2 represents OH, Cl or $OC_{1-2}$ alkyl, all other groups are as defined in claim 1)

e)

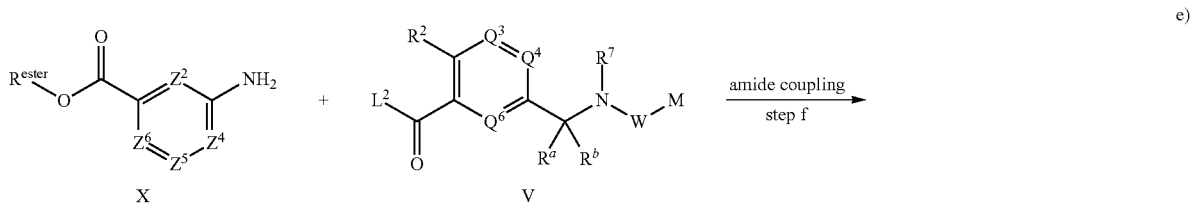

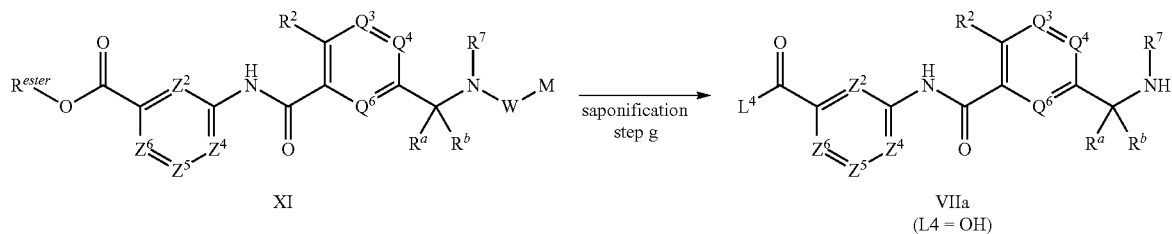

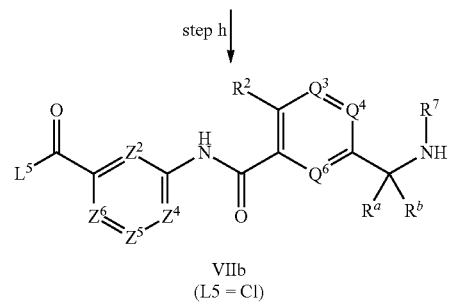

In step f the compounds X and V are coupled as described above for step a-c to furnish XI. The saponification step g wherein the ester XI is converted to the corresponding acid VIIa can be performed for example under acidic conditions (e.g. with HCl, $H_2SO_4$, trifluoro acetic acid etc.), under hydrogenolytic conditions with a suitable catalyst (e.g. Pd on charcoal, Pd-black etc.) or under basic conditions with a suitable base (e.g. LiOH, NaOH, KOH, $Ba(OH)_2$) to furnish the corresponding carboxylic acid VIIa, which can be directly used in the coupling step c described above using the coupling reagents mentioned before.

Alternatively, the carboxylic acid can be transformed in step h into the corresponding acid chloride VIIb by using for example thionyl chloride, oxalyl chloride or 1-chloro-N,N,2-trimethyl-propenylamine in a suitable solvent (e.g. DMF, THF, acetonitrile etc.) or without a solvent preferably at temperatures between 0° C.-100° C.

Precursor IV can be prepared according to reaction sequence depicted in scheme f) wherein $L^4$ in XII is a suitable leaving group as defined for $L^2$ above (for example OH or Cl or $O—C_{1-2}$ alkyl).

Scheme f ($L^4$ in XII is a suitable leaving group as defined above (for example OH or Cl or $O—C_{1-2}$ alkyl) all other groups are as defined in claim 1)

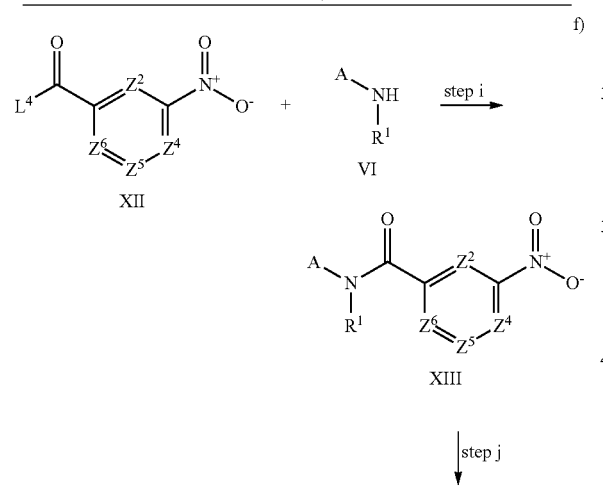

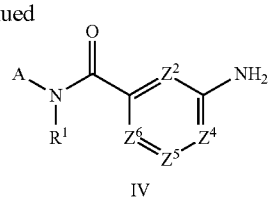

In step i the compounds XII and VI are coupled as described above for step a-c to furnish XIII.

The reduction of the nitro group in XIII in step j can be performed with $H_2$/Raney-Nickel, $H_2$/Palladium on carbon, Fe-powder/aqueous $NH_4Cl$, Fe/HCl, Zn/HCl, $Na_2S_2O_4$, $SnCl_2$/HCl, Zn/HCl or $NaBH_4$/CuCl or according to procedures described in the literature for example R. Larock, Comprehensive Organic Transformations, VCH Verlagsgemeinschaft, Weinheim (1989). Appropriate solvent for this step is for example dichloromethane, tetrahydrofuran (THF), acetonitrile, dimethylformamide (DMF), dimethylacetamide, N methylpyrrolidone, ethanol, methanol, isopropanol or mixtures of the above mentioned solvents.

The precursors XII in Scheme f are commercially available or known from the literature or can be prepared as described in the experimental part or can be prepared in analogy to literature procedures which are known by those skilled in the art.

Precursor V can be prepared according to one of the reaction sequences depicted in schemes g)-i).

For example precursor V and Va wherein $L^5$ represents OH can be prepared according to scheme g, wherein $R^{acyl}$ represents a $C_{1-6}$ alkyl group which might be substituted by one or more fluorine atoms (preferably a $CF_3$ group).

Scheme g ($L^5$ represents preferably OH, $R^{acyl}$ represents a $C_{1-6}$ alkyl group which might be substituted by one or more fluorine atoms (e.g. a $CF_3$ group), all other groups are as defined in claim 1)

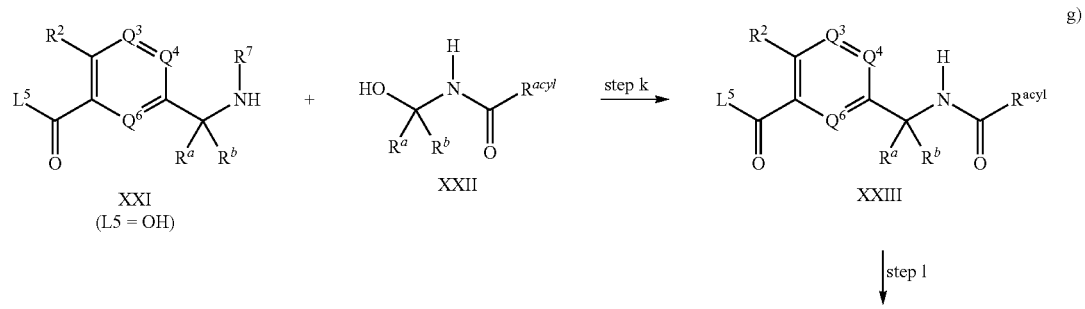

-continued

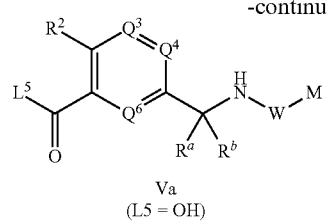

Va
(L5 = OH)

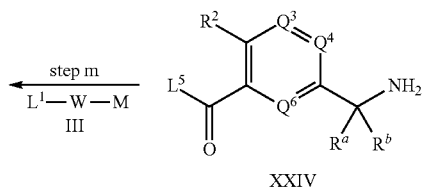

XXIV

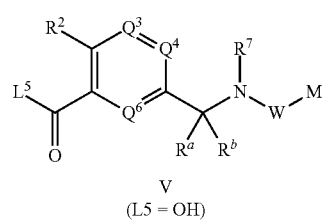

V
(L5 = OH)

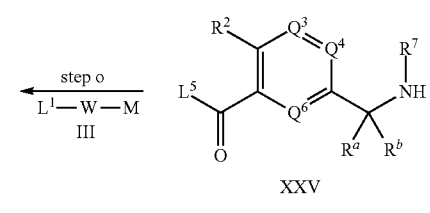

XXV

The reaction of XXI with XXII in step k is performed under strong acidic conditions (e.g. in conc. $H_2SO_4$) preferably at room temperature.

In step l the amino function in XXIII is liberated under standard conditions for example under basic conditions (e.g with NaOH, KOH, KOtBu) in an appropriate solvent (e.g. THF, methanol or ethanol) or under acidic conditions (e.g. with HCl, $H_2SO_4$) at room temperature.

The amine XXIV can then be directly coupled in step m with III under standard amide coupling conditions as described above for step a, b or c to furnish compound Va.

Alternatively, the amine XXIV can be first derivatised in step n at the nitrogen using standard reactions, for example nucleophilic substitutions, reductive aminations or Pd-catalyzed Buchwald-Hartwig-type coupling reactions and afterwards converted in step o to V ($L^5$=OH) under conditions as described above.

It is clear for a person skilled in the art that all carboxylic acid derivatives XXIII, XXIV, XXV and Va and V wherein $L^5$ represents OH can be converted into the corresponding esters by using standard esterification methods or into the corresponding acyl chlorides by using the methods already described above.

Alternatively, precursor V can also be prepared according to scheme h, wherein $L^6$ is preferably OH or $OC_{1-2}$ alkyl, and LG1 is a standard leaving group, preferably chloro, bromo, iodo, a $CH_3S(O)_2$—O-group or a $CF_3S(O)_2$—O-group.

Scheme h ($L^6$ represents preferably OH, or $OC_{1-2}$ alkyl, and $LG^1$ is a standard leaving group, preferably chloro, bromo, iodo, a $CH_3S(O)_2$—O-group or $CF_3S(O)_2$—O-group, all other groups are as defined in claim 1)

h)

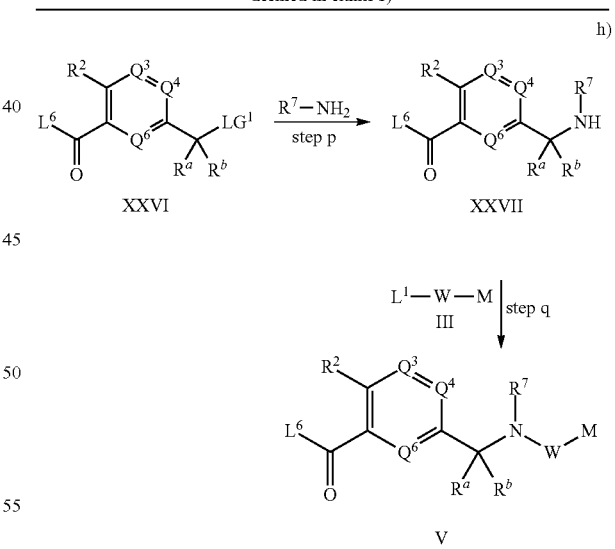

In step p the amino group is introduced in a nucleophilic substitution reaction preferably with an excess of the amine $R^7$—$NH_2$ at around room temperature or above (e.g. up to 40-180° C.), optionally in the presence of a suitable base (e.g. sodium hydride, sodium bicarbonate, potassium carbonate, pyrrolidinopyridine, pyridine, triethylamine, tributylamine, trimethylamine, dimethylaminopyridine, diisopropylamine, diisopropylethylamine, 1,8-diazabicyclo[5.4.0]undec-7-ene, sodium hydroxide, N-ethyldiisopropylamine, N-(methylpolystyrene)-4-(methylamino)pyridine, potassium bis(trimethylsilyl)-amide, sodium bis(trimethylsilyl)amide, potassium tert-butoxide, lithium diisopropylamide, lithium 2,2,6,6-tetramethylpiperidine or mixtures thereof) in an appropriate solvent (e.g. tetrahydrofuran, pyridine, toluene, dichloromethane, chloroform, acetonitrile, dimethylformamide, dimethylsulfoxide, trifluoromethylbenzene, dioxane, triethylamine, water or mixtures thereof).

In step q amine XXVII is converted into V using conditions already described above.

Alternatively, precursor V can also be prepared according to scheme h, wherein $L^6$ is preferably OH or $OC_{1-2}$ alkyl, and LG1 is a standard leaving group, preferably a chloro, bromo, iodo, a $CH_3S(O)_2$—O-group or a $CF_3S(O)_2$—O-group or —OH.

Scheme i ($L^6$ represents preferably OH, or $OC_{1-2}$ alkyl, and $LG^1$ is a standard leaving group, preferably chloro, bromo, iodo, a $CH_3S(O)_2$—O-group or $CF_3S(O)_2$—O-group or —OH, all other groups are as defined in claim 1)

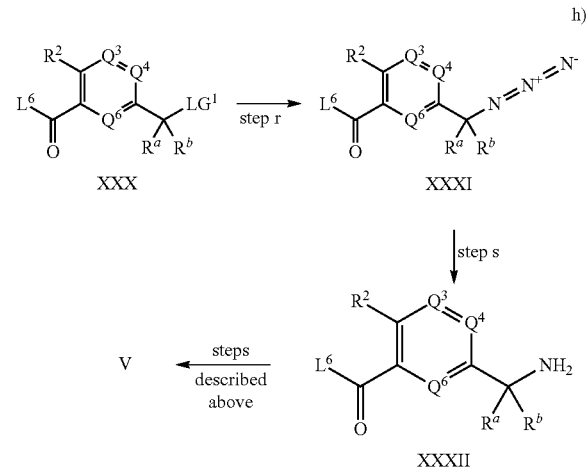

In step r compound XXX wherein $LG^1$ is a standard leaving group is carefully reacted with an azide source (e.g. $NaN_3$) in a suitable solvent (e.g DMSO, DMF, acetonitrile, toluene etc) preferably at room temperature or below, or when $LG^1$ is —OH the reaction may also be performed with diphenyl phosphoryl azide in a suitable solvent (e.g DMSO, DMF, acetonitrile, toluene etc) preferably at room temperature or below, optionally in presence of a suitable base (e.g. 1,8-diazabicyclo-[5,4,0]undec-7-ene).

In step s the azide XXXI is converted into the amine XXXII under standard conditions for example with triphenyl phosphine/ammonia in a suitable solvent like THF, via hydrogenation with a suitable catalyst like palladium-on-charcoal or $PtO_2$ or according to procedures described in the literature for example R. Larock, Comprehensive Organic Transformations, VCH Verlagsgemeinschaft, Weinheim (1989).

Compound XXXII can then be transferred into compound V by conversions already described above.

The precursors III and VI in the above mentioned Schemes are commercially available or known from the literature or can be prepared as described in the experimental part or can be prepared in analogy to literature procedures which are known by those skilled in the art.

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis*", $3^{rd}$ edition, T. W. Greene & P. G. M. Wutz, Wiley-Interscience (1999).

The conditions for all individual steps in the above mentioned schemes e.g. protection/deprotection steps, reductive aminations, amide formations and others are well known to the expert and are described in the standard literature such as the Houben-Weyl: Methoden der organischen Chemie, Georg-Thieme-Verlag, Stuttgart and are exemplified in more detail in the experimental section.

The esterification reaction is optionally carried out in a solvent such as methylene chloride, N,N-dimethylformamide, benzene, toluene, chlorobenzene, tetrahydrofuran, 1,4-dioxane, or mixtures thereof or particularly advantageously in the corresponding alcohol optionally in the presence of an acid, e.g. hydrochloric acid, or a dehydrating agent, e.g. isobutyl chloroformate, thionyl chloride, trimethylchlorosilane, sulfuric acid, methanesulfonic acid, p-toluenesulfonic acid, phosphorus trichloride, phosphorus pentoxide, N,N'-carbonyldiimidazole, N,N'-dicyclohexylcarbodiimide, triphenylphosphine combined with carbon tetrachloride, or combinations thereof optionally in the presence of 4-dimethylaminopyridine and/or 1-hydroxybenzotriazole. The reactions are conducted between 0 and 150° C., preferably between 0 and 80° C.

The ester formation may also be carried out by reacting a compound which contains a carboxy group with a corresponding alkyl halide in the presence of a base.

The subsequent alkylation is optionally carried out in methylene chloride, N,N-dimethylformamide, benzene, toluene, chlorobenzene, tetrahydrofuran, 1,4-dioxane, or mixtures thereof with an alkylating agent such as a corresponding halide or sulfonic acid ester, e.g. methyl iodide, ethyl bromide, dimethyl sulfate, or benzyl chloride, optionally in the presence of a tertiary organic base or an inorganic base at temperatures between 0 and 150 cc, preferably between 0 and 100° C.

The subsequent introduction of a chlorine, bromine, or iodine atom into an aromatic substructure may be carried out by reacting the aromatic compound with an appropriate electrophile of the respective halogen atom. Suited chlorine and bromine electrophiles may be e.g. N-halosuccinimide, HOCl, HOBr, tert-BuOCl, tert-BuOBr, chlorine, bromine, dibromoisocyanuric acid, pyridinium dichlorobromate, pyridinium tribromide, or sulfuryl chloride that may be used alone or in combination with an acid, e.g. hydrochloric acid, hydrobromic acid, tetrafluoroboric acid, triflic acid, sulfuric acid, or acetic acid, or a Lewis acid, e.g. iron(III) halide, boron trifluoride hydrate, boron trifluoride etherate, or aluminum halide. Further useful combinations may be LiBr and ceric ammonium nitrate, KCl or KBr with Oxone®, or KBr and sodium perborate. Suited iodine electrophiles may be generated from iodine and an oxidizing agent such as nitric acid, sulfur trioxide, manganese dioxide, $HIO_3$, hydrogen peroxide, sodium periodate, peroxydisulfates, and Oxone®. Further suited iodine electrophiles may be e.g. iodine chloride, dichloroiodates, and N-iodosuccinimide. These iodine electrophiles are optionally used without an additive or in the presence of an acid such as acetic acid, trifluoroacetic acid, or sulfuric acid or a Lewis acid such as boron trifluoride hydrate or copper salts. If a nitro group is to be introduced appropriate nitro electrophile sources may be, for instance, nitric acid, acetyl nitrate, ceric ammonium nitrate, sodium nitrate, $N_2O_5$, alkyl nitrate, and nitronium tetrafluoroborate. Some of these reagents may be used without an additive, though, several of them are better used in combination with an acid, e.g. sulfuric acid or triflic acid, acetic anhydride, trifluoroacetic anhydride, Lewis acid, e.g. ytterbium triflate or iron acetate, $P_2O_5$, or a base. The $SO_3H$ group may be introduced by reacting the aromatic compound with, for example, concentrated sulfuric acid, $SO_3$, $ClSO_3H$, or $ClSO_2NMe_2$ combined with indium triflate. Reacting the aromatic compound with $ClSO_3H$ gives the corresponding chlorosulfonylated derivative that may be hydrolyzed to the sulfonic acid. Acylating the aromatic part is conducted using an acyl electrophile that may be generated from the respective acyl halide, e.g. chloride, or acyl anhydride and a Lewis acid such as aluminum halide, diethylaluminum halide, indium halide, iron(III) halide, tin(IV) halide, boron trifluoride, titanium(IV) halide, or a Brønsted acid, e.g. sulfuric acid or triflic acid. The formyl group is preferably introduced using the so-called Vilsmeier or Vilsmeier-Haack conditions: dialkylformamide combined with phosgene, thionyl chloride, $POCl_3$, or oxalyl chloride. Preferred solvents for the electrophilic substitutions described may differ depending on the electrophile employed; in the following some more generally applicable are mentioned: methylene chloride, 1,2-dichloroethane, chlorobenzene, dichlorobenzene, ether, 1,4-dioxane, fluorinated hydrocarbons, hexanes, quinoline, and acetonitrile. Temperatures preferably applied range from 0 to 180° C.

The subsequent replacement of an aromatic amino group is initiated by diazotization of the amino group using a nitrous acid or nitrosonium source or equivalent such as a nitrite salt combined with an acid, e.g. sodium nitrite and hydrochloric acid, nitrosonium tetrafluoroborate, or an alkylnitrite, e.g. tert-butyl nitrite or iso-amyl nitrite. The diazotization is optionally carried out in methylene chloride, 1,2-dichloroethane, N,N-dimethylformamide, N-methylpyrrolidinone, benzene, toluene, chlorobenzene, tetrahydrofuran, water, ethyl acetate, alcohol, ether, 1,2-dimethoxyethane, 1,4-dioxane, or mixtures thereof at temperatures between −10 and 100° C. (diazotization of amino groups is detailed in, for example, Angew. Chem. Int. Ed. 1976, 15, 251). The subsequent displacement of the diazo group with a cyano group, chlorine, or bromine atom using copper cyanide, chloride, or bromide, respectively, is known as the Sandmeyer reaction (see e.g. March's Advanced Organic Chemistry, Michael B. Smith and Jerry March, John Wiley & Sons Inc., 6. Ed., New Jersey, 2007 and references quoted therein); the reaction is optionally conducted between −10 and 120° C. in one of the solvents or mixtures mentioned above. The replacement of the diazo group with a fluorine atom may be achieved with a tetrafluoroborate salt or tetrafluoroboric acid and heating to 20 to 160° C.; the reaction is known as the Schiemann reaction. Iodine may be introduced by treatment of the diazo compound with an iodide salt, e.g. sodium iodide, preferably using water or an aqueous solvent mixture at temperatures between 0 and 120° C. The diazo group is replaced with hydroxy using water or an aqueous solvent mixture at temperatures between 0 and 180° C. The reaction usually works without further additives but the addition of copper oxide or strong acid may be advantageous. Mercapto or alkylmercapto may be introduced via their corresponding disulfide salts or dialkyldisulfides at temperatures between 0 and 120° C.; depending on the sulfur species used an inert solvent or aqueous solvent system may be preferred (see e.g. Synth. Commun. 2001, 31, 1857 and references quoted therein).

The subsequent replacement of an aromatic amino group by an aryl group may be accomplished via the corresponding diazo compound obtainable as described above. The reaction with an aryl nucleophile, preferably an aryl boronic acid, boronic ester, trifluoroborate, zinc halide, or stannane, is conducted in the presence of a transition metal species derived from palladium, nickel, rhodium, copper, or iron, preferably palladium. The active catalyst may be a complex of the transition metal with ligands such as e.g. phosphines, phosphites, imdiazole carbenes, imidazolidine carbenes, dibenzylideneacetone, allyl, or nitriles, an elemental form of the transition metal such as palladium on carbon or nanoparticles, or salts such as chloride, bromide, acetate, or trifluoroacetate. The diazo compound is preferably employed as its tetrafluoroborate salt optionally in water, N-methylpyrrolidinone, N,N-dimethylformamide, methylene chloride, benzene, toluene, tetrahydrofuran, ethyl acetate, alcohol, ether, 1,2-dimethoxyethane, 1,4-dioxane, or mixtures thereof at temperatures between 10 and 180° C., preferably between 20 and 140° C.

The subsequent replacement of an aromatic chloro, bromo, or iodo atom or an aromatic trifluoromethylsulfonyloxy, mesyloxy, or tosyloxy group with an amino, aryl, alkenyl, alkynyl, or alkyl residue is preferably mediated by a transition metal species derived from palladium, nickel, copper, or iron. The active catalyst may be a complex of the transition metal with ligands such as phosphines, e.g. tri-tert-butylphosphine, tricyclohexylphosphine, 2-(substituted phenyl)phenyl-dicyclohexylphosphines, 2-(substituted phenyl)phenyl-di-tert-butylphosphines, 1,1'-bis(diphenylphosphino)ferrocene, triphenylphosphine, tritolylphosphine, or trifuryl-phosphine, phosphites, 1,3-disubstituted imdiazole carbenes, 1,3-disubstituted imidazolidine carbenes, dibenzylideneacetone, allyl, or nitriles, an elemental form of the transition metal such as palladium on carbon or nanoparticles of iron or palladium, or a salt such as fluoride, chloride, bromide, acetate, triflate, or trifluoroacetate. The replacement reaction is preferably conducted with a trifluoroborate, boronic acid, or boronic ester (Suzuki or Suzuki-type reaction), zinc halide (Negishi or Negishi-type reaction), stannane (Stille or Stille-type reaction), silane (Hiyama or Hiyama-type reaction), magnesium halide (Kumada or Kumada-type reaction) of the aryl, alkenyl, or alkyl residue to be introduced. The terminal alkyne is preferably used as such or as its zinc acetylide derivative. Depending on the nature of the electrophilic and nucleophilic reaction partners additives such as halide salts, e.g. lithium chloride, potassium fluoride, tetrabutylammonium fluoride, hydroxide sources such as potassium hydroxide or potassium carbonate, silver salts such as silver oxide or triflate, and/or copper salts such as copper chloride or copper thiophene-2-carboxylate may be advantageous or even essential. Copper iodide is a preferred additive in the coupling with terminal alkynes (Sonogashira reaction). The coupling reactions are preferably conducted in benzene, toluene, ether, tetrahydrofuran, 1,2-dimethoxyethane, 1,4-dioxane, N,N-dimethylformamide, N,N-dimethylacetamide, N-methylpyrrolidinone, alcohol, water, or mixtures thereof, though, depending on the nucleophile some of them are less or not suited at all. Preferred temperatures are in the range from −10 to 180° C.

The subsequent reduction of a cyano group to obtain an aminomethyl group is preferably conducted with hydrogen in the presence of a transition metal species or with a hydride.

Suited transition metals may be derived from palladium, nickel, platinum, rhodium, or ruthenium such as palladium on charcoal, palladium hydroxide, platinum oxide, or Raney nickel that may be used in solvents such as ethyl acetate, alcohols, e.g. methanol or ethanol, dichloromethane, tetrahydrofuran, ether, benzene, toluene, N,N-dimethylformamide, or N-methylpyrrolidinone at hydrogen pressures between 1 and 10 bar and at temperatures between 0 and 160° C. Additives such as acids, e.g. hydrochloric acid, methanesulfonic acid, sulfuric acid, or acetic acid, may be beneficial for the reduction with transition metal catalysts. Among the preferred hydride sources are e.g. borohydrides, e.g. sodium borohydride, potassium tri-sec-butylborohydride, borane, or lithium triethylborohydride, and alanates, e.g. lithium aluminum hydride or diisobutylaluminum hydride. Some of these reagents are best used in combination with nickel chloride or cobalt chloride as sodium borohydride. These reagents may be used in e.g. tetrahydrofuran, ether, 1,4-dioxane, 1,2-dimethoxyethane, dichloromethane, 1,2-dichloroethane, benzene, or toluene; some are also compatible with alcoholic or aqueous solutions. Preferred reaction temperatures range from −80 to 160° C., more preferred from −40 to 80° C.

The subsequent transformation of a carboxylic ester into a tertiary hydroxy group is preferably conducted with two or more equivalents of a carbon nucleophile, e.g. alkyl, allyl, alkenyl, aryl, or alkynyl lithium, magnesium, or cerium compound, in tetrahydrofuran, ether, 1,4-dioxane, 1,2-dimethoxyethane, toluene, hexanes, or mixtures thereof, at temperatures of −80 to 80° C.

The compounds according to the invention are advantageously also obtainable using the methods described in the examples that follow, which may also be combined for this purpose with methods known to the skilled man from the literature.

Compounds of formula I may be isolated from their reaction mixtures using conventional techniques.

Biological Assays

Assay A: mPGES-1 Enzyme Assay

The basis of the assay used is to measure the inhibition of microsomal prostaglandin $E_2$ synthase-1 (mPGES-1) dependent prostaglandin (PG) $E_2$ formation from $PGH_2$ by different compounds. Thus, the formation of $PGE_2$ is used as signal and a lowering of this signal can be interpreted as inhibition of mPGES-1. Similar assays to measure inhibition of mPGES-1 have previously been described in the literature [1, 2].

List of Reagents Used:
  Glutathione (Sigma, G-4251)
  Freeze culture in Rosetta *E coli* expression strain.
  LB growth media with Ampillicillin (Amp) final concentration in culture 50 μg/mL
  Chloroamphenicol stock 34 mg/mL (chloro) final concentration in culture 34 μg/mL
  Sterile growth flasks for 500 mL-1 liter cultures
  0.1 M $KP_i$ buffer pH 7.4
  9.25% HCl
  $PGH_2$ (0.25 mM)
  Fe (II) $Cl_2$ tetrahydrate, 99% (Sigma, 220229)
  384-well plate with compounds
  96-well plate, polypropylene (Thermo fast 96 skirted VWR)
  384-well plate polypropylene PCR plate (Greiner 785201)
  Greiner 384-well plate pp (In vitro cat. no. 781280)
  Adhesive sealing film for 96-well plates (Sigma-Aldrich)
  Aluminium foil (PCR foil, 310-0030-127-471 from Labora)
  PBS (GIBCO 14040)
  Prostaglandin $E_2$ Assay (Cisbio, cat. no. 62P2APEC)
  Biomek FX robot (Beckman Coulter)
  Biomek NX robot (Beckman Coulter)
  Multidrop; micro or combi (ThermoLabsystems)
  Plate reader: Safire2 (Tecan)

Microsomes from Rosetta *E. coli* bacteria expressing recombinant human mPGES-1 can be derived as described below:

Inoculate 5 mL LB with Amp and Chloro with bacteria from freeze culture. Incubate over night at 37° C. with 200 rpm. Thereafter, inoculate 500-800 mL LB containing Amp and Chloro with the 5 mL on culture and grow to OD640 of 0.6-0.8. Chill the culture to +4° C. before induction. Induce the culture with IPTG at a final concentration of 400 μM. Express the protein at room temp 18-23° C. with 200 rpm shaking over night.

The following steps can be performed on the following day:
1. Spin down the cells in 250 mL centrifuge flasks for 15 min at 7000 rpm
2. Dissolve the pellet from 250 mL culture in 12.5 mL homogenization buffer
3. Disintegrate the cells by sonication, 4×10 seconds at 35% amplitude
4. Add 2.5 mL MgCl2 (100 mM) and DNase 12.5 μL (0.8 mg/mL) and incubate on ice for 30 min
5. Spin down the bacteria debris and save the supernatant, 7000 rpm for 15 min
6. Isolate the protein containing membranes in the supernatant by ultracentrifugation 45000×g for 1 hour.
7. Discard the supernatant and dissolve the pellet in 20 mM KPi buffer and aliquot the enzyme and store aliquots at −80° C.

Before each experiment is performed an aliquot of the enzyme is thawed and it can then be dissolved in 0.1 M $KP_i$ pH 7.4 buffer containing 2.5 mM GSH. 50 μL of this enzyme solution is subsequently dispensed in a 384-well plate at room temperature. 0.5 μL of the inhibitor dissolved in DMSO is thereafter added to each well and incubated for 25 minutes at room temperature. Subsequently, 2 μL of $PGH_2$ dissolved in an appropriate solvent is added to each well and after one minute at room temperature, the acidified stop solution containing $FeCl_2$ is added. 4 μL of the total volume is transferred to a separate plate and diluted 750-fold in two separate steps before quantification of $PGE_2$.

In order to quantitate the amount of $PGE_2$ that has been formed, a homogenous time resolved fluorescent (HTRF) detection of $PGE_2$ can be performed by the use of a commercially available kit from CisBio essentially according to the manufacturer's protocol. Briefly, 10 μL of the diluted sample is transferred to a white 384-well plate and the following steps can be performed in a sequential manner at room temperature or as indicated.

5 μL reconstitution buffer as supplied by the manufacturer is added to the negative control (NC) wells.
  The plate is covered with adhesive sealing film.
  The plate can now be centrifuged at 1200 rpm for 1 minute.
  The NC samples are covered with sealing film.
  250 μL d2 labeled $PGE_2$ (d2-$PGE_2$) can be diluted in 4750 μL reconstitution buffer as supplied by the manufacturer
  250 μL Eu3+-cryptate can be diluted in 4750 μL reconstitution buffer as supplied by the manufacturer 5 μL d2-PGE$_2$ can now be added to rows 1 to 24, by using a multidrop. The sealing film is thereafter removed from the NC wells.

5 μL Eu3+-cryptate labeled anti-PGE$_2$ can now be added to rows 1 to 24 by using a Multidrop.

The plate can now be covered with sealing film.

The plate can now be centrifuge at 1200 rpm for 1 minute and place at 4° C. overnight.

After the over night incubation the fluorescence is measured by the use of an appropriate microplate reader. The fluorescence of Eu3+-cryptate and d2-PGE$_2$ are measured using the following excitation and emission wavelength, europium cryptate: $\lambda_{max}^{ex}$=307 nm, $\lambda_{max}^{em}$=620 nm and d2: $\lambda_{max}^{ex}$=620 nm, $\lambda_{max}^{em}$=665 nm), respectively. The extent of the specific HTRF is measured as a ratio of the emission intensity at 665 nm vs. that at 620 nm. A standard curve using synthetic PGE$_2$ is used to quantify the amount of PGE$_2$ in unknown samples. The degree of inhibition can be calculated as percent inhibition by dividing the amount of PGE$_2$ formed in unknown samples by the amount of PGE$_2$ formed in control samples.

Assay B: mPGES-1 Enzyme Assay (Modified)

The aim of this assay is to determine the affinity of a test compound for the mPGES-1 enzyme.

47 μl of recombinant human mPGES-1 (~0.5 μg protein/well) containing microsomal suspension in a buffer containing GSH, (2.5 mmol/L L-Glutathione reduced, dissolved in 0.1 mol/L Phosphat Buffer pH 7.4) is dispensed in a 384-well plate and thereafter 1 μl of the test compound(s) is/are added and incubated for 25 minutes at room temperature. The enzyme reaction is started by the addition of 2 ul PGH2 (final conc. 2 μM) dissolved in water-free Diglyme. After 60 seconds the reaction is terminated by addition of a stop solution containing FeCl$_2$ (10 μL 0.074 mol/l FeCl$_2$). The samples are diluted between 1:25 in PBS (Phosphate Buffered Saline). 10 μl of the diluted samples are transferred to 384-well low volume plate. In order to quantify the amount of PGE$_2$ that has been formed, a homogenous time resolved fluorescent (HTRF) detecting of PGE$_2$ has been performed using a commercially available kit from Cisbio according to the manufactures recommendation. This HTRF-based assay has been described in detail (see: Goedken et al., J Biomol Screen, 2008, 13(7), 619-625). Briefly, the diluted samples are mixed with 5111 PGE$_2$-d$_2$ conjugate and 5 μl anti-PGE$_2$ cryptate conjugate. After an incubation period of the plates over night, the fluorescence is measured by the use of an appropriate microplate reader.

The fluorescence of Europium cryptate (maxex=307 nm, maxem=620 nm) and d2-PGE$_2$ (maxex=620 nm, maxem=665 nm) are measured.

The extent of the specific HTRF is measured as a ratio of the emission intensity at 665 nm vs. that at 620 nm at an excitation pulse of 320 nm. The quantification plate contains also wells with different concentrations of PGE$_2$ as calibration curve for the calculation of the PGE$_2$ concentrations from the HTRF ratio values.

From all mPGES enzyme assay the background is subtracted and the IC$_{50}$ is calculated over a nonlinear regression with conventional software.

LITERATURE REFERENCES

1. Riendeau, D., R. Aspiotis, D. Ethier, Y. Gareau, E. Grimm, J. Guay, S. Guiral, H. Juteau, J. Mancini, N. Methot, J. Rubin, and R. Friesen, *Inhibitors of the inducible microsomal prostaglandin E2 synthase (mPGES-1) derived from MK-886.* Bioorg Med Chem Lett, 2005. 15(14): p. 3352-3355.
2. Cote, B., L. Boulet, C. Brideau, D. Claveau, D. Ethier, R. Frenette, M. Gagnon, A. Giroux, J. Guay, S. Guiral, J. Mancini, E. Martins, F. Masse, N. Methot, D. Riendeau, J. Rubin, D. Xu, H. Yu, Y. Ducharme, and R. Friesen, *Substituted phenanthrene imidazoles as potent, selective, and orally active mPGES-1 inhibitors.* Bioorg Med Chem Lett, 2007. 17(24): p. 6816-6820.

Test Results:

Table 1 demonstrates the mPGES-1 inhibitory effect (IC$_{50}$) measured for selected examples in the HTRF assays as described above. These data reflect a successful mPGES-1 inhibition for the given compound examples.

TABLE 1 mPGES-1 inhibitory effect (IC$_{50}$ values in nM) of compounds of the invention in the biological assays A (compounds 1-41, 54, 55, 62, 73) or biological assay B (all other compounds)

| example | IC50 [nM] |
|---|---|
| 1 | ~1600 |
| 2 | 4 |
| 3 | 22 |
| 4 | 1 |
| 5 | 2 |
| 6 | 2 |
| 7 | 4 |
| 8 | 7 |
| 9 | 2 |
| 10 | ~900 |
| 11 | 4 |
| 12 | 3 |
| 13 | 13 |
| 14 | 4 |
| 15 | 2 |
| 16 | 14 |
| 17 | 16 |
| 18 | 2 |
| 19 | 4 |
| 20 | ~3000 |
| 21 | ~1800 |
| 22 | 2 |
| 23 | 1 |
| 24 | 2 |
| 25 | 1 |
| 26 | 3 |
| 27 | 2 |
| 28 | 4 |
| 29 | 2 |
| 30 | 1 |
| 31 | 2 |
| 32 | 2 |
| 33 | 2 |
| 34 | 2 |
| 35 | ~500 |
| 36 | 6 |
| 37 | 1 |
| 38 | 4 |
| 39 | 18 |
| 40 | 5 |
| 41 | 3 |
| 42 | 3 |
| 43 | 120 |
| 44 | 15 |
| 45 | 4 |
| 46 | 5 |
| 47 | 6 |
| 48 | 6 |

TABLE 1-continued mPGES-1 inhibitory effect (IC$_{50}$ values in nM) of compounds of the invention in the biological assays A (compounds 1-41, 54, 55, 62, 73) or biological assay B (all other compounds)

| example | IC50 [nM] |
|---|---|
| 49 | 120 |
| 50 | 34 |
| 51 | 5 |
| 52 | 4 |
| 53 | 11 |
| 54 | 9 |
| 55 | 59 |
| 56 | 128 |
| 57 | 2 |
| 58 | 3 |
| 59 | 5 |
| 60 | 26 |
| 61 | 5 |
| 62 | 11 |
| 63 | 5 |
| 64 | 4 |
| 65 | 4 |
| 66 | 5 |
| 67 | 5 |
| 68 | 9 |
| 69 | 4 |
| 70 | 5 |
| 71 | 10 |
| 72 | 4 |
| 73 | 7 |
| 74 | 47 |
| 75 | 6 |
| 76 | 12 |
| 77 | 2 |
| 78 | 2 |
| 79 | 5 |
| 80 | 10 |
| 81 | 2 |
| 82 | 8 |
| 83 | 7 |
| 84 | 6 |
| 85 | 6 |
| 86 | 5 |
| 87 | 5 |
| 88 | 9 |
| 89 | 4 |
| 90 | 9 |
| 91 | 6 |
| 92 | 6 |
| 93 | 7 |
| 94 | 6 |
| 95 | 8 |
| 96 | 5 |
| 97 | 79 |
| 98 | 43 |
| 99 | 7 |
| 100 | 5 |
| 101 | 9 |
| 102 | >100 |
| 103 | 237 |
| 104 | 10 |
| 105 | 5 |
| 106 | 6 |
| 107 | 5 |
| 108 | 5 |
| 109 | 13 |
| 110 | 17 |
| 111 | 7 |
| 112 | 16 |
| 113 | 4 |
| 114 | 10 |
| 115 | 15 |
| 116 | 6 |
| 117 | 40 |
| 118 | 98 |
| 119 | 5 |
| 120 | 7 |
| 121 | 11 |
| 122 | 7 |
| 123 | 48 |
| 124 | 5 |
| 125 | 5 |
| 126 | 4 |
| 127 | 19 |
| 128 | 5 |
| 129 | 5 |
| 130 | 4 |
| 131 | 9 |
| 132 | 6 |
| 133 | 6 |
| 134 | 7 |
| 135 | 7 |
| 136 | 7 |
| 137 | 9 |
| 138 | 5 |
| 139 | 6 |
| 140 | 8 |
| 141 | 5 |
| 142 | 6 |
| 143 | 6 |
| 144 | 7 |
| 145 | 10 |
| 146 | 14 |
| 147 | 8 |
| 148 | 1 |
| 149 | 4 |
| 150 | 2 |
| 151 | 1 |
| 152 | 11 |
| 153 | 5 |
| 154 | 9 |
| 155 | 150 |
| 156 | 1 |
| 157 | 22 |
| 158 | 2 |
| 159 | 7 |
| 160 | 7 |
| 161 | 13 |
| 162 | 8 |
| 163 | 6 |
| 164 | 79 |
| 165 | 8 |
| 166 | 8 |
| 167 | 47 |
| 168 | 105 |
| 169 | 9 |
| 170 | 50 |
| 171 | 6 |
| 172 | 6 |
| 173 | 48 |
| 174 | 8 |
| 175 | 9 |
| 176 | 50 |
| 177 | 2 |
| 178 | 7 |
| 179 | 4 |
| 180 | 2 |
| 181 | 2 |

Method of Treatment

The present invention relates to compounds of formula I which are useful in the prevention and/or treatment of a disease and/or condition in which the inhibition of prostaglandin E synthases, in particular that of the microsomal prostaglandin $E_2$ synthase-1 (mPGES-1) is of therapeutic benefit, including but not limited to the treatment and/or prevention of inflammatory diseases and/or associated conditions.

The term "inflammation" will be understood to include any inflammatory disease, disorder or condition per se, any condition that has an inflammatory component associated with it, and/or any condition characterised by inflammation as a symptom, including inter alia acute, chronic, ulcerative, specific, allergic and necrotic inflammation, and other forms of inflammation known to those skilled in the art. The term thus also includes, for the purposes of this invention, inflammatory pain, pain generally and/or fever.

Where a condition has an inflammatory component associated with it, or a condition characterised by inflammation as a symptom, the skilled person will appreciate that compounds of the invention may be useful in the treatment of the inflammatory symptoms and/or the inflammation associated with the condition.

Compounds of the invention may also have effects that are not linked to inflammatory mechanisms, such as in the reduction of bone loss in a subject. Such conditions include osteoporosis, osteoarthritis, Paget's disease and/or periodontal diseases.

A further aspect of the present invention relates to a compound of formula I as a medicament. Another aspect of the present invention is the use of compounds of formula I for the treatment and/or prevention of a disease and/or condition in which the inhibition of the mPGES-1 is of therapeutic benefit.

A further aspect of the present invention is the use of a compound of formula I for the treatment and/or prevention of inflammatory diseases and/or associated conditions.

The present invention also relates to the use of compounds of formula I for the treatment and/or prevention of the following diseases and conditions:

1. Rheumatic diseases or autoimmune diseases or muscoskeletal diseases: all forms of rheumatic diseases including e.g. soft tissue rheumatism, rheumatoid arthritis, polymyalgia rheumatica, reactive arthritis, tenosynovitis, gout or metabolic arthritis, bursitis, tendonitis, juvenile arthritis, spondyloarthropathies like e.g. spondylitis, ankylosing spondylitis, psoriatric arthropathy; sarcoidosis, fibromyalgia, myositis, polymyositis, osteoarthritis, traumatic arthritis, collagenoses of any origin e.g. systemic lupus erythematosus, scleroderma, dermatomyositis, Still's Disease, Sjögren syndrome, Felty syndrome; rheumatic fever and rheumatic heart disease, diseases of blood vessels like vasculitis, polyarthritis nodosa, Behcet's syndrome, giant cell arthritis, Wegener's granulomatosis, Henoch-Schönlein purpura; psoriatic arthritis, fungal arthritis, in particular including pain associated with any of the aforementioned conditions;

2. Headaches such as migraines with and without aura, tension-type headaches, cluster headaches and headaches with different origins;

3. Sympathetically maintained pain like complex regional pain syndrome Type I and II;

4. Neuropathic pain such as low back pain, hip pain, leg pain, non-herpetic neuralgia, post herpetic neuralgia, diabetic neuropathy, nerve injury-induced pain, acquired immune deficiency syndrome (AIDS) related neuropathic pain, head trauma, toxin and chemotherapy caused nerve injuries, phantom limb pain, multiple sclerosis, root avulsions, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, postthoracotomy syndrome, stump pain, repetitive motion pain, neuropathic pain associated hyperalgesia and allodynia, alcoholism and other drug-induced pain;

5. Cancer pain induced by or associated with tumors such as bone tumors, lymphatic leukemia; Hodgkin's disease, malignant lymphoma; lymphogranulomatoses; lymphosarcoma; solid malignant tumors; extensive metastases;

6. Visceral disorders such as chronic pelvic pain, pancreatitis, peptic ulcer, interstitial cystitis, cystitis, renal colic, angina, dysmenorrhoea, menstruation, gynaecological pain, irritable bowel disease (IBS), inflammatory bowel disease, Crohn's disease and ulcerative colitis, nephritis, prostatitis, vulvodynia, non-ulcer dyspepsia, non-cardiac chest pain, myocardial ischemia;

7. Inflammation associated diseases of ear, nose, mouth and throat like influenza and viral/bacterial infections such as the common cold, allergic rhinitis (seasonal and perennial), pharyngitis, tonsillitis, gingivitis, larhyngitis, sinusitis, and vasomotor rhinitis, fever, hay fever, thyroiditis, otitis, dental conditions like toothache, perioperative and post-operative conditions, trigeminal neuralgia, uveitis; iritis, allergic keratitis, conjunctivitis, blepharitis, neuritis nervi optici, choroiditis, glaucoma and sympathetic opthalmia, as well as pain thereof;

8. Neurological diseases such as cerebral oedema and angioedema, cerebral dementia like e.g. Parkinson's and Alzheimers disease, senile dementia; multiple sclerosis, epilepsy, drug resistant epilepsy, stroke, myasthenia gravis, brain and meningeal infections like encephalomyelitis, meningitis, including HIV as well as schizophrenia, delusional disorders, autism, affective disorders and tic disorders;

9. Work-related diseases like pneumoconiosis, including aluminosis, anthracosis, asbestosis, chalicosis, ptilosis, siderosis, silicosis, tabacosis and byssinosis;

10. Lung diseases such as asthma including allergic asthma (atopic or non-atopic) as well as exercise-induced bronchoconstriction, occupational asthma, viral- or bacterial exacerbation of asthma, other non-allergic asthmas and "wheezy-infant syndrome", Chronic obstructive pulmonary disease (COPD) including emphysema, adult respiratory distress syndrome, bronchitis, pneumonia, adult respiratory distress syndrome (ARDS), pigeon fancier's disease, farmers lung;

11. Skin diseases such as psoriasis and eczema, dermatitis, sunburn, burns as well as aprains and strains and tissue trauma;

12. Vascular and heart diseases which are inflammation-related like artheriosclerosis including cardiac transplant atherosclerosis, panarteritis nodosa, periarteritis nodosa, arteritis temporalis, Wegner granulomatosis, giant cell arthritis, reperfusion injury and erythema nodosum, thrombosis (e.g. deep vein thrombosis, renal, hepathic, portal vein thrombosis); coronary artery disease, aneurysm, vascular rejection, myocardial infarction, embolism, stroke, thrombosis including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries, artery restenosis;

13. Diabetes-associated symptoms such as diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion);

14. Benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers effecting epithelial cells throughout the body; neoplasias like gastrointestinal cancer, Barrett's esophagus, liver cancer, bladder cancer, pancreatic cancer, ovarian cancer, prostate cancer, cervical cancer, lung cancer, breast cancer and skin cancer; adenomatous polyps, including familial adenomatous polyposis (FAP) as well preventing polyps from forming in patients at risk of FAP.

15. Various other disease states and conditions like epilepsy, septic shock e.g. as antihypovolemic and/or antihypotensive agents, sepsis, osteoporosis, benign prostatic hyperplasia and hyperactive bladder, nephritis, pruritis, vitiligo, disturbances of visceral motility at respiratory, genitourinary, gastrointestinal or vascular regions, wounds, allergic skin reactions, mixed-vascular and non-vascular syndromes, septic shock associated with bacterial infections or with trauma, central nervous system injury, tissue damage and postoperative fever, syndromes associated with itching.

Preferred according to the present invention is the use of a compound of formula I for the treatment and/or prevention of pain; in particular pain that is associated with any one of the diseases or conditions listed above.

Another aspect of the present invention is a method for the treatment and/or prevention of above mentioned diseases and conditions, which method comprises the administration of an effective amount of a compound of formula I to a human being.

Dosage

The dose range of the compounds of formula I applicable per day is usually from 0.01 to 5000 mg, preferably from 1 to 2000 mg, more preferably from 5 to 500 mg, most preferably 10 to 250 mg. Each dosage unit may conveniently contain from 2 to 500 mg, preferably 5 to 250 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Formulations

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. A further aspect of the invention is a pharmaceutical formulation including a compound of formula I in admixture with a pharmaceutically acceptable adjuvant, diluent or carrier.

Combination Therapy

The compounds according to the present invention can be combined with other treatment options known to be used in the art in connection with a treatment of any of the indications the treatment of which is in the focus of the present invention.

Among such treatment options that are considered suitable for combination with the treatment according to the present inventions are:

non-steroidal antiinflammatory drugs (NSAIDs) including COX-2 inhibitors;
opiate receptor agonists;
Cannabionoid agonists or inhibitors of the endocannabinoid pathway
Sodium channel blockers;
N-type calcium channel blockers;
serotonergic and noradrenergic modulators;
corticosteroids;
histamine H1 receptor antagonists;
histamine H2 receptor antagonists;
proton pump inhibitors;
leukotriene antagonists and 5-lipoxygenase inhibitors;
local anesthetics;
VR1 agonists and antagonists;
Nicotinic acetylcholine receptor agonists;
P2X3 receptor antagonists;
NGF agonists and antagonists or anti-NGF antibodies;
NK1 and NK2 antagonists;
Bradykinin B1 antagonists
CCR2 antagonists
iNOS or nNOS or eNOS inhibitors
NMDA antagonist;
potassium channel modulators;
GABA modulators;
serotonergic and noradrenergic modulators;
anti-migraine drugs;
neuropathic pain drugs such as pregabaline or duloxetine.

Said list is not considered to have a limiting character.

In the following representative examples of such treatment options shall be given.

Non-steroidal antiinflammatory drugs (NSAIDs) including COX-2 inhibitors: propionic acid derivatives (alminoprofen, benoxaprofen, bucloxic acid, carprofen, fenhufen, fenoprofen, flubiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefenamic acid, and tolfenamic acid), biphenylcarboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib) and the like;

Antiviral drugs like acyclovir, tenovir, pleconaril, peramivir, pocosanol and the like.

Antibiotic drugs like gentamicin, streptomycin, geldanamycin, doripenem, cephalexin, cefaclor, ceftazichine, cefepime, erythromycin, vancomycin, aztreonam, amoxicillin, bacitracin, enoxacin, mafenide, doxycycline, chloramphenicol and the like;

Opiate receptor agonists: morphine, propoxyphene (Darvon), tramadol, buprenorphin and the like;

Glucocorticosteroids such as bethamethasone, budesonide, dexamethasone, hydrocortisone, methylprednisolone, prednisolone, prednisone, triamcinolone and deflazacort; immunosuppressive, immunomodulatory, or cytsostatic drugs inlcuding but not limited to hydroxychlorquine, D-penicillamine, sulfasalizine, auranofin, gold mercaptopurine, tacrolimus, sirolimus, mycophenolate mofetil, cyclosporine, leflunomide, methotrexate, azathioprine, cyclophosphamide and glatiramer acetate and novantrone, fingolimod (FTY720), minocycline and thalidomide and the like;

anti-TNF antibodies or TNF-receptor antagonists such as but not limited to Etanercept, Infliximab, Adalimumab (D2E7), CDP 571, and Ro 45-2081 (Lenercept), or biologic agents directed against targets such as but not limited to CD-4, CTLA-4, LFA-1, IL-6, ICAM-1, C5 and Natalizumab and the like;

IL-1 receptor antagonists such as but not limited to Kineret;

Sodium channel blockers: carbamazepine, mexiletine, lamotrigine, tectin, lacosamide and the like.

N-type calcium channel blockers: Ziconotide and the like.

Serotonergic and noradrenergic modulators: paroxetine, duloxetine, clonidine, amitriptyline, citalopram;

Histamine H1 receptor antagonists: bromophtniramint, chlorpheniramine, dexchlorpheniramine, triprolidine, clemastine, diphenhydramine, diphenylpyraline, tripelennamine, hydroxyzine, methdiJazine, promethazine, trimeprazine, azatadine, cyproheptadine, antazoline, pheniramine pyrilamine, astemizole, terfenadine, loratadine, cetirizine, deslo-ratadine, fexofenadine and levocetirizine and the like;

Histamine H2 receptor antagonists: cimetidine, famotidine and ranitidine and the like;

Proton pump inhibitors: omeprazole, pantoprazole and esomeprazole and the like;

Leukotriene antagonists and 5-lipoxygenase inhibitors: zafirlukast, mon-telukast, pranlukast and zileuton and the like;

Local anesthetics such as ambroxol, lidocaine and the like;

Potassium channel modulators: like retigabine;

GABA modulators: lacosamide, pregabalin, gabapentin and the like;

Anti-migraine drugs: sumatriptan, zolmitriptan, naratriptan, eletriptan, telcegepant and the like;

NGF antibodies such as RI-724 and the like.

Combination therapy is also possible with new principles for the treatment of pain e.g. P2X3 antagonists, VR1 antagonists, NK1 and NK2 antagonists, NMDA antagonists, mGluR antagonists and the like.

The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased pharmacological effect, or some other beneficial effect of the combination compared with the individual components.

EXPERIMENTAL SECTION

Preparation of Examples for Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

ABBREVIATIONS aq. aqueous solution
Boc tert-butoxycarbonyl
tBu tert-Butyl
BSTFA N,O-Bis(trimethylsilyl)trifluoracetamide
conc. concentrated
DCC N,N'-Dicyclohexylcarbodiimide
DCM dichloromethane
DIPEA N-ethyl-diisopropylamine
DMSO dimethylsulphoxide
DMF N,N-dimethylformamide
DMAP 4-Dimethylaminopyridine
EDC 3-(3-Dimethylaminopropyl)-1-ethyl-carbodiimide
Et ethyl
EtOH ethanol
EtOAc ethyl acetate
satd. saturated
h hour(s)
HATU O-(7-azabenzotriazol-1-yl)-N,N,N',N'-tetramethyluronium-hexafluorophosphate
HBTU O-Benzotriazole-1-yl-N,N,N',N'-tetramethyluronium-hexafluorophosphate
HPLC high performance liquid chromatography
HOAc acetic acid
i. vac. in vacuo
KOtBu potassium tert. Butylate
MeOH methanol
MeCN acetonitrile
M mol/L
min minute(s)
MS mass spectrometry
Pd/C palladium on carbon
PE petrol ether
Piv-Cl pivaloyl chloride
PPA propanephosphonic acid cycloanhydride
prep. preparative
quant. quantitative
Ra-Ni Raney-Nickel
$R_f$ retention factor
$R_t$ retention time in min
rt room temperature
TBME tert.-butyl-methyl-ether
TBTU O-(benzotriazol-1-yl)-N,N,N',N'-tetramethyluronium tetrafluoroborate
TEA triethylamine
TFA trifluoroacetic acid
THF tetrahydrofuran
tert. tertiary
TLC Thin layer chromatography Analytical Methods The TLC data was obtained by using the following tic plates
a) Silica gel plates 60 F254 Merck No 1.05714.0001 abbreviated in the experimental part as "silica gel"
b) Reversed phase plates: RP-8 F 254s Merck No: 1.15684.0001 abbreviated in the experimental part as "RP-8".
c) Aluminiumoxide plates 60 F254 Merck 1.05713.0001 abbreviated in the experimental part as "Alox"

The $R_f$ values given were determined without chamber saturation.

Flash chromatography purifications were performed using silica gel from Millipore (MATREX™, 35 bis 70 μm) or Alox (E. Merck, Darmstadt, Aluminiumoxid 90 standardisiert, 63 bis 200 μm, Artikel-Nr: 1.01097.9050).

The HPLC/MS data were obtained under the following conditions for the methods MC-1 to MC-9 and A.

Agilent 1100 with quarternary pump, Gilson G215 Autosampler, Agilent 6140 Quadrupole LC/MS and HP diode array detector.

The diode array detection took place in a wavelength range from 210-550 nm

Range of mass-spectrometric detection: m/z 120 to m/z 1000

The following solvents were used as mobile phase:

E1: water with 0.15% formic acid
E2: acetonitrile
E4: methanol
E5: water with 0.1% trifluoracetic acid
E6: water with 0.032% NH₄OH Method MC-1
Eluent Gradient:

| time in min | % E1 | % E2 | flow rate in mL/min |
|---|---|---|---|
| 0.0 | 95 | 5 | 1.6 |
| 1.00 | 10 | 90 | 1.6 |
| 2.50 | 10 | 90 | 1.6 |
| 2.75 | 95 | 5 | 1.6 |

Stationary phase: Zorbax Stable Bond C18, 1.8 μm, 3.0×30 mm

Method MC-2
Eluent Gradient:

| time in min | % E1 | % E4 | flow rate in mL/min |
|---|---|---|---|
| 0.0 | 95 | 5 | 1.6 |
| 4.50 | 10 | 90 | 1.6 |
| 5.00 | 10 | 90 | 1.6 |
| 5.50 | 90 | 10 | 1.6 |

Stationary phase: Xbridge C18, 3.5 μm, 4.6×75 mm

Method MC-3
Eluent Gradient:

| time in min | % E1 | % E2 | flow rate in mL/min |
|---|---|---|---|
| 0.0 | 95 | 5 | 1.6 |
| 2.00 | 10 | 90 | 1.6 |
| 5.00 | 10 | 90 | 1.6 |
| 5.50 | 90 | 10 | 1.6 |

Stationary phase: Zorbax Stable Bond C18, 4.6×75 mm

Method MC-4
Eluent Gradient:

| time in min | % E1 | % E2 | flow rate in mL/min |
|---|---|---|---|
| 0.0 | 95 | 5 | 1.6 |
| 2.25 | 10 | 90 | 1.6 |
| 2.50 | 10 | 90 | 1.6 |
| 2.75 | 95 | 5 | 1.6 |

Stationary phase: Zorbax Stable Bond C18, 1.8 μm, 3.0×30 mm

Method MC-5
Eluent Gradient:

| time in min | % E1 | % E2 | flow rate in mL/min |
|---|---|---|---|
| 0.0 | 95 | 5 | 1.6 |
| 2.00 | 50 | 50 | 1.6 |
| 2.25 | 10 | 90 | 1.6 |
| 2.50 | 10 | 90 | 1.6 |
| 2.75 | 95 | 5 | 1.6 |

Stationary phase: Zorbax Stable Bond C18, 1.8 μm, 3.0×30 mm

Method MC-6
Eluent Gradient Analog to MC-4:
  Stationary phase: Xbridge C18, 2.5 μm, 3.0×30 mm Method MC-7
Eluent Gradient:

| time in min | % E1 | % E2 | flow rate in mL/min |
|---|---|---|---|
| 0.0 | 95 | 5 | 1.6 |
| 4.50 | 10 | 90 | 1.6 |
| 5.00 | 10 | 90 | 1.6 |
| 5.50 | 90 | 10 | 1.6 |

Stationary phase: Zorbax Stable Bond C18, 3.5 μm, 4.6×75 mm

Method MC-8
Eluent Gradient:

| time in min | % E1 | % E2 | flow rate in mL/min |
|---|---|---|---|
| 0.0 | 95 | 5 | 1.6 |
| 4.00 | 50 | 50 | 1.6 |
| 4.50 | 10 | 90 | 1.6 |
| 5.00 | 10 | 90 | 1.6 |
| 5.50 | 90 | 10 | 1.6 |

Stationary phase: YMC-Pack ODS-AQ; 3 μm, 4.6×75 mm

Method MC-9
Eluent Gradient:

| time in min | % E6 | % E4 | flow rate in mL/min |
|---|---|---|---|
| 0.0 | 95 | 5 | 1.3 |
| 2.00 | 50 | 50 | 1.3 |
| 2.2 | 10 | 90 | 1.3 |
| 2.5 | 10 | 90 | 1.3 |
| 2.55 | 0 | 100 | 1.3 |
| 3.1 | 0 | 100 | 1.3 |

Stationary phase: Xbridge C18; 2.5 μm; 3.0×30 mm; 40° C.

Method A
Eluent Gradient:

| time in min | % E1 | % E4 | flow rate in mL/min |
|---|---|---|---|
| 0.0 | 95 | 5 | 30 |
| 4.00 | 10 | 90 | 30 |
| 10.00 | 10 | 90 | 30 |
| 11.00 | 90 | 10 | 30 |

Stationary phase: Zorbax Stable Bond C18, 5 µm, 30×100 mm

Alternatively, the following methods were used, abbreviated CC:

HP1100 HPLC+DAD (Wavelength range: 210 nm to 500 nm), and Gilson 215 Autosampler RP-HPLC MS analyses were performed on a Waters ZQ2000 mass spectrometer. The diode array detection took place in a wavelength range from 210-500 nm (Range of mass-spectrometric detection: m/z 120 to m/z 820).

Method CC-1:
Eluent Gradient

| time in min | % E5 | % E4 | flow rate in mL/min |
|---|---|---|---|
| 0.0 | 95 | 5 | 1.5 |
| 1.3 | 0 | 100 | 1.5 |
| 2.5 | 0 | 100 | 1.5 |
| 2.6 | 95 | 5 | 1.5 |

Stationary phase: Waters Sunfire C18, 3.5 µm, 4.6×50 mm, 40° C.
Method CC-2:
Eluent Gradient

| time in min | % E5 | % E2 | flow rate in mL/min |
|---|---|---|---|
| 0.0 | 95 | 5 | 1.5 |
| 2.0 | 0 | 100 | 1.5 |
| 2.5 | 0 | 100 | 1.5 |
| 2.6 | 95 | 5 | 1.5 |

Stationary phase: Waters Sunfire C18, 3.5 µm, 4.6×50 mm, 40° C.
Method CC-3:
Eluent gradient

| time in min | % E5 | % E4 | flow rate in mL/min |
|---|---|---|---|
| 0.0 | 95 | 5 | 1.5 |
| 1.5 | 0 | 100 | 1.5 |
| 3.0 | 0 | 100 | 1.5 |
| 3.7 | 95 | 5 | 1.5 |

Stationary phase: Waters Sunfire C18, 3.5 µm, 4.6×50 mm, 40° C.
Method CC-4:
Eluent Gradient

| time in min | % E5 | % E4 | flow rate in mL/min |
|---|---|---|---|
| 0.0 | 80 | 20 | 2 |
| 1.7 | 0 | 100 | 2 |
| 2.5 | 0 | 100 | 2 |
| 2.6 | 80 | 20 | 2 |

Stationary phase: Waters Sunfire C18, 3.5 µm, 4.6×50 mm, 60° C.
Method CC-5:
Eluent Gradient

| time in min | % E6 | % E4 | flow rate in mL/min |
|---|---|---|---|
| 0.0 | 95 | 5 | 1.5 |
| 2.0 | 5 | 95 | 1.5 |

Stationary phase: XBridge C18, 3.5 µm, 4.6×50 mm, 40° C.
Method CC-6:
Eluent Gradient

| time in min | % E5 | % E4 | flow rate in mL/min |
|---|---|---|---|
| 0.0 | 95 | 5 | 1.5 |
| 1.3 | 0 | 100 | 1.5 |
| 3.0 | 0 | 100 | 1.5 |
| 3.4 | 95 | 5 | 1.5 |

Stationary phase: Waters Sunfire C18, 3.5 µm, 4.6×50 mm, 40° C.
Method CC-7:
Eluent Gradient

| time in min | % E6 | % E4 | flow rate in mL/min |
|---|---|---|---|
| 0.0 | 95 | 5 | 1.0 |
| 2.0 | 0 | 100 | 1.0 |
| 2.5 | 0 | 100 | 1.0 |
| 2.6 | 95 | 5 | 1.0 |

Stationary phase: XBridge C18, 1.7 µm, 2.1×50 mm, 60° C.
Method CC-8:
Eluent Gradient

| time in min | % E5 | % E2 | flow rate in mL/min |
|---|---|---|---|
| 0.0 | 95 | 5 | 1.5 |
| 2.0 | 5 | 95 | 1.5 |

Stationary phase: XBridge C18, 3.5 µm, 4.6×50 mm, 40° C.
Method CC-9:
Eluent gradient

| time in min | % E1 | % E4 | flow rate in mL/min |
|---|---|---|---|
| 0.0 | 95 | 5 | 1.5 |
| 2.0 | 5 | 95 | 1.5 |

Stationary phase: XBridge C18, 3.5 µm, 4.6×50 mm, 40° C.
Method CC-10:
Eluent Gradient

| time in min | % E6 | % E4 | flow rate in mL/min |
|---|---|---|---|
| 0.0 | 80 | 20 | 2.0 |
| 1.7 | 0 | 100 | 2.0 |

-continued
| time in min | % E6 | % E4 | flow rate in mL/min |
|---|---|---|---|
| 2.5 | 0 | 100 | 2.0 |
| 2.6 | 20 | 20 | 2.0 |
Stationary phase: XBridge C18, 3.5 μm, 4.6×50 mm, 60° C.
Example 1
N-(4-Chloro-3-methylaminocarbonyl-phenyl)-2-methyl-5-[(1-methylcyclohexylcarbonylamino)methyl]-benzamide
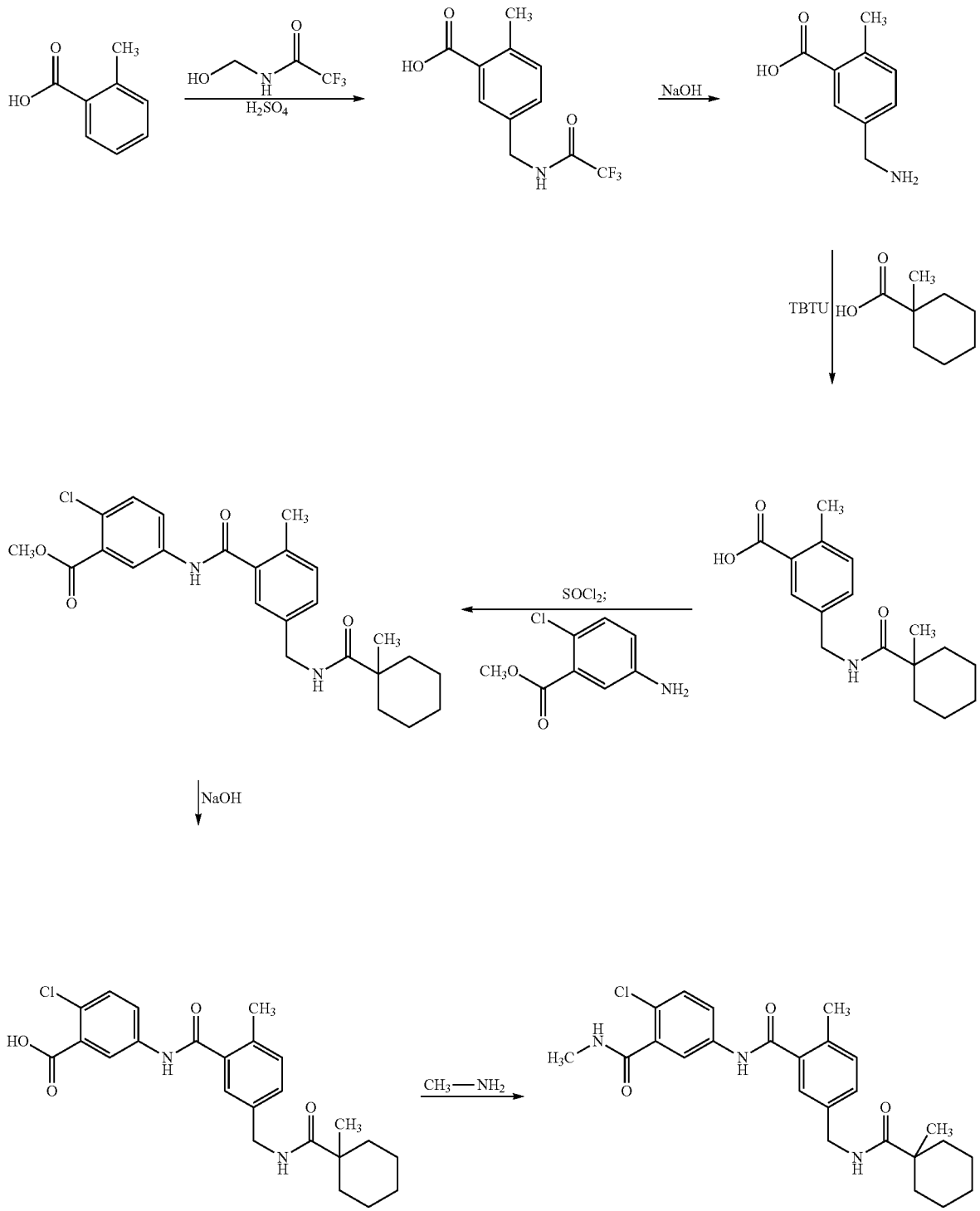

(a) 2-Methyl-5-(trifluoromethylcarbonylamino-methylbenzoic acid

N-(Hydroxymethyl)trifluoroacetamide (300 mmol; 42.9 g) was added to a mixture of 2-methylbenzoic acid (300 mmol; 40.8 g) and concentrated $H_2SO_4$ (750 mL). The mixture was stirred at rt overnight and poured into ice water. The precipitate was collected by filtration, dried and recrystallised from toluene/butan-2-one (7:1) to give the desired product. Yield: 31 g (40%). MS [M−H]⁻=260.

(b) 5-(Aminomethyl)-2-methylbenzoic acid hydrochloride

A mixture of 2-methyl-5-(trifluoromethylcarbonylamino-methyl)benzoic acid (15 mmol; 4.00 g), 1 M NaOH (36 mL) and THF (40 mL) was stirred at rt for 3 h. 4 M aq. HCl solution (5 mL) was added. Concentration under reduced pressure gave the sub-title compound as a mixture with NaCl which was used without further purification in the next step.

(c) 2-Methyl-5-[(1-methylcyclohexylcarbonylamino) methyl]benzoic acid

TBTU (15 mmol; 4.9 g) was added to a mixture of 1-methylcyclohexylcarboxylic acid (15 mmol; 2.2 g), TEA (9.6 mL) and DMF (130 mL) at rt. After 10 min a mixture of 5-aminomethyl-2-methylbenzoic acid (6.3 g crude mixture with NaCl, see step (b) above) was added. After 3 h at rt the reaction mixture was concentrated, water was added and the formed precipitate was washed with water, dried and purified by preparative HPLC. Yield: 3.6 g (83%). MS [M+H]⁺=290; TLC: $R_f$=0.49 (silica gel, DCM:EtOH 9:1).

(d) 2-Methyl-5-[(1-methylcyclohexylcarbonylamino) methyl]benzoyl chloride

A mixture of 2-methyl-5-[(1-methylcyclohexylcarbonylamino)methyl]benzoic acid (0.250 g, 0.864 mmol), 0.16 mL thionyl chloride, 15 mL DCM and 10 μL DMF were heated at reflux for 2 h and concentrated. The crude acid chloride was used without further purification.

(e) N-(4-Chloro-3-methoxycarbonyl-phenyl)-2-methyl-5-[(1-methylcyclohexylcarbonylamino)methyl]-benzamide A mixture of 2-methyl-5-[(1-methylcyclohexylcarbonylamino)methyl]benzoyl chloride (0.266 g, 0.864 mmol) in 5 mL THF was added to methyl 5-amino-2-chloro-benzoate (0.160 g, 0.864 mmol) and 0.42 mL TEA in 10 mL THF. The mixture was stirred overnight and concentrated. EtOAc was added to the residue and the organic phase was washed with water and 2 M aq. HCl solution and dried with $Na_2SO_4$. The crude mixture was purified via MPLC. Yield: 0.21 g (53%). MS [M+H]⁺=457 (Cl isotope pattern); TLC: $R_f$=0.44 (silica gel, DCM:EtOH 19:1).

(f) N-(4-Chloro-3-hydroxycarbonyl-phenyl)-2-methyl-5-[(1-methylcyclohexylcarbonylamino)methyl]-benzamide A mixture of 2-N-(4-chloro-3-methoxycarbonyl-phenyl)-2-methyl-5-[(1-methylcyclohexylcarbonylamino)methyl]-benzamide (0.190 g, 0.416 mmol) and 0.42 mL 4 M NaOH in 10 mL MeOH was stirred for 8 h at rt and 16 h at 50° C. The crude mixture was concentrated, diluted with water and acidified with 6 M aq. HCl solution. The precipitate was filtered and dried. Yield: 0.170 g (92%). MS [M+H]⁺=443 (Cl isotope pattern), TLC: $R_f$=0.18 (RP-8, MeOH:5%-aq NaCl-solution 6:4).

(g) N-(4-Chloro-3-methylaminocarbonyl-phenyl)-2-methyl-5-[(1-methylcyclohexylcarbonylamino)methyl]-benzamide TBTU (0.373 mmol; 0.120 g) and TEA (0.118 mL) was added to a mixture of N-(4-chloro-3-hydroxycarbonyl-phenyl)-2-methyl-5-[(1-methylcyclohexylcarbonylamino)methyl]-benzamide (0.339 mmol; 0.150 g) and 10 mL THF. The mixture was stirred for 15 min, then 0.423 mL methylamine solution (2 M in THF) was added and it was stirred overnight. The mixture was concentrated, diluted with THF and filtered through a pad of aluminium oxide and concentrated to furnish the title compound.

Yield: 36 mg (23%).
$C_{25}H_{30}ClN_3O_3$ (455.97)
Mass spectrum: [M+H]⁺=456 (Cl-isotope pattern)
HPLC: $R_t$=1.38 min (Method MC-1).

Example 2

N-[4-Fluoro-3-(4-bromophenyl)aminocarbonyl-phenyl]-2-chloro-5-(tert-butylcarbonylamino)methyl-benzamide

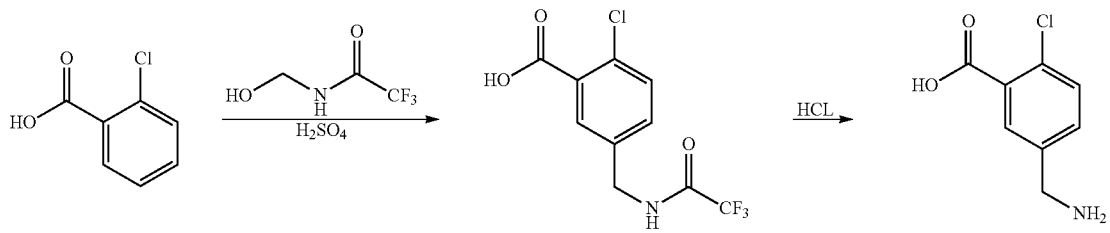

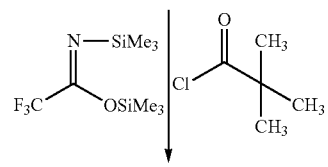

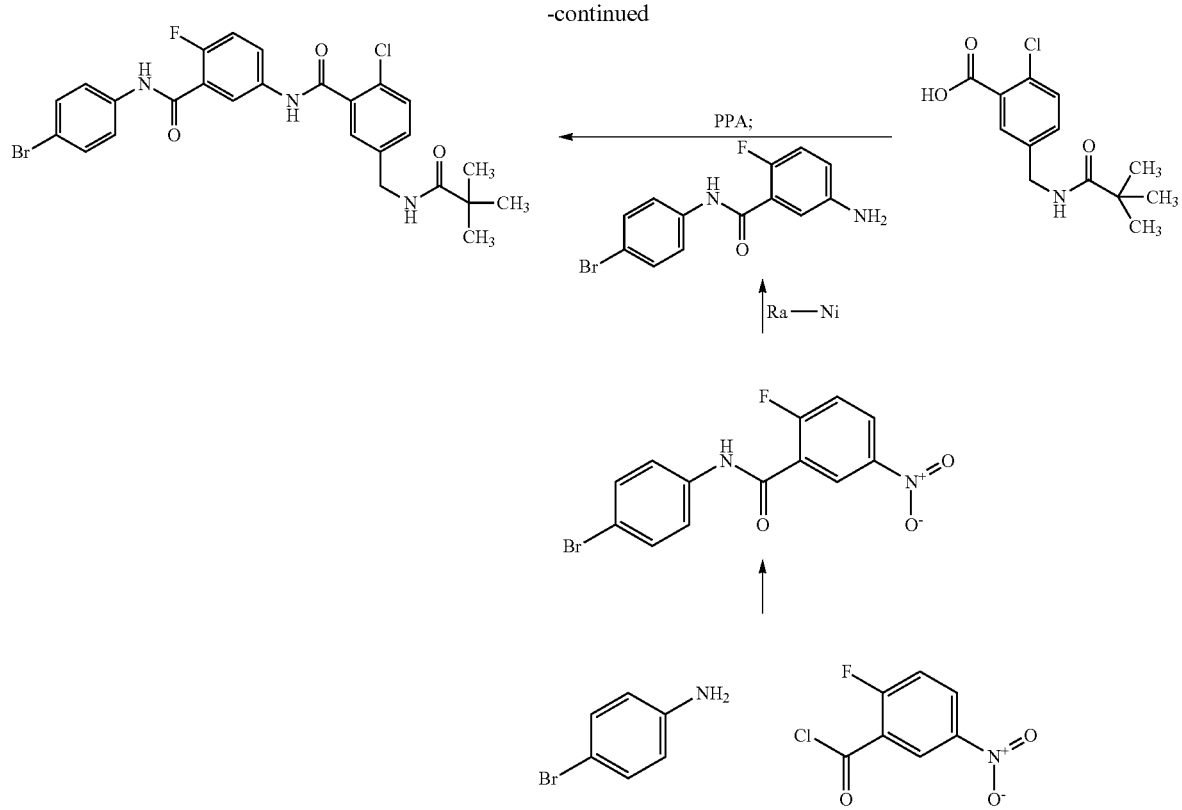

(a) 2-Chloro-5-(trifluoromethylcarbonylamino-methyl)benzoic acid

N-(Hydroxymethyl)trifluoroacetamide (70 mmol; 10.0 g) was added to a mixture of 2-chlorobenzoic acid (70 mmol; 10.9 g) and conc. $H_2SO_4$ (120 mL). The mixture was stirred at rt overnight, poured into ice water and stirred for 2 h. The precipitate was collected by filtration, dried and recrystallised from toluene/butan-2-one (7:1) to give the subtitle compound. Yield: 9.6 g (49%). MS [M−H]⁻=280 (Cl isotope pattern), TLC: $R_f$=0.57 (RP-8, MeOH:5%-aq NaCl-solution 6:4).

(b) 5-(Aminomethyl)-2-chloro-benzoic acid hydrochloride

A mixture of 2-chloro-5-(trifluoromethylcarbonylamino-methyl)benzoic acid (7.8 mmol; 2.20 g), and 1 M aq. HCl solution (50 mL) was stirred overnight at 50° C. and 6 h at 70° C. Additional conc. HCl (5 mL) was added and it was stirred for an additional 16 h at 70° C. The mixture was concentrated and the white crystalline precipitate was collected.

Yield: 1.72 g (99%). MS [M−H]⁻=186 (Cl isotope pattern), TLC: $R_f$=0.79 (RP-8, MeOH:5%-aq NaCl-solution 6:4).

(c) 2-Chloro-5-(tert-butylcarbonylamino)methyl-benzoic acid

A mixture of 5-(aminomethyl)-2-methylbenzoic acid hydrochloride (3.2 g, 14 mmol), BSTFA (2.26 mL, 14 mmol) and 50 mL THF was heated to reflux for 1 h and cooled to 0° C. 10 mL of TEA were added, followed by 1.77 mL (14 mmol) Piv-Cl in 50 mL THF. The mixture was stirred overnight at rt, concentrated i.vac., diluted with water and acidified with 22 mL glacial acetic acid. After 30 min it was extracted 3× with DCM, the organic phase was dried with $Na_2SO_4$, concentrated i.vac and purified via MPLC. Yield: 2.57 g (66%). MS [M+H]⁺=270 (Cl-isotope pattern); HPLC: $R_t$=4.09 min (Method MC-2).

(d) N-(4-Bromophenyl)-2-fluoro-5-nitro-benzoic acid amide

A mixture of 2-fluoro-5-nitro-benzoyl chloride (1.1 g, 5.4 mmol) in 20 mL DCM was added dropwise to 4-bromoaniline (929 mg, 5.4 mmol), 0.905 mL TEA in 20 mL DCM. The mixture was stirred for 6 days, successively washed with satd. $NaHCO_3$-solution and 2 M aq. HCl solution and dried with $Na_2SO_4$. After filtration and concentration i. vac. the subtitle compound was obtained. Yield: 1.57 g (86%). MS [M+H]⁺= 339 (Br-isotope pattern); TLC: $R_f$=0.96 (silica gel, DCM:EtOH 9:1).

(e) N-(4-Bromophenyl)-2-fluoro-5-amino-benzoic acid amide

A mixture of N-(4-Bromophenyl)-2-fluoro-5-nitro-benzoic acid amide (1.57 g, 4.6 mmol) and 500 mg Ra-Ni in 100 mL THF was stirred for 20 h under an atmosphere of hydrogen (3 bar). After filtration and concentration i. vac. the subtitle compound was obtained. Yield: 1.46 g (quantitative). MS [M+H]⁺=309 (Br-isotope pattern); TLC: $R_f$=0.68 (silica gel, DCM:EtOH 9:1).

(f) N-[4-Fluoro-3-(4-bromophenyl)aminocarbonyl-phenyl]-2-chloro-5-(tert-butylcarbonylamino)methyl-benzamide PPA (0.142 mL 50% solution in DMF) was added dropwise to a mixture of N-(4-bromophenyl)-2-fluoro-5-amino-benzoic acid amide (57 mg, 0.19 mmol), 2-chloro-5-(tert-butyl-carbonylamino)methyl-benzoic acid (50 mg, 0.19 mmol), 64 μL TEA and 10 mL THF. The reaction was refluxed overnight, additional PPA (0.14 mL) was added and it was refluxed for additional 4.5 h. The crude reaction mixture was concentrated i.vac., EtOAc was added and the organic phase was washed with 2 M aq. HCl, satd. NaHCO$_3$, dried with Na$_2$SO$_4$ and purified via HPLC (Method A) to furnish the title compound.

Yield: 24 mg (23%).

C$_{26}$H$_{24}$BrClFN$_3$O$_3$ (560.84)

Mass spectrum: [M+H]$^+$=560 (Br/Cl-isotope pattern)

TLC: R$_f$=0.49 (silica gel, DCM:EtOH 9:1).

Example 3

N-[4-Chloro-3-(4-bromophenyl)aminocarbonyl-phenyl]-2-chloro-5-(tert-butylcarbonylamino)methyl-benzamide

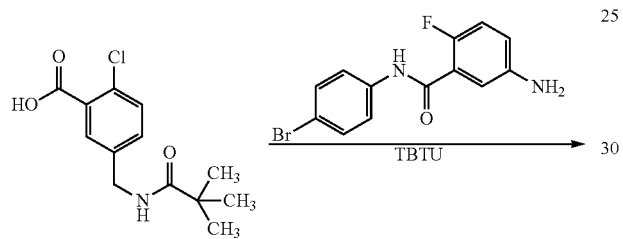

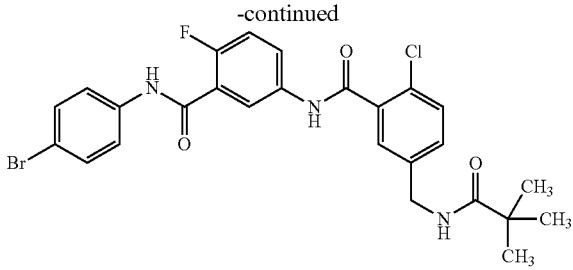

A mixture of TBTU (108 mg, 0.338 mmol), TEA (0.128 mL), 2-chloro-5-(tert-butylcarbonylamino)methyl-benzoic acid (83 mg, 0.31 mmol) and 5 mL THF was stirred for 15 min at rt. Then N-(4-bromophenyl)-2-chloro-5-amino-benzoic acid amide (100 mg, 0.31 mmol, prepared analogously to 2d/2e) was added and it was stirred for 3 h at rt and for additional 3 h at reflux. The mixture was concentrated i.vac., EtOAc was added and the organic phase was washed with 1M NaOH, water, 2M aq. HCl-solution, water and brine and dried with Na$_2$SO$_4$. The crude mixture was concentrated i.vac. and purified by chromatography (silica gel, petrol ether/EtOAc 60/40→55/45) to furnish the title compound.

Yield: 80 mg (45%).

C$_{26}$H$_{24}$BrCl$_2$N$_3$O$_3$ (577.30)

Mass spectrum: [M+H]$^+$=576 (Br/Cl$_2$-isotope pattern)

TLC: R$_f$=0.4 (silica gel, DCM:EtOH 19:1).

HPLC: R$_t$=1.52 min (Method MC-1).

Example 4

N-[4-Methoxy-3-(4-bromophenyl)aminocarbonyl-phenyl]-2-chloro-5-(tert-butylcarbonylamino)methyl-benzamide

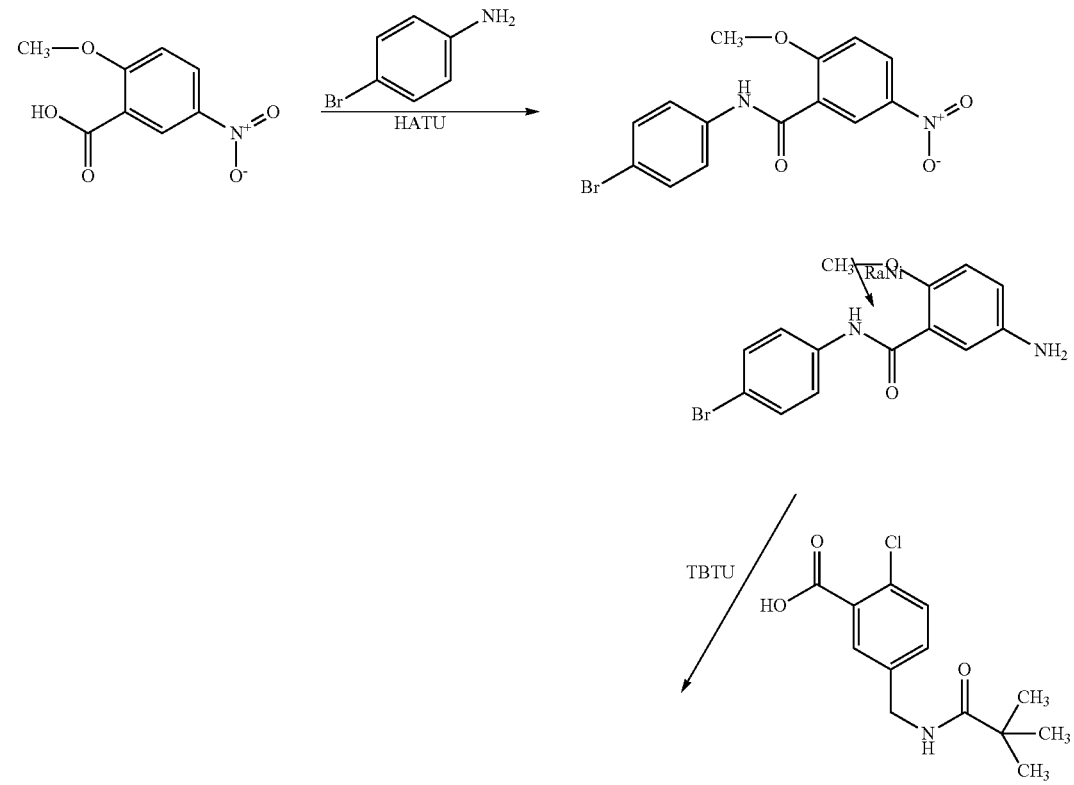

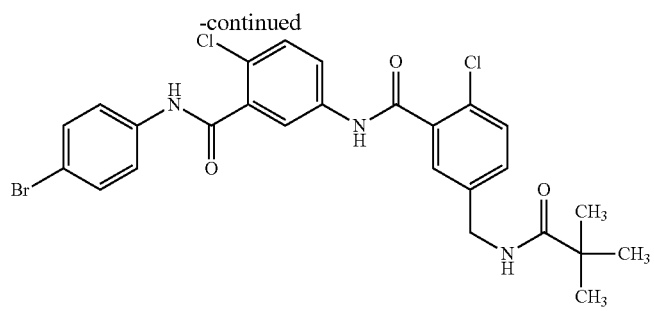

(a) N-(4-Bromophenyl)-2-methoxy-5-nitro-benzoic acid amide

A mixture of 2-methoxy-5-nitro-benzoic acid (2.00 g, 10.1 mmol), HATU (3.86 g, 10.1 mmol), TEA (4.23 mL) and 100 mL THF was stirred for 30 min. Then 4-bromoaniline (1.75 g, 10.1 mmol) was added and the mixture was stirred for 3 days and concentrated. The crude material was dissolved in EtOAc and the organic phase was washed with satd. aq. $NaHCO_3$. The precipitate was collected and again dissolved in EtOAc and washed with water and satd. $NaHCO_3$. The organic phase was dried with $Na_2SO_4$, filtered and concentrated to furnish the subtitle compound. Yield: 930 mg (26%). MS $[M+H]^+$= 351 (Br-isotope pattern); TLC: $R_f$=0.94 (silica gel, DCM: EtOH 9:1).

(b) N-(4-Bromophenyl)-2-methoxy-5-amino-benzoic acid amide

A mixture of N-(4-bromophenyl)-2-methoxy-5-nitro-benzoic acid amide (930 mg, 2.6 mmol) and 140 mg Ra-Ni in 40 mL THF was stirred for 20 h under an atmosphere of hydrogen (3 bar). After filtration and concentration i. vac. the subtitle compound was obtained. Yield: 890 mg (quantitative). MS $[M+H]^+$=321 (Br-isotope pattern); TLC: $R_f$=0.60 (silica gel, DCM:EtOH 9:1).

(c) N-[4-Methoxy-3-(4-bromophenyl)aminocarbonyl-phenyl]-2-chloro-5-(tert-butylcarbonylamino)methyl-benzamide TBTU (40 mg, 0.125 mmol) in 0.25 mL DMF was added to 2-chloro-5-(tert-butylcarbonylamino)methyl-benzoic acid (34 mg, 0.125 mmol), followed by 50 μL TEA and the mixture was stirred for 5 min. Then N-(4-bromophenyl)-2-methoxy-5-amino-benzoic acid amide in 0.25 mL DMF was added and it was stirred overnight. The crude mixture was filtered through aluminium oxide and the solid phase was washed 4× with 1 mL DMF/MeOH 9:1. The combined organic phase was concentrated i.vac. dissolved in Acetonitrile/HCOOH, filtered and dried via lyophilisation to furnish the title compound.

Yield: 54 mg (75%).
$C_{27}H_{27}BrClN_3O_4$ (572.88)
Mass spectrum: $[M+H]^+$=572 (Br/Cl-isotope pattern)
HPLC: $R_t$=3.35 min (Method MC-3).

Example 5

N-[4-(2,2-Difluoroethyl)oxy-3-[trans-(4-trifluoromethyl-cyclohexyl)amino]carbonyl-phenyl]-2-chloro-5-(tert-butylcarbonylamino)methyl-benzamide

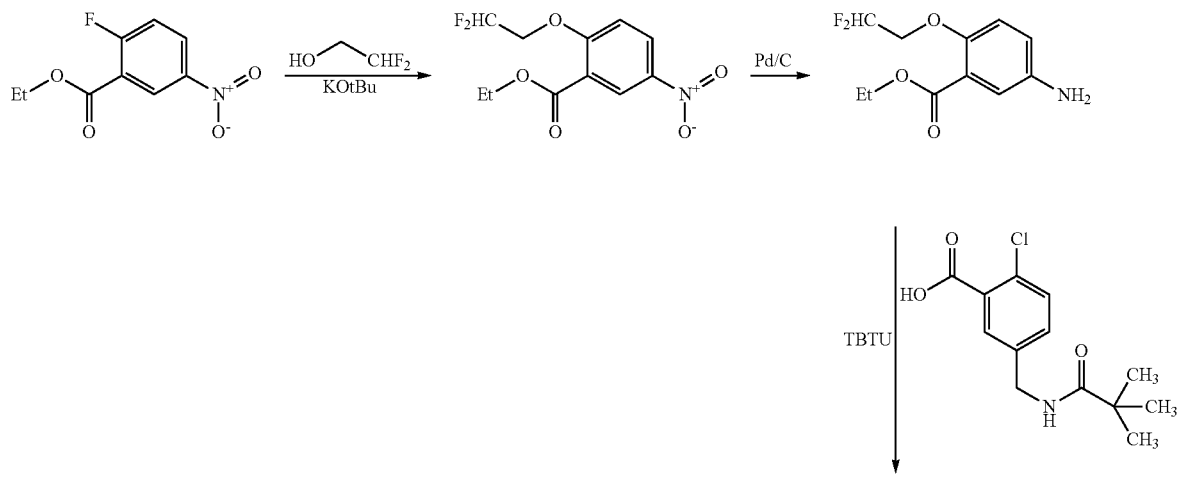

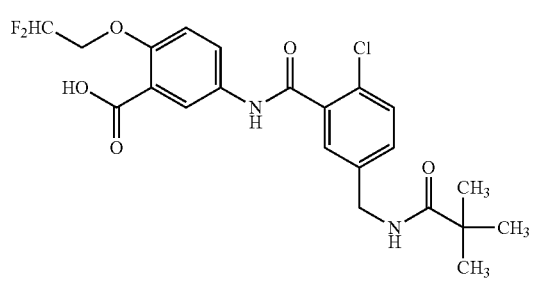
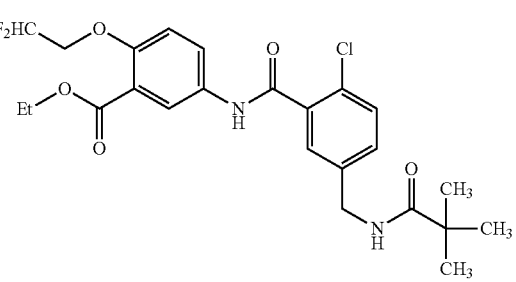

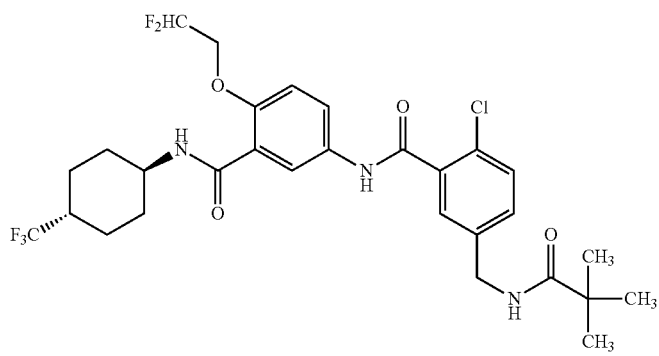

(a) Ethyl 2-(2,2-Difluoroethyl)oxy-5-nitro-benzoate

A mixture of 2,2-difluoroethanol (0.178 mL, 2.82 mmol) and KOtBu (0.319 g, 2.70 mmol) in 10 mL THF was stirred for 5 min, then ethyl 2-fluoro-5-nitrobenzoate (0.500 g, 2.35 mmol) was added and it was stirred at rt overnight. Additional 60 μL 2,2-difluoroethanol and 110 mg KOtBu were added and it was stirred for 2 h. The mixture was diluted with $H_2O$, concentrated i.vac. and extracted 2× with EtOAc. The combined organic layers were dried with $Na_2SO_4$ and concentrated to furnish the subtitle compound. Yield: 0.52 g (81%); TLC: $R_f$=0.85 (silica gel, DCM:EtOH 99:1).

(b) Ethyl 5-amino-2-(2,2-difluoroethyl)oxy-benzoate

A mixture of ethyl 2-(2,2-difluoroethyl)oxy-5-nitro-benzoate (600 mg, 2.18 mmol) and 80 mg 10% Pd/C in 30 mL MeOH was stirred for 6.5 h under an atmosphere of hydrogen (3 bar). After filtration and concentration i. vac. the subtitle compound was obtained. Yield: 500 mg, (94%). MS $[M+H]^+$= 246; TLC: $R_f$=0.2 (silica gel, DCM:EtOH 99:1).

(c) N-[4-(2,2-Difluoroethyl)oxy-3-ethoxycarbonyl-phenyl]-2-chloro-5-(tert-butylcarbonylamino)methyl-benzamide Prepared analogously to Example 4c from 2 ethyl 5-amino-2-(2,2-difluoroethyl)oxy-benzoate and 2-chloro-5-(tert-butylcarbonylamino)methyl-benzoic acid with TBTU and TEA in THF. Yield: (quantitative). MS $[M+H]^+$=497 (Cl isotope pattern); TLC: $R_f$=0.35 (silica gel, DCM:EtOH 19:1).

(d) N-[4-(2,2-Difluoroethyl)oxy-3-hydroxycarbonyl-phenyl]-2-chloro-5-(tert-butylcarbonylamino)methyl-benzamide A mixture of N-[4-(2,2-difluoroethyl)oxy-3-ethoxycarbonyl-phenyl]-2-chloro-5-(tert-butylcarbonylamino)methyl-benzamide (0.470 mg, 0.946 mmol) and 1.4 mL 2M NaOH in 5.0 mL EtOH was stirred at rt for 3 h and concentrated i.vac. Water was added and it was acidified with 2 M HCl. The resulting precipitate was filtered, washed with water and dried. Yield: (86%). MS $[M+H]^+$=469 (Cl isotope pattern); TLC: $R_f$=0.25 (silica gel, DCM:EtOH 9:1).

(e) N-[4-(2,2-Difluoroethyl)oxy-3-[trans-(4-trifluoromethyl-cyclohexyl)amino]carbonyl-phenyl]-2-chloro-5-(tert-butylcarbonylamino)methyl-benzamide Prepared analogously to Example 4c from N-[4-(2,2-difluoroethyl)oxy-3-hydroxycarbonyl-phenyl]-2-chloro-5-(tert-butylcarbonylamino)methyl-benzamide and trans-4-trifluoromethyl-cyclohexylamine with TBTU and TEA in THF.
Yield: 70 mg (quantitative).
$C_{29}H_{33}ClF_5N_3O_4$ (618.035)
Mass spectrum: $[M+H]^+$=618 (Cl-isotope pattern)
TLC: $R_f$=0.7 (silica gel, DCM:EtOH 9:1)
HPLC: $R_t$=1.48 min (Method MC-1).

Example 6

N-[2-(2,2-Difluoroethyl)oxy-3-(4-bromophenyl)aminocarbonyl-pyridin-5-yl]-2-chloro-5-(tert-butyl-carbonylamino)methyl-benzamide

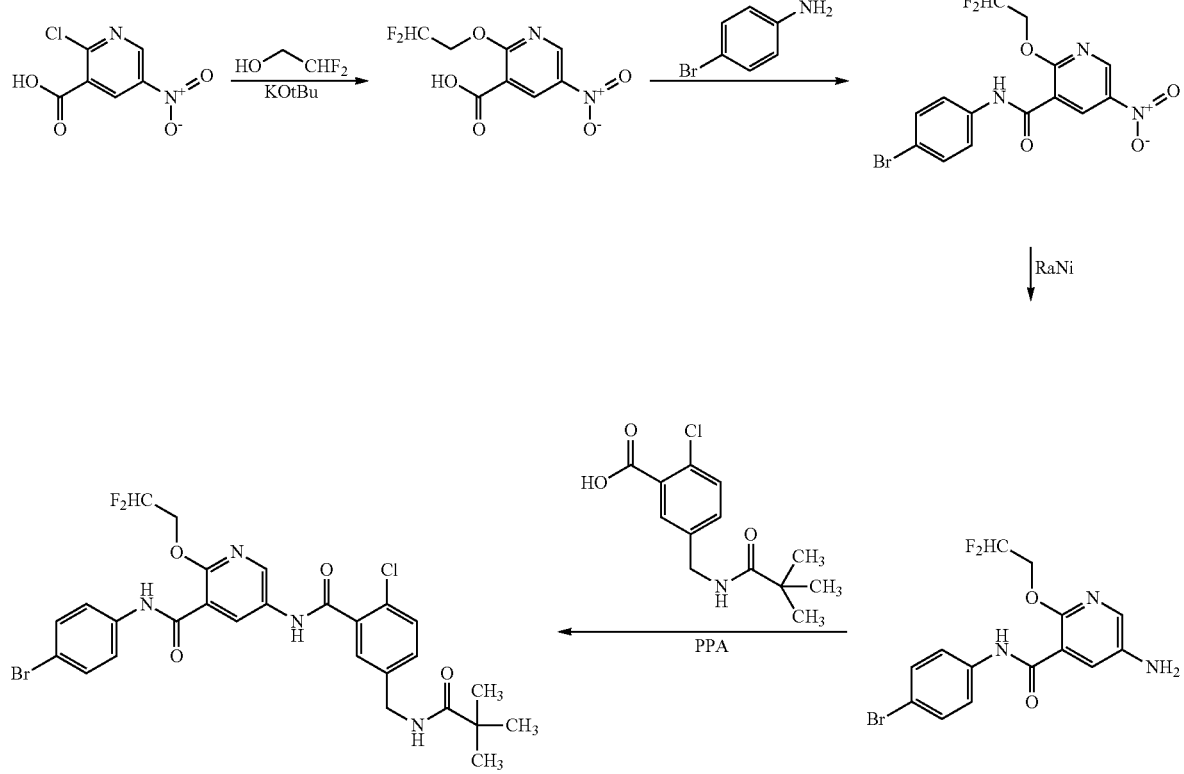

(a) 2-(2,2-Difluoroethyl)oxy-5-nitro-nicotinic acid

Prepared analogously to Example 5a from 2 chloro-5-nitro nicotinic acid and 2,2-difluoroethanol with KOtBu in THF. Yield: (25%). MS [M−H]⁻=247; TLC: $R_f$=0.13 (silica gel, DCM:EtOH 9:1).

(b) 2-(2,2-Difluoroethyl)oxy-5-nitro-nicotinic acid chloride

A mixture of 2-(2,2-difluoroethyl)oxy-5-nitro-nicotinic acid (310 mg, 1.25 mmol), 2.0 mL thionyl chloride, 5.0 mL DCM and one drop of DMF was refluxed for 4 h and concentrated i.vac. The corresponding acid chloride was directly used for the next step without further purification.

(c) N-(4-Bromophenyl)-2-(2,2-difluoroethyl)oxy-5-nitronicotinic acid amide

The acid chloride (obtained in step 6b) in 5 mL DCM was added dropwise to a mixture of 4-bromoaniline (214 mg, 1.25 mmol) and 0.21 mL TEA in 5 mL DCM and it was stirred at rt overnight. The resulting precipitate was filtered, washed 2× with DCM and dried to furnish the subtitle compound. Yield: 350 mg, (70%). MS [M+H]⁺=402 (Br-isotope pattern); TLC: $R_f$=0.97 (silica gel, DCM:EtOH 9:1).

(d) N-(4-Bromophenyl)-2-(2,2-difluoroethyl)oxy-5-amino-nicotinic acid amide

Prepared analogously to Example 4b from N-(4-bromophenyl)-2-(2,2-difluoroethyl)oxy-5-nitronicotinic acid amide and Ra-Ni in THF. Yield: (quantitative). MS [m+H]⁺=372 (Br-isotope pattern); TLC: $R_f$=0.60 (silica gel, DCM:EtOH 9:1).

(e) N-[2-(2,2-Difluoroethyl)oxy-3-(4-bromophenyl)aminocarbonyl-pyridin-5-yl]-2-chloro-5-(tert-butyl-carbonylamino)methyl-benzamide Prepared analogously to Example 2f from N-(4-bromophenyl)-2-(2,2-difluoroethyl)oxy-5-amino-nicotinic acid amide and 2-chloro-5-(tert-butylcarbonylamino)methyl-benzoic acid with PPA and TEA in THF. Purification via HPLC (Method A)

Yield: 26 mg (23%).

C₂₇H₂₆BrClF₂N₄O₄ (623.873)

Mass spectrum: [M+H]⁺=623 (Br/Cl-isotope pattern)

TLC: $R_f$=0.39 (silica gel, DCM:EtOH 9:1)

Example 7

N-[4-(2,2-Difluoroethyl)oxy-3-(4-fluoro-3-chlorophenyl)aminocarbonyl-phenyl]-2-chloro-5-(tert-butylcarbonylamino)methyl-benzamide

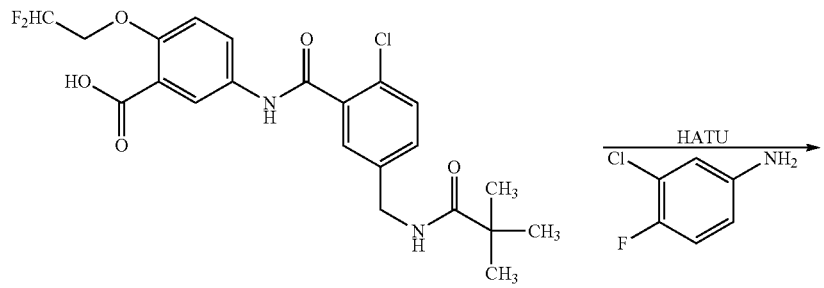

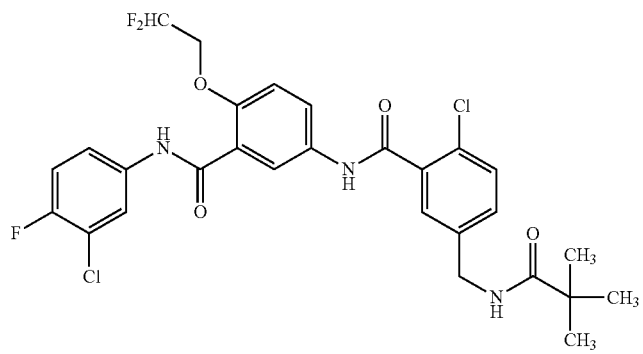

HATU (43 mg, 0.11 mmol) was added to N-[4-(2,2-difluoroethyl)oxy-3-hydroxycarbonyl-phenyl]-2-chloro-5-(tert-butylcarbonylamino)methyl-benzamide (50.0 mg, 0.107 mmol) in 5.0 mL THF, followed by 52 µL TEA and the mixture was stirred for 15 min. Then 3-chloro-4-fluoroaniline (15.5 mg, 0.107 mmol) was added and it was stirred for 4 h at rt. The crude mixture was concentrated, EtOAc was added and the organic phase was washed with satd. aq. NaHCO$_3$-solution, water and satd. NaCl-solution. The organic phase was dried with Na$_2$SO$_4$ and concentrated i. vac. to give the title compound.

Yield: 50 mg (79%).
C$_{28}$H$_{26}$Cl$_2$F$_3$N$_3$O$_4$ (596.424)
Mass spectrum: [M+H]$^+$=596 (Cl$_2$-isotope pattern)
HPLC: R=1.57 min (Method MC-1). TLC: R$_f$=0.25 (silica gel, DCM:EtOH 19:1).

Example 8

N-[4-Methoxy-3-(4-trifluoromethyl-pyridin-2-yl)aminocarbonyl-phenyl]-2-chloro-5-(tert-butylcarbonylamino)methyl-benzamide

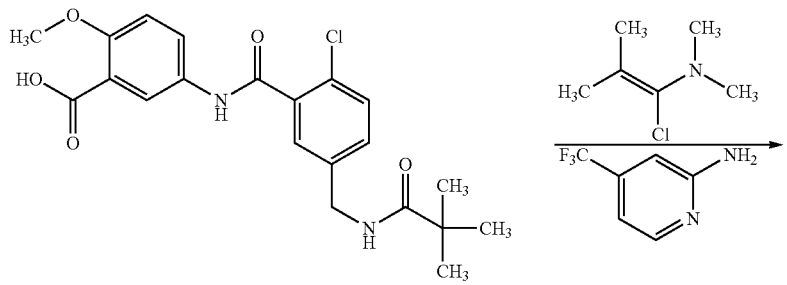

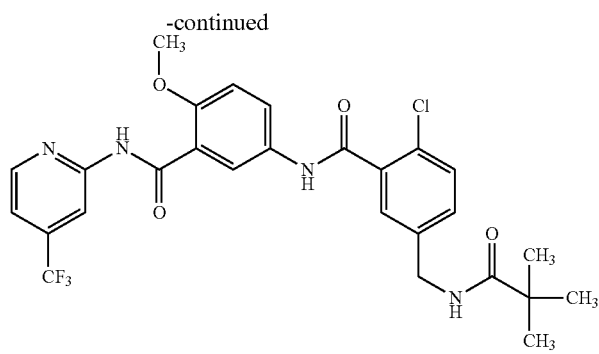

1-Chloro-N,N,2-trimethylpropenylamine (23 was added to a mixture of N-[4-methoxy-3-hydroxycarbonyl-phenyl]-2-chloro-5-(tert-butylcarbonylamino)methyl-benzamide (60.0 mg, 0.143 mmol, prepared from ethyl 5-amino-2-methoxy benzoate in analogy to step 5c and 5d) in 2.0 mL THF and it was stirred for 2 h. additional 80 μL of 1-chloro-N,N,2-trimethylpropenylamine were added and it was stirred for another 2 h. Then TEA (0.100 mL) and 2-amino-4-trifluormethyl-pyridine (23.2 mg, 0.143 mmol) were added and it was stirred overnight. The reaction mixture was concentrated and purified via prep. HPLC (method A) to furnish the title compound.

Yield: 45 mg (56%).

$C_{27}H_{26}ClF_3N_4O_4$ (562.968); Mass spectrum: $[M+H]^+=$ 563 (Cl-isotope pattern)

TLC: $R_f$=0.58 (silica gel, DCM:EtOH 9:1).

Example 9

N-[4-Methoxy-3-(4-bromophenyl)aminocarbonyl-phenyl]-2-chloro-5-(2,2,2-trifluoro-1,1-dim ethyl-ethyl)carbonylaminomethyl-benzamide

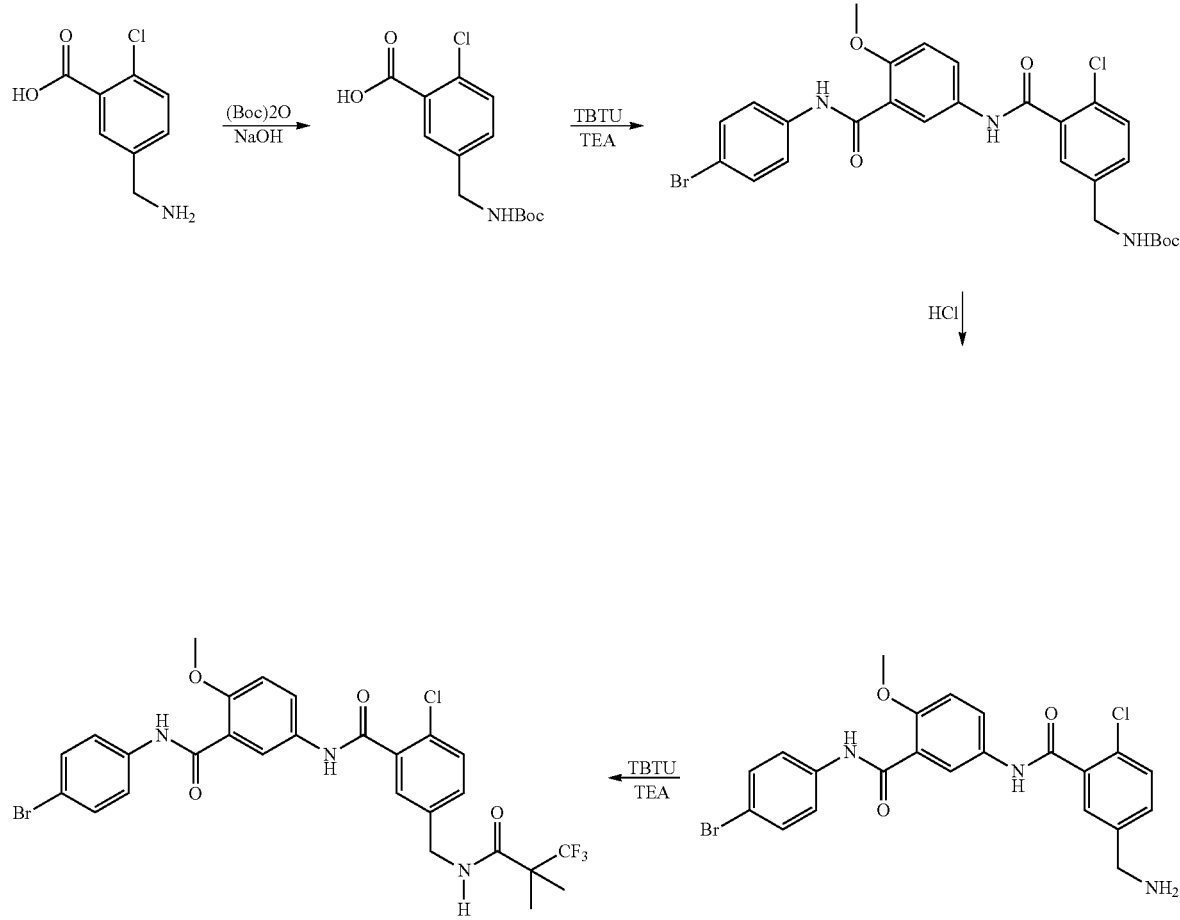

(a) 5-(tert.Butoxycarbonylamino)methyl-2-chloro benzoic acid

At 0° C. 0.2 N NaOH (144 mL) was dropped to a mixture of 3.2 g 5-(aminomethyl)-2-chloro-benzoic acid (14.4 mmol) in 50 mL THF and it was stirred for 15 min. Then 3.14 g Boc$_2$O (14.4 mmol) was added in 50 mL THF and it was stirred for 30 min at 0° C. and overnight at rt. The mixture was concentrated i. vac. and it was acidified at 0° C. with satd. KHSO$_4$ solution (pH 3-4) and stirred for 1 h. The precipitate was filtered and dried to furnish the subtitle compound. Yield: 2.69 g, (65%). MS [M–H]$^−$=284 (Cl-isotope pattern).

(b) N-[4-Methoxy-3-(4-bromophenyl)aminocarbonyl-phenyl]-2-chloro-5-(tert-butoxycarbonylamino)methyl-benzamide Prepared analogously to Example 4c from N-(4-bromophenyl)-2-methoxy-5-amino-benzoic acid amide and 5-(tert.butoxycarbonylamino)methyl-2-chloro benzoic acid with TBTU and TEA. Yield: (85%). MS [m+H]$^+$=588 (Br/Cl-isotope pattern); TLC: R$_f$=0.60 (silica gel, DCM:EtOH 9:1).

(c) N-[4-Methoxy-3-(4-bromophenyl)aminocarbonyl-phenyl]-2-chloro-5-aminomethyl-benzamide A mixture of 2.66 g N-[4-methoxy-3-(4-bromophenyl)aminocarbonyl-phenyl]-2-chloro-5-(tert.butoxycarbonylamino)methyl-benzamide (4.51 mmol) 25 mL 4M HCl in dioxane and 50 mL dioxane was stirred for 2 h at rt and 60 min at 50° C. and concentrated i.vac. to furnish the subtitle compound. Yield: (quantitative). MS [M+H]$^+$=488 (Br/Cl-isotope pattern).

(d) N-[4-Methoxy-3-(4-bromophenyl)aminocarbonyl-phenyl]-2-chloro-5-(2,2,2-trifluoro-1,1-dimethyl-ethyl)carbonylaminomethyl-benzamide To 1.0 mL of a 0.13 M solution of 3,3,3-trifluoro-2,2-dimethyl-propionic acid (0.13 mmol) in DMF was added 1.0 mL of a 0.1 M solution of N-[4-methoxy-3-(4-bromophenyl)aminocarbonyl-phenyl]-2-chloro-5-aminomethyl-benzamide (0.10 mmol) in DMF and triethylamine (70 μL, 0.50 mmol). Then 1.0 mL of a 0.115 M solution of TBTU (0.115 mmol) in DMF was added and the mixture was stirred overnight. The reaction mixture was directly purified via prep. HPLC to furnish the title compound.

C$_{27}$H$_{24}$BrCl F$_3$N$_3$O$_4$ (626.9); MS: [m+H]$^+$=626 (Br/Cl pattern)
HPLC: R$_t$=1.98 min (Method CC-1).

Example 10

N-[4-Chloro-3-cyclopropylaminocarbonyl-phenyl]-2-chloro-5-(5-chloro-thien-2-yl)carbonylaminomethyl-benzamide

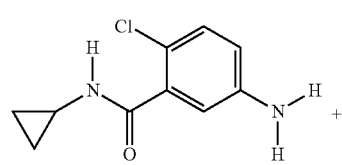
+

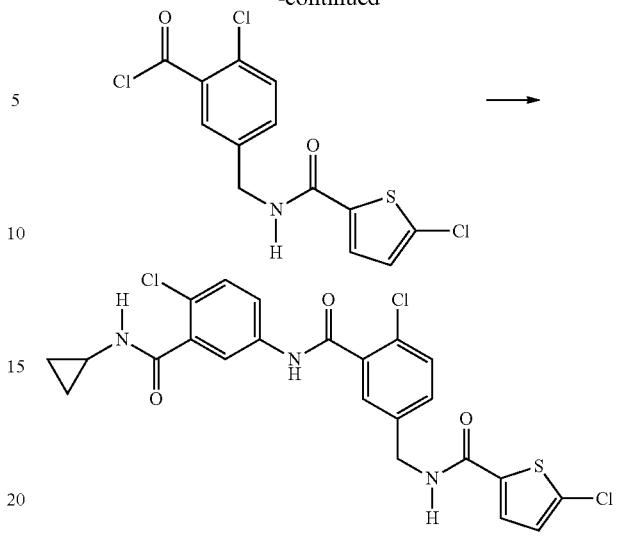

To 2.0 mL of a 0.05 M solution of 5-amino-2-chloro-N-cyclopropyl-benzamide (0.10 mmol) in acetonitrile was added pyridine (20 μL, 0.25 mmol) and then 1.0 mL of a 0.05 M solution of 2-chloro-5-(5-chloro-thien-2-yl)carbonylaminomethyl-benzoyl chloride (0.10 mmol, prepared from 5-(aminomethyl)-2-chloro-benzoic acid in analogy to step 1c and 1d) in acetonitrile. The reaction mixture was stirred overnight at 60° C., diluted with 200 μL of distilled water and filtered over Alox B. The Alox B pad was washed three times with 2.0 mL 9:1 DMF/MeOH-solution and the combined filtrate was concentrated in vacuo. The residue was dissolved in 2.0 mL of DMF and purified via prep. HPLC.

C$_{23}$H$_{18}$Cl$_3$N$_3$O$_3$S (522.8)
Mass spectrum: [M+H]$^+$=522/524/526 (Cl$_3$ pattern)
HPLC: R$_t$=1.94 min (Method CC-1).

Example 36

N-[4-Methoxy-3-(4-bromophenyl)aminocarbonyl-phenyl]-2-chloro-5-cyclopropylsulphonylaminomethyl-benzamide

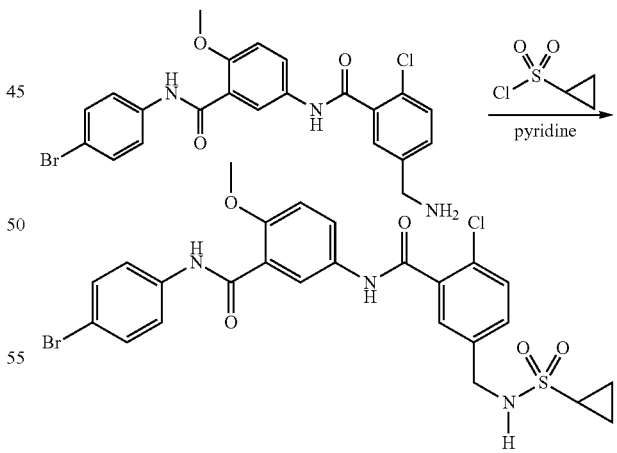

A mixture of 52.5 mg N-[4-methoxy-3-(4-bromophenyl)aminocarbonyl-phenyl]-2-chloro-5-aminomethyl-benzamide (0.10 mmol), 16.8 mg cyclopropylsulphonic acid chloride (0.12 mmol), 1.0 mL pyridine and 4.0 mL acetonitrile was stirred overnight, concentrated, dissolved in 3 mL DMF and purified by prep. HPLC.

C$_{25}$H$_{23}$BrCl N$_3$O$_5$S (592.89)
Mass spectrum: [M+H]$^+$=592 (Br/Cl pattern)
HPLC: R=2.25 min (Method CC-3).

Example 37

N-[4-(4-Methyl-piperidin-1-yl)-3-(4-bromophenyl)aminocarbonyl-phenyl]-2-chloro-5-(tert-butylcarbonylamino)methyl-benzamide

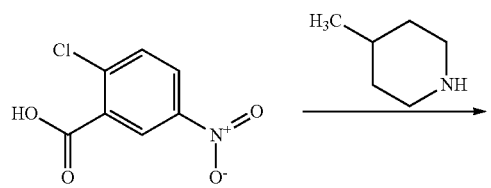

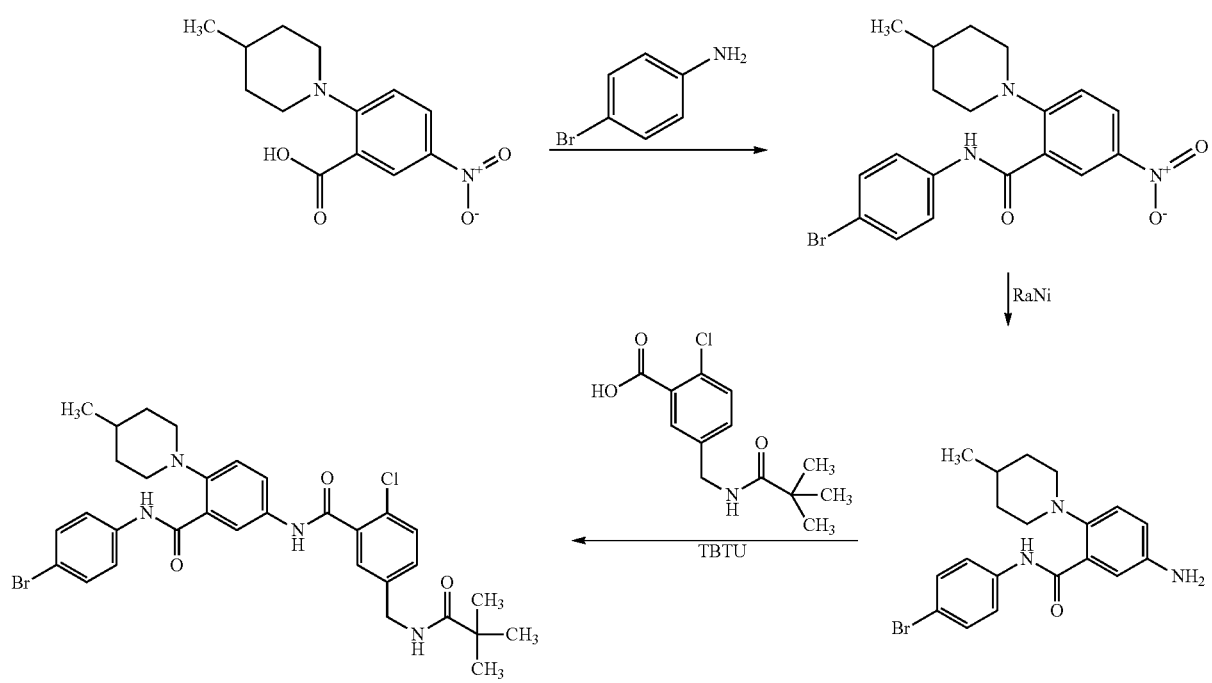

(a) 2-(4-Methyl-piperidin-1-yl)-5-nitro-benzoic acid

A mixture of 10.0 g 2-chloro-5-nitro benzoic acid (50 mmol) and 13 mL 4-methyl-piperidine was refluxed for 2 h, 100 mL 1 N aq. HCl solution was added and it was extracted with 100 mL DCM. The organic phase was dried with $Na_2SO_4$, concentrated and purified via chromatography (silica gel, eluent: DCM:MeOH 100:1) to furnish the subtitle compound. MS $[m+H]^+=265$.

(b) N-(4-Bromophenyl)-2-(4-methyl-piperidin-1-yl)-5-nitro-benzoic acid amide Prepared analogously to Example 8 from 2-(4-methyl)piperidin-1-yl-5-nitro-benzoic acid and 4-bromoaniline with 1-chloro-N,N,2-trimethylpropenylamine and TEA in THF. Yield: (quantitative). MS $[M+H]^+=418$ (Br-isotope pattern); TLC: $R_f=0.9$ (silica gel, DCM:EtOH 19:1).

(c) N-(4-Bromophenyl)-2-(4-methyl-piperidin-1-yl)-5-amino-benzoic acid amide Prepared analogously to Example 4b from N-(4-bromophenyl)-2-(4-methyl-piperidin-1-yl)-5-nitro-benzoic acid amide and Ra-Ni in THF. Yield: (quantitative). MS $[M+H]^+=388$ (Br-isotope pattern); $R_t=1.36$ min (Method MC-1).

(d) N-[4-(4-Methyl-piperidin-1-yl)-3-(4-bromophenyl)aminocarbonyl-phenyl]-2-chloro-5-(tert-butylcarbonylamino)methyl-benzamide Prepared analogously to Example 4c from N-(4-bromophenyl)-2-(4-methyl-piperidin-1-yl)-5-amino-benzoic acid amide and 2-chloro-5-(tert-butylcarbonylamino)methyl-benzoic acid with to TBTU and TEA in THF. Purification via chromatography (silica gel, eluent PE:EtOAc 6:4)

Yield: 120 mg (46%).
$C_{32}H_{36}BrClN_4O_3$ (640.01)
Mass spectrum: $[M+H]^+=639$ (Br/Cl-isotope pattern)
TLC: $R_f=0.45$ (silica gel, eluent DCM:EtOH 19:1)
HPLC: $R_t=1.79$ min (Method MC-1).

Example 38

N-[4-(Cyclopropylmethyloxy)-3-[trans-(4-trifluoromethyl-cyclohexyl)amino]carbonyl-phenyl]-2-chloro-5-(tert-butylcarbonylamino)methyl-benzamide

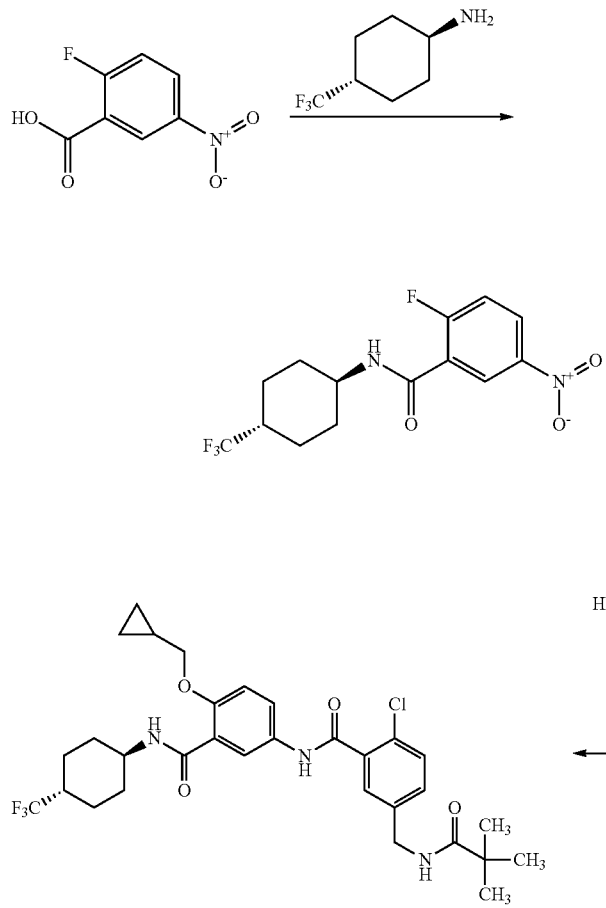

(a) 2-Fluoro-N-[trans-(4-trifluoromethyl-cyclohexyl]-5-nitro-benzoic acid amide

Prepared analogously to Example 2d from 2-fluoro-5-nitro-benzoic acid chloride and trans-4-trifluoromethyl-cyclohexylamine with TEA in DCM. Yield: (89%). MS [m+H]$^+$= 335; TLC: R$_f$=0.85 (silica gel, DCM:EtOH 19:1).

(b) 2-(Cyclopropylmethyloxy)-N-[trans-(4-trifluoromethyl-cyclohexyl]-5-nitro-benzoic acid amide A mixture of 24 μL cyclopropyl-methanol (0.299 mmol) and NaH (16 mg, 50% dispersion in mineral oil) in 2.0 mL DMF was stirred for 30 min, then 2-fluoro-N-[trans-(4-trifluoromethyl-cyclohexyl]-5-nitro-benzoic acid amide (0.100 mg, 0.299 mmol) was added and it was stirred for another 1.5 h. Water was carefully added and the water phase was extracted with EtOAc (3×). The organic layer was dried with Na$_2$SO$_4$ and concentrated to give the crude subtitle compound which was used without further purification. Yield: (quantitative). MS [m+H]$^+$=387; HPLC: R$_t$=1.57 min (Method MC-1).

(c) 2-(Cyclopropylmethyloxy)-N-[trans-(4-trifluoromethyl-cyclohexyl]-5-amino-benzoic acid amide Prepared analogously to Example 2e from 2-(cyclopropylmethyloxy)-N-[trans-(4-trifluoromethyl-cyclohexyl]-5-nitro-benzoic acid amide with Pd/C in MeOH. Yield: (81%). MS [M+H]$^+$=357; TLC: R$_f$=0.25 (silica gel, DCM:EtOH 19:1).

(d) N-[4-(Cyclopropylmethyloxy)-3-[trans-(4-trifluoromethyl-cyclohexyl)amino]carbonyl-phenyl]-2-chloro-5-(tert-butylcarbonylamino)methyl-benzamide Prepared analogously to Example 7 from 2-(cyclopropylmethyloxy)-N-[trans-(4-trifluoromethyl-cyclohexyl]-5-amino-benzoic acid amide and 2-chloro-5-(tert-butylcarbonylamino)methyl-benzoic acid with HATU and TEA in THF. Purification via chromatography (silica gel, eluent DCM:MeOH 98:2)

Yield: 100 mg (89%). C$_{31}$H$_{37}$ClF$_3$N$_3$O$_4$ (608.10)

MS: [M+H]$^+$=608 (Cl-isotope pattern);

TLC: R$_f$=0.35 (silica gel, eluent DCM:EtOH 19:1); HPLC: R$_t$=1.57 min (Method MC-1).

Example 42

N-[4-(2,2-Difluoroethyl)oxy-3-(4-bromophenyl)aminocarbonyl-phenyl]-2-trifluormethyl-5-(tert-butylcarbonylamino)methyl-benzamide

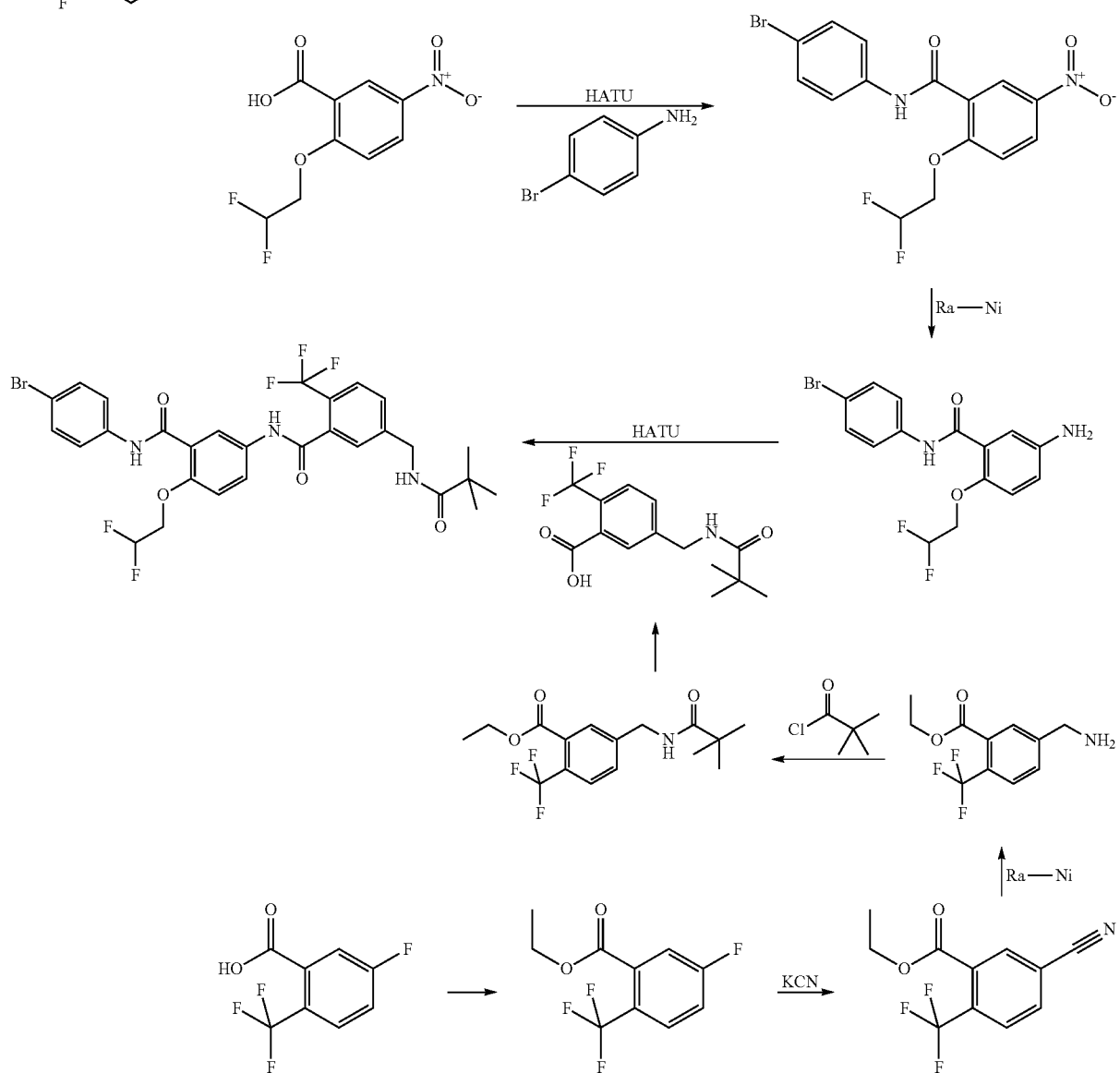

(a) 2-(2,2-Difluoro-ethoxy)-5-nitro-benzoic acid 2,2-Difluoroethanol (0.376 mL; 5.94 mmol) was dissolved in THF (15 mL), KOtBu (0.702 g; 5.94 mmol) was added and it was stirred for 5 min. 2-Fluor-5-nitro-benzoic acid (1.0 g; 5.4 mmol) was added and additional KOtBu (0.5 g and 0.2 g) was added after 2 h and 5 h. Additional 2-fluor-5-nitro-benzoic acid (50 µL) was added and it was stirred over night. The solvent was removed i.vac. and the residue was diluted with water, acidified with 2M aq. HCl-solution, extracted with EtOAc, dried over $Na_2SO_4$ and concentrated i. vac.

Yield: 1.2 g (95%); MS [M−H]⁻=246; TLC: (silica gel; DCM/EtOH 9/1) $R_f$=0.4

(b) N-(4-Bromo-phenyl)-2-(2,2-difluoro-ethoxy)-5-nitro-benzamide 2-(2,2-Difluoro-ethoxy)-5-nitro-benzoic acid (1.06 g; 4.29 mmol) was dissolved in THF (20 mL) HATU (1.712 g; 4.5 mmol) and TEA (1.788 mL; 12.8 mmol) were added and it was stirred at rt for 10 min. 4-Bromoaniline (0.738 g; 4.29 mmol) was added, the mixture was stirred at rt over night.

Then 5% aq. NaHCO$_3$ solution was added, the precipitate was collected by filtration, washed with water and dried i. vac.

Yield: 1.5 g (87%); MS [M+H]$^+$=401/3 (Br-isotope pattern); TLC: (silica gel; DCM/EtOH 98/2) R$_f$=0.7

(c) 5-Amino-N-(4-bromo-phenyl)-2-(2,2-difluoro-ethoxy)-benzamide

Prepared analogously to Example 4b from N-(4-bromo-phenyl)-2-(2,2-difluoro-ethoxy)-5-nitro-benzamide and Ra-Ni/H$_2$ in THF.

MS: (2M+H)$^+$=741; TLC (silica gel; DCM/EtOH 98/2) R$_f$=0.2

(d) 5-Fluoro-2-trifluoromethyl-benzoic acid ethyl ester

A mixture of 5-fluoro-2-trifluoromethyl-benzoic acid (3.0 g; 10 mmol) and 25 mL HCl in EtOH was heated at reflux over night. The mixture was cooled to rt and evaporated i.vac.

Yield: 2.47 g (73%); MS [M+H]$^+$=236; TLC (RPB; MeOH: 5% NaCl-Lsg 6/4) R$_f$=0.16

(e) 5-Cyano-2-trifluoromethyl-benzoic acid ethyl ester

KCN (1.09 g; 16.7 mmol) was added to a mixture of 5-fluoro-2-trifluoromethyl-benzoic acid ethyl ester (2.47 g; 10.46 mmol) and 20 mL DMSO. The mixture was warmed to 60° C.-100° C. and stirred for 1 week. The mixture was diluted with water and extracted with EtOAc (2×), the combined organic phases were washed with brine, dried over Na$_2$SO$_4$ and evaporated i. vac. The residue was purified by prep. HPLC.

Yield: 530 mg (21%); MS: [M+H]$^+$=243; TLC (silica gel; DCM/EtOH 9:1) R$_f$=0.9

(f) 5-Aminomethyl-2-trifluoromethyl-benzoic acid ethyl ester

A mixture of 5-cyano-2-trifluoromethyl-benzoic acid ethyl ester (250 mg; 1.03 mmol) and 100 mg Ra-Ni in 20 mL NH$_3$ in MeOH was stirred for 17 h under an atmosphere of hydrogen (3 bar). After filtration and concentration i.vac. the subtitle compound was obtained. Yield: 250 mg (98%); MS: [m+H]$^+$=248; TLC (silica gel; DCM/EtOH 9/1) R$_f$=0.28.

(g) 5-(tert-Butylcarbonylamino)methyl-2-trifluoromethyl-benzoic acid ethyl ester Piv-Cl (0.137 mL; 1.11 mmol) was added to a mixture of 5-aminomethyl-2-trifluoromethyl-benzoic acid ethyl ester (250 mg; 1.01 mmol), 10 mL THF and TEA (10 mL; 71.8 mmol) and it was stirred over night. After concentration i.vac. the residue was diluted with water and extracted with EtOAc, the organic layer was washed with brine, dried with Na$_2$SO$_4$, and concentrated i. vac.

Yield: 310 mg (93%); MS [m+H]$^+$=332; TLC (silica gel; DCM/EtOH 9/1) R$_f$=0.72

(h) 5-(tert-Butylcarbonylamino)methyl-2-trifluoromethyl-benzoic acid

A mixture of 5-(tert-butylcarbonylamino)methyl-2-trifluoromethyl-benzoic acid ethyl ester (310 mg; 0.94 mmol), 5 mL EtOH and 1 M aq. NaOH solution (1.87 mL, 1.87 mmol) was stirred overnight. Additional 4 M NaOH (0.5 mL, 2 mmol) was added and it was stirred for 2 h. The mixture was concentrated i.vac. and the residue was diluted with water, acidified with 4 M aq. HCl solution, stirred for 2 h then filtered and washed with water. The resulting precipitate is filtered and dried (55° C.).

Yield: 210 mg (74%); MS: [m+H]$^+$=304; TLC (RPB; MeOH/5% NaCl 6/4) R$_f$: 0.49

(i) N-[4-(2,2-Difluoroethyl)oxy-3-(4-bromophenyl) aminocarbonyl-phenyl]-2-trifluormethyl 5-(tert-butylcarbonylamino)methyl-benzamide A mixture of 5-(tert-butylcarbonylamino)methyl-2-trifluoromethyl-benzoic acid (50 mg; 0.13 mmol) HATU (53.8 mg, 0.14 mmol) and TEA (0.066 mL 0.47 mmol) in 2 mL THF was stirred for 15 min at rt. 5-Amino-N-(4-bromo-phenyl)-2-(2,2-difluoro-ethoxy)-benzamide (40.8 mg; 0.13 mmol) was added and it was stirred over night. The solvent was evaporated and the residue was purified by prep HPLC.

Yield: 60 mg (68%)

C$_{29}$H$_{27}$BrF$_5$N$_3$O$_4$ (656.44); MS: [m+H]$^+$=656 (Br-isotope pattern);

TLC (silicagel, DCM/EtOH 9/1) R$_f$=0.68.

Example 43

N-[4-(2,2-Difluoroethyl)oxy-3-(4-bromophenyl) aminocarbonyl-phenyl]-6-fluor-2-chlor-3-(trifluormethylcarbonylamino)methyl-benzamide

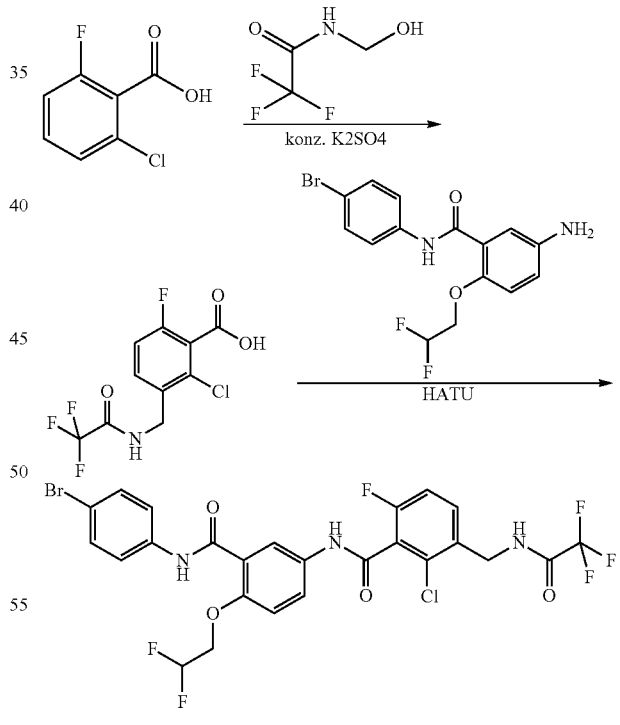

(a) 2-Chlor-6-flour-3-(trifluormethylcarbonylamino) methyl-benzoic acid

N-(Hydroxymethyl)trifluoracetamide (0.82 g; 5.73 mmol) was added to a mixture of 10 mL conc. H$_2$SO$_4$ and 2-chlor-6-fluorobenzoic acid (1 g; 5.73 mmol) under ice bath cooling and stirred at rt overnight. The mixture was poured into ice, DCM was added, the resulting precipitate was filtered, washed with DCM and water and dried. The residue was purified by HPLC.

Yield: 400 mg (23%; Purity: 95%) MS: [M−H]⁻=298

(b) N-[4-(2,2-Difluoroethyl)oxy-3-(4-bromophenyl)aminocarbonyl-phenyl]-6-fluor-2-chlor-3-(trifluormethylcarbonylamino)methyl-benzamide A mixture of 2-chlor-6-flour-3-(trifluormethylcarbonylamino)methyl-benzoic acid (40.3 mg; 0.13 mmol), HATU (53.8 mg; 0.14 mmol) and TEA (0.066 mL, 0.47 mmol) in THF (2 mL) was stirred for 15 min at rt. 5-Amino-N-(4-bromo-phenyl)-2-(2,2-difluoro-ethoxy)-benzamide (50 mg; 0.13 mmol) was added and it was stirred for 2 days. The solvent was removed and the residue was purified by prep. HPLC.

Yield: 55 mg (63%) $C_{25}H_{17}BrClF_6$ (652.77);
MS: [M+H]⁺: 652 (Br/Cl-isotope pattern); TLC (silica gel; DCM/EtOH 9/1) $R_f$: 0.63;

Example 44

N-[4-(2,2-Difluoroethyl)oxy-3-(4-bromophenyl)aminocarbonyl-phenyl]-6-fluor-2-chlor-3-(tert-butylcarbonylamino)methyl-benzamide

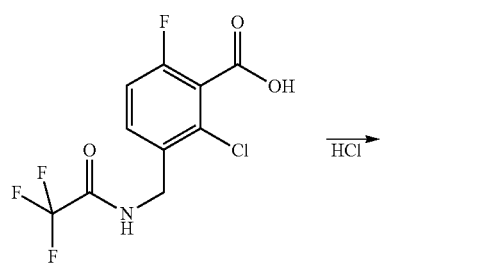

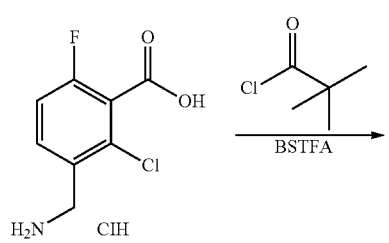

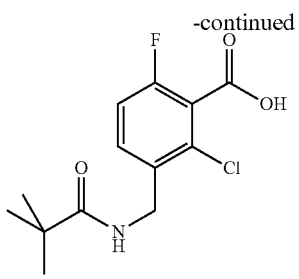

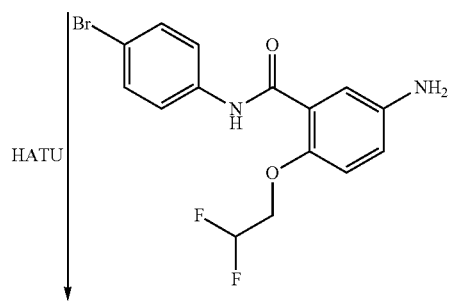

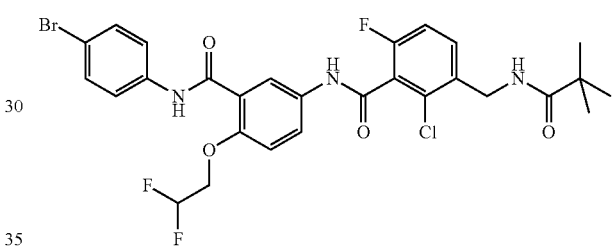

(a) 3-Aminomethyl-2-chlor-6-fluorobenzoic acid

A mixture of 2-chlor-6-flour-3-(trifluormethylcarbonylamino)methyl-benzoic acid (350 mg; 1.17 mmol) in 10 mL 6M aq. HCl solution was stirred at rt over 2 days. The mixture was warmed to 80° C. and stirred over night. The solvent was removed to furnish the subtitle compound.
Yield: 270 mg (96%); MS: [m+H]⁺=204; TLC (RPB; MeOH/5% NaCl-Lsg 6/4) $R_f$: 0.88

(b) 2-Chloro-3-(tert-butylcarbonylamino-methyl)-6-fluoro-benzoic acid

BSTFA (0.18 mL; 1.15 mmol) was added to a mixture of 3-aminomethyl-2-chlor-6-fluorobenzoic acid (270 mg; 1.12 mmol, HCl-salt) in 8 mL THF, it was stirred at reflux for 20 min, and then cooled in an ice bath. TEA (0.783 mL; 5.62 mmol) and Piv-Cl (142 µL; 1.16 mmol) in 2 mL THF were added and it was stirred overnight. The solvent was removed i.vac. and the residue was diluted with water and 10 mL HOAc, extracted (3x) with DCM, dried over $Na_2SO_4$ and concentrated i vac.
Yield: 330 mg (102%); MS: [m+H]⁺=288

(c) N-[4-(2,2-Difluoroethyl)oxy-3-(4-bromophenyl)aminocarbonyl-phenyl]-6-fluor-2-chlor-3-(tert-butylcarbonylamino)methyl-benzamide Prepared analogously to 43b from 2-chloro-3-(tert-butylcarbonylamino-methyl)-6-fluoro-benzoic acid and 5-amino-N-(4-bromo-phenyl)-2-(2,2-difluoro-ethoxy)-benzamide with HATU and TEA in THF.
Yield: 48 mg (56%); $C_{28}H_{26}BrClF_3N_3O_4$ (640.88)
MS: [M+H]⁺=640 (Br/Cl isotope pattern); TLC (silica gel DCM/EtOH 9/1) $R_f$: 0.68

Example 45
N-[4-(2,2-Difluoroethyl)oxy-3-(4-bromophenyl)aminocarbonyl-phenyl]-6-chlor-2-fluor-3-(tert-butyl-carbonylamino)methyl-benzamide
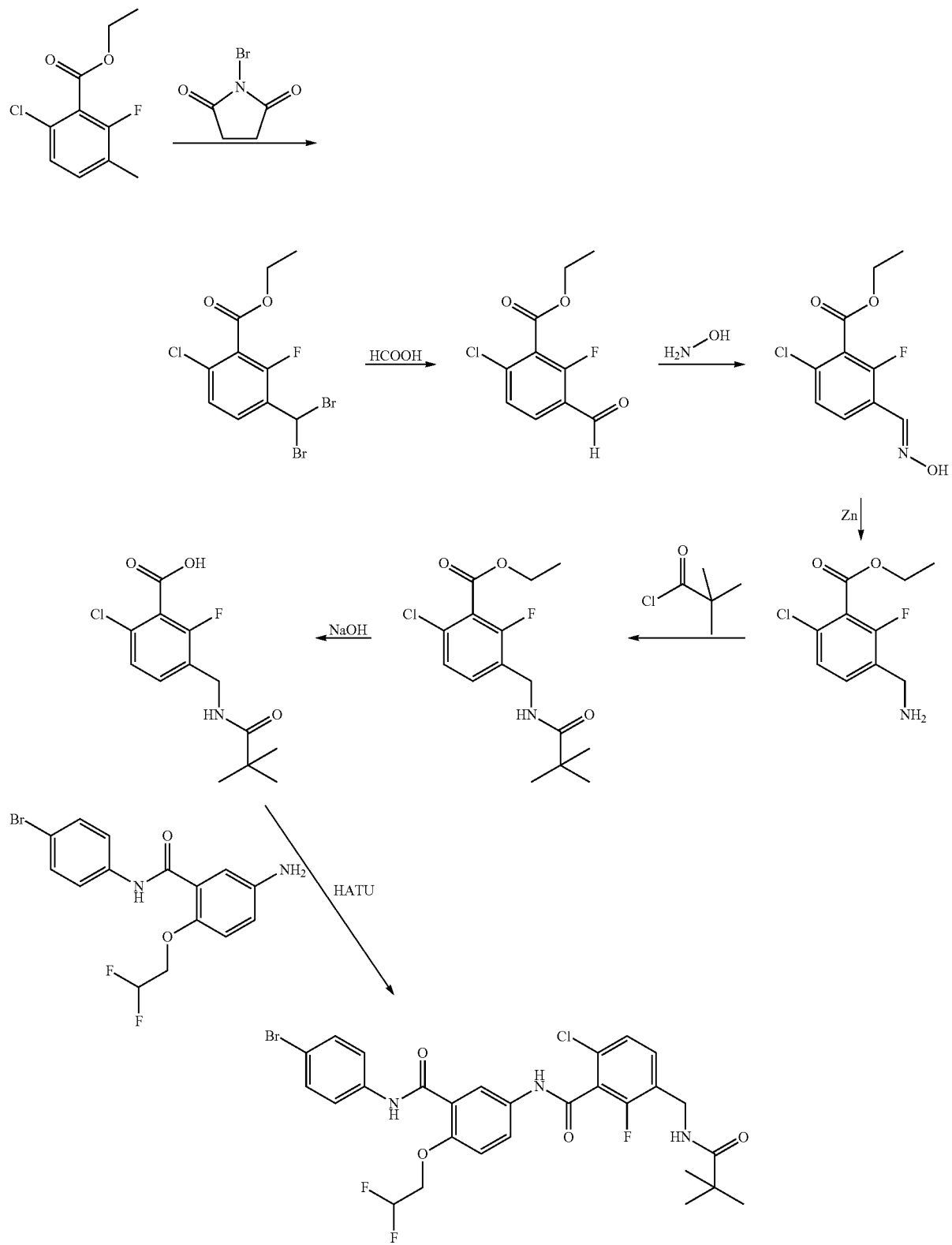

(a) (a) 6-Chloro-3-dibromomethyl-2-fluoro-benzoic acid ethyl ester

A mixture of 6-chloro-2-fluoro-3-methyl-benzoic acid ethylester (5 g; 23.1 mmol), 2,2-azobis(isobutyronitrile) (84 mg; 0.51 mmol), N-bromosuccinimide (9.04 g; 50.8 mmol) in 55 mL CCl$_4$ was stirred under irradiation (300W UV-lamp) for 1.5 h at reflux. The precipitate was filtered and concentrated i. vac. to furnish the subtitle compound.

Yield: quantitative; MS: [M+H]$^+$=373; HPLC: R$_t$=2.37 min (Method MC-6)

(b) 6-Chloro-2-fluoro-3-formyl-benzoic acid ethyl ester

A mixture of 6-chloro-3-dibromomethyl-2-fluoro-benzoic acid ethyl ester (9 g; 24 mmol) and HCOOH (60 mL) was stirred at reflux overnight. The solvent was evaporated, and the residue was diluted with satd. NaHCO$_3$, extracted with EtOAc and dried with Na$_2$SO$_4$.

Yield: 4.04 g (73%); MS: [m+H]$^+$=231; HPLC: R$_t$=1.95 min (Method MC-6)

(c) 6-Chloro-2-fluoro-3-(hydroxyimino-methyl)-benzoic acid ethyl ester

A mixture of 6-chloro-2-fluoro-3-formyl-benzoic acid ethyl ester (4.04 g; 17.52 mmol), hydroxylamine (50% aq. solution, 4.29 mL; 70 mmol) in MeOH (60 mL) was stirred at 55° C. for 1.5 h. The mixture was concentrated i. vac., diluted with EtOAc, washed with brine, dried over Na$_2$SO$_4$ and concentrated i.vac. to furnish the subtitle compound.

Yield: 4.21 g (98%); HPLC: R$_t$=1.9 min (Method MC-6); MS: [m+H]$^+$=246

(d) 3-Aminomethyl-6-chloro-2-fluoro-benzoic acid ethyl ester

A mixture of 6-chloro-2-fluoro-3-(hydroxyimino-methyl)-benzoic acid ethyl ester (4.21 g; 17.14 mmol), MeOH (200 mL), 10 M HCl in EtOH (51.42 mL; 514.2 mmol) and Zn (4.483 g; 68.56 mmol) was refluxed for 2.5 h. Additional Zn (2.24 g; 34.25 mmol) was added, and it was refluxed for 1 h and stirred at rt overnight. The mixture was concentrated i.vac., diluted with sat. NaHCO$_3$-solution and EtOAc. The mixture was filtered, the organic layer was separated, dried with Na$_2$SO$_4$ and concentrated i. vac.

Yield: quantitative; MS: [m+H]$^+$=232; HPLC: R$_t$=1.23 min (Method MC-6)

(e) 2-Fluoro-3-(tert-butylcarbonylamino-methyl)-6-chloro-benzoic acid ethyl ester A mixture of 3-aminomethyl-6-chloro-2-fluoro-benzoic acid ethyl ester (70 mg; 0.3 mmol), TEA (0.105 mL; 0.76 mmol) in THF (3 mL) was added dropwise to a mixture of Piv-Cl (38.3 µL; 0.31 mmol) in THF (1 mL) and it was stirred at rt for 1.5 h. The mixture was concentrated i. vac. diluted with half saturated aq. NaCl and extracted with EtOAc. The organic phase was dried with Na$_2$SO$_4$ and concentrated i. vac.

Yield: 70 mg (73%); MS: [m+H]$^+$=316 (Cl$_2$ isotope pattern); HPLC: R$_t$=2.02 min (Method MC-6)

(f) 2-Fluoro-3-(tert-butylcarbonylamino-methyl)-6-chloro-benzoic acid

A mixture of 2-fluoro-3-(tert-butylcarbonylamino-methyl)-6-chloro-benzoic acid ethyl ester (70 mg; 0.22 mmol) in 1 M aq. NaOH solution (0.44 mL; 0.44 mmol) and EtOH (2 mL) was stirred at rt overnight. Additional 1 M aq. NaOH solution (0.88 mL; 0.88 mmol) was added and it was stirred at 60° C. for 2 h. The mixture was concentrated i. vac., diluted with water, acidified with 4 M aq. HCl solution, extracted with DCM, dried over Na$_2$SO$_4$ and evaporated i. vac.

Yield: quantitative; MS: [M+H]$^+$=288 (Cl$_2$ isotope pattern); HPLC: R$_t$=1.44 min (Method MC-6)

(q) N-[4-(2,2-Difluoroethyl)oxy-3-(4-bromophenyl)aminocarbonyl-phenyl]-6-chlor-2-fluor-3-(tert-butylcarbonylamino)methyl-benzamide Prepared analogously to 43b from 2-fluoro-3-(tert-butylcarbonylamino-methyl)-6-chloro benzoic acid (41 mg; 0.13 mmol), 5-amino-N-(4-bromo-phenyl)-2-(2,2-difluoro-ethoxy)benzamide (50 mg; 0.13 mmol), HATU (54 mg; 0.14 mmol), TEA (0.066 mL; 0.47 mmol) in THF (2 mL).

Yield: 4.8 mg (6%) C$_{28}$H$_{26}$BrClF$_3$N$_3$O$_4$ (640.88)

MS: [M+H]$^+$=640 (Br/Cl isotope pattern); HPLC: R$_t$=5.19 min (Method MC-7)

Example 46

N-[4-(2,2-Difluoroethyl)oxy-3-(4-fluoro-3-chloro-phenyl)aminocarbonyl-phenyl]-6-chloro-2-fluoro-3-(tert-butylcarbonylamino)methyl-benzamide

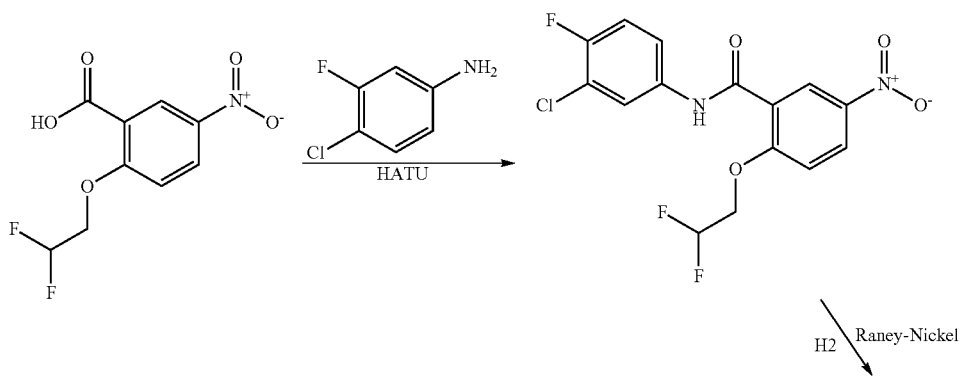

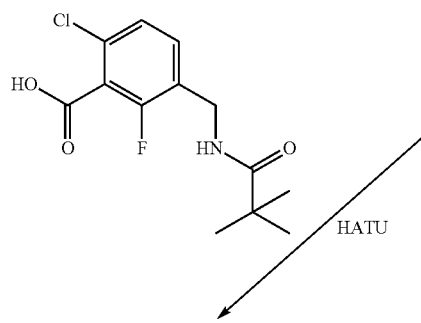

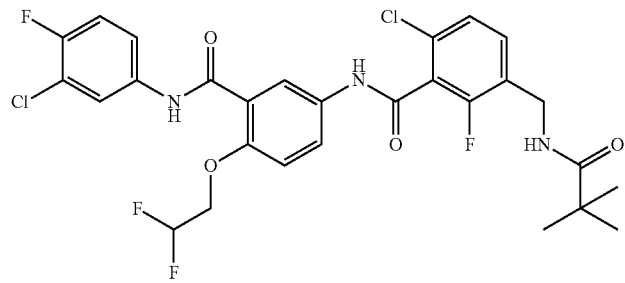

(a) N-(3-Chloro-4-fluoro-phenyl)-2-(2,2-difluoro-ethoxy)-5-nitro-benzamide

Prepared analogously to 42b from 2-(2,2-difluoro-ethoxy)-5-nitrobenzoic acid (0.8 g; 3.24 mmol), 3-chloro-4-fluoroaniline (471 mg; 3.24 mmol), HATU (1.292 g; 3.4 mmol), TEA (1.35 mL; 9.71 mmol) in THF (20 mL).

Yield: quantitative; MS: [M+H]$^+$=375 (Cl isotope pattern); HPLC: $R_t$=2.27 min (Method MC-6)

(b) N-(3-Chloro-4-fluoro-phenyl)-2-(2,2-difluoro-ethoxy)-5-amino-benzamide

Prepared analogously to 4b from N-(3-chloro-4-fluoro-phenyl)-2-(2,2-difluoro-ethoxy)-5-nitro-benzamide (0.67 g; 1.79 mmol), Ra-Ni/H$_2$ (70 mg; 3 bar) in THF (10 mL).

Yield: 590 mg (96%); MS: [m+H]$^+$=345 (Cl isotope pattern); HPLC: $R_t$=1.8 min (Method MC-6)

(c) N-[4-(2,2-Difluoroethyl)oxy-3-(4-fluoro-3-chloro-phenyl)aminocarbonyl-phenyl]-6-chloro-2-fluoro-3-(tert-butylcarbonylamino)methyl-benzamide Prepared analogously to 43b from 2-fluoro-3-(tert-butyl-carbonylamino-methyl)-6-chloro-benzoic acid (74 mg; 0.26 mmol) and N-(3-chloro-4-fluoro-phenyl)-2-(2,2-difluoro-ethoxy)-5-amino-benzamide (88 mg; 0.26 mmol) with HATU (195 mg; 0.51 mmol) and DIPEA (0.202 mL; 0.1.16 mmol) in THF (1 mL)

Yield: 21 mg (13%). C$_{28}$H$_{25}$Cl$_4$F$_4$N$_3$O$_4$ (614.41)

MS: [m+H]$^+$=614; HPLC: $R_t$=2.32 min (Method MC-6).

Example 47

N-[4-(2,2-Difluoroethyl)oxy-3-(4-bromophenyl)aminocarbonyl-phenyl]-2,6-dichloro-3-(2,2,2-trifluoro-1,1-dimethyl-ethyl)carbonylaminomethyl-benzamide

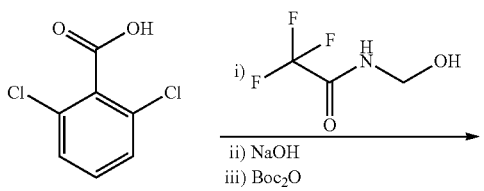

-continued

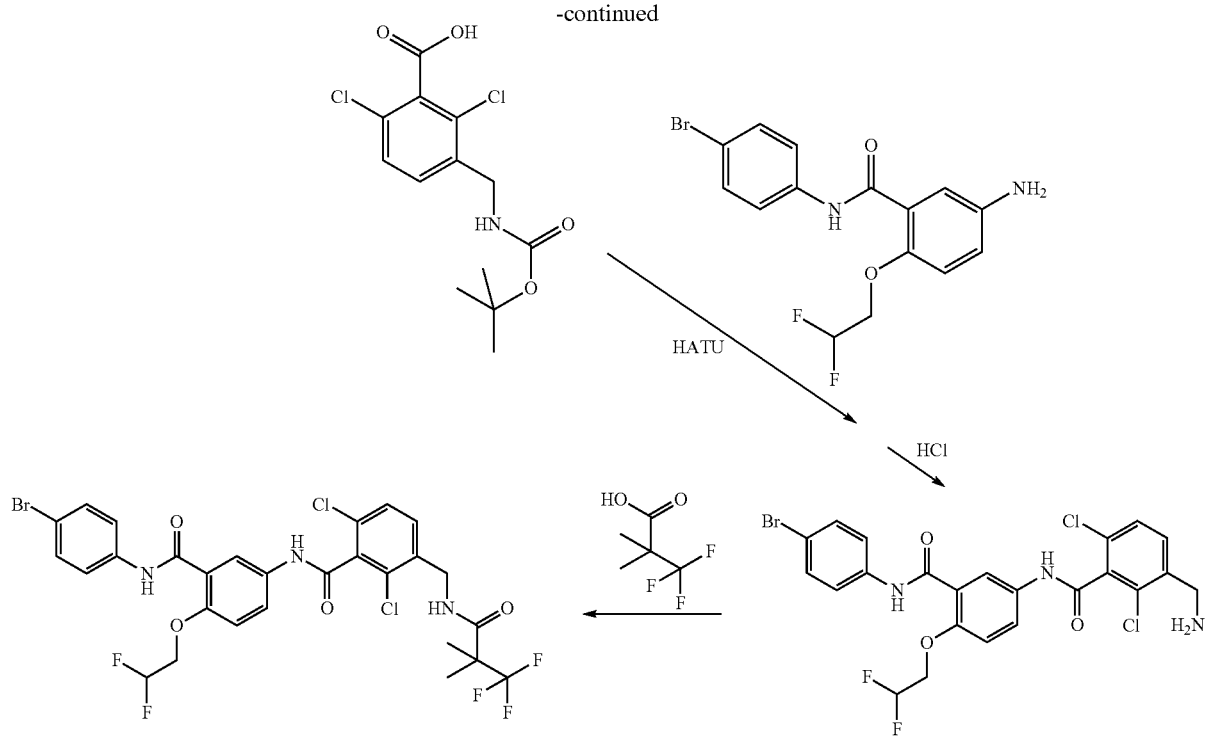

(a) 3-(tert-Butoxycarbonylamino-methyl)-2,6-dichloro-benzoic acid

Step i): A mixture of 2,6-dichlorobenzoic acid (4 g; 20.94 mmol), conc. $H_2SO_4$ (50 mL) and N-(hydroxymethyl)trifluoroacetamide (2.996 g; 20.94 mmol) was stirred at rt overnight. The mixture was diluted with 500 mL crushed ice and 200 mL $H_2O$, the precipitate was filtered and dried to give crude 3-(trifluoromethylcarbonylamino-methyl)-2,6-dichloro-benzoic acid.

Step ii): A mixture of the crude 3-(trifluoromethylcarbonylamino-methyl)-2,6-dichloro-benzoic acid prepared above, 200 mL MeOH, 100 mL $H_2O$ and 40 mL 4 M aq. NaOH solution was stirred at rt for 4 h. Then it was acidified with 25 mL 4 M aq. HCl solution, concentrated i. vac. and the residue was diluted with 50 mL MeOH. The precipitate was filtered off and dried to give crude 3-aminomethyl-2,6-dichloro-benzoic acid.

Step iii): A mixture of crude 3-aminomethyl-2,6-dichloro-benzoic acid, 100 mL dioxane, 10 mL $H_2O$, 10 mL TEA and di-tert-butyldicarbonate (4.57 g; 20.9 mmol) was stirred for 2 h at rt. The solvent was evaporated and the residue was purified by prep. HPLC (Eluents: $H_2O+1\%\ NH_4OH/MeOH$)

Yield: 1.7 g (25%).

MS: $[M-BOC+H]^+=220$ ($Cl_2$ isotope pattern); HPLC: $R_t=2.15$ min (Method CC-6).

(b) N-[4-(2,2-Difluoroethyl)oxy-3-(4-bromophenyl) aminocarbonyl-phenyl]-2,6-dichloro-3-(aminomethyl)-benzamide A mixture of 3-(tert-butoxycarbonylamino-methyl)-2,6-dichloro-benzoic acid (250 mg; 0.78 mmol), HATU (326 mg; 0.86 mmol), DIPEA (500 µL; 2.91 mmol), 5-amino-N-(4-bromophenyl)-2-(2,2-difluoro-ethoxy)-benzamide (290 mg; 0.78 mmol) in 15 mL DMF was stirred at rt overnight. The solvent was removed, 10 mL dioxane and 15 mL 4 M HCl in dioxane were added and it was stirred for 30 min at rt. The solvent was removed, 10 mL DMF and 5 mL $H_2O$ were added and the crude mixture was purified by prep. HPLC.

Yield: 280 mg (63%);

MS: $[m+H]^+=574$ (Br; $Cl_2$ isotope pattern); HPLC: $R_t$: 1.91 min (Method CC-4)

(c) N-[4-(2,2-Difluoroethyl)oxy-3-(4-bromophenyl) aminocarbonyl-phenyl]-2,6-dichloro-3-(2,2,2-trifluoro-1,1-dimethyl-ethyl)carbonylaminomethyl-benzamide A mixture of 3,3,3-trifluoro-2,2-dimethyl-propionic acid (91 mg; 0.59 mmol); TEA (343 µl; 2.44 mmol), TBTU (172 mg; 0.54 mmol) in DMF was stirred for 20 min at rt. N-[4-(2,2-difluoroethyl)oxy-3-(4-bromophenyl)aminocarbonyl-phenyl]-2,6-dichloro-3-(methylamino)benzamide (280 mg; 0.49 mmol) was added and it was stirred 30 min at rt. The mixture was concentrated and directly purified by prep. HPLC (Eluents: $H_2O+1\%\ NH_4OH/MeOH$).

Yield: 15 mg (4%); $C_{28}H_{23}BrCl_2F_5N_3O_4$ (711.3); MS: $[M+H]^+=710$ (Br, $Cl_2$ isotope pattern); HPLC: $R_t$: 2.34 min (Method CC-4)

Example 48
N-[4-(2,2-Difluoroethyl)oxy-3-[trans-(4-trifluoromethylcyclohexyl)amino]carbonylphenyl]-2,6-dichloro-3-(tert-butylcarbonylamino)methyl-benzamide
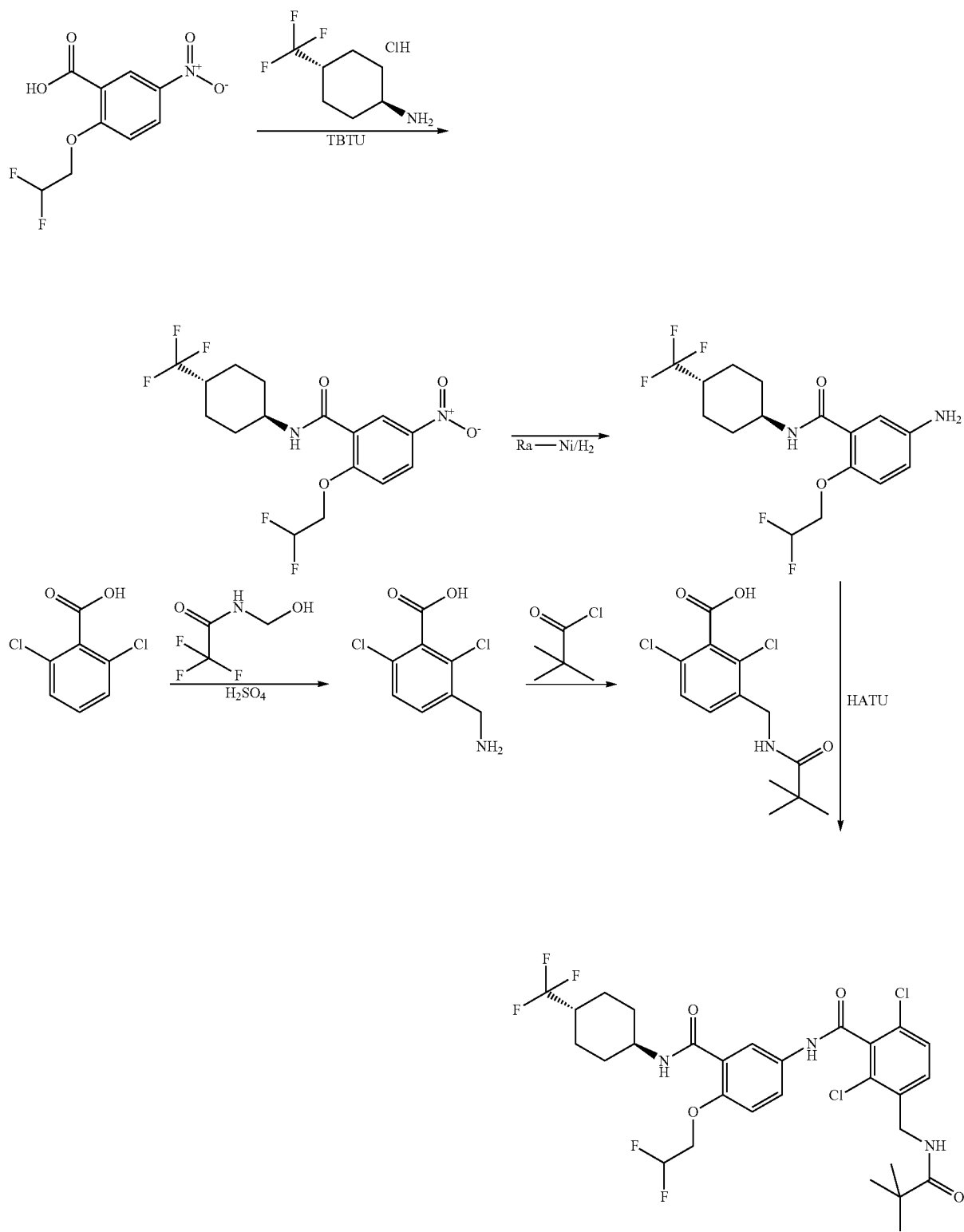

(a) 2-(2,2-Difluoro-ethoxy)-5-nitro-N-trans-(4-trifluoromethyl-cyclohexyl)-benzamide A mixture of 2-(2,2-difluoro-ethoxy)-5-nitro-benzoic acid (1.214 g; 4.91 mmol), TBTU (1,656 g; 5.16 mmol), TEA (2.389 mL; 17.1 mmol) in THF (50 mL) was stirred for 15 min at rt. Trans-4-Trifluoromethylcyclohexylamine (1.00 g; 4.91 mmol) was added and it was stirred at RT over 3 days. The mixture was extracted with EtOAc, and the organic phase was washed with saturated aq. $NaHCO_3$ and dried with $Na_2SO_4$ and concentrated i. vac. The crude was purified by prep. HPLC to obtain the subtitle compound.

Yield: 1.5 g (77%); MS: $[M+H]^+$=397; HPLC: $R_t$=2.19 min (Method MC-6)

(b) 5-Amino-2-(2,2-difluoro-ethoxy)-N-trans-(4-trifluoromethyl-cyclohexyl)-benzamide Prepared analogously to 4b from 2-(2,2-difluoro-ethoxy)-5-nitro-N-trans-(4-trifluoromethylcyclohexyl)-benzamide (0.8 g; 2.02 mmol), 10% Pd/C (80 mg), $H_2$ (3 bar) in MeOH (30 mL).

Yield: 720 mg (97%) MS: $[m+H]^+$=367; HPLC: $R_t$=2.31 min (Method MC-2)

(c) 3-Aminomethyl-2,6-dichloro-benzoic acid n-(Hydroxymethyl)trifluoroacetamide (11.23 g; 78.5 mmol) was added to a mixture of 2,6-dichlorobenzoic acid (15 g; 78.5 mmol) in conc. $H_2SO_4$ (180 mL) and it was stirred at rt overnight. The mixture was poured into 1.8 L crushed ice/$H_2O$, the precipitate was filtered off and dried. The crude was diluted with 150 mL MeOH and 80 mL 2 M aq. NaOH solution and stirred at rt for 2 h. The solvent was removed, the residue was diluted with $H_2O$ and extracted 2× with DCM. The aq. layer was acidified with 70 mL 4 M aq. HCl solution, washed with DCM and concentrated. The residue was diluted with 400 mL EtOH, filtered and concentrated i. vac. to obtain the subtitle compound.

Yield: 13.82 g (69%); MS: $[m+H]^+$=220; HPLC: $R_t$=1.77 min (Method CC-4)

(d) 2,6-Dichloro-3-(tert-butylcarbonylamino-methyl)-benzoic acid

Piv-Cl (2.9 mL; 23.55 mmol) was added to a mixture of 3-aminomethyl-2,6-dichloro-benzoic acid hydrochloride (5 g; 19.5 mmol) in 100 mL MeCN and pyridine (5 mL; 61.95 mmol) and it was stirred at rt over 3 days. The mixture was concentrated, diluted with $H_2O$ and acidified with 4 M aq. HCl solution. The precipitate was filtered off, washed with $H_2O$ and dried.

Yield: 5.64 g (95%); MS: $(M+H)^+$=304; HPLC: $R_t$=1.79 min (Method CC-4)

(e) N-[4-(2,2-Difluoroethyl)oxy-3-[trans-(4-trifluoromethyl-cyclohexyl)amino]carbonyl-phenyl]-2,6-dichloro-3-(tert-butylcarbonylamino)methyl-benzamide Prepared analogously to 43b from 2,6-dichloro-3-(tert-butylcarbonylamino-methyl)-benzoic acid (67 mg; 0.22 mmol) and 5-amino-2-(2,2-difluoro-ethoxy)-N-trans-(4-trifluoromethylcyclohexyl)-benzamide (121 mg; 0.33 mmol) with HATU (168 mg; 0.44 mmol) and DIPEA (0.173 mL; 0.99 mmol) in THF (1 mL).

Yield: 59 mg (41%). $C_{29}H_{32}Cl_2F_5N_3O_4$ (652.48)

MS: $[m+H]^+$=652 ($Cl_2$ isotope pattern); HPLC: $R_t$=2.93 min (Method MC-3).

Example 49

N-[4-Fluoro-3-(4-bromophenyl)aminocarbonyl-phenyl]-2,6-difluoro-3-(tert-butylcarbonylamino)methyl-benzamide

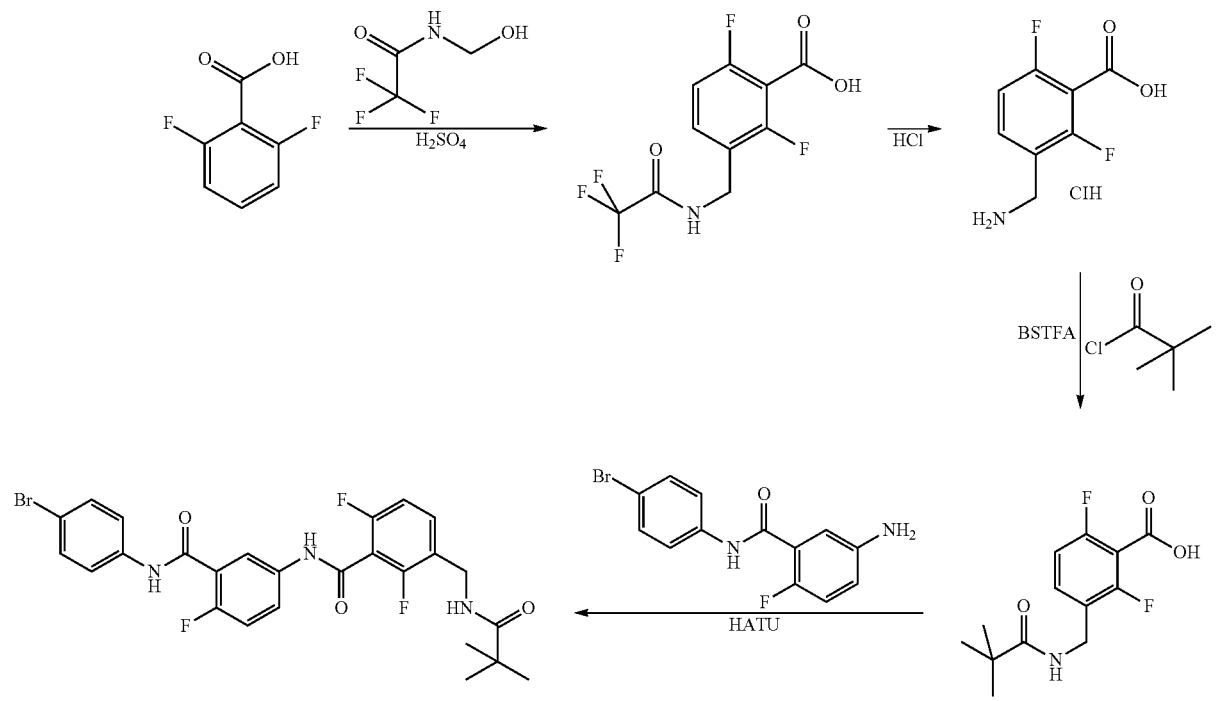

(a) 2,6-Difluoro-3-(trifluormethylcarbonylamino) methyl-benzoic acid

Prepared analogously to 43a with 2,6-difluorobenzoic acid and n-(hydroxymethyl)trifluoroacetamide in conc. $H_2SO_4$.
Yield: 1.24 g (75%); MS: [M–H]–=282; HPLC: $R_t$=1.30 min (Method MC-6)

(b) 3-Aminomethyl-2,6-difluorobenzoic acid

Prepared analogously to 44a with 2,6-difluoro-3-(trifluormethylcarbonylamino)methyl-benzoic acid in 6 M aq. HCl.
Yield: 960 mg (98%); MS: $[m+H]^+$=188; HPLC: $R_t$=0.149 min (Method MC-6)

(c) 2,6-Difluoro-3-(tert-butylcarbonylamino-methyl)-benzoic acid

Prepared analogously to 44b with 3-aminomethyl-2,6-difluorobenzoic acid, Piv-Cl, BSTFA and TEA in THF. Yield: 1.2 g (77%); MS: $[m+H]^+$=272; HPLC: $R_t$=1.38 min (Method MC-6)

(d) N-[4-Fluoro-3-(4-bromophenyl)aminocarbonyl-phenyl]-2,6-difluoro-3-(tert-butylcarbonylamino) methyl-benzamide Prepared analogously to 44c with 2,6-difluoro-3-tert-butylcarbonylamino-methyl)-benzoic acid (60 mg; 0.22 mmol) and N-(4-bromophenyl)-2-fluoro-5-amino-benzoic acid amide (103 mg; 0.33 mmol) with HATU (168 mg; 0.44 mmol) and DIPEA (0.173 mL; 1 mmol) in THF (1 mL).
Yield: 80 mg (64%) $C_{26}H_{23}BrF_3N_3O_3$ (562.38)
MS: $[M+H]^+$=562; HPLC: $R_t$=2.23 min (Method MC-6)

Example 51/52

N-[4-(2,2-Difluoroethyl)oxy-3-(4-bromophenyl) aminocarbonyl-phenyl]-6-chloro-2-methyl-3-(tert-butylcarbonylamino)methyl-benzamide (Exp. 51)
N-[4-(2,2-Difluoroethyl)oxy-3-(4-bromophenyl) aminocarbonyl-phenyl]-2-chloro-6-methyl-3-(tert-butylcarbonylamino)methyl-benzamide (Exp. 52)

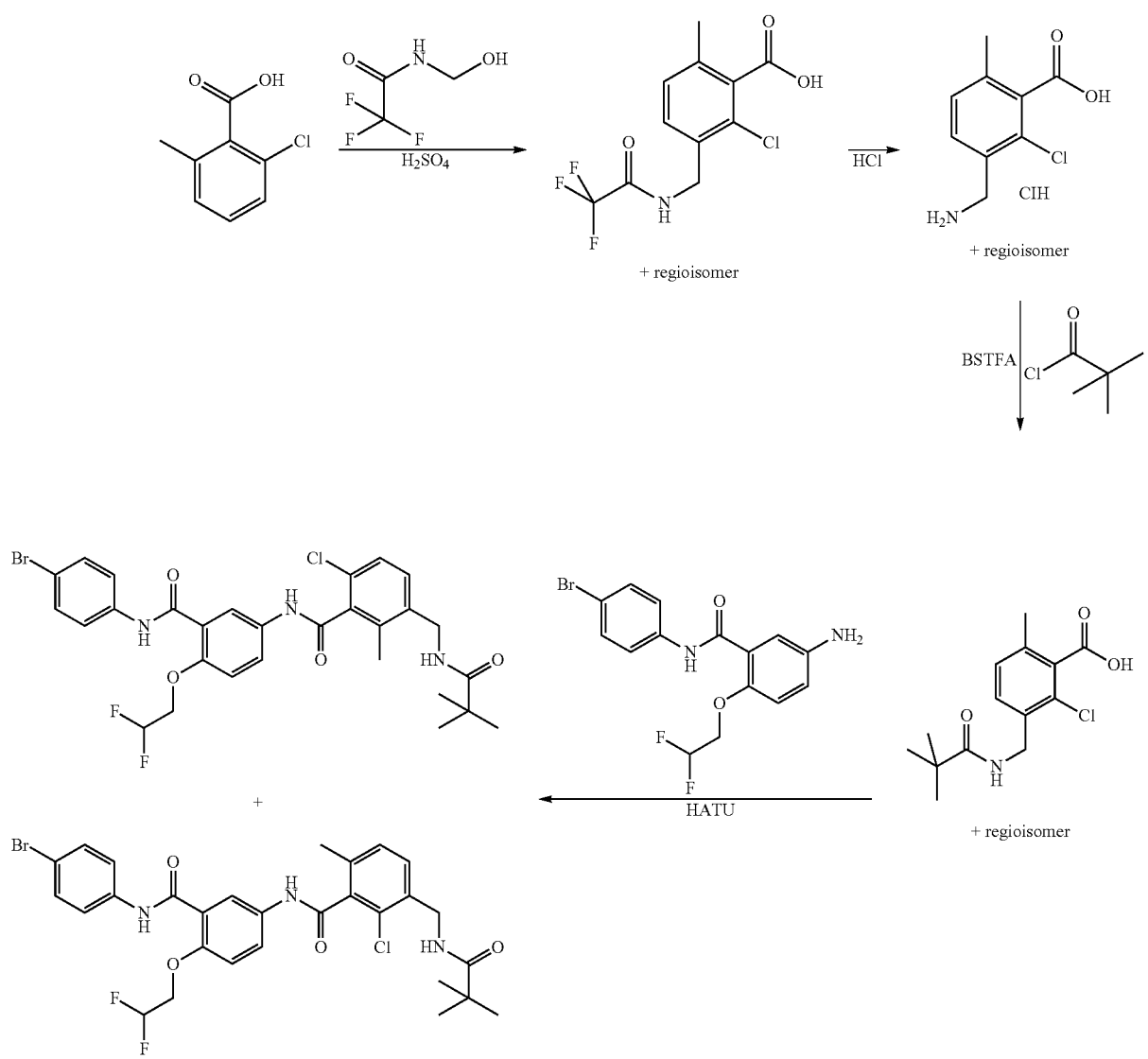

(a) 2-Chloro-6-methyl-difluoro-3-(trifluormethylcarbonylamino)methyl-benzoic acid/2-methyl-6-chloro-difluoro-3-(trifluormethylcarbonylamino)methyl-benzoic acid Prepared analogously to 43a with 2-chloro-6-methylbenzoic acid (1 g; 5.86 mmol) and N(hydroxymethyl)trifluoroacetamide (0.839 g; 5.86 mmol) in conc. $H_2SO_4$ (10 mL).

Yield: 330 mg; (19%; mixture of regioisomers); MS: $[M-H]^-=294$; HPLC: $R_t=4.55$ min (Method MC-8)

(b) 3-Aminomethyl-2-chloro-6-methylbenzoic acid/3-Aminomethyl-2-methyl-6-chlorobenzoic acid Prepared analogously to 44a with 2-chloro-6-methyl-difluoro-3-(trifluormethylcarbonylamino)methyl-benzoic acid/2-methyl-6-chloro-difluoro-3-(trifluormethylcarbonylamino)methyl-benzoic acid (5.62 g 19 mmol) in 6 M aq. HCl solution. Yield: 4.37 g; (97%; mixture of regioisomers); MS: $[M-H]^-=198$; HPLC: $R_t=0.189$ min (Method MC-6)

(c) 2-Chloro-6-methyl-3-(tert-butylcarbonylamino-methyl)-benzoic acid/2-methyl-6-chloro-3-(tert-butylcarbonylamino-methyl)-benzoic acid Prepared analogously to 44b with 3-aminomethyl-2-chloro-6-methylbenzoic acid/3-aminomethyl-2-methyl-6-chlorobenzoic acid (4.37 g; 18.5 mmol), Piv-Cl (2.346 mL; 19 mmol), BSTFA (2.956 mL; 18.8 mmol) and TEA (12.88 mL; 95.55 mmol) in 150 mL THF.

Yield: 4.73 g; (90%; mixture of regioisomers); MS: $[m+H]^+=284$; HPLC: $R_t=1.53$ min (Method MC-6)

(d) N-[4-(2,2-Difluoroethyl)oxy-3-(4-bromophenyl)aminocarbonyl-phenyl]-6-chloro-2-methyl-3-(tert-butylcarbonylamino)methyl-benzamide (Exp. 51) N-[4-(2,2-Difluoroethyl)oxy-3-(4-bromophenyl)aminocarbonyl-phenyl]-2-chloro-6-methyl-3-(tert-butylcarbonylamino)methyl-benzamide (Exp. 52)

A mixture of 2-chloro-6-methyl-3-(tert-butylcarbonylamino-methyl)-benzoic acid/2-methyl-6-chloro-3-(tert-butylcarbonylamino-methyl)-benzoic acid (115 mg; 0.4 mmol); HATU (161 mg; 0.42 mmol); TEA (0.197 mL; 1.41 mmol) in THF was stirred at rt for 15 min. 5-Amino-N-(4-bromo-phenyl)-2-(2,2-difluoro-ethoxy)-benzamide was added and it was stirred for 2 days at rt and 9 d at reflux. The crude mixture was first purified by MPLC (210 mL $SiO_2$; Eluents: PE/EtOAc 100/0→25/75) and the regioisomeric were separated on a prep. chiral HPLC (Daicel IC; 250 mm×4.6 mm; 4 mL/min; 10 min; 30% MeOH with a few drops $(CH_3)_2NH$).

Example 51

Yield: 58 mg (23%); $C_{29}H_{29}BrClF_2N_3O_4$ (636.91)
MS: $[M+H]^+=636$; TLC (silica gel; PE/EtOAc 3/7); $R_f=0.61$

Example 52

Yield: 90 mg (34%); $C_{29}H_{29}BrClF_2N_3O_4$ (636.91)
MS: $[M+H]^+=636$; TLC (silica gel; PE/EtOAc 3/7); $R_f=0.50$

Example 53

N-[4-(2-Methoxy)ethoxy-3-(trans-4-trifluoromethyl-cyclohexyl)aminocarbonyl-phenyl]-2-chloro-5-[1-(trifluoromethyl)cyclopropyl]carbonylaminomethyl-benzamide

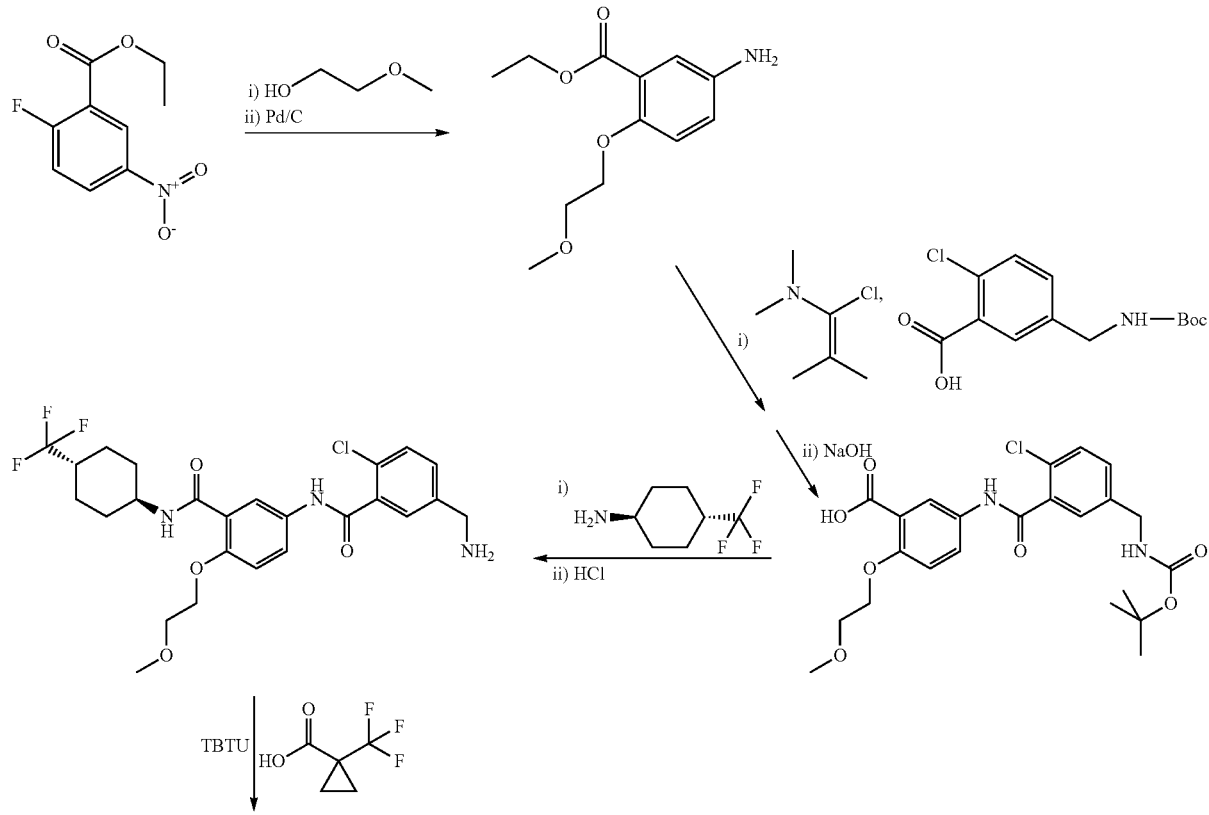

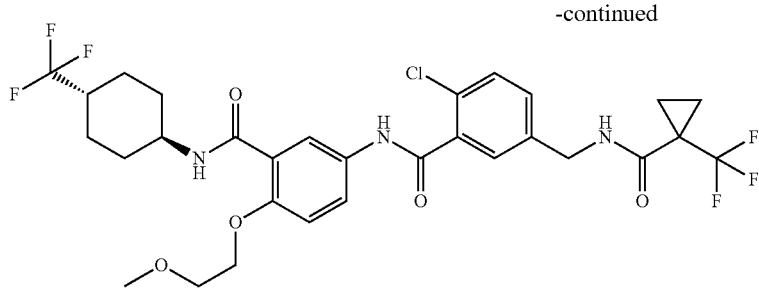

(a) 5-Amino-2-[2-(methoxy)ethoxy]-benzoic acid ethyl ester

Step i) 2-Fluor-5-nitro-benzoic acid ethylester (1 g; 4.69 mmol) was added to a mixture of 2-(methoxy)ethanol (370 µL; 4.69 mmol); KOtBu (0.578 g; 5.16 mmol) in DMF (10 mL) and stirred at rt over night. The mixture was diluted with water, extracted with EtOAc, dried over $Na_2SO_4$ and concentrated i. vac.

Step ii) The residue was mixed with 10 mL MeOH; 10 mL THF and Pd/C (80 mg) and hydrogenated (3 bar) for 3 h. The mixture was filtered, concentrated i. vac. and purified by prep. HPLC. Yield: 200 mg (18%); MS: $[M+H]^+=240$; HPLC: $R_t=2.40$ min (Method CC-5).

(b) 5-[5-(tert-Butoxycarbonylamino-methyl)-2-chloro-benzoylamino]-2-[2-(methoxy)ethoxy]-benzoic acid 1-Chloro-N,N,2-trimethylpropenylamine (166 µL; 1.25 mmol) was added to a mixture of 5-(tert-butoxycarbonylamino)methyl-2-chloro benzoic acid (263 mg; 0.92 mmol) in MeCN (10 mL) and stirred at rt for 15 min. Pyridine (198 µL; 2.51 mmol) and 5-amino-2-(2-methoxyethoxy)-benzoic acid ethyl ester (200 mg; 0.84 mmol) was added and it was stirred at rt overnight. The mixture was filtered through a pad of Alox B, washed with DMF/MeOH 9/1 and concentrated i. vac. The residue was mixed with 15 mL MeOH and 15 mL 2 M aq NaOH and stirred for 3 days at rt. After concentration, the residue was diluted with 10 mL 4M aq. HCl, extracted with EtOAc, dried with $Na_2SO_4$ and concentrated i. vac. The crude was mixed with 50 mL Dioxan; 5 mL $H_2O$ and di-tert-butyldicarbonate (200 mg), stirred at rt for 2 h and concentrated. Yield: 380 mg (95%); MS: $[M+H]^+=479$ (Cl isotope pattern); HPLC: $R_t=2.01$ min (Method CC-4)

(c) N-[4-[2-(Methoxy)ethoxy]-3-(trans-4-trifluoromethylcyclohexyl)aminocarbonyl-phenyl]-2-chloro-5-aminomethyl-phenyl Step i) Prepared analogously to example 8 with 5-[5-(tert-butoxycarbonylamino-methyl)-2-chloro-benzoylamino]-2-(2-methoxy-ethoxy)-benzoic acid (190 mg; 0.4 mmol); trans-4-(trifluoromethyl)cyclohexylamine hydrochloride (89 mg; 0.44 mmol); 1-chloro-N,N,2-trimethylpropenylamine (79 µL; 0.6 mmol); pyridine (94 µL; 1.19 mmol) in 5 mL MeCN.

Step ii) The above product is mixed with 5 mL Dioxan and 5 mL 4 M HCl in Dioxan and stirred for 1 h at rt. The mixture was concentrated and purified by prep HPLC.

Yield: 74 mg (35%); MS: $[m+H]^+=528$; HPLC $R_t=1.83$ min (Method CC-4)

(d) N-[4-(2-Methoxy)ethoxy-3-(trans-4-trifluoromethylcyclohexyl)aminocarbonyl-phenyl]-2-chloro-5-[1-(trifluoromethyl)cyclopropyl]carbonylaminomethyl-benzamide Prepared analogously to 47c with N-[4-(2-Methoxy)ethoxy-3-(trans-4-trifluoromethylcyclohexyl)aminocarbonyl-phenyl]-2-chloro-5-aminomethyl-phenyl (25 mg; 0.05 mmol); 1-trifluoromethylcyclopropane-1-carboxylic acid (9 mg; 0.06 mmol), TBTU (17 mg; 0.05 mmol), TEA (20 µL; 0.14 mmol) in 3 mL DMF.

Yield: 16 mg (50%); $C_{30}H_{32}ClF_6N_3O_5$ (664.04)

MS: $[M+H]^+=664$ (Cl isotope pattern); HPLC: $R_t=2.69$ min (Method CC-5)

Example 54

N-[3,4-Difluoro-5-(4-bromophenyl)aminocarbonyl-phenyl]-2-chloro-5-(tert-butylcarbonylamino)methyl-benzamide

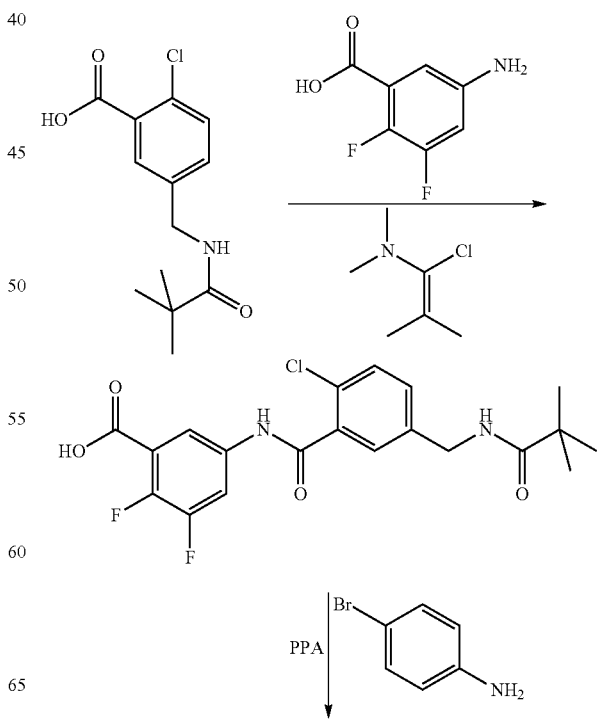

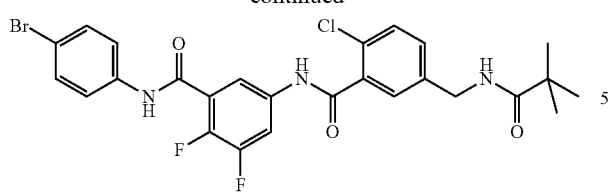

(a) 5-{2-Chloro-5-[(tert-butylcarbonylamino)-methyl]-benzoylamino}-2,3-difluoro-benzoic acid Prepared analogously to example 8 with 5-(tert-butoxycarbonylamino)methyl-2-chloro benzoic acid (0.2 g; 0.75 mmol); 1-chloro-N,N,2-trimethylpropenylamine (0.124 mL; 0.9 mmol); 5-amino-2,3-difluorobenzoic acid (0.13 g; 0.75 mmol) and TEA (0.261 mL; 0.88 mmol) in 20 mL THF. Yield: 290 mg (91%); MS: [m+H]$^+$ 425; HPLC: $R_t$=1.29 min (Method MC-1)

(b) N-[3,4-Difluoro-5-(4-bromophenyl)aminocarbonyl-phenyl]-2-chloro-5-(tert-butylcarbonylamino)methyl-benzamide Prepared analogously to example 2f with 5-{2-Chloro-5-[(tert-butylcarbonylamino)-methyl]-benzoylamino}-2,3-difluoro-benzoic acid (0.29 g; 0.68 mmol); 4-bromoaniline (0.117 g; 0.68 mmol); PPA (0.523 mL; 0.89 mmol; 50% solution in DMF) and TEA (0.237 mL; 1.71 mmol).

Yield: 40 mg (10%) C$_{26}$H$_{23}$BrClF$_2$N$_3$O$_3$ (578.83)

MS: [m+H]$^+$=578 (Br, Cl isotope pattern); TLC (silicagel; DCM/EtOH 95/5) R$_f$=0.31

Example 55

N-[4-Methyl-3-(4-bromophenyl)aminocarbonyl-phenyl]-2-chloro-5-(tert-butylcarbonylamino)methyl-benzamide

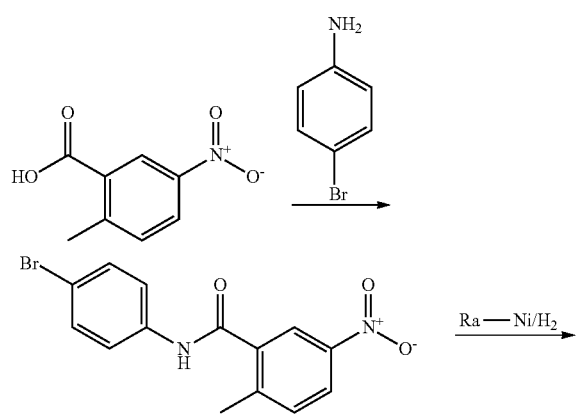

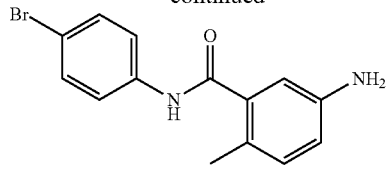

(a) N-(4-Bromo-phenyl)-2-methyl-5-nitro-benzamide

Prepared analogously to example 8 with 2-methyl-5-nitrobenzoic acid (0.1 g; 0.55 mmol); 4-bromoaniline (95 mg; 0.55 mmol); 1-chloro-N,N,2-trimethylpropenylamine (88 µL; 0.66 mmol); TEA (0.192 mL; 1.38 mmol) in THF. Yield: 0.18 g (97%);

MS ([M+H]+=335 (Br isotope pattern); TLC (silica gel; DCM/EtOH 95/5) R$_f$=0.75

(b) 5-Amino-N-(4-bromo-phenyl)-2-methyl-benzamide

Prepared analogously to example 2e with N-(4-bromo-phenyl)-2-methyl-5-nitro-benzamide (0.18 g; 0.54 mmol) and Ra-Ni (20 mg), 3 bar H$_2$. Yield: 0.14 g (85%) MS: [m+H]$^+$= 305; HPLC R$_t$=1.2 min (Method MC-1); TLC (silica gel; DCM/EtOH 95/5) R$_f$=0.3

(c) N-[4-Methyl-3-(4-bromophenyl)aminocarbonyl-phenyl]-2-chloro-5-(tert-butylcarbonylamino)methyl-benzamide Prepared analogously to example 7 with 5-(tert-butylcarbonylamino)methyl-2-chloro benzoic acid (50 mg; 0.19 mmol); 5-amino-N-(4-bromo-phenyl)-2-methyl-benzamide (57 mg; 0.19 mmol); HATU (78 mg; 0.2 mmol) in TEA (77 µL; 0.56 mmol) and 5 mL THF.

Yield: 40 mg (39%) C$_{27}$H$_{27}$BrClN$_3$O$_3$ (556.88); MS: [M+H]$^+$=556 (Cl isotope pattern); HPLC: R$_t$=1.5 min (Method MC-1); TLC (silica gel; DCM/EtOH 95/5) R$_f$=0.3.

Example 56
N-[4-(trans-4-trifluoromethylcyclohexyl)amino-3-[trans-(4-trifluoromethylcyclohexyl)amino]carbonyl-phenyl]-2-chloro-5-(tert-butylcarbonylamino)methyl-benzamide
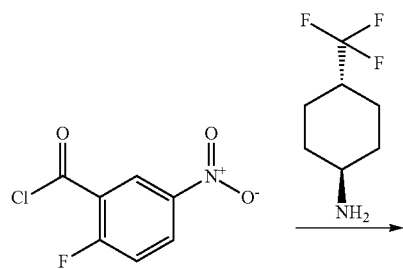
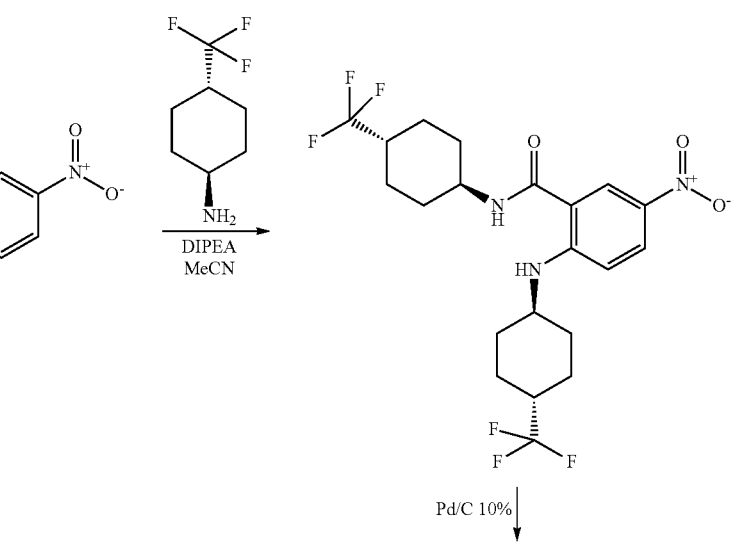
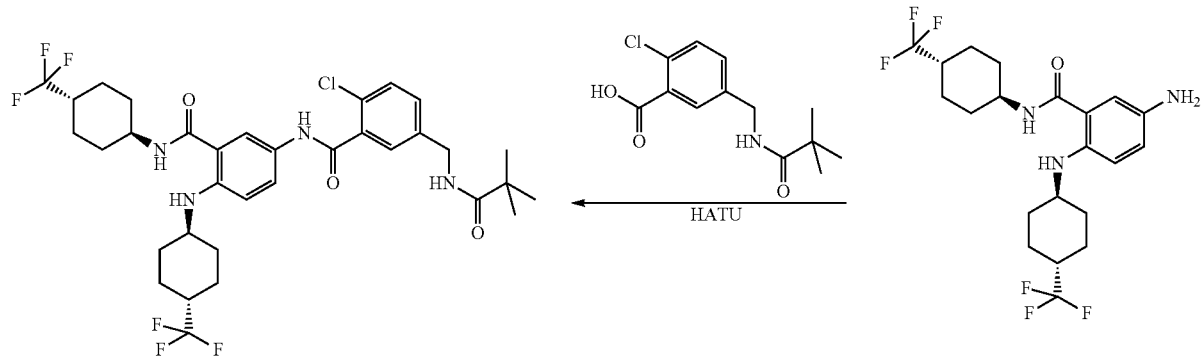

(a) 2-Fluoro-5-nitro-N-trans-(4-trifluoromethyl-cyclohexyl)-benzamide

Prepared analogously to example 2d with 2-fluoro-5-nitrobenzoylchloride (0.55 g; 2.7 mmol) and trans-4-(trifluoromethyl)cyclohexylamine×HCl (0.55 g; 2.7 mmol) in DCM with TEA.

Yield: 0.8 g (89%) MS [m+H]$^+$=335; HPLC: R$_t$=1.42 min (Method MC-1); TLC: (silica gel; DCM/EtOH 95/5) R$_f$=0.85

(b) 5-Nitro-N-trans-(4-trifluoromethyl-cyclohexyl)-2-trans-(4-trifluoromethyl-cyclohexylamino)-benzamide A mixture of 2-fluoro-5-nitro-N-trans-(4-trifluoromethyl-cyclohexyl)-benzamide (50 mg; 0.15 mmol); trans-4-(trifluoromethyl)cyclohexylamine×HCl (31 mg; 0.15 mmol); DIPEA (77 µL; 0.45 mmol) in MeCN (1 mL) was stirred at reflux for 3.5 h. Additional 150 µL DIPEA was added and it was stirred for another 2 h at reflux. The mixture was diluted with water, extracted with EtOAc, dried with Na$_2$SO$_4$ and concentrated.

Yield: 65 mg (90%) MS [M+H]$^+$=482 HPLC: R$_t$=1.82 min (Method MC-1)

(c) 5-Amino-N-trans-(4-trifluoromethyl-cyclohexyl)-2-trans-(4-trifluoromethyl-cyclohexylamino)-benzamide Prepared analogously to example 42c from 5-nitro-N-trans-(4-trifluoromethyl-cyclohexyl)-2-trans-(4-trifluoromethyl-cyclohexylamino)-benzamide (65 mg; 0.14 mmol), 10% Pd/C/H$_2$ (10 mg; 3 bar) in 10 mL MeOH. Yield: 45 mg (74%); MS: [m+H]$^+$=452; HPLC: R$_t$=1.43 min (Method MC-1); TLC (silica gel; DCM/EtOH 98/2) R$_f$=0.2

(d) N-[4-(trans-4-trifluoromethylcyclohexyl)amino-3-[trans-(4-trifluoromethyl-cyclohexyl)amino]carbonyl-phenyl]-2-chloro-5-(tert-butylcarbonylamino)methyl-benzamide Prepared analogously to example 7 with 5-(tert-butylcarbonylamino)methyl-2-chloro benzoic acid (27 mg; 0.1 mmol); 5-amino-N-trans-(4-trifluoromethyl-cyclohexyl)-2-trans-(4-trifluoromethyl-cyclohexylamino)-benzamide (45 mg; 0.1 mmol); HATU (42 mg; 0.11 mmol) in TEA (42 µL; 0.3 mmol) and THF (2 mL). Purification with prep HPLC (Method A)

Yield: 50 mg (71%) C$_{34}$H$_{41}$ClF$_6$N$_4$O$_3$ (703.16)

MS: [m+H]$^+$=703; HPLC: R$_t$=1.69 min (Method MC-1); TLC (silica gel;

DCM/EtOH 95/5) R$_f$=0.5

Example 57

N-[4-(4-Fluoro-piperidin-1-yl)-3-(3-chloro-4-fluorophenyl)aminocarbonyl-phenyl]-2-fluoro-6-chloro-3-[(2,2,2-trifluoro-1,1-dimethyl-ethyl)carbonylamino]methyl-benzamide

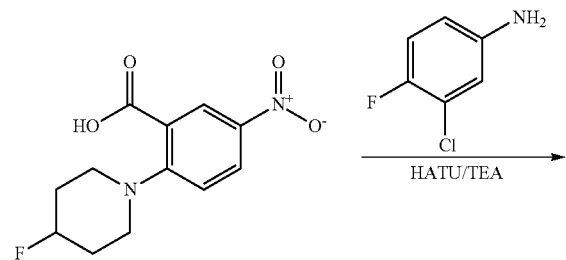

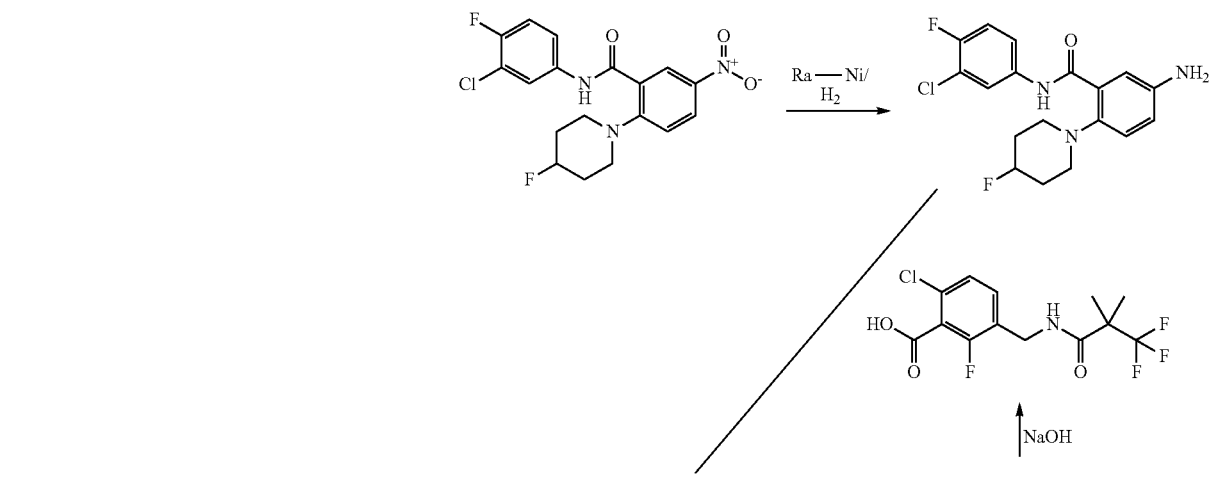

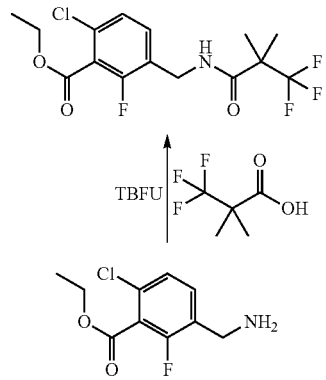

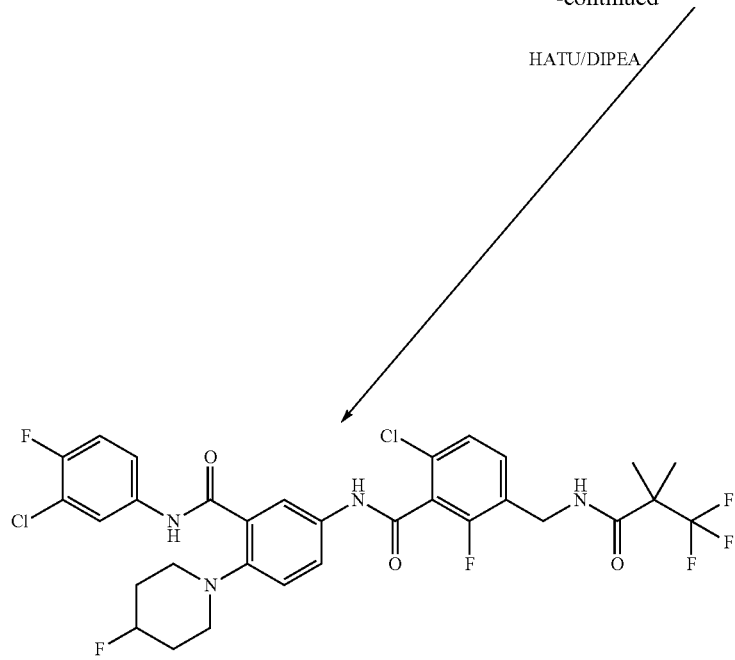

(a) N-(3-Chloro-4-fluorophenyl)-2-(4-fluoro-piperidin-1-yl)-5-nitro-benzamide

Prepared analogously to example 7 with 2-(4-fluoro-piperidin-yl)-5-nitrobenzoic acid (1.08 g; 4.03 mmol), 3-chloro-4-fluoro-aniline (0.586 g; 4.03 mmol); HATU (1.607 g; 4.23 mmol) in TEA (1.679 mL; 12 mmol) and 30 mL THF.

Yield: 1.89 g (83%) MS: [M+H]$^+$=396 (Cl isotope pattern); HPLC: $R_t$=2.33 min (Method MC-6)

(b) N-(3-Chloro-4-fluorophenyl)-2-(4-fluoro-piperidin-1-yl)-5-amino-benzamide

Prepared analogously to example 4b with N-(3-chloro-4-fluorophenyl)-2-(4-fluoro-piperidin-1-yl)-5-nitro-benzamide (1.89 g; 3.34 mmol), Ra-Ni/H$_2$ (230 mg/3 bar) in 50 mL THF.

Yield: quantitative MS: MS: [m+H]$^+$=366 (Cl isotope pattern); HPLC: $R_t$=1.91 min (Method MC-6)

(c) 2-Fluoro-6-chloro-3-[(2,2,2-trifluoro-1,1-dimethyl-ethyl)carbonylamino]methyl-benzoic acid ethyl ester Prepared analogously to example 4c with 3,3,3-trifluoro-2,2-dimethyl-propionic acid (651 mg; 4.17 mmol); 2-Fluoro-6-chloro-benzoic acid ethyl ester (920 mg; 3.97 mmol); TBTU (1.339 g; 4.17 mmol) and TEA (1.382 mL; 9.93 mmol).

Yield: 1.02 g (69%); MS: [m+H]$^+$=370 (Cl isotope pattern); HPLC: $R_t$=2.15 min (Method MC-6)

(d) 2-Fluoro-6-chloro-3-[(2,2,2-trifluoro-1,1-dimethyl-ethyl)carbonylamino]methyl-benzoic acid Prepared analogously to example 45f with 2-fluoro-6-chloro-3-[(2,2,2-trifluoro-1,1-dimethylethyl)carbonylamino]methyl-benzoic acid ethylester (1.02 g; 2.76 mmol) in 1 M aq. NaOH with 25 mL EtOH. The solvent was evaporated, diluted with 4 M aq HCl and extracted with DCM, dried with Na$_2$SO$_4$ and concentrated i.vac to obtain the subtitle compound.

Yield: 690 mg (73%); MS: [M+H]$^+$=342 (Cl isotope pattern); HPLC: $R_t$=1.67 min (Method MC-6)

(e) N-[4-(4-Fluoro-piperidin-1-yl)-3-(3-chloro-4-fluorophenyl)aminocarbonyl-phenyl]-2-fluoro-6-chloro-3-[(2,2,2-trifluoro-1,1-dimethyl-ethyl)carbonylamino]methyl-benzamide Prepared analogously to example 7 with 2-fluoro-6-chloro-3-[(2,2,2-trifluoro-1,1-dimethylethyl)carbonylamino]methylbenzoic acid (55 mg; 0.16 mmol); 5 N-(3-chloro-4-fluorophenyl)-2-(4-fluoro-piperidin-1-yl)-5-amino-benzamide (59 mg; 0.16 mmol); HATU (67 mg; 0.18 mmol) in DIPEA (0.126 mL; 0.72 mmol) and 1 mL THF. The mixture was purified by prep. HPLC (Method A).

Yield: 54 mg (49%); C$_{31}$H$_{28}$Cl$_2$F$_6$N$_4$O$_3$ (689.47);
MS: [m+H]$^+$=689 (Cl$_2$ isotope pattern); HPLC: $R_t$=3.2 min (Method MC-3)

Example 58

N-[4-(4-Trifluoromethyl-piperidin-1-yl)-3-(trans-4-trifluoromethylcyclohexyl)aminocarbonyl-phenyl]-2-chloro-5-(tert-butylcarbonylamino)methyl-benzamide

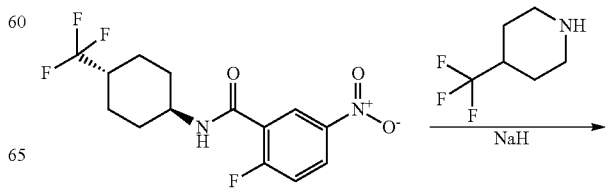

-continued

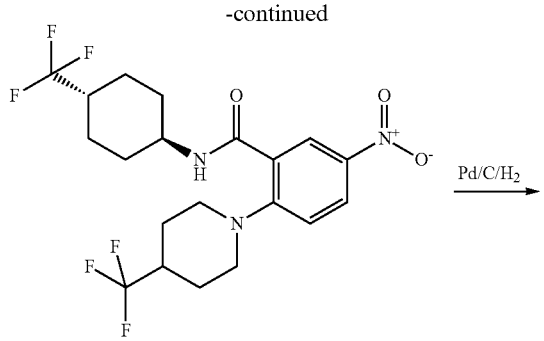

(a) 5-Nitro-2-(4-trifluoromethyl-piperidin-yl)-N-(trans-4-trifluoromethylcyclohexyl)benzamide Prepared analogously to example 38b with 4-(trifluoromethyl)piperidine (32 mg; 0.21 mmol) and NaH (11 mg; 0.23 mmol; 50% dispersion in mineral oil); 2-fluoro-5-nitro-N-(trans-4-trifluoromethyl-cyclohexyl)-benzamide (70 mg; 0.21 mmol) in 2 mL DMF.
Yield: 80 mg (82%); MS: $[m+H]^+=468$; HPLC: $R_t=1.56$ min (Method MC-1)

(b) 5-Amino-2-(4-trifluoromethyl-piperidin-yl)-N-(trans-4-trifluoromethylcyclohexyl)benzamide Prepared analogously to example 42c with 5-nitro-2-(4-trifluoromethyl-piperidin-yl)-N-(trans-4-trifluoromethylcyclohexyl)benzamide (80 mg; 0.17 mmol) and Pd/C 10%/H$_2$ (20 mg; 50 psi) in 10 mL MeOH.
Yield: 60 mg (80%); MS: $[m+H]^+=438$; HPLC: $R_t=1.37$ min (Method MC-1)

(c) N-[4-(4-Trifluoromethyl-piperidin-1-yl)-3-(trans-4-trifluoromethylcyclohexyl)aminocarbonyl-phenyl]-2-chloro-5-(tert-butylcarbonylamino)methyl-benzamide Prepared analogously to example 7 with 5-(tert-butylcarbonylamino)methyl-2-chloro benzoic acid (37 mg; 0.14 mmol); 5-amino-2-(4-trifluoromethyl-piperidin-yl)-N-(trans-4-trifluoromethylcyclohexyl)benzamide (60 mg; 0.14 mmol); HATU (57 mg; 0.15 mmol) in TEA (57 µL; 0.41 mmol) and 5 mL THF. Purification via chromatography (silica gel (80 mL), eluent PE/EtOAc 60/40→50/50).
Yield: 60 mg (64%); $C_{33}H_{39}ClF_6N_4O_3$ (689.13); MS: $[M+H]^+=689$; HPLC: $R_t=1.63$ min (Method MC-1)

Example 59

N-[4-(4-Trifluoromethyl-piperidin-1-yl)-3-(cyclopropylmethyl)aminocarbonyl-phenyl]-2,6-dichloro-3-[(2,2,2-trifluoro-1,1-dimethyl-ethyl)carbonylamino]methyl-benzamide

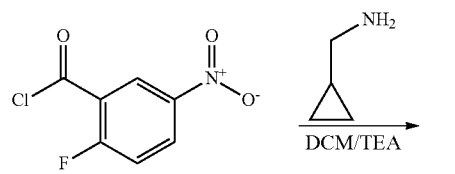

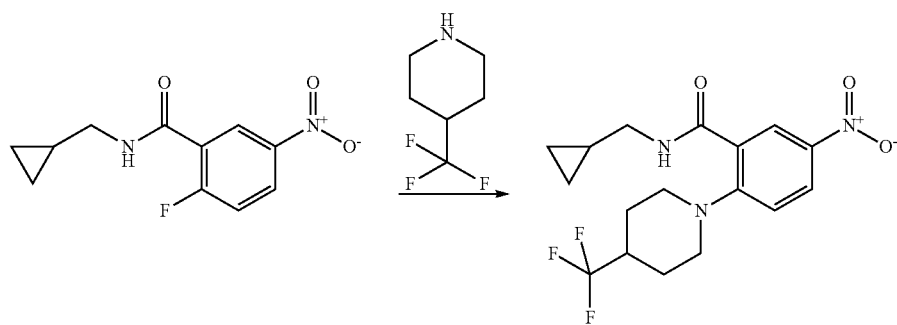

-continued

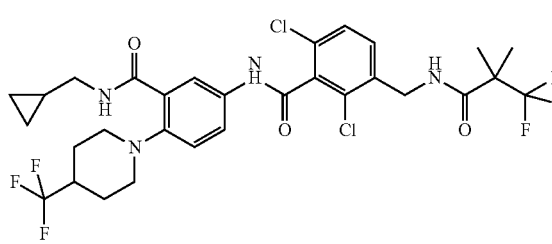
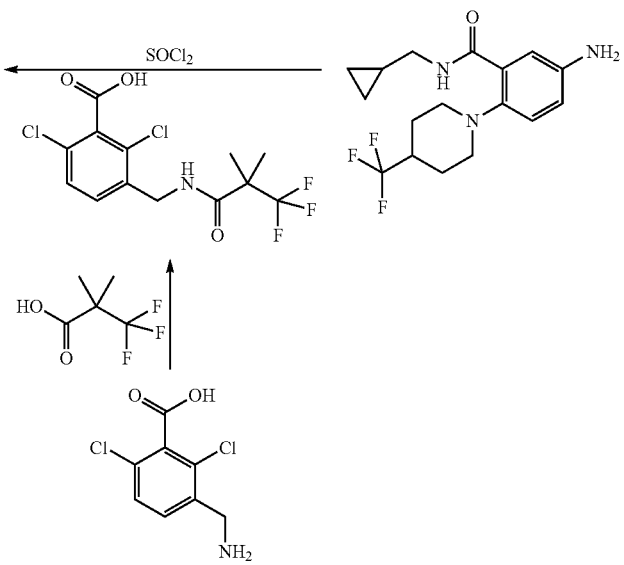

(a) 5-Nitro-2-fluoro-N-cyclopropylmethyl-benzamide

Prepared analogously to example 2d with 5-nitro-2-fluoro-benzoic acid chloride (5.498 g; 27 mmol); cyclopropanem-ethylamine (2.34 mL; 27 mmol) in TEA (5.66 mL; 40.5 mmol) and 200 mL DCM.

Yield: 6.33 g (98%); MS: $[m+H]^+=239$; HPLC: $R_t=1.67$ min (Method MC-6)

(b) 5-Nitro-2-(4-trifluoromethyl-piperidin-1-yl)-N-cyclopropylmethylbenzamide Prepared analogously to example 56b with 5-nitro-2-fluoro-N-cyclopropylmethylbenzamide (250 mg; 1.05 mmol); 4-(trifluoromethyl)piperidine hydrochloride (219 mg; 1.15 mmol) in DIPEA (0.898 mL; 5.25 mmol) and 5 mL MeCN.

Yield: 370 mg (95%); MS: $[m+H]^+=372$; HPLC: $R_t=2.17$ min (Method MC-6)

(c) 5-Amino-2-(4-trifluoromethyl-piperidin-1-yl)-N-cyclopropylmethylbenzamide Prepared analogously to example 42c with 5-nitro-2-(4-trifluoromethyl-piperidin-yl)-N-cyclopropylmethylbenzamide (370 mg; 1 mmol) and Pd/C 10%/$H_2$ (60 mg/3 bar) in 60 mL THF. Yield: quantitative; MS: $[M+H]^+=342$; HPLC: $R_t=1.68$ min (Method MC-6)

(d) 2,6-Dichloro-3-[(2,2,2-trifluoro-1,1-dimethyl-ethyl)carbonylamino]methyl-benzoic acid Prepared analogously to example 8 with 2,6-dichloro-3-aminomethyl-benzoic acid×HCl (0.257 g; 1 mmol); 1-chloro-N,N,2-trimethylpropenylamine (0.2 mL; 1.51 mmol); 3,3,3-trifluoro-2,2-dimethyl-propionic acid (0.19 g; 1.22 mmol) and pyridine (0.4 mL; 4.96 mmol) in 10 mL MeCN. Yield: 117 mg (33%); MS: $[m+H]^+$ 358 ($Cl_2$ isotope pattern); HPLC: $R_t=1.97$ min (Method CC-4)

(e) N-[4-(4-Trifluoromethyl-piperidin-1-yl)-3-(cyclopropyl-methyl)aminocarbonyl-phenyl]-2,6-dichloro-3-[(2,2,2-trifluoro-1,1-dimethyl-ethyl)carbonylamino]methyl-benzamide A mixture of 2,6-dichloro-3-[(2,2,2-trifluoro-1,1-dimethyl-ethyl)carbonylamino]methyl-benzoic acid (67 mg; 0.17 mmol) and thionylchloride was stirred at reflux for 2 h. The mixture was concentrated, diluted with 2 mL MeCN and mixed with 5-amino-2-(4-trifluoromethyl-piperidin-1-yl)-N-cyclopropylmethylbenzamide (55 mg; 0.16 mmol) in 1 mL MeCN and DIPEA (83 µL; 0.48 mmol). After stirring overnight, the mixture was concentrated i.vac. and purified by chromatography (silica gel, eluent DCM+0-15% MeOH+$NH_3$ [9/1]).

Yield: 20 mg (18%); $C_{30}H_{32}Cl_2F_6N_4O_3$ (681.5);

MS: $[M+H]^+=681$ ($Cl_2$ isotope pattern); HPLC: $R_t=2.32$ min (Method CC-4)

Example 60

N-[4-(3,3-Difluoro-azetidin-1-yl)-3-(4-bromphenyl)aminocarbonyl-phenyl]-2-chloro-5-(tert-butylcarbonylamino)methyl-benzamide

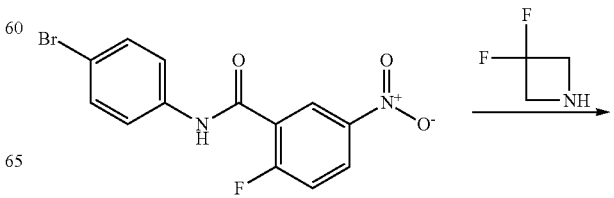

-continued

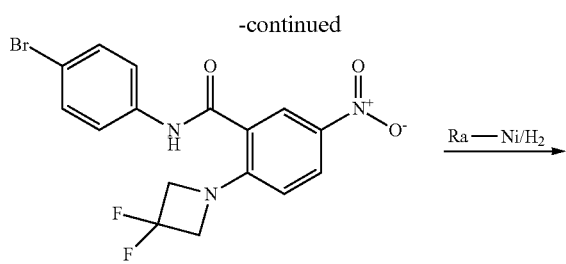

mmol); 5-amino-N-(4-bromo-phenyl)-2-(3,3-difluoro-azetidin-1-yl)benzamide (55 mg; 0.14 mmol); HATU (60 mg; 0.16 mmol) in TEA (60 µL; 0.43 mmol) and 2 mL THF. The mixture was purified via chromatographie (silica gel (80 mL); DCM/EtOH 98/2→97/3).

Yield: 70 mg (77%); $C_{29}H_{28}BrClF_2N_4O_3$ (633.91)

MS: $[M+H]^+$=633 (Br; Cl isotope pattern); HPLC: $R_t$=1.52 min (Method MC-1)

TLC $R_f$=0.35 (silica gel; DCM/EtOH 95/5)

Example 62

N-[4-(dimethylamino)-3-(trans-4-trifluoromethylcyclohexyl)aminocarbonyl-phenyl]-2-chloro-5-(tert-butylcarbonylamino)methyl-benzamide

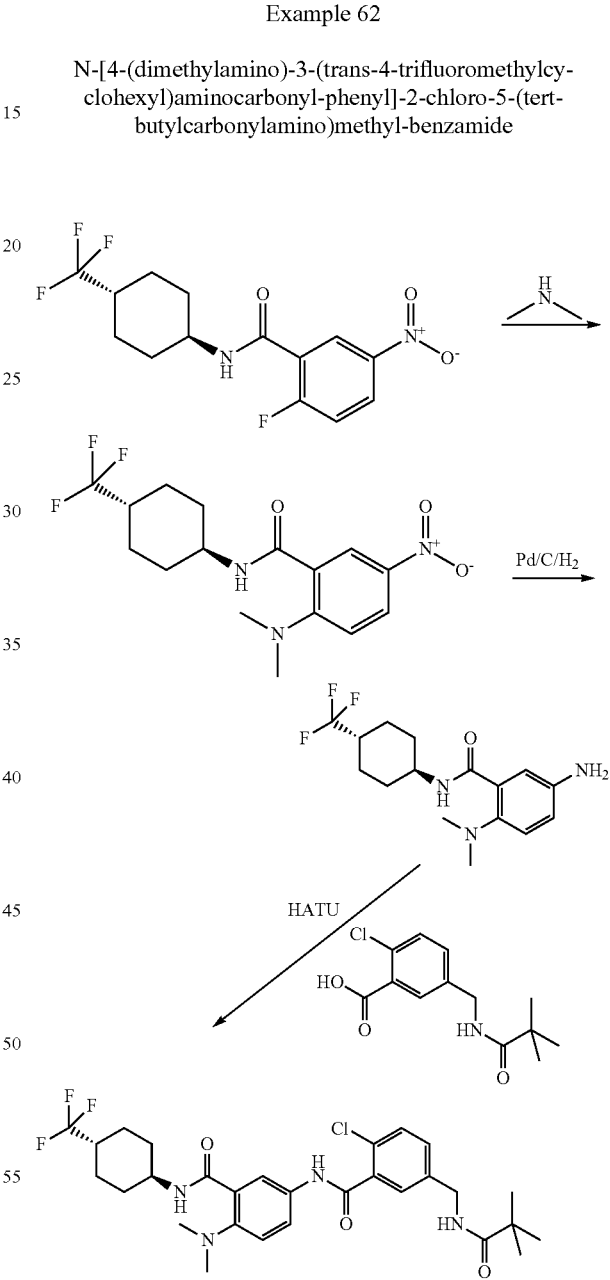

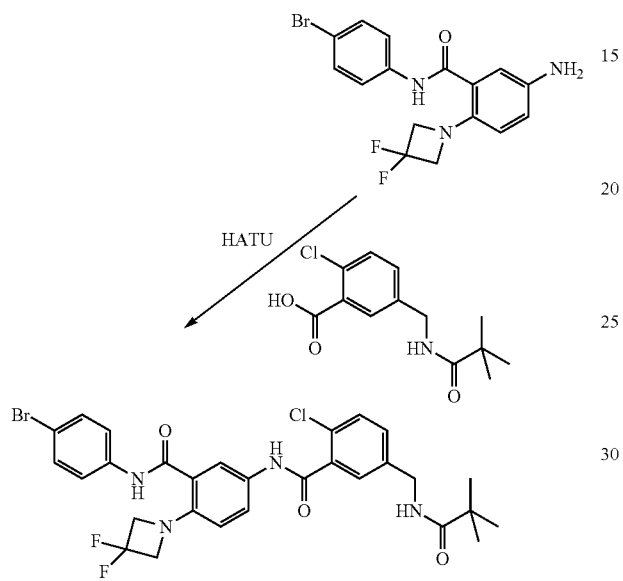

(a) N-(4-Bromo-phenyl)-2-(3,3-difluoro-azetidin-1-yl)-5-nitro-benzamide

Prepared analogously to example 56b with N-(4-bromophenyl)-2-fluoro-5-nitro-benzamide (0.1 g; 0.29 mmol); 3,3-difluoro-azetidine×HCl (42 mg; 0.32 mmol) in DIPEA (0.252 mL; 1.47 mmol) and 1 mL MeCN.

Yield: 60 mg (49%); MS: $[m+H]^+$=410 (Br isotope pattern); HPLC: $R_t$=1.51 min (Method MC-1)

(b) 5-Amino-N-(4-Bromo-phenyl)-2-(3,3-difluoro-azetidin-1-yl)benzamide

Prepared analogously to example 4b with N-(4-bromophenyl)-2-(3,3-difluoro-azetidin-1-yl)-5-nitro-benzamide (60 mg; 0.15 mmol) with Ra-Ni/H$_2$ (10 mg/50 psi) in 15 mL THF.

Yield: 56 mg (100%); MS: $[M+H]^+$=382 (Br isotope pattern); HPLC: $R_t$=1.29 min (Method MC-1)

(c) N-[4-(3,3-Difluoro-azetidin-1-yl)-3-(4-bromphenyl)aminocarbonyl-phenyl]-2-chloro-5-(tert-butylcarbonylamino)methyl-benzamide Prepared analogously to example 7 with 5-(tert.butylcarbonylamino)methyl-2-chloro benzoic acid (39 mg; 0.14

(a) 2-Dimethylamino-5-nitro-N-(trans-4-trifluoromethyl-cyclohexyl)-benzamide

A mixture of 2-fluoro-5-nitro-N-(trans-4-trifluoromethyl-cyclohexyl)-benzamide (50 mg; 0.15 mmol) in 40% aq. dimethylamine (2 mL; 15.8 mmol) was stirred at rt for 1 h. The mixture was diluted with THF and concentrated. The crude was diluted with H₂O and extracted with EtOAc. The organic layer was dried with Na₂SO₄ and concentrated i.vac.

Yield: 50 mg (93%); MS: [m+H]⁺=360; HPLC: $R_t$=1.41 min (Method MC-1)

(b) 5-Amino-2-dimethylamino-N-(trans-4-trifluoromethyl-cyclohexyl)-benzamide

Prepared analogously to example 4b with 2-dimethylamino-5-nitro-N-(trans-4-trifluoromethylcyclohexyl)-benzamide (50 mg; 0.14 mmol) with Pd/C/H₂ (15 mg/50 psi) in 10 mL MeOH. Yield: quantitative; MS: [m+H]⁺=330; HPLC: $R_t$=1.14 min (Method MC-1)

(c) N-[4-(dimethylamino)-3-(trans-4-trifluoromethylcyclohexyl)aminocarbonyl-phenyl]-2-chloro-5-(tert-butylcarbonylamino)methyl-benzamide Prepared analogously to example 7 with 5-(tert.butylcarbonylamino)methyl-2-chloro benzoic acid (41 mg; 0.15 mmol); 5-amino-2-dimethylamino-N-(trans-4-trifluoromethyl-cyclohexyl)benzamide (50 mg; 0.15 mmol); HATU (64 mg; 0.17 mmol) in TEA (64 μL; 0.46 mmol) and 2 mL THF and purified via chromatographie (silica gel (80 mL); PE/EtOAc 55/45→47/53).

Yield: 20 mg (23%); C₂₉H₃₆ClF₃N₄O₃ (581.07)

MS: [M+H]⁺=581 (Cl isotope pattern); HPLC: $R_t$=1.37 min (Method MC-1);

TLC (silica gel; DCM/EtOH 95/5) $R_f$=0.25

Example 65

N-[4-(2-Methoxy)ethoxy-3-(4-bromphenyl)aminocarbonyl-phenyl]-2-chloro-5-(2,2,2-trifluoro-1-methyl-ethyl)carbonylaminomethyl-benzamide

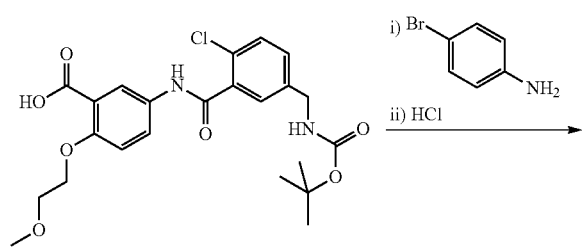

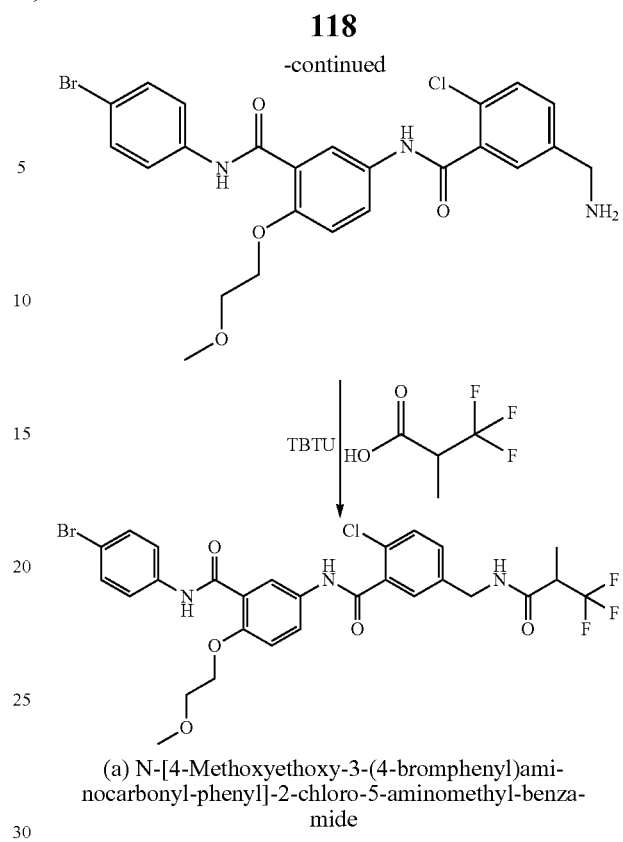

(a) N-[4-Methoxyethoxy-3-(4-bromphenyl)aminocarbonyl-phenyl]-2-chloro-5-aminomethyl-benzamide Prepared analogously to example 53c with 5-[5-(tert-butoxycarbonylamino-methyl)-2-chloro-benzoylamino]-2-(2-methoxy-ethoxy)-benzoic acid (190 mg; 0.4 mmol); 1-chloro-N,N,2-trimethylpropenylamine (79 μL; 0.6 mmol); 4-bromoaniline (75 mg; 0.44 mmol); pyridine (94 μL; 1.19 mmol) in 5 mL MeCN and 4 M HCl in dioxan Yield: 160 mg (76%); MS: [m+H]⁺=532; HPLC: $R_t$=1.93 min (Method CC-4)

(b) N-[4-Methoxyethoxy-3-(4-bromphenyl)aminocarbonyl-phenyl]-2-chloro-5-(2,2,2-trifluoro-1-methyl-ethyl)carbonylaminomethyl-benzamide Prepared analogously to example 53d with 3,3,3-trifluoro-2-methyl-propionic acid (10 mg; 0.07 mmol); N-[4-methoxyethoxy-3-(4-bromphenyl)aminocarbonyl-phenyl]-2-chloro-5-aminomethyl-benzamide (32 mg; 0.06 mmol); TBTU (21 mg; 0.07 mmol) in TEA (25 μL; 0.18 mmol) and 3 mL DMF.

Yield: 15.5 mg (39%); C₂₈H₂₆BrClF₃N₃O₅ (656.88);

MS: [M+H]⁺=656 (Br; Cl isotope pattern); HPLC: $R_t$=2.73 min (Method CC-5)

Example 66

N-[4-(Tetrahydrofuran-3-yloxy)-3-(4-bromophenyl)aminocarbonyl-phenyl]-2-chloro-5-(tert-butyl-carbonylaminomethyl)-benzamide

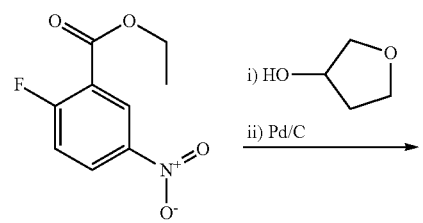

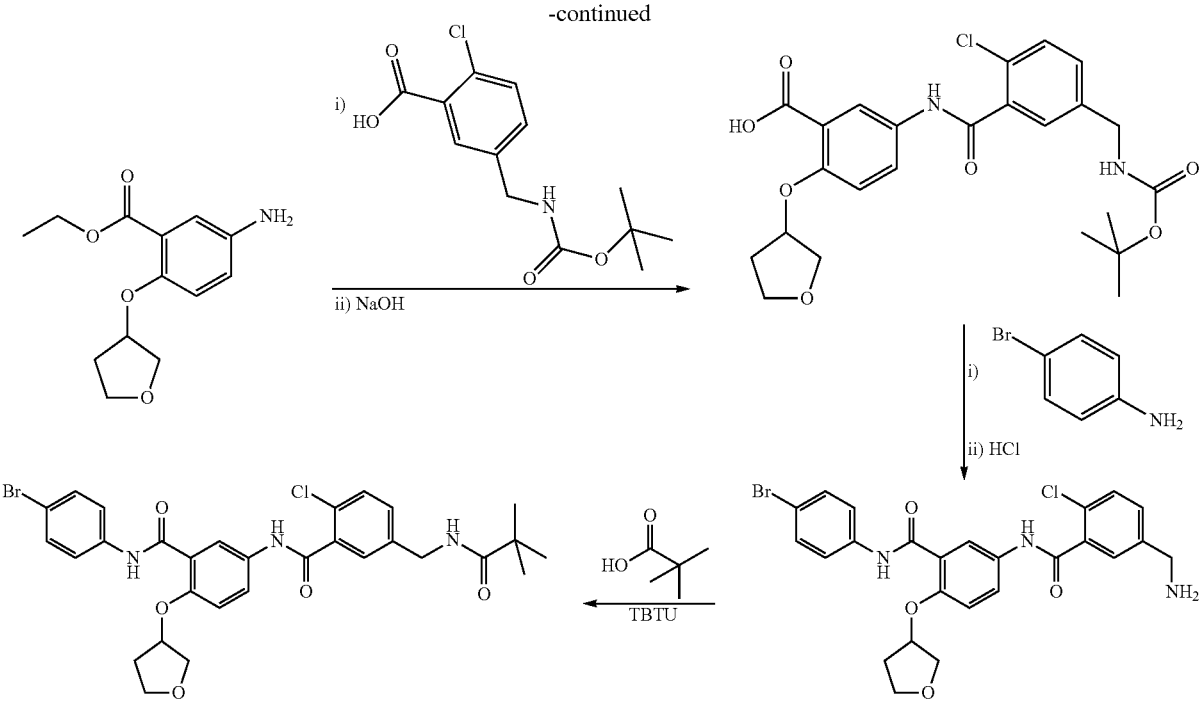

(a) 5-Amino-2-(tetrahydrofuran-3-yloxy)-benzoic acid ethylester

Prepared analogously to example 53a with 2-fluoro-5-nitro-benzic acid ethylester (1 g; 4.69 mmol); tetrahydrofuran-3-ol (379 µL; 4.69 mmol); KOtBu (578 mg; 5.16 mmol) in DMF and for step ii) 10 mL MeOH; 5 mL THF and Pd/C (40 mg), H$_2$ (3 bar).

Yield: 250 mg (21%); MS: [M+H]$^+$=252; HPLC R$_t$=2.38 min (Method CC-5)

(b) 5-[5-(tert-Butoxycarbonylamino-methyl)-2-chloro-benzoylamino]-2-(tetrahydrofuran-3-yloxy)-benzoic acid Prepared analogously to example 53b with 5-(tert-butoxycarbonylamino-methyl)-2-chloro-benzoic acid (284 mg; 0.99 mmol); 1-chloro-N,N,2-trimethylpropenylamine (197 µL; 1.49 mmol); 5-amino-2-(tetrahydrofuran-3-yloxy)-benzoic acid (250 mg; 0.99 mmol); pyridine (236 µL; 2.98 mmol) in 10 mL MeCN. followed by saponification with NaOH.

Yield: 220 mg (45%); MS: [M+H]$^+$=391; HPLC R$_t$=1.97 min (Method CC-4)

(c) N-[4-(Tetrahydrofuran-3-yloxy)-3-(4-bromophenyl)aminocarbonyl-phenyl]-2-chloro-5-aminomethyl-phenyl Prepared analogously to 53c with 5-[5-(tert-butoxycarbonylamino-methyl)-2-chloro-benzoylamino]-2-(tetrahydrofuran-3-yloxy)-benzoic acid (120 mg; 0.24 mmol); 4-bromoaniline (47 mg; 0.28 mmol); 1-chloro-N,N,2-trimethylpropenylamine (50 µL; 0.38 mmol); pyridine (60 µL; 0.75 mmol) in 5 mL MeCN, followed by BOC-deprotection with 4 M HCl in dioxan.

Yield: 83 mg (62%); MS: [M+H]$^+$=544 (Br; Cl isotope pattern); HPLC R$_t$=1.88 min (Method CC-4)

(d) N-[4-(Tetrahydrofuran-3-yloxy)-3-(4-bromophenyl)aminocarbonyl-phenyl]-2-chloro-5-(tert-butyl-carbonylaminomethyl)-benzamide Prepared analogously to example 53d with N-[4-(tetrahydrofuran-3-yloxy)-3-(4-bromophenyl)aminocarbonyl-phenyl]-2-chloro-5-aminomethyl-phenyl (28 mg; 0.05 mmol); 2,2-dimethylpropionic acid (5.3 mg; 0.05 mmol); TBTU (18 mg; 0.06 mmol) in TEA (22 µL; 0.15 mmol) and 3 mL DMF.

Yield: 13 mg (40%); C$_{30}$H$_{31}$BrClN$_3$O$_5$ (628.94);

MS: [M+H]$^+$=656 (Br; Cl isotope pattern); HPLC: R$_t$=2.73 min (Method CC-5).

Example 73

N-[2-(2,2-Difluoroethyl)oxy-3-(4-bromophenyl)aminocarbonyl-pyridin-5-yl]-2-chloro-5-[(2,2,2-trifluoro-1,1-dimethyl-ethyl)carbonylamino]methyl-benzamide

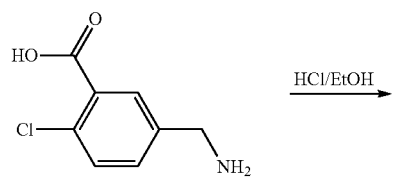

HCl/EtOH

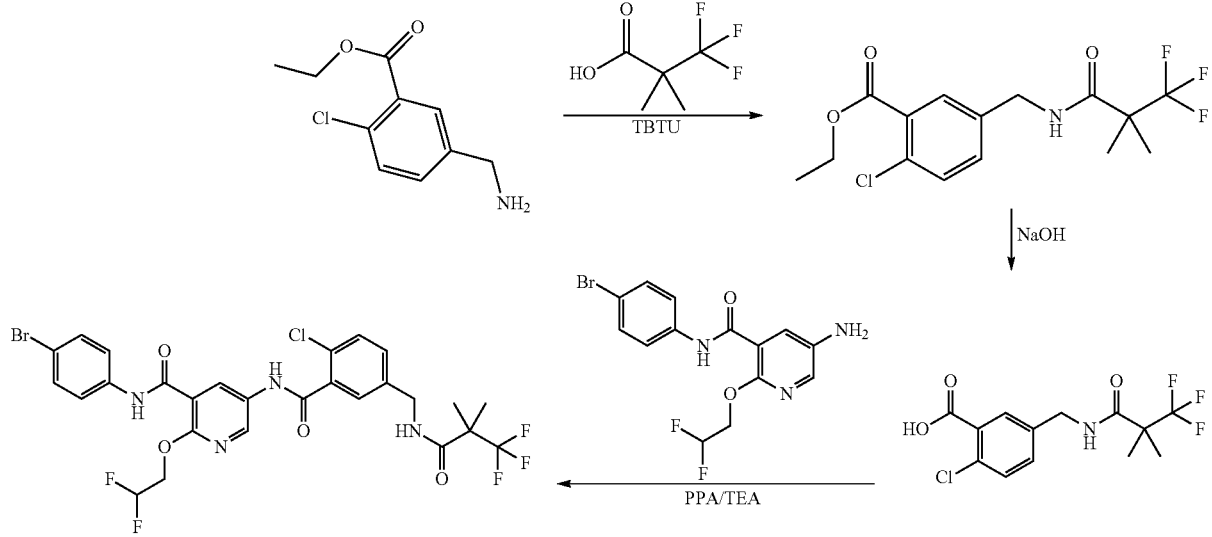

(a) 5-Aminomethyl-2-chloro-benzoic acid ethyl ester

Prepared analogously to example 42d with 5-aminomethyl-2-chlorobenzoic acid (2 g; 9.01 mmol) in 20 mL HCl in EtOH. Yield: 2.38 g (90%); MS: [M+H]$^+$=214 (Cl isotope pattern); HPLC: R$_t$=1.20 min (Method MC-6)

(b) 2-Chloro-5-[(2,2,2-trifluoro-1,1-dimethyl-ethyl)carbonylamino]methyl-benzoic acid ethyl ester Prepared analogously to example 8 with 5-aminomethyl-2-chloro-benzoic acid ethyl ester (2.2 g; 8.8 mmol); 3,3,3-trifluoro-2,2-dimethylpropionic acid (1.442 g; 9.24 mmol); TBTU (2.965 g; 9.24 mmol) in TEA (3.673 mL; 26.39 mmol) and 90 mL THF.

Yield: 2.06 g (67%); MS: [M+H]$^+$=352 (Cl isotope pattern); HPLC: R$_t$=2.11 min (Method MC-6)

(c) 2-Chloro-5-[(2,2,2-trifluoro-2,2-dimethyl-ethyl)carbonylamino]methyl-benzoic acid Prepared analogously to example 42 h with 2-chloro-5-[(2,2,2-trifluoro-1,1-dimethylethyl)carbonylamino]methyl-benzoic acid ethyl ester (2.06 g; 5.86 mmol) in 1 M aq NaOH (23.5 mL; 23.4 mmol) and 50 mL EtOH. Yield: 880 mg (46%); MS: [M+H]$^+$=324 (Cl isotope pattern); HPLC: R$_t$=1.11 min (Method MC-9)

(d) N-[2-(2,2-Difluoroethyl)oxy-3-(4-bromophenyl)aminocarbonyl-pyridin-5-yl]-2-chloro-5-[(2,2,2-trifluoromethyl-1,1-dimethyl-ethyl)carbonylamino]methyl-benzamide Prepared analogously to example 2f with 2-chloro-5-[(2,2,2-trifluoro-2,2-dimethylethyl)carbonylamino-methyl]-benzoic acid (50 mg; 0.15 mmol); N-(4-bromophenyl)-2-(2,2-difluoroethyl)oxy-5-amino-nicotinic acid amide (66 mg; 0.18 mmol); PPA (118 µL; 0.2 mmol; 50% in DMF); TEA (54 µL; 0.39 mmol) in 10 mL THF.

Yield: 28 mg (27%); C$_{27}$H$_{23}$BrClF$_5$N$_4$O$_4$ (677.84)
MS: [m+H]$^+$=677 (Br; Cl isotope pattern); TLC (silica gel; DCM/EtOH 9/1) R$_f$=0.74

Example 75

N-[2-(2,2-Difluoroethoxy)-3-(3-chloro-5-fluorophenyl)aminocarbonyl-pyridin-5-yl]-2,6-dichloro-5-(tert-butylcarbonylamino)methyl-benzamide

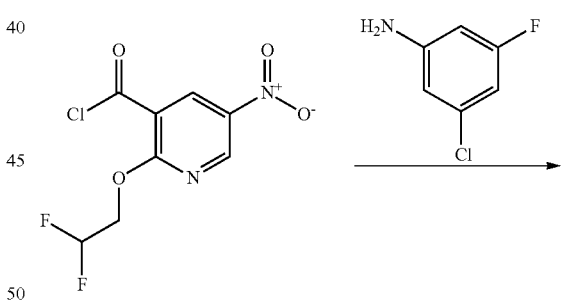

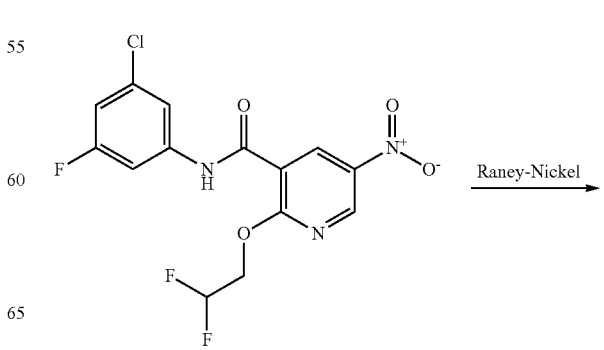

123
-continued

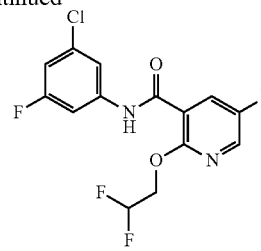

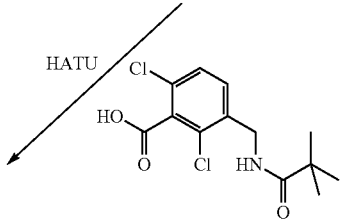

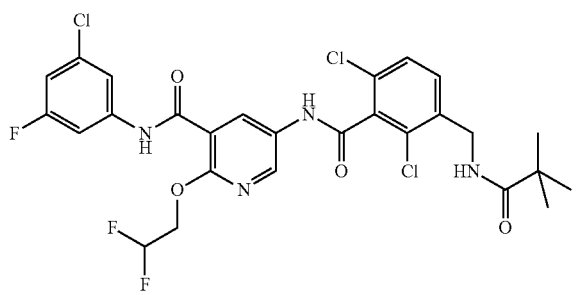

(a) N-(3-Chloro-5-fluoro-phenyl)-2-(2,2-difluoro-ethoxy)-5-nitro-nicotinamide

Prepared analogously to example 6c with 2-(2,2-difluoro-ethoxy)-5-nitro-nicotinic acid chloride (prepared analogously to 6b) (179 mg; 0.67 mmol); 3-chloro-5-fluoroaniline (98 mg; 0.67 mmol) and TEA (112 μL; 0.81 mmol) in 5 mL DCM. Yield: 230 mg (91%); MS: [m+H]⁺=376 (Cl isotope pattern); HPLC: $R_t$=2.35 min (Method MC-6)

(b) 5-Amino-N-(3-chloro-5-fluoro-phenyl)-2-(2,2-difluoro-ethoxy)-nicotinamide

Prepared analogously to example 6d with N-(3-chloro-5-fluoro-phenyl)-2-(2,2-difluoroethoxy)-5-nitro-nicotinamide (230 mg; 0.61 mmol); Ra-Ni/H₂ (50 mg; 3 bar) in 8 mL. Yield: quantitative; MS: [M+H]⁺=346 (Cl isotope pattern); HPLC: $R_t$=2.1 min (Method MC-6)

(c) N-[2-(2,2-Difluoroethoxy)-3-(3-chloro-5-fluorophenyl)aminocarbonyl-pyridin-5-yl]-2,6-dichloro-5-(tert-butylcarbonylamino)methyl-benzamide Prepared analogously to example 7 with 2,6-dichloro-3-(tert-butylcarbonylamino-methyl)benzoic acid (100 mg; 0.33 mmol); 5-amino-N-(3-chloro-5-fluoro-phenyl)-2-(2,2-difluoroethoxy)-nicotinamide (114 mg; 0.33 mmol); HATU (250 mg; 0.66 mmol) and DIPEA (0.258 mL; 1.48 mmol) in 1 mL THF.

124

Yield: 22 mg (8%); C₂₇H₂₄Cl₃F₃N₄O₄ (631.86); MS: [M+H]⁺=631 (Cl isotope pattern); HPLC: $R_t$=2.44 min (Method MC-6)

Example 77

N-[4-(2,2-Difluoroethyl)oxy-3-(4-fluoro-3-chlorophenyl)aminocarbonyl-phenyl]-6-chloro-2-fluoro-3-[(2,2,2-trifluoro-1,1-dimethyl-ethyl)carbonylamino]methyl-benzamide

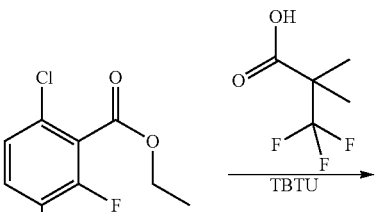

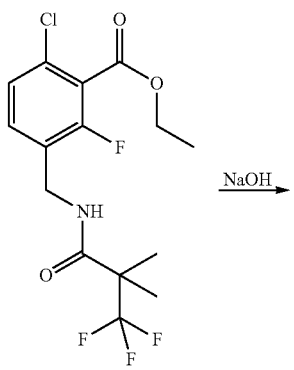

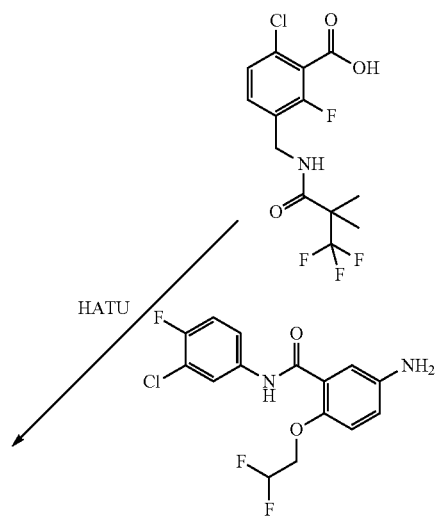

(prepared analogously to 46a and 46b)

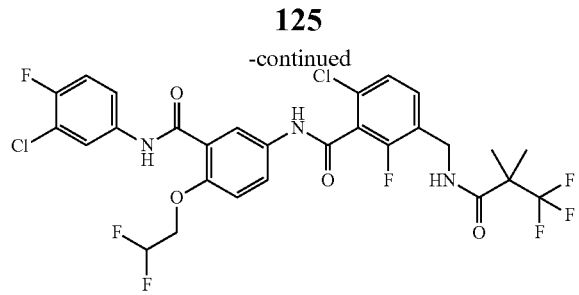

(a) 2-Fluoro-6-chloro-3-[(2,2,2-trifluoro-1,1-dimethyl-ethyl)carbonylamino]methyl-benzoic acid ethyl ester Prepared analogously to example 9b with 3-aminomethyl-6-chloro-2-fluoro-benzoic acid ethyl ester (920 mg; 3.97 mmol); 3,3,3-trifluoro-2,2-dimethylpropionic acid (651 mg; 4.17 mmol); TBTU (1.339 g; 4.17 mmol) and TEA (1.382 mL; 4.17 mmol) in 40 mL THF.

Yield: 1.02 g (69%); MS: [m+H]$^+$=370 (Cl isotope pattern); HPLC: R$_t$=2.15 min (Method MC-6)

(b) 2-Fluoro-6-chloro-3-[(2,2,2-trifluoro-1,1-dimethyl-ethyl)carbonylamino}methyl-benzoic acid Prepared analogously to example 42 h with 2-fluoro-6-chloro-3-[(2,2,2-trifluoro-1,1-dimethylethyl)carbonylamino]methyl-benzoic acid ethyl ester (1.02 g; 2.76 mmol) in 1 M aq NaOH (5.517 mL; 5.52 mmol) in 25 mL EtOH.

Yield: 690 mg (73%); MS: [m+H]$^+$=342 (Cl isotope pattern); HPLC: R$_t$=1.67 min (Method MC-6)

(c) N-[4-(2,2-Difluoroethyl)oxy-3-(4-fluoro-3-chloro-phenyl)aminocarbonyl-phenyl]-6-chloro-2-fluoro-3-[(2,2,2-trifluoro-1,1-dimethyl-ethyl)carbonylamino]methyl-benzamide Prepared analogously to example 43b with 2-fluoro-6-chloro-3-[(2,2,2-trifluoro-1,1-dimethylethyl)carbonylamino]methyl-benzoic acid (55 mg; 0.16 mmol); N-(3-chloro-5-fluoro-phenyl)-2-(2,2-difluoroethyl)oxy-5-amino-benzamide (56 mg; 0.16 mmol); HATU (67 mg; 0.18 mmol) and DIPEA (126 µL; 0.72 mmol) in 1 mL THF.

Yield: 45 mg (42%); C$_{28}$H$_{22}$Cl$_2$F$_7$N$_3$O$_4$ (668.39);
MS: [M+H]$^+$=668 (Cl$_2$ isotope pattern); HPLC: R$_t$=2.38 min (Method MC-6)

Example 82

N-[4-(2,2-difluoroethyl)oxy-3-(trans-4-trifluoromethylcyclohexyl)aminocarbonyl-phenyl]-2-chloro-5-[(2,2,2-trifluoro-1,1-dimethyl-ethyl)carbonylamino}methyl-benzamide

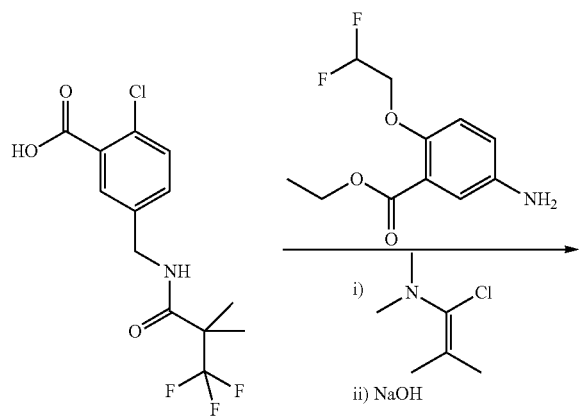

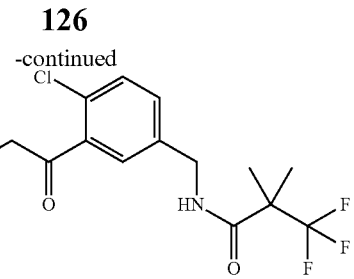

(a) N-[4-(2,2-Difluoro-ethyl)oxy-3-hydroxycarbonyl-phenyl]-2-chloro-5-[(2,2,2-trifluoro-1,1-dimethyl-ethyl)carbonylamino]m ethyl-benzamide Step i) 1-Chloro-N,N,2-trimethylpropenylamine (3.35 mL; 25.4 mmol) was added to a mixture of 2-chloro-5-[(2,2,2-trifluoro-1,1-dimethyl-ethyl)carbonylamino]methyl-benzoic acid (5.47 g; 16.9 mmol) in 100 mL MeCN and it was stirred at rt for 10 min. Pyridine (4.68 mL; 59.1 mmol) and 2-(2,2-difluoroethyl)oxy-5-aminocarboxylic acid ethyl ester×HCl (4.76 g; 16.9 mmol) were added, it was stirred at rt overnight and the mixture was concentrated.

Step ii) The residue was mixed with 50 mL MeOH and 50 mL 2 M aq NaOH, stirred for 3 d at rt, concentrated and the residue was acidified with 4M aq. HCl, filtered and dried. The crude was purified via chromatography (silica gel; eluents: DCM+15-70% MeOH/NH$_4$OH=9/1). Yield: 8.3 g (94%); MS: [m+H]$^+$=523 (Cl isotope pattern); HPLC: R$_t$=2.05 min (Method CC-6)

(b) N N-[4-(2,2-difluoroethyl)oxy-3-(trans-4-trifluoromethylcyclohexyl)aminocarbonyl-phenyl]-2-chloro-5-[(2,2,2-trifluoro-1,1-dimethyl-ethyl)carbonylamino]methyl-benzamide 1-Chloro-N,N,2-trimethylpropenylamine (19.8 µL; 0.15 mmol) was added to a mixture of N-[4-(2,2-Difluoro-ethyl)oxy-3-hydroxycarbonyl-phenyl]-2-chloro-5-[(2,2,2-trifluoro-1,1-dimethylethyl)carbonylamino]methyl-benzamide (52 mg; 0.1 mmol) in 1.5 mL MeCN and it was stirred at rt for 20 min. A mixture of trans-4-trifluoromethylcyclohexylamine×HCl (20.4 mg; 0.1 mmol) and pyridine (24 µL; 0.3 mmol) in 1.5 mL MeCN were added and it was stirred at rt overnight. The mixture was diluted with a mixture of 2 mL DMF/H$_2$O 19/1 and purified by prep. HPLC.

Yield: 18.9 mg (28%); C$_{29}$H$_{30}$ClF$_8$N$_3$O$_4$ (672.01)
MS: [M+H]$^+$=672; HPLC: R$_t$=1.69 (Method CC-7)

Example 145

N-[4-(2,2-difluoroethyl)oxy-3-(4-fluoro-3-chlorophenyl)aminocarbonyl-phenyl]-2,6-dichloro-3-[(2,2,2-trifluoro-1,1-dimethyl-ethyl)carbonylamino]methyl-benzamide

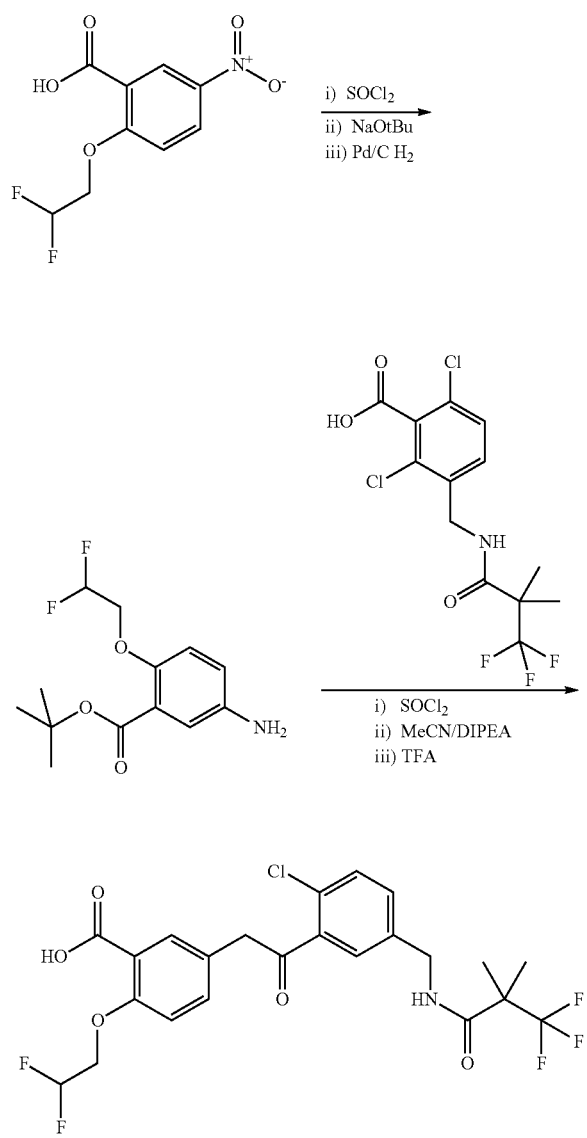

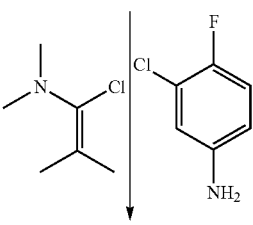

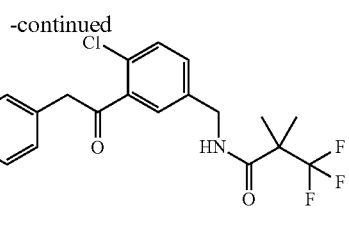

(a) 5-Amino-2-(2,2-difluoroethyl)oxy-benzoic acid tert-butyl ester

Step i) A mixture of 5-nitro-2-(2,2-difluoroethyl)oxy-benzoic acid (5 g; 20.2 mmol) in 50 mL SOCl$_2$ was stirred at reflux for 2 h and concentrated.

Step ii) The residue was diluted with 100 mL THF and dropped under ice cooling to a mixture of NaOtBu (2.916 g; 30.35 mmol) in 100 mL THF, and it was stirred at rt for 3 h. After concentration, the residue was diluted with 100 mL DCM, washed with water, dried with Na$_2$SO$_4$ and concentrated i.vac.

Step iii) The crude was mixed with 100 mL MeOH, 100 mL THF and Pd/C (200 mg), hydrogenated (4 bar) overnight, filtered and concentrated. Yield: 520 mg (94%); [M-tBu]$^+$=217; HPLC: R$_t$=1.54 min (Method CC-4)

(b) N-4-(2,2-Difluoro-ethoxy)-3-hydroxycarbonyl-phenyl-2,6-chloro-3-[(2,2,2-trifluoro-1,1-dim ethyl-ethyl)carbonylamino]methyl-benzamide Step i) Prepared analogously to example 6b with 2,6-dichloro-3-[(2,2,2-trifluoro-1,1-dimethylethyl)carbonylamino]methyl-benzoic acid (2.293 g; 5.76 mmol) in 100 mL SOCl$_2$.

Step ii) The acid chloride was mixed with 100 mL MeCN and dropped to a mixture of 5-amino-2-(2,2-difluoroethyl)oxy-benzoic acid tert-butyl ester (1.5 g; 5.49 mmol); DIPEA (2.833 mL; 16.47 mmol) in 100 mL MeCN, and it was stirred at rt for 3 h and concentrated.

Step iii) The residue was diluted with 100 mL DCM; 5 mL H$_2$O and 100 mL TFA, stirred at rt for 3 d, concentrated and purified by prep. HPLC.

Yield: 1.68 g (55%); [M+H]+=557 HPLC; R$_t$=1.92 min (Method CC-9)

(c) N-[4-(2,2-difluoroethyl)oxy-3-(4-fluoro-3-chlorophenyl)aminocarbonyl-phenyl]-2,6-dichloro-3-[(2,2,2-trifluoro-1,1-dimethyl-ethyl)carbonylamino]methyl-benzamide Prepared analogously to example 82b with 1-chloro-N,N,2-trimethylpropenylamine (25 µL; 0.19 mmol); N-4-(2,2-difluoro-ethoxy)-3-hydroxycarbonyl-phenyl-2,6-chloro-3-[(2,2,2-trifluoro-1,1-dimethyl-ethyl)carbonylamino]methyl-benzamide (56 mg; 0.1 mmol) in 2 mL MeCN and 3-chloro-4-fluoroaniline (14.5 mg; 0.1 mmol); DIPEA (51.6 µL; 0.3 mmol) in 1 mL MeCN. Yield: 30.2 mg (44%); C$_{28}$H$_{22}$Cl$_3$F$_6$N$_3$O$_4$ (684.84)

MS: [M+H]$^+$=684; HPLC: R$_t$=2.01 min (Method CC-4)

Example 160

N-[4-(2,2-Difluoroethyl)oxy-3-(4-bromophenyl)aminocarbonyl-phenyl]-2-chloro-5-[(2-methyl-1-methoxy-ethyl)carbonylamino]methyl-benzamide

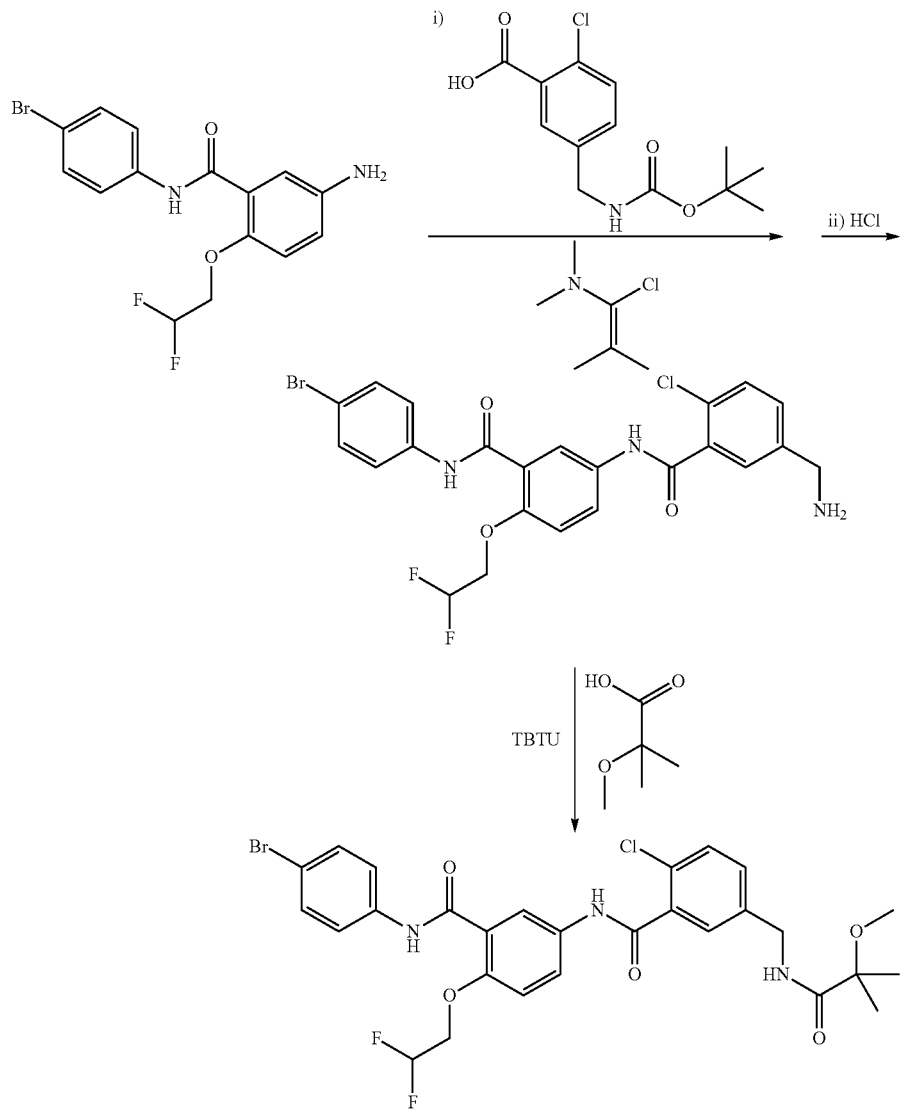

(a) N-[4-(2,2-Difluoroethyl)oxy-3-(4-bromophenyl)aminocarbonyl-phenyl]-2-chloro-5-aminomethyl-benzamide Step i) prepared analogously to example 53c with 5-(tert-butoxycarbonylamino-methyl)-2-chloro-benzoic acid (1.8 g; 6.3 mmol); 1-chloro-N,N,2-trimethylpropenylamine (1.25 mL; 9.45 mmol); 5-amino-N-bromophenyl-2-(2,2-difluoro-ethoxy)-benzamide (2.33 g; 6.3 mmol); pyridine (1.49 mL; 18.9 mmol) in 20 mL MeCN. Step ii) The residue was mixed with 50 mL dioxan and 50 mL 4 M HCl in dioxan, stirred at rt for 3 h and concentrated i.vac. The residue was mixed with 100 mL water and 10 mL 25% aq $NH_3$, and the precipitate was filtered off and dried.

Yield: 3.2 g (94%) MS: $[M+H]^+=538$; HPLC $R_t=1.96$ min (Method CC-6)

(b) N-[4-(2,2-Difluoroethyl)oxy-3-(4-bromophenyl)aminocarbonyl-phenyl]-2-chloro-5-[(2-methyl-1-methoxy-ethyl)carbonylamino]methyl-benzamide N-4-(2,2-Difluoroethyl)oxy-3-(4-bromophenyl)aminocarbonyl-2-chloro-5-aminomethyl-benzamide (54 mg; 0.1 mmol) in 1 mL DMF was added to a mixture of 2-methoxy-2-methyl-propionic acid (13.2 mg; 0.1 mmol); TEA (35 µL; 0.25 mmol) and TBTU (32 mg; 0.1 mmol) in 1 mL DMF and it was stirred at rt overnight. The mixture was purified by prep. HPLC.

Yield: 23 mg (36%) $C_{29}H_{29}BrClF_2N_3O_5$ (638.9);
MS: $[M+H]^+=638$ HPLC: $R_t=1.67$ min (Method CC-7)

Example 177

N-[4-(4-Trifluoromethyl-piperidin-1-yl)-3-(4-bromophenyl)aminocarbonyl-phenyl]-2,6-dichloro-5-(tert-butylcarbonylamino)methyl-benzamide

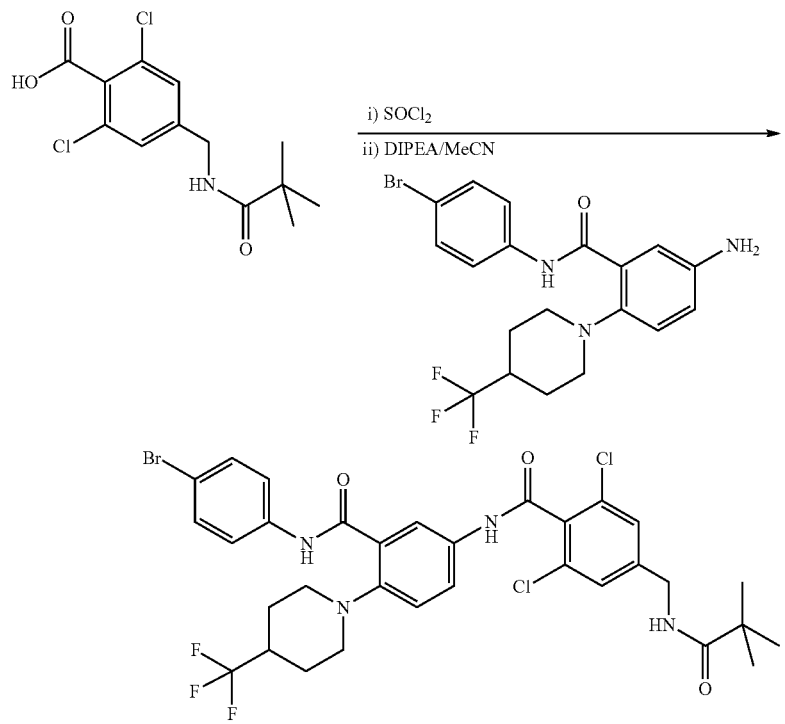

A mixture of 2,6-dichloro-5-(tert-butylcarbonylamino) methyl benzoic acid (30.4 mg; 0.1 mmol) and 2 mL $SOCl_2$ was stirred at reflux for 2 h and concentrated. The residue was diluted with 2 mL MeCN and added to a mixture of 5-amino-N-(4-bromo-phenyl)-2-(4-trifluoromethyl-piperidin-1-yl)-benzamide (21 mg; 0.1 mmol) and DIPEA (50 μL; 0.29 mmol) in 1 mL MeCN, and it was stirred at 60° C. overnight. The mixture was diluted with 2 mL DMF and purified by prep. HPLC Yield: 2.2 mg (3%); $C_{32}H_{32}BrCl_2F_3N_4O_3$ (728.4); MS: $[m+H]^+=727$; HPLC: $R_t=2.16$ min (Method CC-4)

The following examples were prepared in analogy to the methods described above.

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 11 | (structure shown) | $C_{29}H_{32}ClF_6N_3O_4$ 636.03 | 636 | $R_f$= 0.5 (silica gel, DCM:EtOH 19:1) | 3 |

-continued

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 12 | 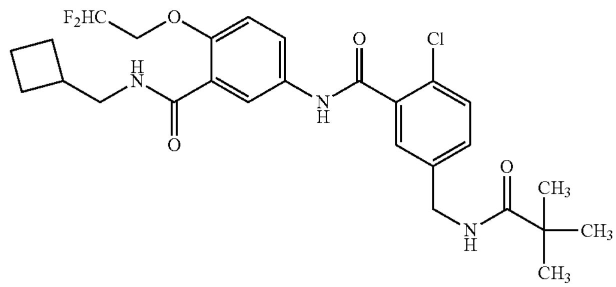 [SMILES: CC(C)(C)C(=O)NCc1ccc(Cl)c(C(=O)Nc2ccc(OCC(F)F)c(C(=O)NCC3CCC3)c2)c1] | $C_{27}H_{32}ClF_2N_3O_4$ 536.01 | 536 | $R_t$ = 1.42 min MC-1 | 5 |
| 13 | 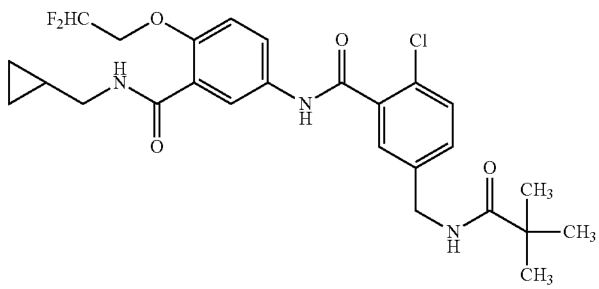 [SMILES: CC(C)(C)C(=O)NCc1ccc(Cl)c(C(=O)Nc2ccc(OCC(F)F)c(C(=O)NCC3CC3)c2)c1] | $C_{26}H_{30}ClF_2N_3O_4$ 521.98 | 522 | $R_t$ = 1.38 min MC-1 | 5 |
| 14 | 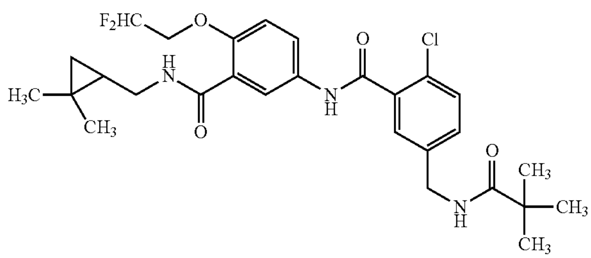 [SMILES: CC(C)(C)C(=O)NCc1ccc(Cl)c(C(=O)Nc2ccc(OCC(F)F)c(C(=O)NCC3CC3(C)C)c2)c1] | $C_{28}H_{34}ClF_2N_3O_4$ 550.04 | 550 | $R_f$ = 0.7 (silica gel, DCM:EtOH 19:1) | 5 |
| 15 | 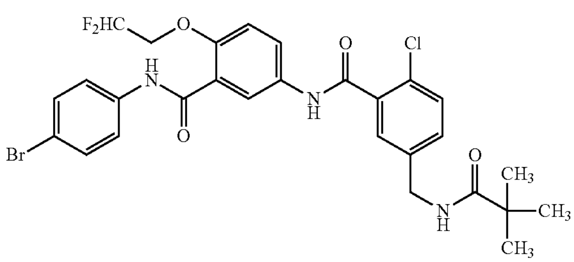 [SMILES: CC(C)(C)C(=O)NCc1ccc(Cl)c(C(=O)Nc2ccc(OCC(F)F)c(C(=O)Nc3ccc(Br)cc3)c2)c1] | $C_{28}H_{27}BrClF_2N_3O_4$ 622.89 | 622 | $R_t$ = 1.53 min MC-1 | 7 |
| 16 | 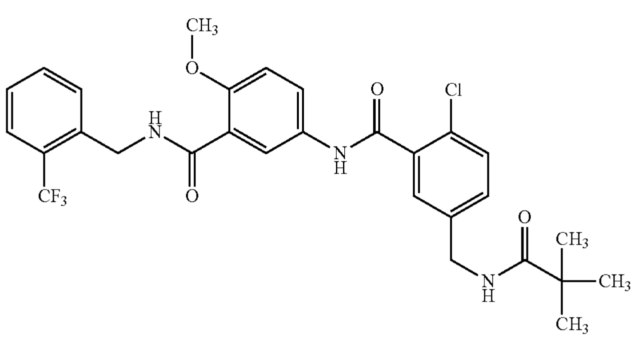 [SMILES: COc1ccc(NC(=O)c2cc(CNC(=O)C(C)(C)C)ccc2Cl)cc1C(=O)NCc1ccccc1C(F)(F)F] | $C_{29}H_{29}ClF_3N_3O_4$ 576.01 | 576 | $R_f$ = 0.63 (silica gel, DCM:EtOH 9:1) | 5 |

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 17 | 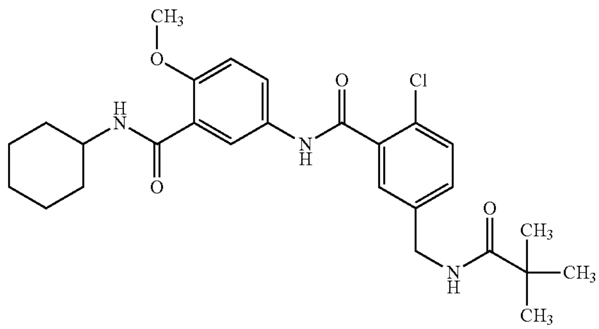 [SMILES: COc1ccc(NC(=O)c2cc(CNC(=O)C(C)(C)C)ccc2Cl)cc1C(=O)NC1CCCCC1] | $C_{27}H_{34}ClN_3O_4$ 500.03 | 500 | $R_f$ = 0.61 (silica gel, DCM:EtOH 9:1) | 5 |
| 18 | 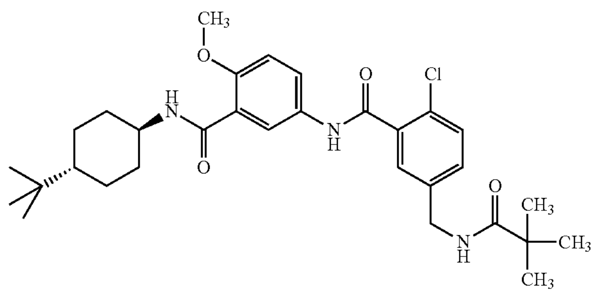 [SMILES: COc1ccc(NC(=O)c2cc(CNC(=O)C(C)(C)C)ccc2Cl)cc1C(=O)N[C@H]1CC[C@H](C(C)(C)C)CC1] | $C_{31}H_{42}ClN_3O_4$ 556.14 | 556 | $R_f$ = 0.72 (silica gel, DCM:EtOH 9:1) | 5 |
| 19 | 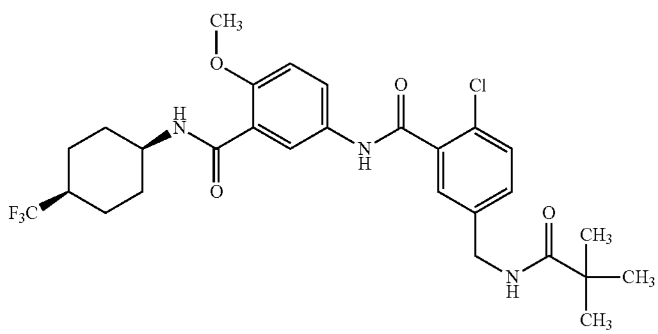 [SMILES: COc1ccc(NC(=O)c2cc(CNC(=O)C(C)(C)C)ccc2Cl)cc1C(=O)N[C@H]1CC[C@@H](C(F)(F)F)CC1] | $C_{28}H_{33}ClF_3N_3O_4$ 568.03 | 568 | $R_f$ = 0.57 (silica gel, DCM:EtOH 9:1) | 5 |
| 20 | 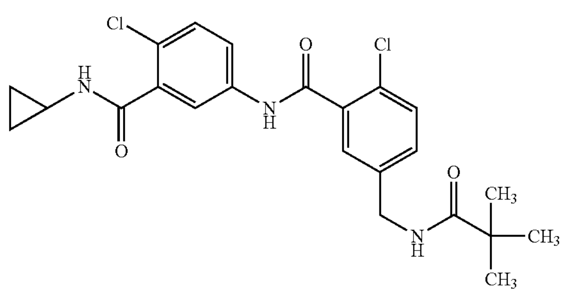 [SMILES: CC(C)(C)C(=O)NCc1ccc(Cl)c(C(=O)Nc2ccc(Cl)c(C(=O)NC3CC3)c2)c1] | $C_{23}H_{25}Cl_2N_3O_3$ 462.37 | 462 | $R_t$ = 1.87 min CC-1 | 10 |
| 21 | 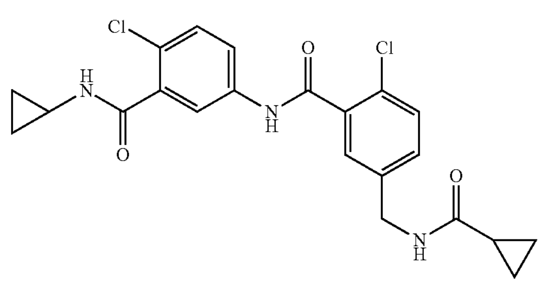 [SMILES: O=C(Nc1ccc(Cl)c(C(=O)NC2CC2)c1)c1cc(CNC(=O)C2CC2)ccc1Cl] | $C_{22}H_{21}Cl_2N_3O_3$ 446.33 | 446 | $R_t$ = 1.81 min CC-1 | 10 |

-continued

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 22 | 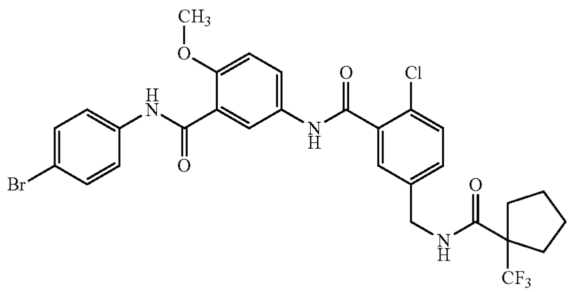 [SMILES: COc1ccc(NC(=O)c2cc(CNC(=O)C3(C(F)(F)F)CCCC3)ccc2Cl)cc1C(=O)Nc1ccc(Br)cc1] | $C_{29}H_{26}BrClF_3N_3O_4$ 652.89 | 652 | $R_t$ = 2.01 min CC-1 | 9 |
| 23 | 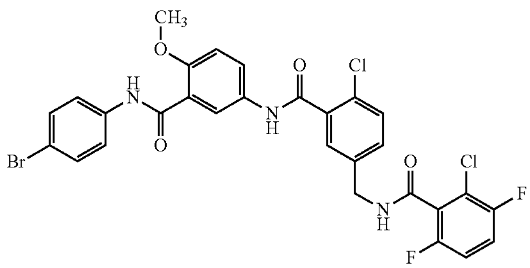 [SMILES: COc1ccc(NC(=O)c2cc(CNC(=O)c3c(F)ccc(F)c3Cl)ccc2Cl)cc1C(=O)Nc1ccc(Br)cc1] | $C_{29}H_{20}BrCl_2F_2N_3O_4$ 663.30 | 662 | $R_t$ = 1.97 min CC-1 | 9 |
| 24 | 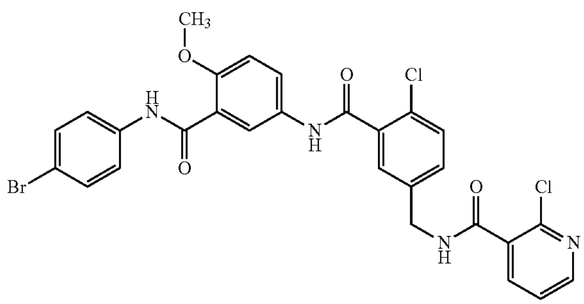 [SMILES: COc1ccc(NC(=O)c2cc(CNC(=O)c3cccnc3Cl)ccc2Cl)cc1C(=O)Nc1ccc(Br)cc1] | $C_{28}H_{21}BrCl_2N_4O_4$ 628.31 | 627 | $R_t$ = 1.94 min CC-1 | 9 |
| 25 | 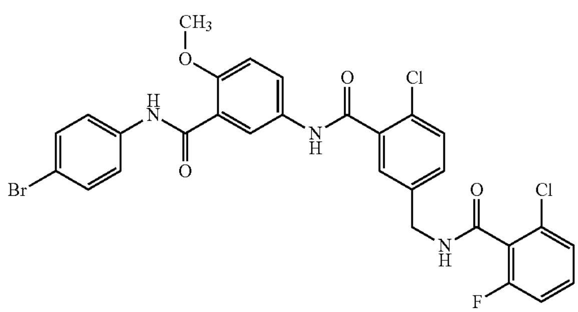 [SMILES: COc1ccc(NC(=O)c2cc(CNC(=O)c3c(F)cccc3Cl)ccc2Cl)cc1C(=O)Nc1ccc(Br)cc1] | $C_{29}H_{21}BrCl_2FN_3O_4$ 645.31 | 644 | $R_t$ = 1.96 min CC-1 | 9 |
| 26 | 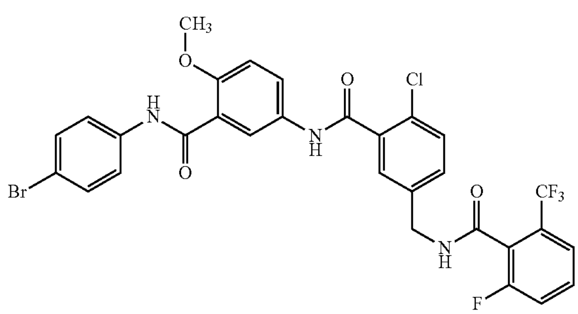 [SMILES: COc1ccc(NC(=O)c2cc(CNC(=O)c3c(F)cccc3C(F)(F)F)ccc2Cl)cc1C(=O)Nc1ccc(Br)cc1] | $C_{30}H_{21}BrClF_4N_3O_4$ 678.86 | 678 | $R_t$ = 1.96 min CC-1 | 9 |

-continued

| Ex. | Structure | Formula/Mw. | Ms* m/z [M + H]+ | R$_f$(TLC) or R$_t$ [min] (HPLC-method) | Prepared in analogy to example |
|---|---|---|---|---|---|
| 27 | 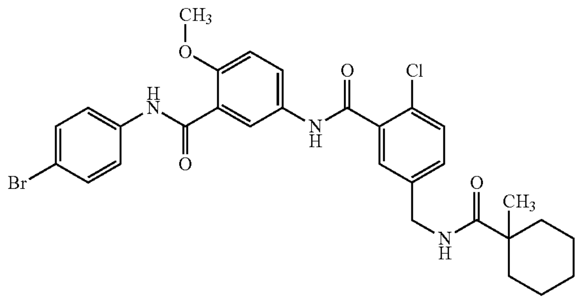 [SMILES: COc1ccc(NC(=O)c2cc(CNC(=O)C3(C)CCCCC3)ccc2Cl)cc1C(=O)Nc1ccc(Br)cc1] | C$_{30}$H$_{31}$BrClN$_3$O$_4$ 612.95 | 612 | R$_t$ = 2.03 min CC-1 | 9 |
| 28 | 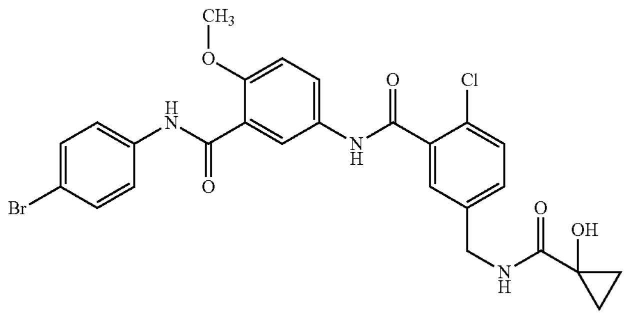 [SMILES: COc1ccc(NC(=O)c2cc(CNC(=O)C3(O)CC3)ccc2Cl)cc1C(=O)Nc1ccc(Br)cc1] | C$_{26}$H$_{23}$BrClN$_3$O$_5$ 572.84 | 572 | R$_t$ = 1.94 min CC-1 | 9 |
| 29 | 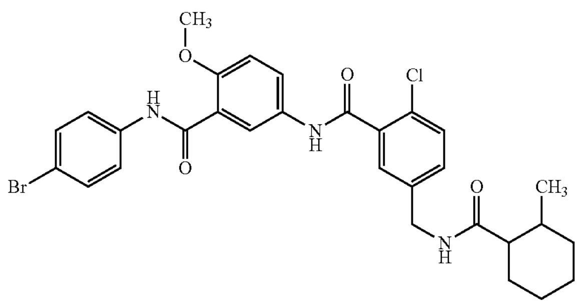 [SMILES: COc1ccc(NC(=O)c2cc(CNC(=O)C3CCCCC3C)ccc2Cl)cc1C(=O)Nc1ccc(Br)cc1] | C$_{30}$H$_{31}$BrClN$_3$O$_4$ 612.95 | 612 | R$_t$ = 2.04 min CC-1 | 9 |
| 30 | 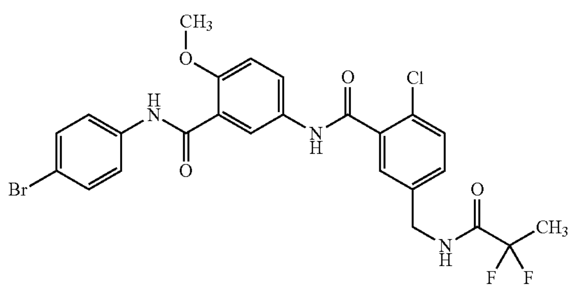 [SMILES: COc1ccc(NC(=O)c2cc(CNC(=O)C(C)(F)F)ccc2Cl)cc1C(=O)Nc1ccc(Br)cc1] | C$_{25}$H$_{21}$BrClF$_2$N$_3$O$_4$ 580.81 | 580 | R$_t$ = 1.95 min CC-1 | 9 |
| 31 | 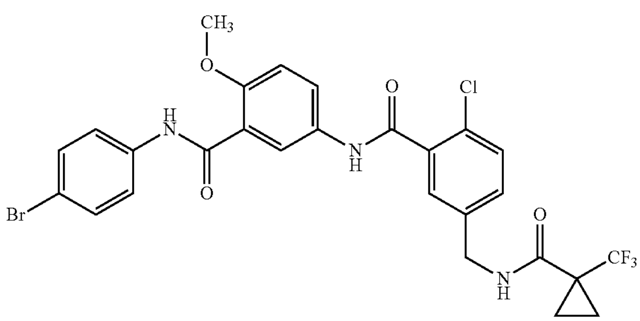 [SMILES: COc1ccc(NC(=O)c2cc(CNC(=O)C3(C(F)(F)F)CC3)ccc2Cl)cc1C(=O)Nc1ccc(Br)cc1] | C$_{27}$H$_{22}$BrClF$_3$N$_3$O$_4$ 624.84 | 624 | R$_t$ = 1.98 min CC-1 | 9 |

-continued

| Ex. | Structure | Formula/Mw. | Ms* m/z [M + H]+ | R$_f$(TLC) or R$_t$ [min] (HPLC-method) | Prepared in analogy to example |
|---|---|---|---|---|---|
| 32 | 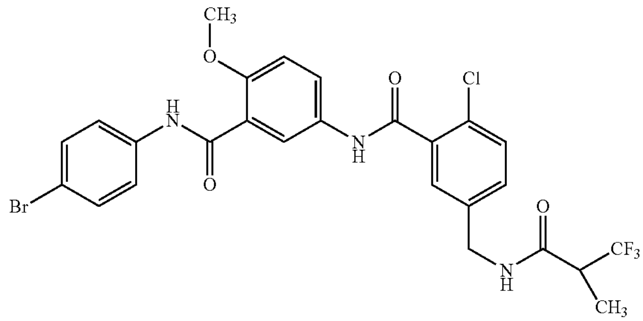 [SMILES: COc1ccc(NC(=O)c2cc(CNC(=O)C(C)C(F)(F)F)ccc2Cl)cc1C(=O)Nc1ccc(Br)cc1] | C$_{26}$H$_{22}$BrClF$_3$N$_3$O$_4$ 612.83 | 612 | R$_t$ = 1.97 min CC-1 | 9 |
| 33 | 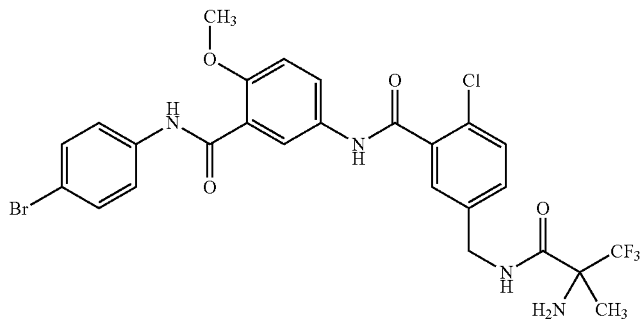 [SMILES: COc1ccc(NC(=O)c2cc(CNC(=O)C(C)(N)C(F)(F)F)ccc2Cl)cc1C(=O)Nc1ccc(Br)cc1] | C$_{26}$H$_{23}$BrClF$_3$N$_4$O$_4$ 627.84 | 627 | R$_t$ = 1.82 min CC-1 | 9 |
| 34 | 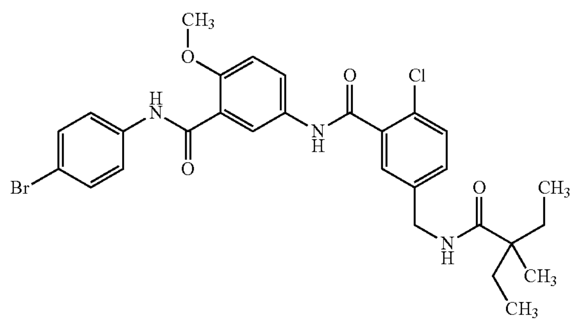 [SMILES: CCC(C)(CC)C(=O)NCc1ccc(Cl)c(C(=O)Nc2ccc(OC)c(C(=O)Nc3ccc(Br)cc3)c2)c1] | C$_{29}$H$_{31}$BrClN$_3$O$_4$ 600.94 | 600 | R$_t$ = 2.03 min CC-1 | 9 |
| 35 | 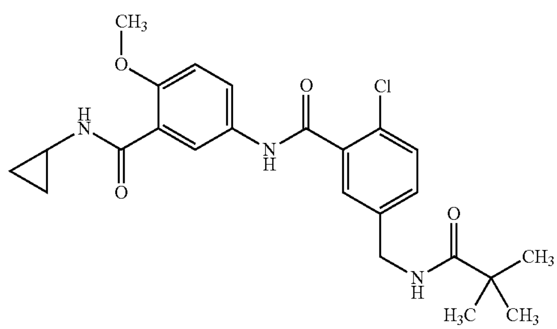 [SMILES: COc1ccc(NC(=O)c2cc(CNC(=O)C(C)(C)C)ccc2Cl)cc1C(=O)NC1CC1] | C$_{24}$H$_{28}$ClN$_3$O$_4$ 457.96 | 458 | R$_t$ = 1.98 min CC-2 | 10 |
| 39 | 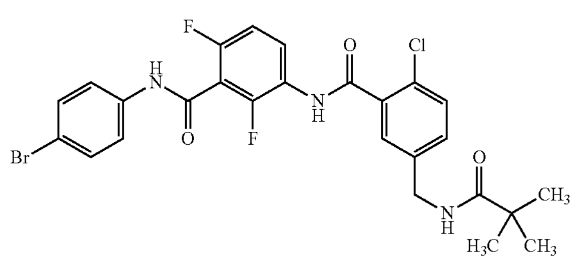 [SMILES: CC(C)(C)C(=O)NCc1ccc(Cl)c(C(=O)Nc2ccc(F)c(C(=O)Nc3ccc(Br)cc3)c2F)c1] | C$_{26}$H$_{23}$ClF$_2$N$_3$O$_3$ 578.83 | 578 | R$_t$ = 1.48 min MC-1 | 38 |

-continued

| Ex. | Structure | Formula/Mw. | Ms* m/z [M + H]+ | R_f (TLC) or R_t [min] (HPLC-method) | Prepared in analogy to example |
|---|---|---|---|---|---|
| 40 | 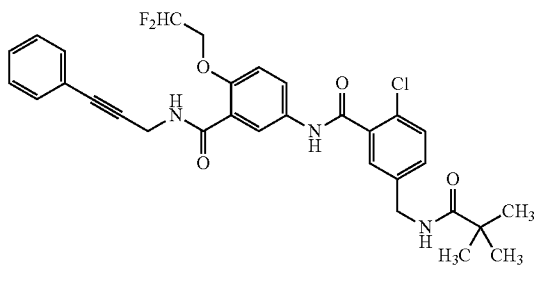 [SMILES: CC(C)(C)C(=O)NCc1ccc(Cl)c(C(=O)Nc2ccc(OCC(F)F)c(C(=O)NCC#Cc3ccccc3)c2)c1] | $C_{31}H_{30}ClF_2N_3O_4$ 582.04 | 582 | $R_t$ = 1.46 min MC-1 | 7 |
| 41 | 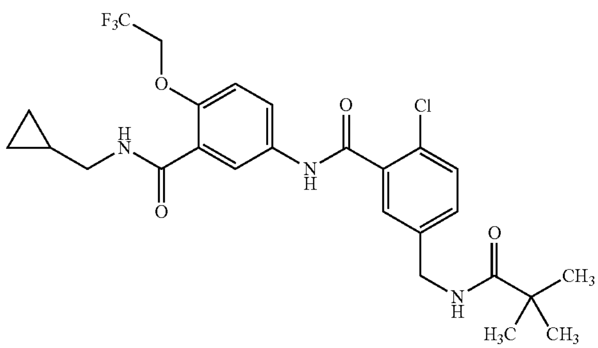 [SMILES: CC(C)(C)C(=O)NCc1ccc(Cl)c(C(=O)Nc2ccc(OCC(F)(F)F)c(C(=O)NCC3CC3)c2)c1] | $C_{26}H_{29}ClF_3N_3O_4$ 539.97 | 540 | $R_t$ = 1.42 min MC-1 | 38 |
| 50 | 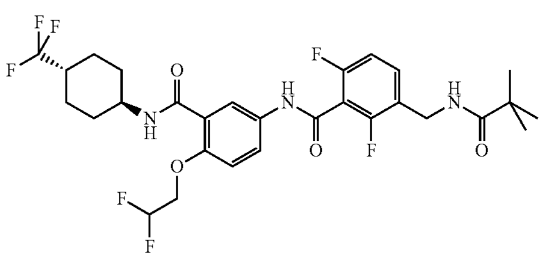 [SMILES: CC(C)(C)C(=O)NCc1ccc(F)c(C(=O)Nc2ccc(OCC(F)F)c(C(=O)N[C@H]3CC[C@H](C(F)(F)F)CC3)c2)c1F] | $C_{29}H_{32}F_7N_3O_4$ 619.57 | 620 | $R_t$ = 2.85 min MC-3 | 48 |
| 61 | 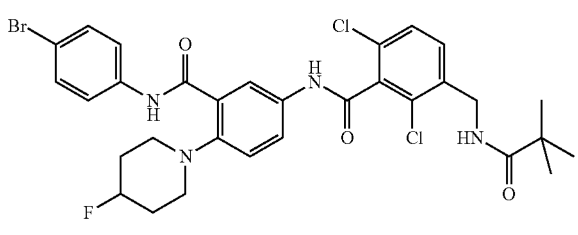 [SMILES: CC(C)(C)C(=O)NCc1ccc(Cl)c(C(=O)Nc2ccc(N3CCC(F)CC3)c(C(=O)Nc3ccc(Br)cc3)c2)c1Cl] | $C_{31}H_{32}BrCl_2FN_4O_3$ 678.42 | 677 | $R_t$ = 3.2 min MC-3 | 60 |
| 63 | 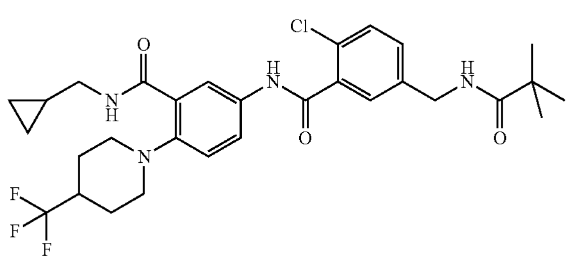 [SMILES: CC(C)(C)C(=O)NCc1ccc(Cl)c(C(=O)Nc2ccc(N3CCC(C(F)(F)F)CC3)c(C(=O)NCC3CC3)c2)c1] | $C_{30}H_{36}ClF_3N_4O_3$ 593.08 | 593 | $R_t$ = 1.52 min MC-1 | 7 |

-continued

| Ex. | Structure | Formula/Mw. | Ms* m/z [M + H]+ | R$_f$(TLC) or R$_t$ [min] (HPLC-method) | Prepared in analogy to example |
|---|---|---|---|---|---|
| 64 | 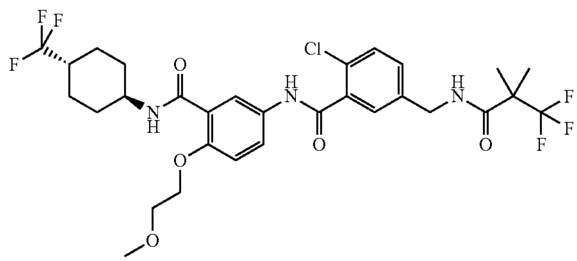 [SMILES: COCCOc1ccc(NC(=O)c2cc(CNC(=O)C(C)(C)C(F)(F)F)ccc2Cl)cc1C(=O)N[C@H]1CC[C@H](C(F)(F)F)CC1] | C$_{30}$H$_{34}$ClF$_6$N$_3$O$_5$ 666.05 | 666 | R$_t$ = 2.7 min CC-5 | 53 |
| 67 | 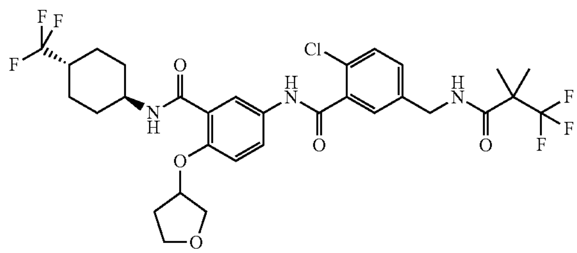 [SMILES: CC(C)(C(=O)NCc1ccc(Cl)c(C(=O)Nc2ccc(OC3CCOC3)c(C(=O)N[C@H]3CC[C@H](C(F)(F)F)CC3)c2)c1)C(F)(F)F] | C$_{31}$H$_{34}$ClF$_6$N$_3$O$_5$ 678.06 | 678 | R$_t$ = 2.68 min CC-5 | 66 |
| 68 | 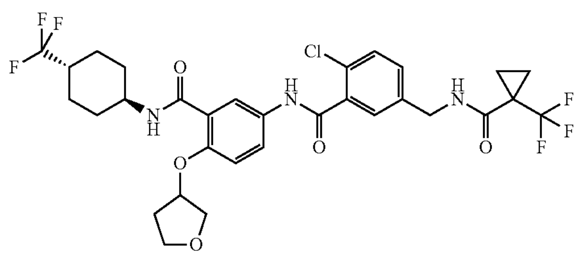 [SMILES: O=C(Nc1ccc(OC2CCOC2)c(C(=O)N[C@H]2CC[C@H](C(F)(F)F)CC2)c1)c1cc(CNC(=O)C2(C(F)(F)F)CC2)ccc1Cl] | C$_{31}$H$_{32}$ClF$_6$N$_3$O$_5$ 676.05 | 676 | R$_t$ = 2.66 min CC-5 | 66 |
| 69 | 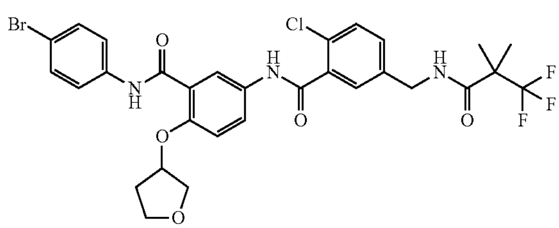 [SMILES: CC(C)(C(=O)NCc1ccc(Cl)c(C(=O)Nc2ccc(OC3CCOC3)c(C(=O)Nc3ccc(Br)cc3)c2)c1)C(F)(F)F] | C$_{30}$H$_{28}$BrClF$_3$N$_3$O$_5$ 682.91 | 682 | R$_t$ = 2.74 min CC-5 | 66 |
| 70 | 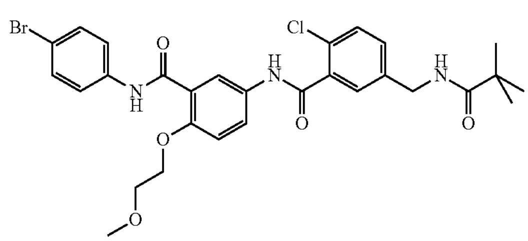 [SMILES: COCCOc1ccc(NC(=O)c2cc(CNC(=O)C(C)(C)C)ccc2Cl)cc1C(=O)Nc1ccc(Br)cc1] | C$_{29}$H$_{31}$BrClN$_3$O$_5$ 616.93 | 616 | R$_t$ = 2.76 min CC-5 | 65 |
| 71 | 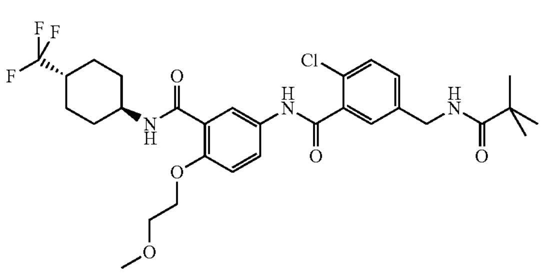 [SMILES: COCCOc1ccc(NC(=O)c2cc(CNC(=O)C(C)(C)C)ccc2Cl)cc1C(=O)N[C@H]1CC[C@H](C(F)(F)F)CC1] | C$_{30}$H$_{37}$ClF$_3$N$_3$O$_5$ 612.08 | 612 | R$_t$ = 2.69 min CC-5 | 53 |

-continued

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 72 | 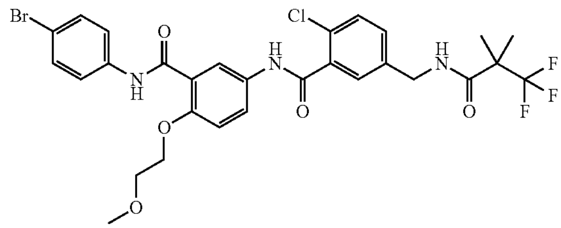 [SMILES: COCCOc1ccc(NC(=O)c2cc(CNC(=O)C(C)(C)C(F)(F)F)ccc2Cl)cc1C(=O)Nc1ccc(Br)cc1] | $C_{29}H_{28}BrClF_3N_3O_5$ 670.9 | 670 | $R_t$ = 2.77 min CC-5 | 65 |
| 74 | 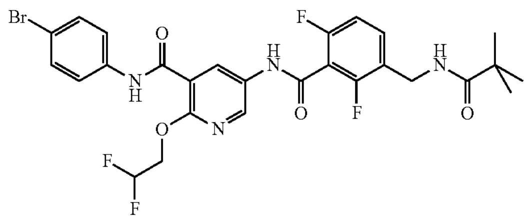 [SMILES: CC(C)(C)C(=O)NCc1ccc(F)c(C(=O)Nc2cnc(OCC(F)F)c(C(=O)Nc3ccc(Br)cc3)c2)c1F] | $C_{27}H_{25}BrF_4N_4O_4$ 625.41 | 625 | $R_t$ = 2.36 min MC-6 | 7 |
| 76 | 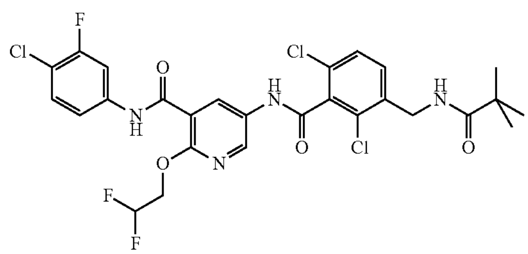 [SMILES: CC(C)(C)C(=O)NCc1ccc(Cl)c(C(=O)Nc2cnc(OCC(F)F)c(C(=O)Nc3ccc(Cl)c(F)c3)c2)c1Cl] | $C_{27}H_{24}Cl_3F_3N_4O_4$ 631.86 | 631 | $R_t$ = 2.39 min MC-6 | 75 |
| 78 | 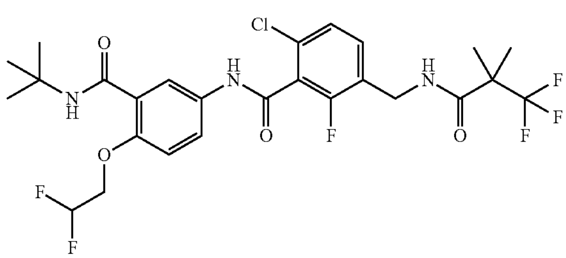 [SMILES: CC(C)(C)NC(=O)c1cc(NC(=O)c2c(Cl)ccc(CNC(=O)C(C)(C)C(F)(F)F)c2F)ccc1OCC(F)F] | $C_{26}H_{28}ClF_6N_3O_4$ 595.96 | 596 | $R_t$ = 2.24 min MC-6 | 75 |
| 79 | 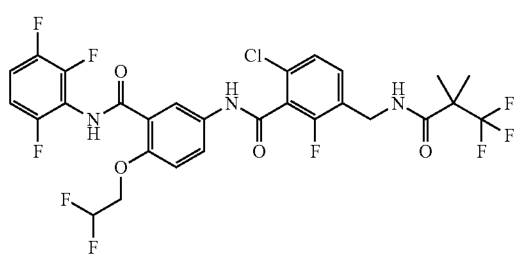 [SMILES: CC(C)(C(=O)NCc1ccc(Cl)c(C(=O)Nc2ccc(OCC(F)F)c(C(=O)Nc3c(F)ccc(F)c3F)c2)c1F)C(F)(F)F] | $C_{28}H_{21}ClF_9N_3O_4$ 669.92 | 670 | $R_t$ = 4.66 min MC-7 | 75 |
| 80 | 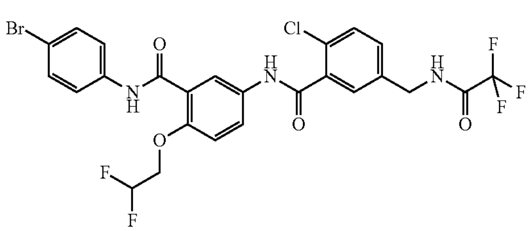 [SMILES: O=C(Nc1ccc(OCC(F)F)c(C(=O)Nc2ccc(Br)cc2)c1)c1cc(CNC(=O)C(F)(F)F)ccc1Cl] | $C_{25}H_{18}BrClF_5N_3O_4$ 634.78 | 634 | $R_t$ = 1.53 min MC-1 | 75 |

-continued

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 81 | 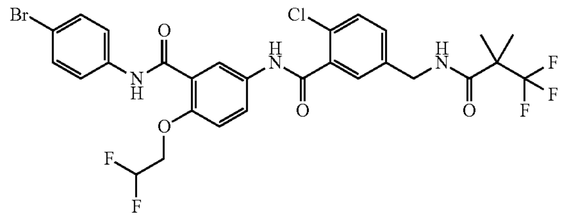 [SMILES: CC(C)(C(=O)NCc1ccc(Cl)c(C(=O)Nc2ccc(OCC(F)F)c(C(=O)Nc3ccc(Br)cc3)c2)c1)C(F)(F)F] | $C_{28}H_{24}BrClF_5N_3O_4$ 676.86 | 676 | $R_t$ = 2.31 min CC-6 | 8 |
| 83 | 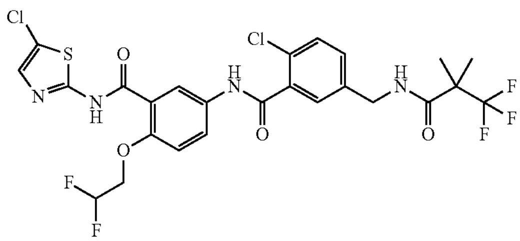 [SMILES: CC(C)(C(=O)NCc1ccc(Cl)c(C(=O)Nc2ccc(OCC(F)F)c(C(=O)Nc3ncc(Cl)s3)c2)c1)C(F)(F)F] | $C_{25}H_{21}Cl_2F_5N_4O_4S$ 639.43 | 639 | $R_t$ = 1.57 min CC-7 | 82 |
| 84 | 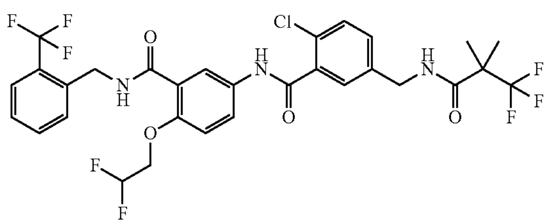 [SMILES: CC(C)(C(=O)NCc1ccc(Cl)c(C(=O)Nc2ccc(OCC(F)F)c(C(=O)NCc3ccccc3C(F)(F)F)c2)c1)C(F)(F)F] | $C_{30}H_{26}ClF_8N_3O_4$ 679.99 | 680 | $R_t$ = 1.67 min CC-7 | 82 |
| 85 | 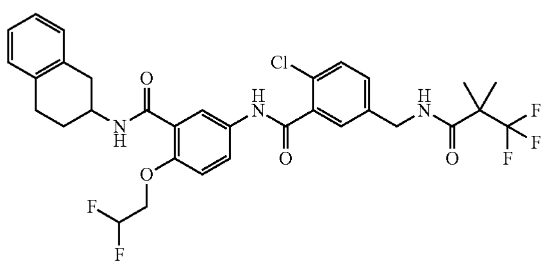 [SMILES: CC(C)(C(=O)NCc1ccc(Cl)c(C(=O)Nc2ccc(OCC(F)F)c(C(=O)NC3CCc4ccccc4C3)c2)c1)C(F)(F)F] | $C_{32}H_{31}ClF_5N_3O_4$ 652.06 | 652 | $R_t$ = 1.72 min CC-7 | 82 |
| 86 | 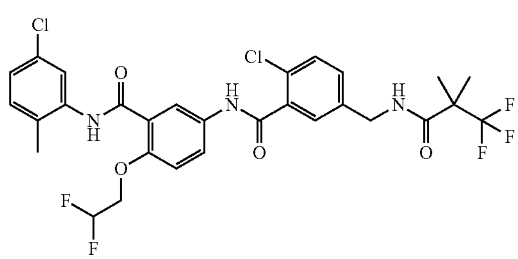 [SMILES: Cc1ccc(Cl)cc1NC(=O)c1cc(NC(=O)c2cc(CNC(=O)C(C)(C)C(F)(F)F)ccc2Cl)ccc1OCC(F)F] | $C_{29}H_{26}Cl_2F_5N_3O_4$ 646.44 | 646 | $R_t$ = 2.03 min CC-1 | 82 |
| 87 | 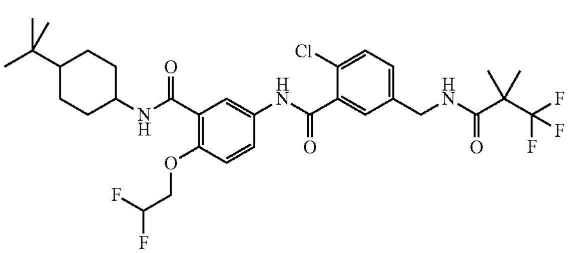 [SMILES: CC(C)(C)C1CCC(NC(=O)c2cc(NC(=O)c3cc(CNC(=O)C(C)(C)C(F)(F)F)ccc3Cl)ccc2OCC(F)F)CC1] | $C_{32}H_{39}ClF_5N_3O_4$ 660.12 | 660 | $R_t$ = 1.87 min CC-7 | 82 |

-continued

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 88 | 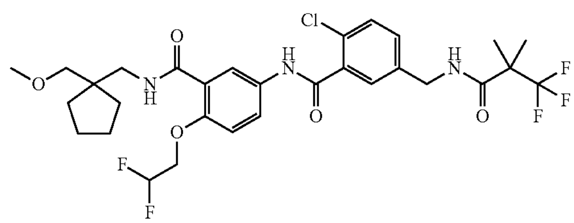 [SMILES: COCC1(CNC(=O)c2cc(NC(=O)c3cc(CNC(=O)C(C)(C)C(F)(F)F)ccc3Cl)ccc2OCC(F)F)CCCC1] | $C_{30}H_{35}ClF_5N_3O_4$ 648.07 | 648 | $R_t$ = 2.3 min CC-2 | 82 |
| 89 | 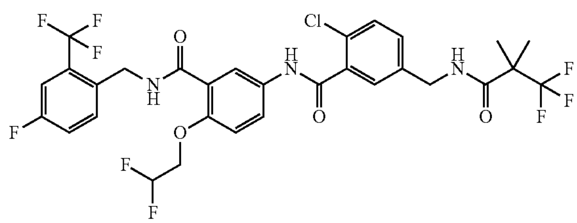 [SMILES: CC(C)(C(=O)NCc1ccc(Cl)c(C(=O)Nc2ccc(OCC(F)F)c(C(=O)NCc3ccc(F)cc3C(F)(F)F)c2)c1)C(F)(F)F] | $C_{30}H_{25}ClF_9N_3O_4$ 697.98 | 698 | $R_t$ = 1.7 min CC-7 | 82 |
| 90 | 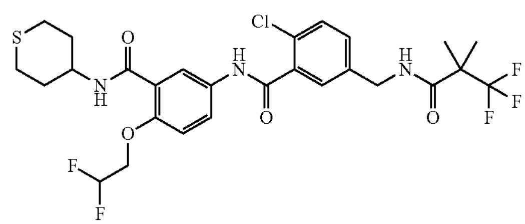 [SMILES: CC(C)(C(=O)NCc1ccc(Cl)c(C(=O)Nc2ccc(OCC(F)F)c(C(=O)NC3CCSCC3)c2)c1)C(F)(F)F] | $C_{27}H_{29}ClF_5N_3O_4S$ 622.05 | 622 | $R_t$ = 1.55 min CC-7 | 82 |
| 91 | 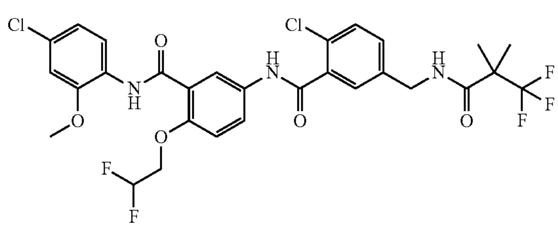 [SMILES: COc1cc(Cl)ccc1NC(=O)c1cc(NC(=O)c2cc(CNC(=O)C(C)(C)C(F)(F)F)ccc2Cl)ccc1OCC(F)F] | $C_{29}H_{26}Cl_2F_5N_3O_5$ 662.44 | 662 | $R_t$ = 1.75 min CC-7 | 82 |
| 92 | 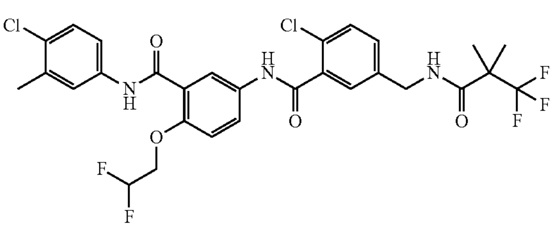 [SMILES: Cc1cc(NC(=O)c2cc(NC(=O)c3cc(CNC(=O)C(C)(C)C(F)(F)F)ccc3Cl)ccc2OCC(F)F)ccc1Cl] | $C_{29}H_{26}Cl_2F_5N_3O_4$ 646.44 | 646 | $R_t$ = 1.76 min CC-7 | 82 |
| 93 | 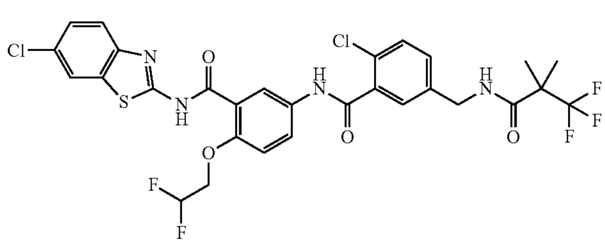 [SMILES: CC(C)(C(=O)NCc1ccc(Cl)c(C(=O)Nc2ccc(OCC(F)F)c(C(=O)Nc3nc4ccc(Cl)cc4s3)c2)c1)C(F)(F)F] | $C_{29}H_{23}Cl_2F_5N_4O_4S$ 689.49 | 689 | $R_t$ = 1.71 min CC-7 | 82 |

-continued

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 94 | 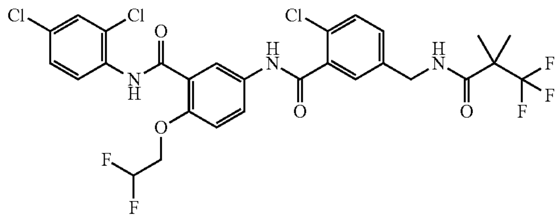 [SMILES: CC(C)(C(=O)NCc1ccc(Cl)c(C(=O)Nc2ccc(OCC(F)F)c(C(=O)Nc3ccc(Cl)cc3Cl)c2)c1)C(F)(F)F] | $C_{28}H_{23}Cl_3F_5N_3O_4$ 666.85 | 666 | $R_t$ = 1.8 min CC-7 | 82 |
| 95 | 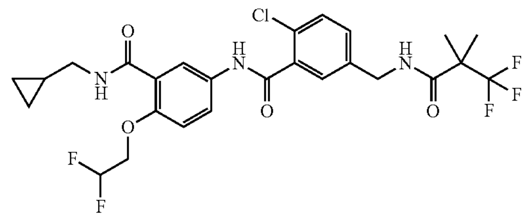 [SMILES: CC(C)(C(=O)NCc1ccc(Cl)c(C(=O)Nc2ccc(OCC(F)F)c(C(=O)NCC3CC3)c2)c1)C(F)(F)F] | $C_{26}H_{27}ClF_5N_3O_4$ 575.96 | 576 | $R_t$ = 1.54 min CC-7 | 82 |
| 96 | 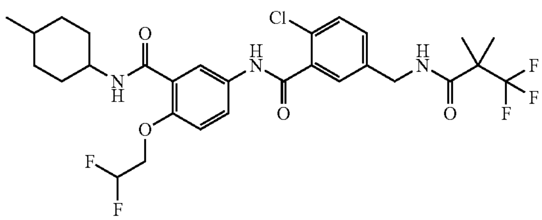 [SMILES: CC1CCC(NC(=O)c2cc(NC(=O)c3cc(CNC(=O)C(C)(C)C(F)(F)F)ccc3Cl)ccc2OCC(F)F)CC1] | $C_{29}H_{33}ClF_5N_3O_4$ 618.04 | 618 | $R_t$ = 1.73 min CC-7 | 82 |
| 97 | 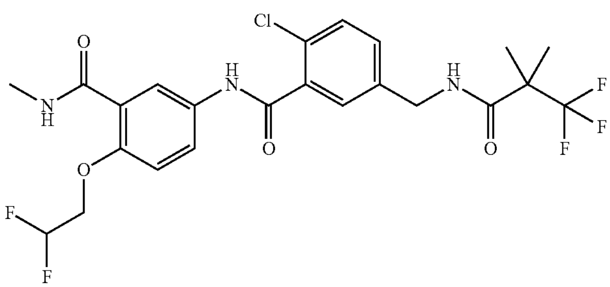 [SMILES: CNC(=O)c1cc(NC(=O)c2cc(CNC(=O)C(C)(C)C(F)(F)F)ccc2Cl)ccc1OCC(F)F] | $C_{23}H_{23}ClF_5N_3O_4$ 535.89 | 536 | $R_t$ = 1.36 min CC-7 | 82 |
| 98 | 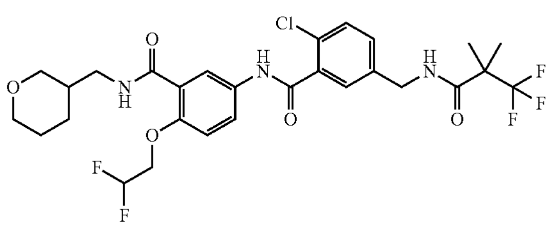 [SMILES: CC(C)(C(=O)NCc1ccc(Cl)c(C(=O)Nc2ccc(OCC(F)F)c(C(=O)NCC3CCCOC3)c2)c1)C(F)(F)F] | $C_{28}H_{31}ClF_5N_3O_5$ 620.01 | 620 | $R_t$ = 1.47 min CC-7 | 82 |
| 99 | 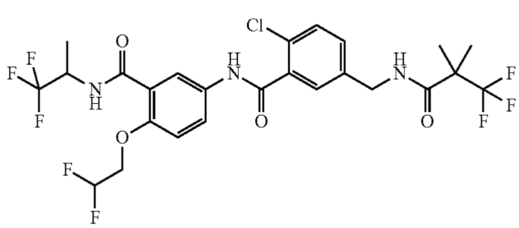 [SMILES: CC(NC(=O)c1cc(NC(=O)c2cc(CNC(=O)C(C)(C)C(F)(F)F)ccc2Cl)ccc1OCC(F)F)C(F)(F)F] | $C_{25}H_{24}ClF_8N_3O_4$ 617.92 | 618 | $R_t$ = 1.55 min CC-7 | 82 |

-continued

| Ex. | Structure | Formula/Mw. | Ms* m/z [M + H]+ | R$_f$(TLC) or R$_t$ [min] (HPLC-method) | Prepared in analogy to example |
|---|---|---|---|---|---|
| 100 | 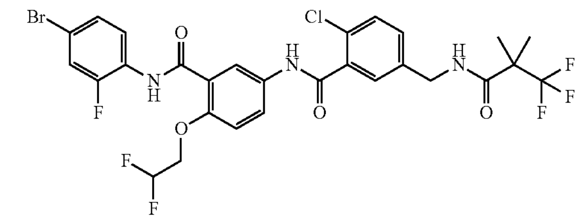 [SMILES: CC(C)(C(=O)NCc1ccc(Cl)c(C(=O)Nc2ccc(OCC(F)F)c(C(=O)Nc3ccc(Br)cc3F)c2)c1)C(F)(F)F] | C$_{28}$H$_{23}$BrClF$_6$N$_3$O$_4$ 694.85 | 694 | R$_t$ = 1.77 min CC-7 | 82 |
| 101 | 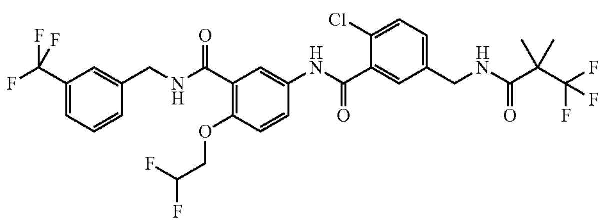 [SMILES: CC(C)(C(=O)NCc1ccc(Cl)c(C(=O)Nc2ccc(OCC(F)F)c(C(=O)NCc3cccc(C(F)(F)F)c3)c2)c1)C(F)(F)F] | C$_{30}$H$_{26}$ClF$_8$N$_3$O$_4$ 679.99 | 680 | R$_t$ = 1.66 min CC-7 | 82 |
| 102 | 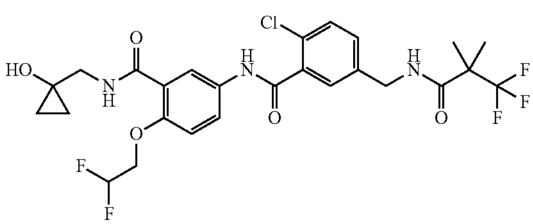 [SMILES: CC(C)(C(=O)NCc1ccc(Cl)c(C(=O)Nc2ccc(OCC(F)F)c(C(=O)NCC3(O)CC3)c2)c1)C(F)(F)F] | C$_{26}$H$_{27}$ClF$_5$N$_3$O$_5$ 591.96 | 592 | R$_t$ = 1.39 min CC-7 | 82 |
| 103 | 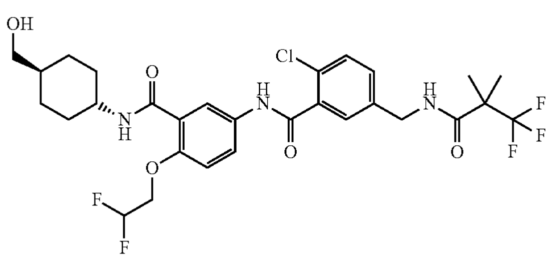 | C$_{29}$H$_{33}$ClF$_5$N$_3$O$_5$ 634.04 | 634 | R$_t$ = 1.45 min CC-7 | 82 |
| 104 | 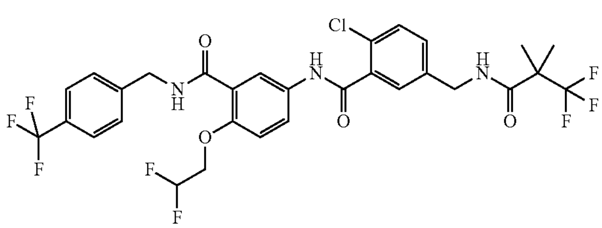 [SMILES: CC(C)(C(=O)NCc1ccc(Cl)c(C(=O)Nc2ccc(OCC(F)F)c(C(=O)NCc3ccc(C(F)(F)F)cc3)c2)c1)C(F)(F)F] | C$_{30}$H$_{26}$ClF$_8$N$_3$O$_4$ 679.99 | 680 | R$_t$ = 1.66 min CC-7 | 82 |
| 105 | 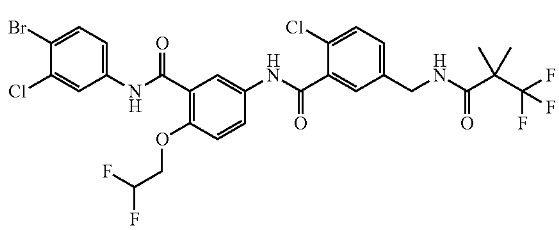 [SMILES: CC(C)(C(=O)NCc1ccc(Cl)c(C(=O)Nc2ccc(OCC(F)F)c(C(=O)Nc3ccc(Br)c(Cl)c3)c2)c1)C(F)(F)F] | C$_{28}$H$_{23}$BrCl$_2$F$_5$N$_3$O$_4$ 711.31 | 710 | R$_t$ = 1.79 min CC-7 | 82 |

-continued
| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 106 | 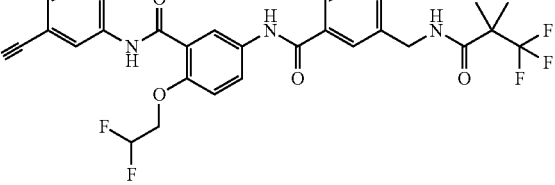 | $C_{29}H_{23}Cl_2F_5N_4O_4$ 657.42 | 657 | $R_t$ = 1.64 min CC-7 | 82 |
| 107 | 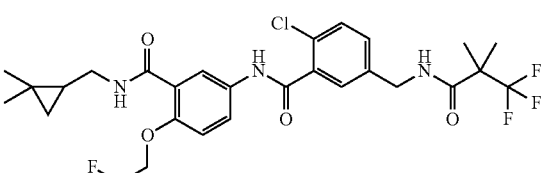 | $C_{28}H_{31}ClF_5N_3O_4$ 604.01 | 604 | $R_t$ = 1.67 min CC-7 | 82 |
| 108 | 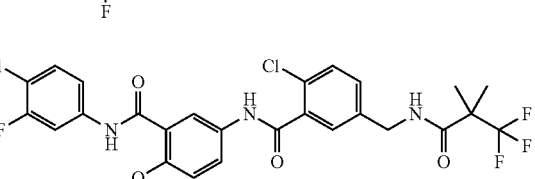 | $C_{28}H_{23}Cl_2F_6N_3O_4$ 650.4 | 650 | $R_t$ = 1.72 min CC-7 | 82 |
| 109 | 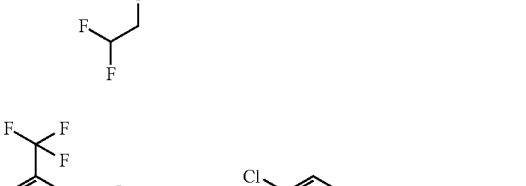 | $C_{28}H_{23}ClF_8N_4O_4$ 666.95 | 667 | $R_t$ = 1.69 min CC-7 | 82 |
| 110 | 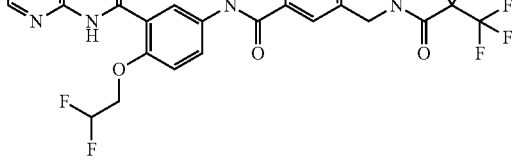 | $C_{25}H_{27}ClF_5N_3O_4$ 563.95 | 564 | $R_t$ = 1.51 min CC-7 | 82 |
| 111 | 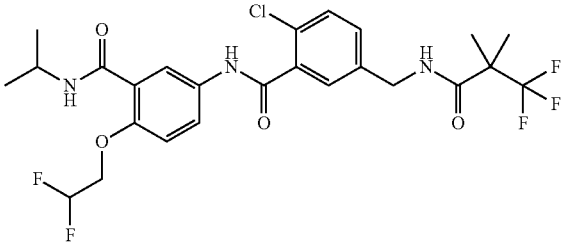 [SMILES: CC(C)NC(=O)c1cc(NC(=O)c2cc(CNC(=O)C(C)(C)C(F)(F)F)ccc2Cl)ccc1OCC(F)F] | $C_{27}H_{29}ClF_5N_3O_4$ 589.99 | 590 | $R_t$ = 1.61 min CC-7 | 82 |

-continued

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 112 | 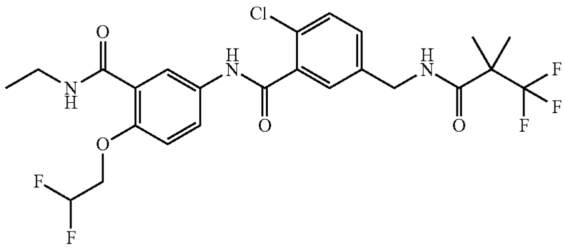 [SMILES: CCNC(=O)c1cc(NC(=O)c2cc(CNC(=O)C(C)(C)C(F)(F)F)ccc2Cl)ccc1OCC(F)F] | $C_{24}H_{25}ClF_5N_3O_4$ 549.92 | 550 | $R_t$ = 1.44 min CC-7 | 82 |
| 113 | 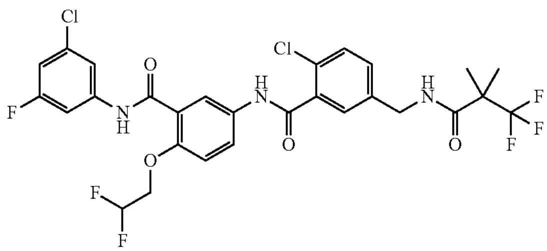 [SMILES: CC(C)(C(=O)NCc1ccc(Cl)c(C(=O)Nc2ccc(OCC(F)F)c(C(=O)Nc3cc(F)cc(Cl)c3)c2)c1)C(F)(F)F] | $C_{28}H_{23}Cl_2F_6N_3O_4$ 650.4 | 650 | $R_t$ = 1.74 min CC-7 | 82 |
| 114 | 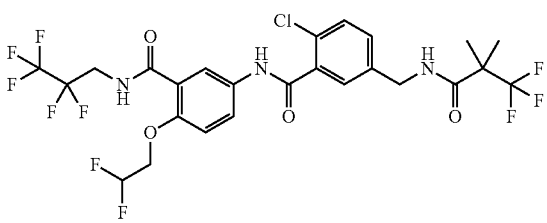 [SMILES: CC(C)(C(=O)NCc1ccc(Cl)c(C(=O)Nc2ccc(OCC(F)F)c(C(=O)NCC(F)(F)C(F)(F)F)c2)c1)C(F)(F)F] | $C_{25}H_{22}ClF_{10}N_3O_4$ 563.9 | 654 | $R_t$ = 1.58 min CC-7 | 82 |
| 115 | 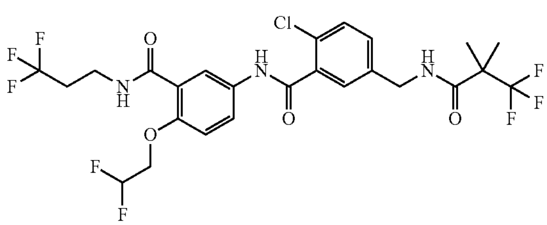 [SMILES: CC(C)(C(=O)NCc1ccc(Cl)c(C(=O)Nc2ccc(OCC(F)F)c(C(=O)NCCC(F)(F)F)c2)c1)C(F)(F)F] | $C_{25}H_{24}ClF_8N_3O_4$ 617.92 | 618 | $R_t$ = 1.51 min CC-7 | 82 |
| 116 | 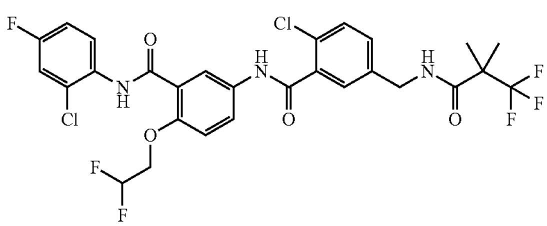 [SMILES: CC(C)(C(=O)NCc1ccc(Cl)c(C(=O)Nc2ccc(OCC(F)F)c(C(=O)Nc3ccc(F)cc3Cl)c2)c1)C(F)(F)F] | $C_{28}H_{23}Cl_2F_6N_3O_4$ 650.4 | 650 | $R_t$ = 1.7 min CC-7 | 82 |
| 117 | 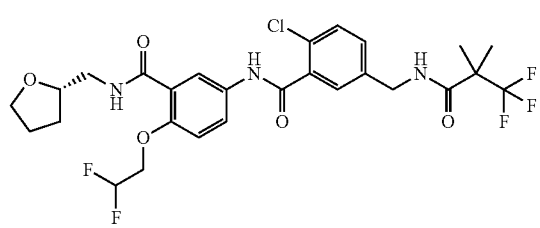 [SMILES: CC(C)(C(=O)NCc1ccc(Cl)c(C(=O)Nc2ccc(OCC(F)F)c(C(=O)NC[C@@H]3CCCO3)c2)c1)C(F)(F)F] | $C_{27}H_{29}ClF_5N_3O_5$ 605.98 | 606 | $R_t$ = 2.09 min CC-2 | 82 |

-continued

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 118 | 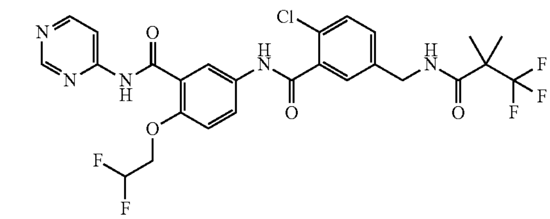 [SMILES: CC(C)(C(=O)NCc1ccc(Cl)c(C(=O)Nc2ccc(OCC(F)F)c(C(=O)Nc3ccncn3)c2)c1)C(F)(F)F] | $C_{26}H_{23}ClF_5N_5O_4$ 599.95 | 600 | $R_t$ = 1.46 min CC-7 | 82 |
| 119 | 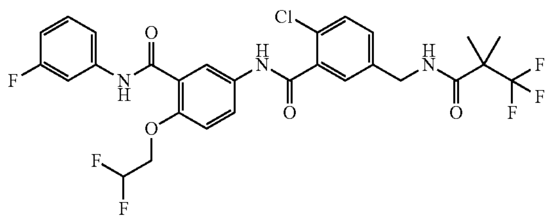 [SMILES: CC(C)(C(=O)NCc1ccc(Cl)c(C(=O)Nc2ccc(OCC(F)F)c(C(=O)Nc3cccc(F)c3)c2)c1)C(F)(F)F] | $C_{28}H_{24}ClF_6N_3O_4$ 615.95 | 616 | $R_t$ = 1.63 min CC-7 | 82 |
| 120 | 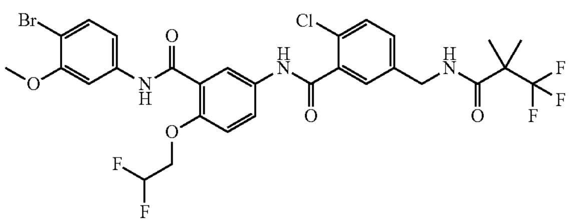 [SMILES: COc1cc(NC(=O)c2cc(NC(=O)c3cc(CNC(=O)C(C)(C)C(F)(F)F)ccc3Cl)ccc2OCC(F)F)ccc1Br] | $C_{29}H_{26}BrClF_5N_3O_5$ 706.89 | 706 | $R_t$ = 1.7 min CC-7 | 82 |
| 121 | 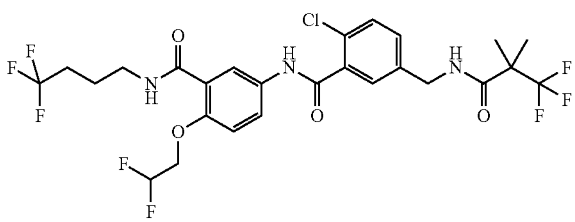 [SMILES: CC(C)(C(=O)NCc1ccc(Cl)c(C(=O)Nc2ccc(OCC(F)F)c(C(=O)NCCCC(F)(F)F)c2)c1)C(F)(F)F] | $C_{26}H_{26}ClF_8N_3O_4$ 631.94 | 632 | $R_t$ = 1.55 min CC-7 | 82 |
| 122 | 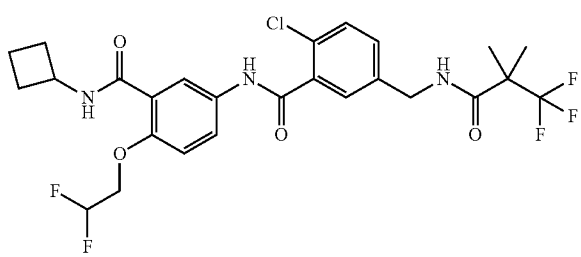 [SMILES: CC(C)(C(=O)NCc1ccc(Cl)c(C(=O)Nc2ccc(OCC(F)F)c(C(=O)NC3CCC3)c2)c1)C(F)(F)F] | $C_{26}H_{27}ClF_5N_3O_4$ 575.96 | 576 | $R_t$ = 1.55 min CC-7 | 82 |
| 123 | 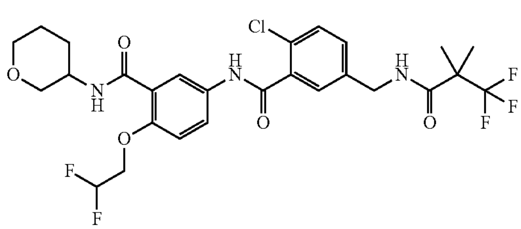 [SMILES: CC(C)(C(=O)NCc1ccc(Cl)c(C(=O)Nc2ccc(OCC(F)F)c(C(=O)NC3CCCOC3)c2)c1)C(F)(F)F] | $C_{27}H_{29}ClF_5N_3O_5$ 605.98 | 606 | $R_t$ = 1.47 min CC-7 | 82 |

-continued

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 124 | 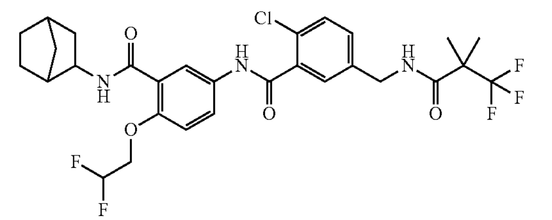 [SMILES: CC(C)(C(=O)NCc1ccc(Cl)c(C(=O)Nc2ccc(OCC(F)F)c(C(=O)NC3CC4CCC3C4)c2)c1)C(F)(F)F] | $C_{29}H_{31}ClF_5N_3O_4$ 616.02 | 616 | $R_t$ = 1.69 min CC-7 | 82 |
| 125 | 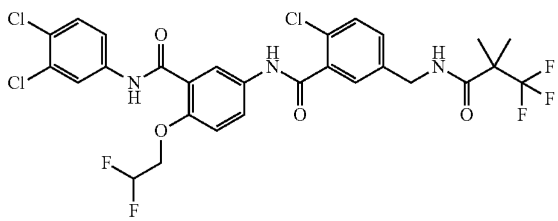 [SMILES: CC(C)(C(=O)NCc1ccc(Cl)c(C(=O)Nc2ccc(OCC(F)F)c(C(=O)Nc3ccc(Cl)c(Cl)c3)c2)c1)C(F)(F)F] | $C_{28}H_{23}Cl_3F_5N_3O_4$ 666.85 | 665 | $R_t$ = 2.44 min CC-2 | 82 |
| 126 | 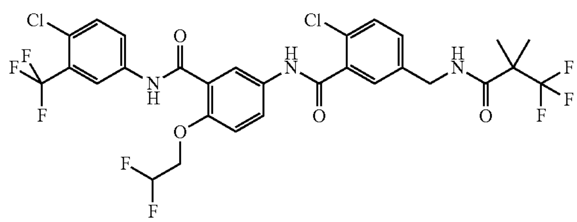 [SMILES: CC(C)(C(=O)NCc1ccc(Cl)c(C(=O)Nc2ccc(OCC(F)F)c(C(=O)Nc3ccc(Cl)c(C(F)(F)F)c3)c2)c1)C(F)(F)F] | $C_{29}H_{23}Cl_2F_8N_3O_4$ 700.41 | 700 | $R_t$ = 1.78 min CC-7 | 82 |
| 127 | 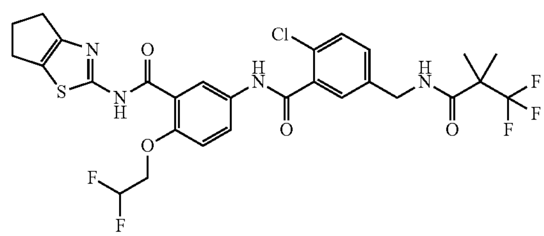 [SMILES: CC(C)(C(=O)NCc1ccc(Cl)c(C(=O)Nc2ccc(OCC(F)F)c(C(=O)Nc3nc4c(s3)CCC4)c2)c1)C(F)(F)F] | $C_{28}H_{26}ClF_5N_4O_4S$ 645.05 | 645 | $R_t$ = 1.67 min CC-7 | 82 |
| 128 | 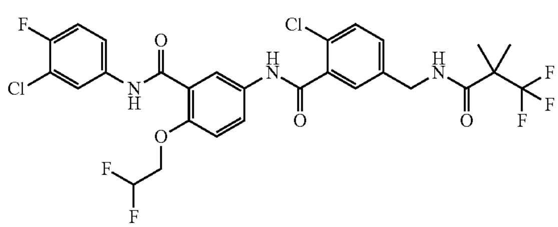 [SMILES: CC(C)(C(=O)NCc1ccc(Cl)c(C(=O)Nc2ccc(OCC(F)F)c(C(=O)Nc3ccc(F)c(Cl)c3)c2)c1)C(F)(F)F] | $C_{28}H_{23}Cl_2F_6N_3O_4$ 650.4 | 650 | $R_t$ = 1.7 min CC-7 | 82 |
| 129 | 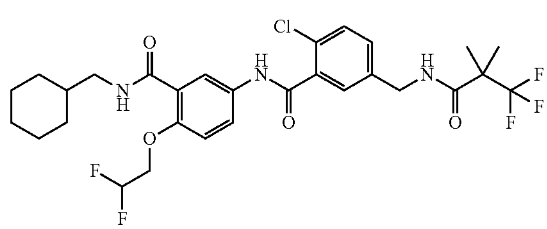 [SMILES: CC(C)(C(=O)NCc1ccc(Cl)c(C(=O)Nc2ccc(OCC(F)F)c(C(=O)NCC3CCCCC3)c2)c1)C(F)(F)F] | $C_{29}H_{33}ClF_5N_3O_4$ 618.04 | 618 | $R_t$ = 1.72 min CC-7 | 82 |

-continued

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 130 | 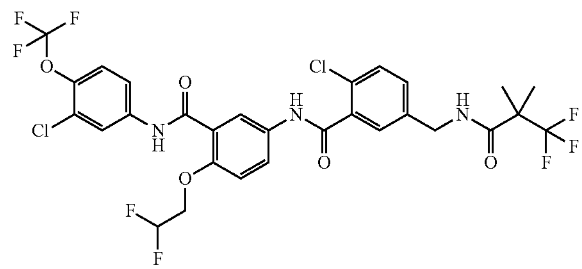 [SMILES: CC(C)(C(=O)NCc1ccc(Cl)c(C(=O)Nc2ccc(OCC(F)F)c(C(=O)Nc3ccc(OC(F)(F)F)c(Cl)c3)c2)c1)C(F)(F)F] | $C_{29}H_{23}Cl_2F_8N_3O_5$ 716.41 | 716 | $R_t$ = 1.8 min CC-7 | 82 |
| 131 | 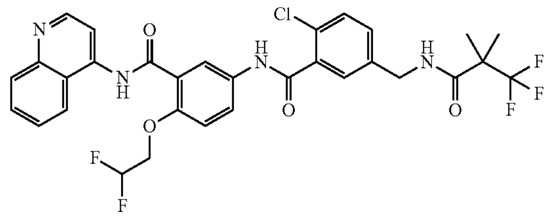 [SMILES: CC(C)(C(=O)NCc1ccc(Cl)c(C(=O)Nc2ccc(OCC(F)F)c(C(=O)Nc3ccnc4ccccc34)c2)c1)C(F)(F)F] | $C_{31}H_{26}ClF_5N_4O_4$ 649.01 | 649 | $R_t$ = 1.57 min CC-7 | 82 |
| 132 | 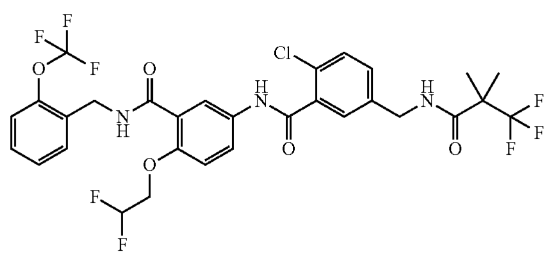 [SMILES: CC(C)(C(=O)NCc1ccc(Cl)c(C(=O)Nc2ccc(OCC(F)F)c(C(=O)NCc3ccccc3OC(F)(F)F)c2)c1)C(F)(F)F] | $C_{30}H_{26}ClF_8N_3O_5$ 695.99 | 696 | $R_t$ = 1.69 min CC-7 | 82 |
| 133 | 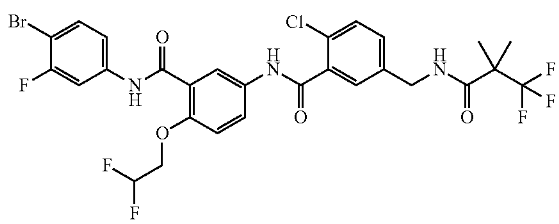 [SMILES: CC(C)(C(=O)NCc1ccc(Cl)c(C(=O)Nc2ccc(OCC(F)F)c(C(=O)Nc3ccc(Br)c(F)c3)c2)c1)C(F)(F)F] | $C_{28}H_{23}BrClF_6N_3O_4$ 694.85 | 694 | $R_t$ = 1.74 min CC-7 | 82 |
| 134 | 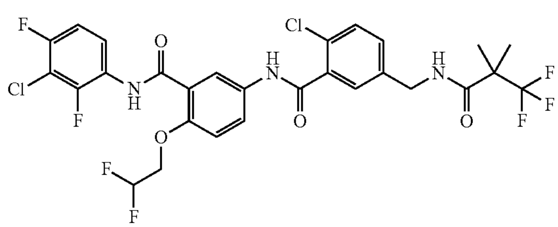 [SMILES: CC(C)(C(=O)NCc1ccc(Cl)c(C(=O)Nc2ccc(OCC(F)F)c(C(=O)Nc3ccc(F)c(Cl)c3F)c2)c1)C(F)(F)F] | $C_{28}H_{22}Cl_2F_7N_3O_4$ 668.39 | 668 | $R_t$ = 1.73 min CC-7 | 82 |
| 135 | 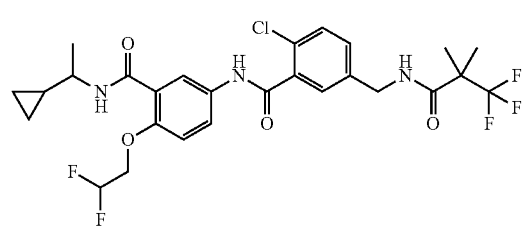 [SMILES: CC(NC(=O)c1cc(NC(=O)c2cc(CNC(=O)C(C)(C)C(F)(F)F)ccc2Cl)ccc1OCC(F)F)C1CC1] | $C_{27}H_{29}ClF_5N_3O_4$ 589.99 | 590 | $R_t$ = 1.59 min CC-7 | 82 |

-continued

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 136 | 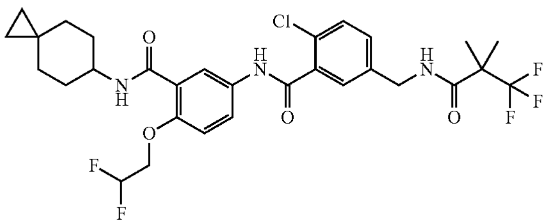 [SMILES: CC(C)(C(=O)NCc1ccc(Cl)c(C(=O)Nc2ccc(OCC(F)F)c(C(=O)NC3CCC4(CC3)CC4)c2)c1)C(F)(F)F] | $C_{30}H_{33}ClF_5N_3O_4$ 630.5 | 630 | $R_t$ = 1.73 min CC-7 | 82 |
| 137 | 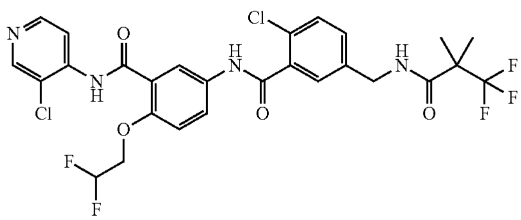 [SMILES: CC(C)(C(=O)NCc1ccc(Cl)c(C(=O)Nc2ccc(OCC(F)F)c(C(=O)Nc3ccncc3Cl)c2)c1)C(F)(F)F] | $C_{27}H_{23}Cl_2F_5N_4O_4$ 633.4 | 633 | $R_t$ = 1.59 min CC-7 | 82 |
| 138 | 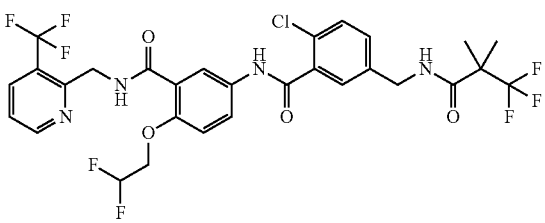 [SMILES: CC(C)(C(=O)NCc1ccc(Cl)c(C(=O)Nc2ccc(OCC(F)F)c(C(=O)NCc3ncccc3C(F)(F)F)c2)c1)C(F)(F)F] | $C_{29}H_{25}ClF_8N_4O_4$ 680.98 | 681 | $R_t$ = 1.61 min CC-7 | 82 |
| 139 | 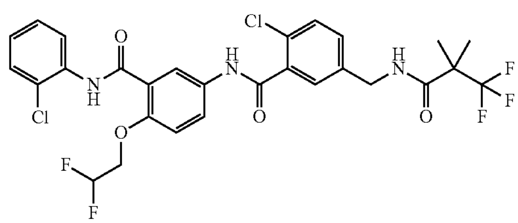 [SMILES: CC(C)(C(=O)NCc1ccc(Cl)c(C(=O)Nc2ccc(OCC(F)F)c(C(=O)Nc3ccccc3Cl)c2)c1)C(F)(F)F] | $C_{28}H_{24}Cl_2F_5N_3O_4$ 632.41 | 632 | $R_t$ = 168 min CC-7 | 82 |
| 140 | 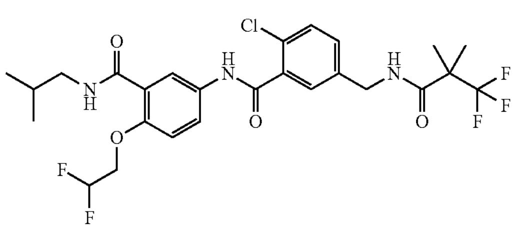 [SMILES: CC(C)CNC(=O)c1cc(NC(=O)c2cc(CNC(=O)C(C)(C)C(F)(F)F)ccc2Cl)ccc1OCC(F)F] | $C_{26}H_{29}ClF_5N_3O_4$ 577.97 | 578 | $R_t$ = 1.58 min CC-7 | 82 |
| 141 | 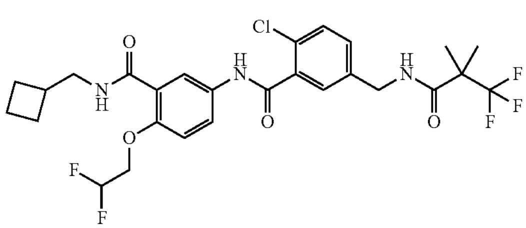 [SMILES: CC(C)(C(=O)NCc1ccc(Cl)c(C(=O)Nc2ccc(OCC(F)F)c(C(=O)NCC3CCC3)c2)c1)C(F)(F)F] | $C_{27}H_{29}ClF_5N_3O_4$ 589.99 | 590 | $R_t$ = 1.62 min CC-7 | 82 |

-continued

| Ex. | Structure | Formula/Mw. | Ms* m/z [M + H]+ | $R_f$(TLC) or $R_t$ [min] (HPLC- method) | Prepared in analogy to example |
|---|---|---|---|---|---|
| 142 | 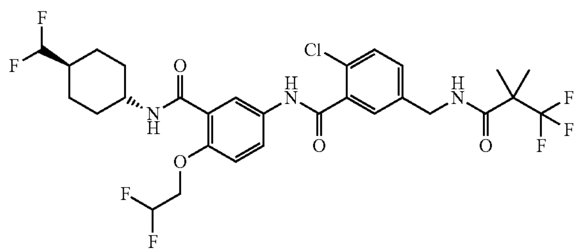 | $C_{29}H_{31}ClF_7N_3O_4$ 654.02 | 654 | $R_t$ = 1.62 min CC-7 | 82 |
| 143 | 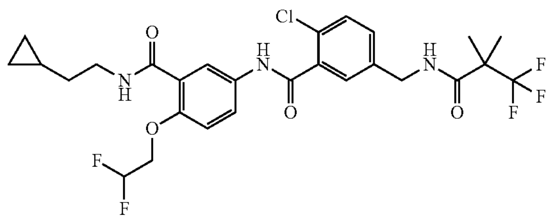 [SMILES: CC(C)(C(=O)NCc1ccc(Cl)c(C(=O)Nc2ccc(OCC(F)F)c(C(=O)NCCC3CC3)c2)c1)C(F)(F)F] | $C_{27}H_{29}ClF_5N_3O_4$ 589.99 | 590 | $R_t$ = 1.59 min CC-7 | 82 |
| 144 | 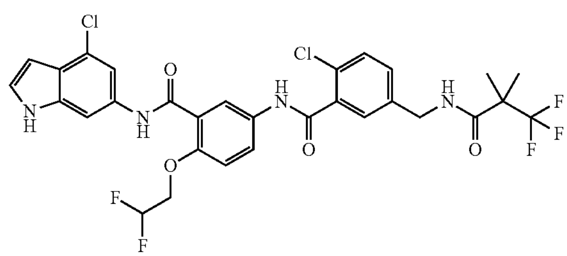 [SMILES: CC(C)(C(=O)NCc1ccc(Cl)c(C(=O)Nc2ccc(OCC(F)F)c(C(=O)Nc3cc(Cl)c4cc[nH]c4c3)c2)c1)C(F)(F)F] | $C_{30}H_{25}Cl_2F_5N_4O_4$ 671.45 | 671 | $R_t$ = 1.64 min CC-7 | 82 |
| 146 | 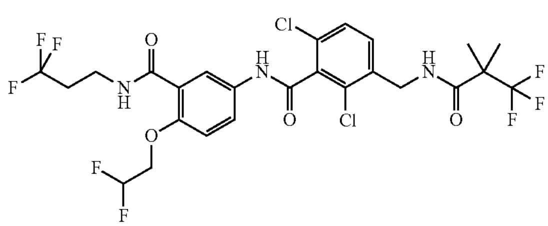 [SMILES: CC(C)(C(=O)NCc1ccc(Cl)c(C(=O)Nc2ccc(OCC(F)F)c(C(=O)NCCC(F)(F)F)c2)c1Cl)C(F)(F)F] | $C_{25}H_{23}Cl_2F_8N_3O_4$ 652.36 | 652 | $R_t$ = 2.29 min CC-8 | 145 |
| 147 | 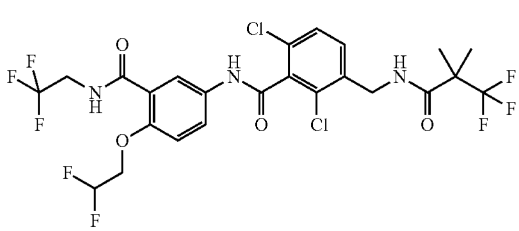 [SMILES: CC(C)(C(=O)NCc1ccc(Cl)c(C(=O)Nc2ccc(OCC(F)F)c(C(=O)NCC(F)(F)F)c2)c1Cl)C(F)(F)F] | $C_{24}H_{21}Cl_2F_8N_3O_4$ 638.34 | 638 | $R_t$ = 2.28 min CC-8 | 145 |
| 148 | 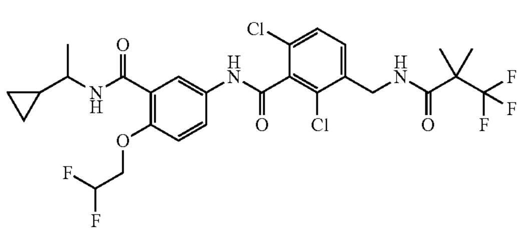 [SMILES: CC(NC(=O)c1cc(NC(=O)c2c(Cl)ccc(CNC(=O)C(C)(C)C(F)(F)F)c2Cl)ccc1OCC(F)F)C1CC1] | $C_{27}H_{28}Cl_2F_5N_3O_4$ 624.43 | 624 | $R_t$ = 2.34 min CC-8 | 145 |

-continued

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 149 | 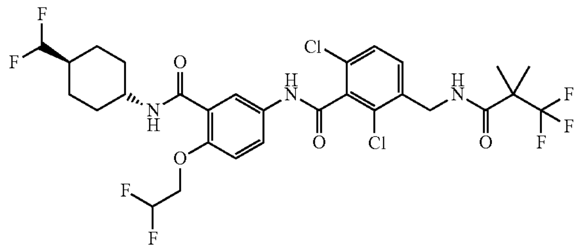 | $C_{29}H_{30}Cl_2F_7N_3O_4$ 688.46 | 688 | $R_t$ = 2.35 min CC-8 | 145 |
| 150 | 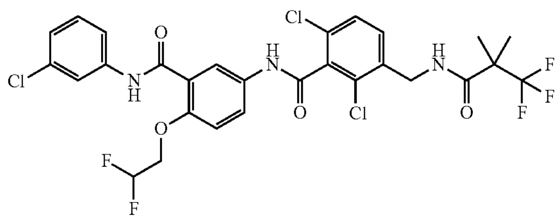 [SMILES: CC(C)(C(=O)NCc1ccc(Cl)c(C(=O)Nc2ccc(OCC(F)F)c(C(=O)Nc3cccc(Cl)c3)c2)c1Cl)C(F)(F)F] | $C_{28}H_{23}Cl_3F_5N_3O_4$ 666.86 | 666 | $R_t$ = 1.48 min CC-8 | 145 |
| 151 | 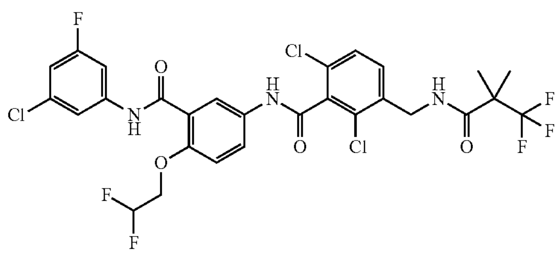 [SMILES: CC(C)(C(=O)NCc1ccc(Cl)c(C(=O)Nc2ccc(OCC(F)F)c(C(=O)Nc3cc(F)cc(Cl)c3)c2)c1Cl)C(F)(F)F] | $C_{28}H_{22}Cl_3F_6N_3O_4$ 684.85 | 684 | $R_t$ = 2.53 min CC-8 | 145 |
| 152 | 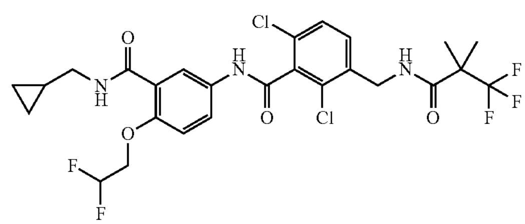 | $C_{26}H_{26}Cl_2F_5N_3O_4$ 610.4 | 610 | $R_t$ = 2.27 min CC-8 | 145 |
| 153 | 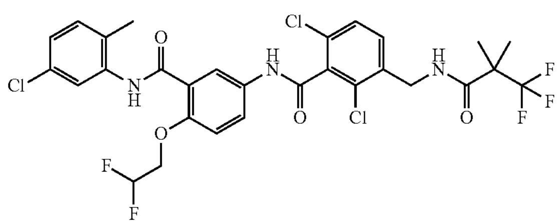 [SMILES: Cc1ccc(Cl)cc1NC(=O)c1cc(NC(=O)c2c(Cl)ccc(CNC(=O)C(C)(C)C(F)(F)F)c2Cl)ccc1OCC(F)F] | $C_{29}H_{25}Cl_3F_5N_3O_4$ 680.88 | 680 | $R_t$ = 2.49 min CC-8 | 145 |
| 154 | 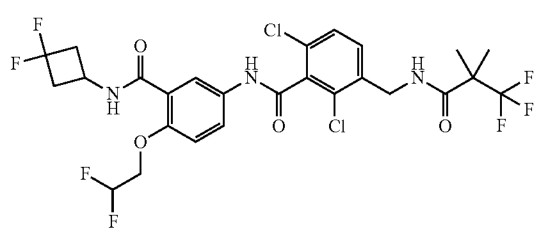 [SMILES: CC(C)(C(=O)NCc1ccc(Cl)c(C(=O)Nc2ccc(OCC(F)F)c(C(=O)NC3CC(F)(F)C3)c2)c1Cl)C(F)(F)F] | $C_{26}H_{24}Cl_2F_7N_3O_4$ 646.38 | 646 | $R_t$ = 2.27 min CC-8 | 145 |

-continued

| Ex. | Structure | Formula/Mw. | Ms* m/z [M + H]+ | $R_f$(TLC) or $R_t$ [min] (HPLC-method) | Prepared in analogy to example |
|---|---|---|---|---|---|
| 155 | 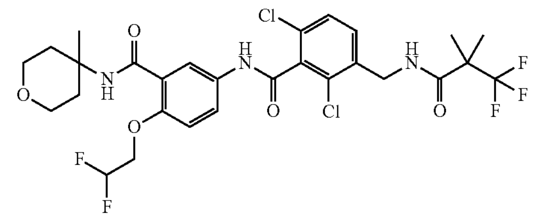 [SMILES: CC1(NC(=O)c2cc(NC(=O)c3c(Cl)ccc(CNC(=O)C(C)(C)C(F)(F)F)c3Cl)ccc2OCC(F)F)CCOCC1] | $C_{28}H_{30}Cl_2F_5N_3O_5$ 654.46 | 654 | $R_t$ = 2.22 min CC-8 | 145 |
| 156 | 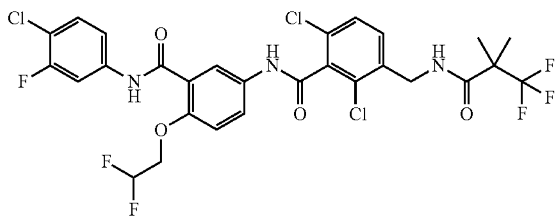 [SMILES: CC(C)(C(=O)NCc1ccc(Cl)c(C(=O)Nc2ccc(OCC(F)F)c(C(=O)Nc3ccc(Cl)c(F)c3)c2)c1Cl)C(F)(F)F] | $C_{28}H_{22}Cl_3F_6N_3O_4$ 684.85 | 684 | $R_t$ = 2.51 min CC-8 | 145 |
| 157 | 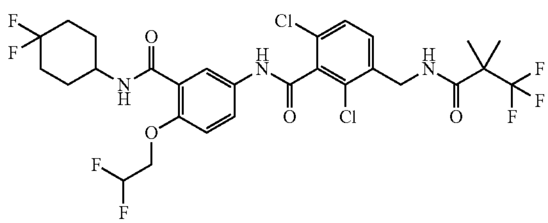 [SMILES: CC(C)(C(=O)NCc1ccc(Cl)c(C(=O)Nc2ccc(OCC(F)F)c(C(=O)NC3CCC(F)(F)CC3)c2)c1Cl)C(F)(F)F] | $C_{28}H_{28}Cl_2F_7N_3O_4$ 674.44 | 674 | $R_t$ = 2.32 min CC-8 | 145 |
| 158 | 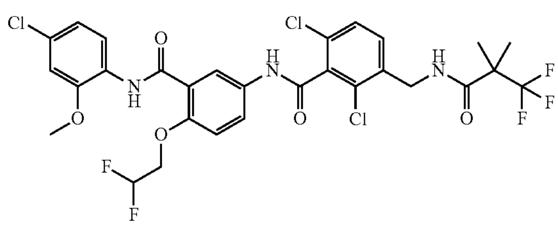 [SMILES: COc1cc(Cl)ccc1NC(=O)c1cc(NC(=O)c2c(Cl)ccc(CNC(=O)C(C)(C)C(F)(F)F)c2Cl)ccc1OCC(F)F] | $C_{29}H_{25}Cl_3F_5N_3O_5$ 696.88 | 696 | $R_t$ = 2.53 min CC-8 | 145 |
| 159 | 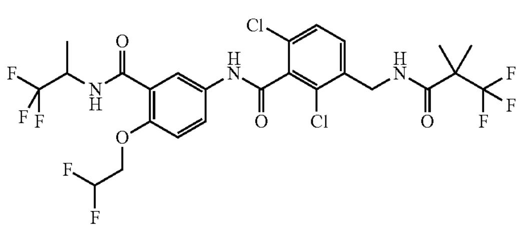 [SMILES: CC(NC(=O)c1cc(NC(=O)c2c(Cl)ccc(CNC(=O)C(C)(C)C(F)(F)F)c2Cl)ccc1OCC(F)F)C(F)(F)F] | $C_{25}H_{23}Cl_2F_8N_3O_4$ 652.36 | 652 | $R_t$ = 2.34 min CC-8 | 145 |
| 161 | 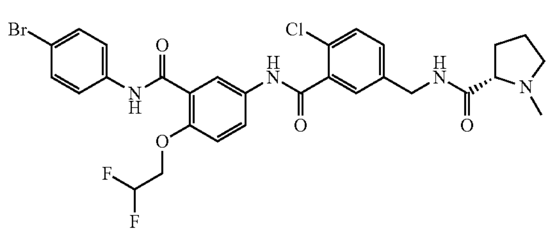 [SMILES: CN1CCC[C@H]1C(=O)NCc1ccc(Cl)c(C(=O)Nc2ccc(OCC(F)F)c(C(=O)Nc3ccc(Br)cc3)c2)c1] | $C_{29}H_{28}BrClF_2N_4O_4$ 649.92 | 649 | $R_t$ = 1.69 min CC-7 | 160 |

-continued
| Ex. | Structure | Formula/Mw. | Ms* m/z [M + H]+ | R$_f$(TLC) or R$_t$ [min] (HPLC-method) | Prepared in analogy to example |
|---|---|---|---|---|---|
| 162 | 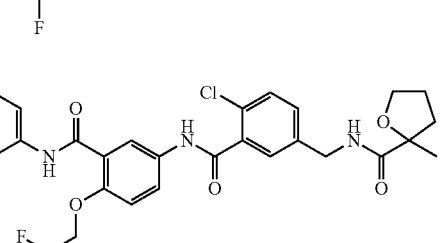 | C$_{27}$H$_{23}$BrClF$_2$N$_3$O$_5$ 622.85 | 622 | R$_t$ = 1.6 min CC-7 | 160 |
| 163 | 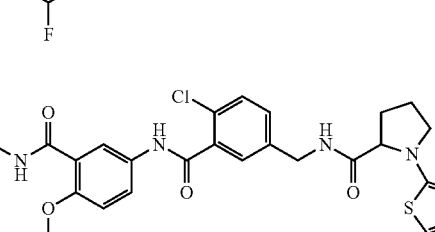 | C$_{29}$H$_{27}$BrClF$_2$N$_3$O$_5$ 650.9 | 650 | R$_t$ = 1.67 min CC-7 | 160 |
| 164 | 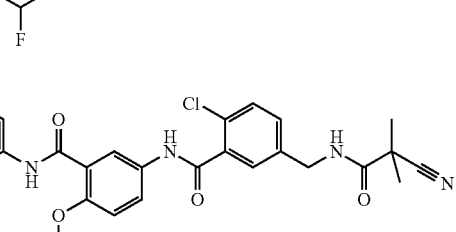 | C$_{31}$H$_{27}$BrClF$_2$N$_5$O$_4$S 719 | 718 | R$_t$ = 1.69 min CC-7 | 160 |
| 165 | 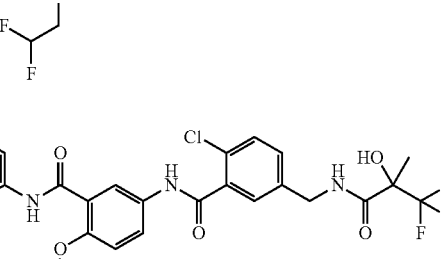 | C$_{28}$H$_{24}$BrClF$_2$N$_4$O$_4$ 633.87 | 633 | R$_t$ = 2.14 min CC-1 | 160 |
| 166 | 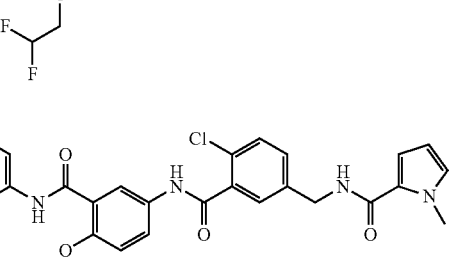 | C$_{27}$H$_{22}$BrClF$_5$N$_3$O$_5$ 678.83 | 678 | R$_t$ = 1.64 min CC-7 | 160 |
| 167 | 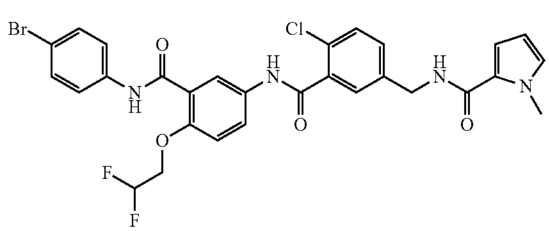 [SMILES: Cn1cccc1C(=O)NCc1ccc(Cl)c(C(=O)Nc2ccc(OCC(F)F)c(C(=O)Nc3ccc(Br)cc3)c2)c1] | C$_{29}$H$_{24}$BrClF$_2$N$_4$O$_4$ 645.88 | 645 | R$_t$ = 2.22 min CC-1 | 160 |

| Ex. | Structure | Formula/Mw. | Ms* m/z [M + H]+ | R_f (TLC) or R_t [min] (HPLC-method) | Prepared in analogy to example |
|---|---|---|---|---|---|
| 168 | 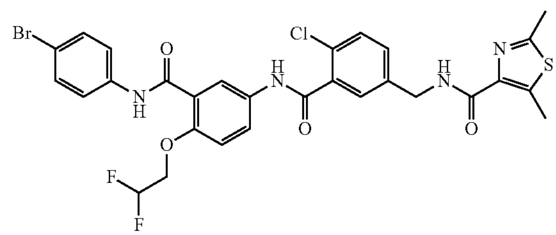 [SMILES: Cc1nc(C(=O)NCc2ccc(Cl)c(C(=O)Nc3ccc(OCC(F)F)c(C(=O)Nc4ccc(Br)cc4)c3)c2)c(C)s1] | C29H24BrClF2N4O4S 677.95 | 677 | R_t = 1.66 min CC-7 | 160 |
| 169 | 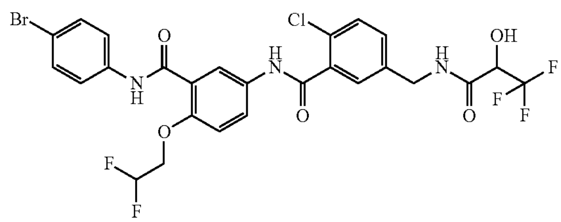 [SMILES: O=C(Nc1ccc(OCC(F)F)c(C(=O)Nc2ccc(Br)cc2)c1)c1cc(CNC(=O)C(O)C(F)(F)F)ccc1Cl] | C26H20BrClF5N3O5 664.81 | 664 | R_t = 1.61 min CC-7 | 160 |
| 170 | 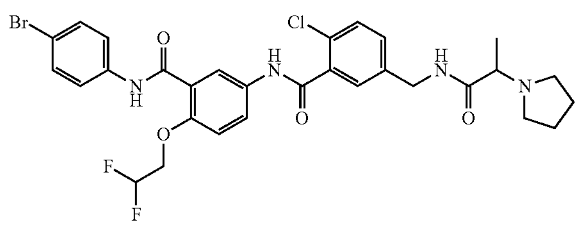 [SMILES: CC(C(=O)NCc1ccc(Cl)c(C(=O)Nc2ccc(OCC(F)F)c(C(=O)Nc3ccc(Br)cc3)c2)c1)N1CCCC1] | C30H30BrClF2N4O4 663.94 | 663 | R_t = 1.72 min CC-7 | 160 |
| 171 | 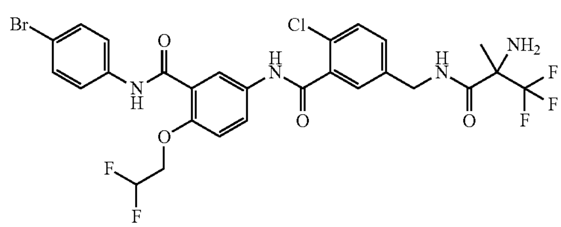 [SMILES: CC(N)(C(=O)NCc1ccc(Cl)c(C(=O)Nc2ccc(OCC(F)F)c(C(=O)Nc3ccc(Br)cc3)c2)c1)C(F)(F)F] | C27H23BrClF5N4O4 677.85 | 677 | R_t = 1.63 min CC-7 | 160 |
| 172 | 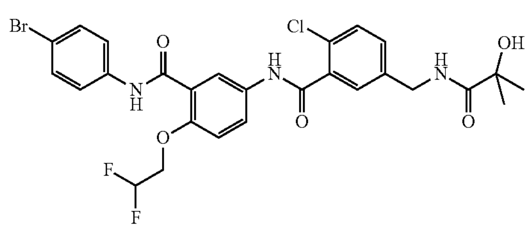 [SMILES: CC(C)(O)C(=O)NCc1ccc(Cl)c(C(=O)Nc2ccc(OCC(F)F)c(C(=O)Nc3ccc(Br)cc3)c2)c1] | C27H25BrClF2N3O5 624.86 | 624 | R_t = 1.6 min CC-7 | 160 |
| 173 | 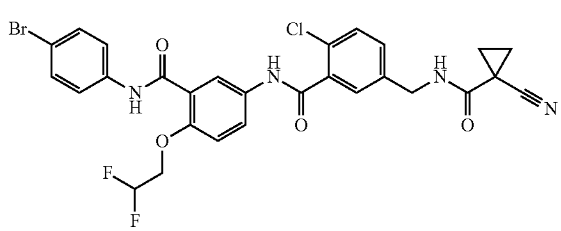 [SMILES: N#CC1(C(=O)NCc2ccc(Cl)c(C(=O)Nc3ccc(OCC(F)F)c(C(=O)Nc4ccc(Br)cc4)c3)c2)CC1] | C28H22BrClF2N4O4 631.86 | 631 | R_t = 1.63 min CC-7 | 160 |

-continued

| Ex. | Structure | Formula/Mw. | Ms* m/z [M + H]+ | R_f (TLC) or R_t [min] (HPLC-method) | Prepared in analogy to example |
|---|---|---|---|---|---|
| 174 | 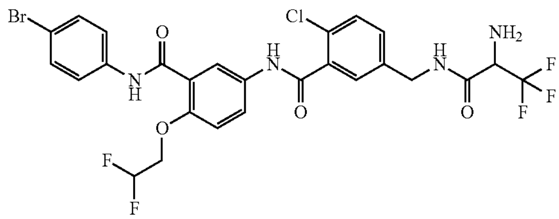 [SMILES: NC(C(=O)NCc1ccc(Cl)c(C(=O)Nc2ccc(OCC(F)F)c(C(=O)Nc3ccc(Br)cc3)c2)c1)C(F)(F)F] | $C_{26}H_{21}BrClF_5N_4O_4$ 663.82 | 663 | $R_t$ = 1.61 min CC-7 | 160 |
| 175 | 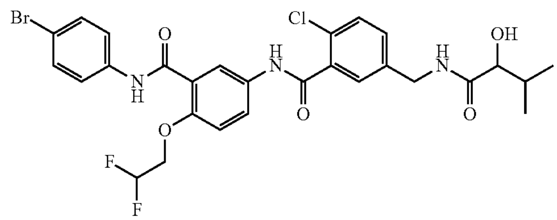 [SMILES: CC(C)C(O)C(=O)NCc1ccc(Cl)c(C(=O)Nc2ccc(OCC(F)F)c(C(=O)Nc3ccc(Br)cc3)c2)c1] | $C_{28}H_{27}BrClF_2N_3O_5$ 638.89 | 638 | $R_t$ = 1.65 min CC-7 | 160 |
| 176 | 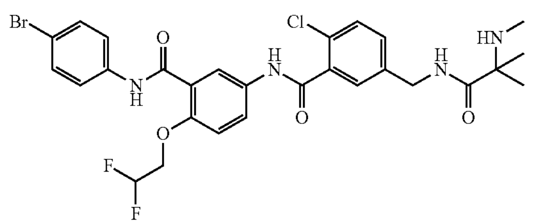 [SMILES: CNC(C)(C)C(=O)NCc1ccc(Cl)c(C(=O)Nc2ccc(OCC(F)F)c(C(=O)Nc3ccc(Br)cc3)c2)c1] | $C_{28}H_{28}BrClF_2N_4O_4$ 637.91 | 637 | $R_t$ = 1.64 min CC-7 | 160 |
| 178 | 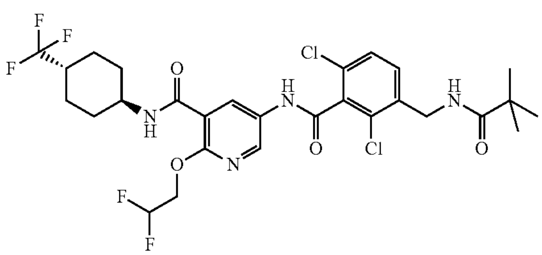 [SMILES: CC(C)(C)C(=O)NCc1ccc(Cl)c(C(=O)Nc2cnc(OCC(F)F)c(C(=O)N[C@H]3CC[C@H](C(F)(F)F)CC3)c2)c1Cl] | $C_{28}H_{31}Cl_2F_5N_4O_4$ 653.47 | 653 | $R_t$ = 1.88 min CC-10 | 177 |
| 179 | 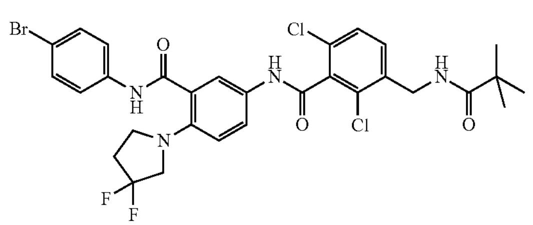 [SMILES: CC(C)(C)C(=O)NCc1ccc(Cl)c(C(=O)Nc2ccc(N3CCC(F)(F)C3)c(C(=O)Nc3ccc(Br)cc3)c2)c1Cl] | $C_{30}H_{29}BrCl_2F_2N_4O_3$ 682.39 | 680 | $R_t$ = 1.9 min CC-10 | 177 |
| 180 | 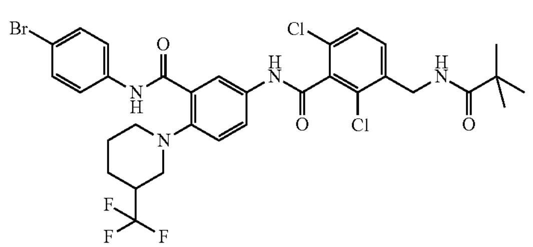 [SMILES: CC(C)(C)C(=O)NCc1ccc(Cl)c(C(=O)Nc2ccc(N3CCCC(C(F)(F)F)C3)c(C(=O)Nc3ccc(Br)cc3)c2)c1Cl] | $C_{32}H_{32}BrCl_2F_3N_4O_3$ 728 | 726 | $R_t$ = 2.8 min CC-10 | 177 |

-continued

| Ex. | Structure | Formula/Mw. | Ms* m/z [M + H]⁺ | $R_f$(TLC) or $R_t$ [min] (HPLC-method) | Prepared in analogy to example |
|---|---|---|---|---|---|
| 181 | [structure] | $C_{31}H_{31}BrCl_2F_2N_4O_3$ 696.42 | 694 | $R_t$ = 2.74 min CC-5 | 177 |

*MS = mass sprectra. In the mass spectra only one m/z-peak with high relative intensity is cited. For all compounds where mass spectra data is given, the isotope patterns are in accordance with the natural occurance of the elements which are present in the given compound.

The invention claimed is:

1. A compound selected from the following compounds:

| # | Structure |
|---|---|
| 1 | [structure] |
| 2 | [structure] |
| 3 | [structure] |
| 4 | [structure] |
| 5 | [structure] |
| 7 | [structure] |
| 8 | [structure] |
| 9 | [structure] |

| # | Structure |
|---|---|
| 10 | 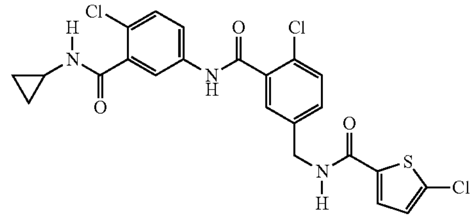 [SMILES: O=C(NCc1ccc(Cl)c(C(=O)Nc2ccc(Cl)c(C(=O)NC3CC3)c2)c1)c1ccc(Cl)s1] |
| 11 | 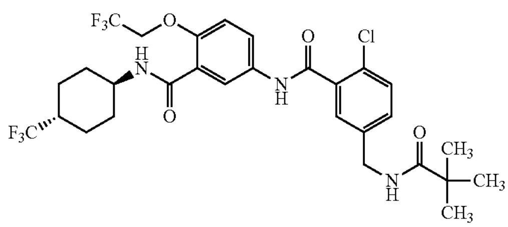 [SMILES: CC(C)(C)C(=O)NCc1ccc(Cl)c(C(=O)Nc2ccc(OCC(F)(F)F)c(C(=O)N[C@H]3CC[C@H](C(F)(F)F)CC3)c2)c1] |
| 12 | 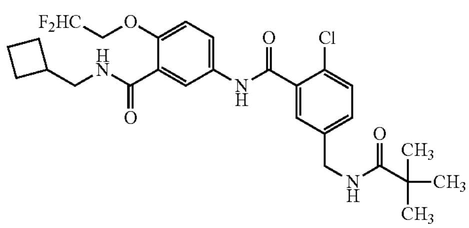 [SMILES: CC(C)(C)C(=O)NCc1ccc(Cl)c(C(=O)Nc2ccc(OCC(F)F)c(C(=O)NCC3CCC3)c2)c1] |
| 13 | 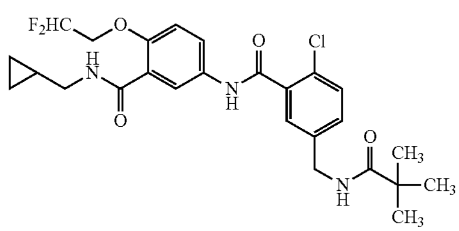 [SMILES: CC(C)(C)C(=O)NCc1ccc(Cl)c(C(=O)Nc2ccc(OCC(F)F)c(C(=O)NCC3CC3)c2)c1] |
| 14 | 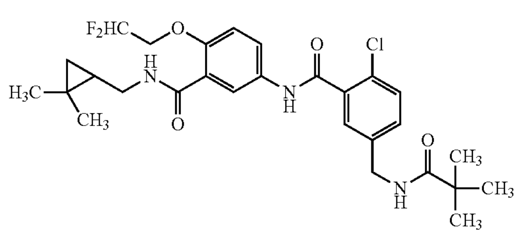 [SMILES: CC(C)(C)C(=O)NCc1ccc(Cl)c(C(=O)Nc2ccc(OCC(F)F)c(C(=O)NCC3CC3(C)C)c2)c1] |
| 15 | 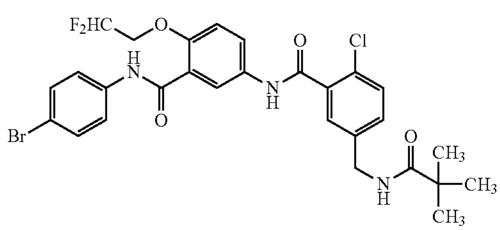 [SMILES: CC(C)(C)C(=O)NCc1ccc(Cl)c(C(=O)Nc2ccc(OCC(F)F)c(C(=O)Nc3ccc(Br)cc3)c2)c1] |
| 16 | |
| 17 | |
| 18 | |
| 19 | |
| 20 | |
| 21 | |

| # | Structure |
|---|---|
| 22 | (structure) |
| 23 | (structure) |
| 24 | (structure) |
| 25 | (structure) |
| 26 | (structure) |
| 27 | (structure) |
| 28 | (structure) |
| 29 | (structure) |
| 30 | (structure) |
| 31 | (structure) |
| 32 | (structure) |
| 33 | (structure) |

| # | Structure |
|---|---|
| 34 | 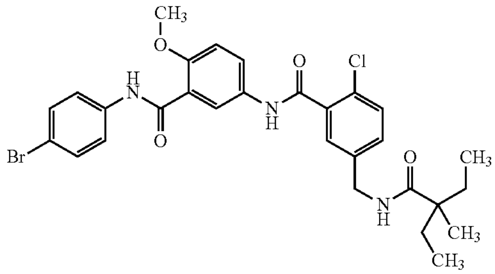 [SMILES: CCC(C)(CC)C(=O)NCc1ccc(Cl)c(C(=O)Nc2ccc(OC)c(C(=O)Nc3ccc(Br)cc3)c2)c1] |
| 35 | 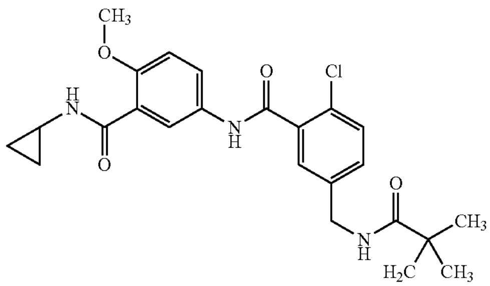 [SMILES: COc1ccc(NC(=O)c2cc(CNC(=O)C(C)(C)C)ccc2Cl)cc1C(=O)NC1CC1] |
| 36 | 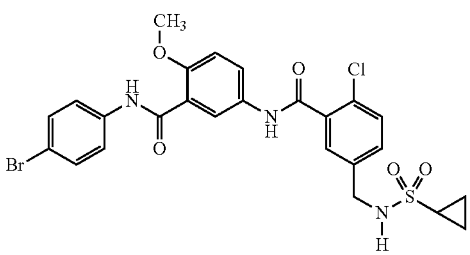 [SMILES: COc1ccc(NC(=O)c2cc(CNS(=O)(=O)C3CC3)ccc2Cl)cc1C(=O)Nc1ccc(Br)cc1] |
| 37 | 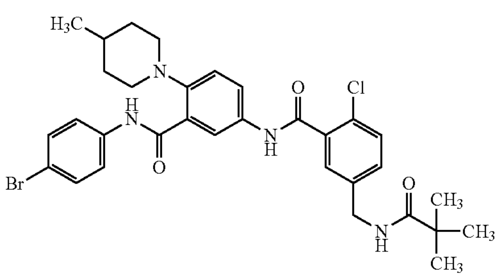 [SMILES: CC1CCN(c2ccc(NC(=O)c3cc(CNC(=O)C(C)(C)C)ccc3Cl)cc2C(=O)Nc2ccc(Br)cc2)CC1] |
| 38 | 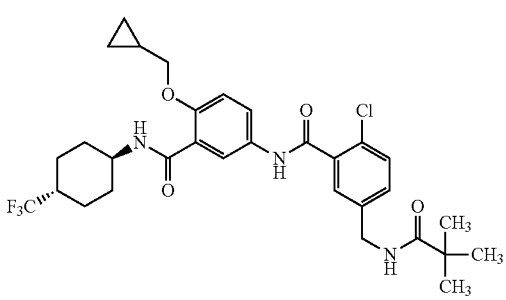 [SMILES: CC(C)(C)C(=O)NCc1ccc(Cl)c(C(=O)Nc2ccc(OCC3CC3)c(C(=O)N[C@H]3CC[C@H](C(F)(F)F)CC3)c2)c1] |

| # | Structure |
|---|---|
| 39 | 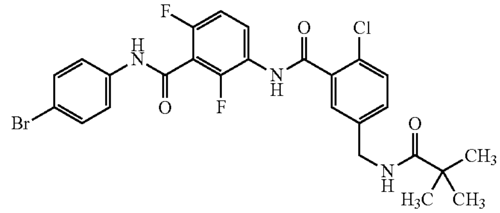 [SMILES: CC(C)(C)C(=O)NCc1ccc(Cl)c(C(=O)Nc2ccc(F)c(C(=O)Nc3ccc(Br)cc3)c2F)c1] |
| 40 | 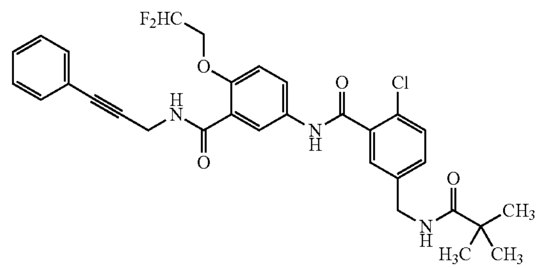 [SMILES: CC(C)(C)C(=O)NCc1ccc(Cl)c(C(=O)Nc2ccc(OCC(F)F)c(C(=O)NCC#Cc3ccccc3)c2)c1] |
| 41 | 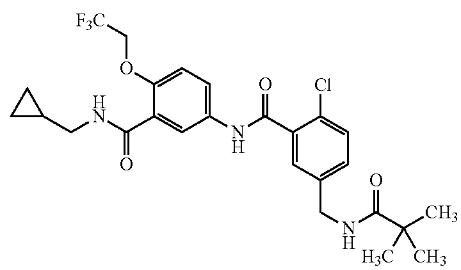 [SMILES: CC(C)(C)C(=O)NCc1ccc(Cl)c(C(=O)Nc2ccc(OCC(F)(F)F)c(C(=O)NCC3CC3)c2)c1] |
| 42 | 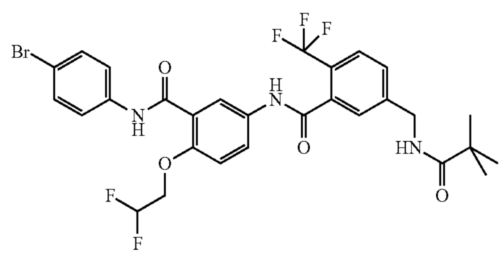 [SMILES: CC(C)(C)C(=O)NCc1ccc(C(F)(F)F)c(C(=O)Nc2ccc(OCC(F)F)c(C(=O)Nc3ccc(Br)cc3)c2)c1] |
| 43 | 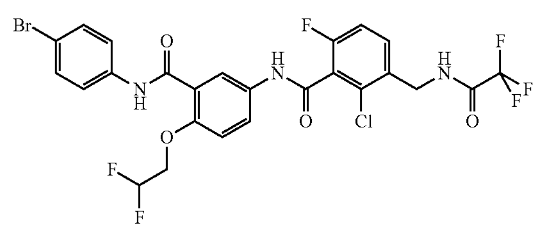 [SMILES: O=C(Nc1ccc(Br)cc1)c1cc(NC(=O)c2c(F)ccc(CNC(=O)C(F)(F)F)c2Cl)ccc1OCC(F)F] |
| 44 | 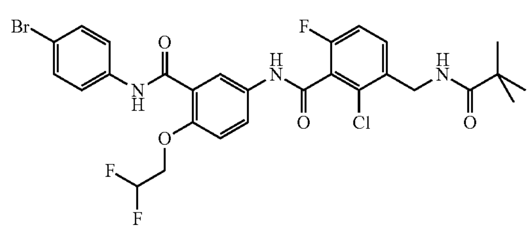 [SMILES: CC(C)(C)C(=O)NCc1ccc(F)c(C(=O)Nc2ccc(OCC(F)F)c(C(=O)Nc3ccc(Br)cc3)c2)c1Cl] |

| # | Structure |
|---|---|
| 45 | 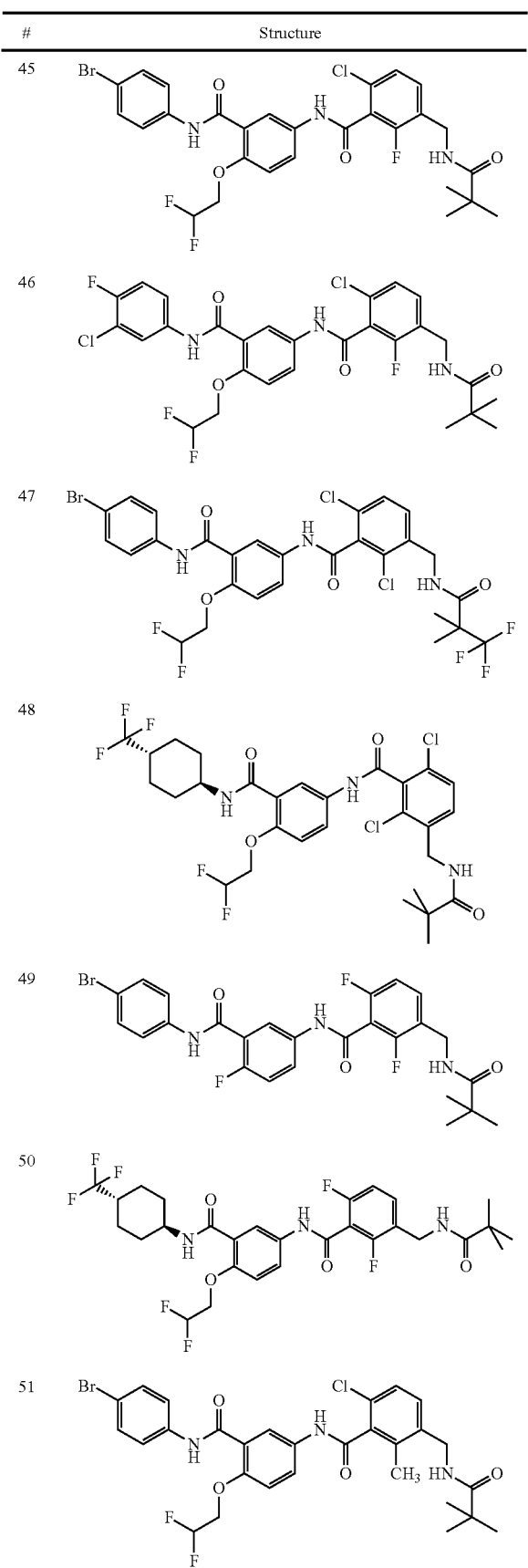 |
| 46 | |
| 47 | |
| 48 | |
| 49 | |
| 50 | |
| 51 | |
| # | Structure |
|---|---|
| 52 | 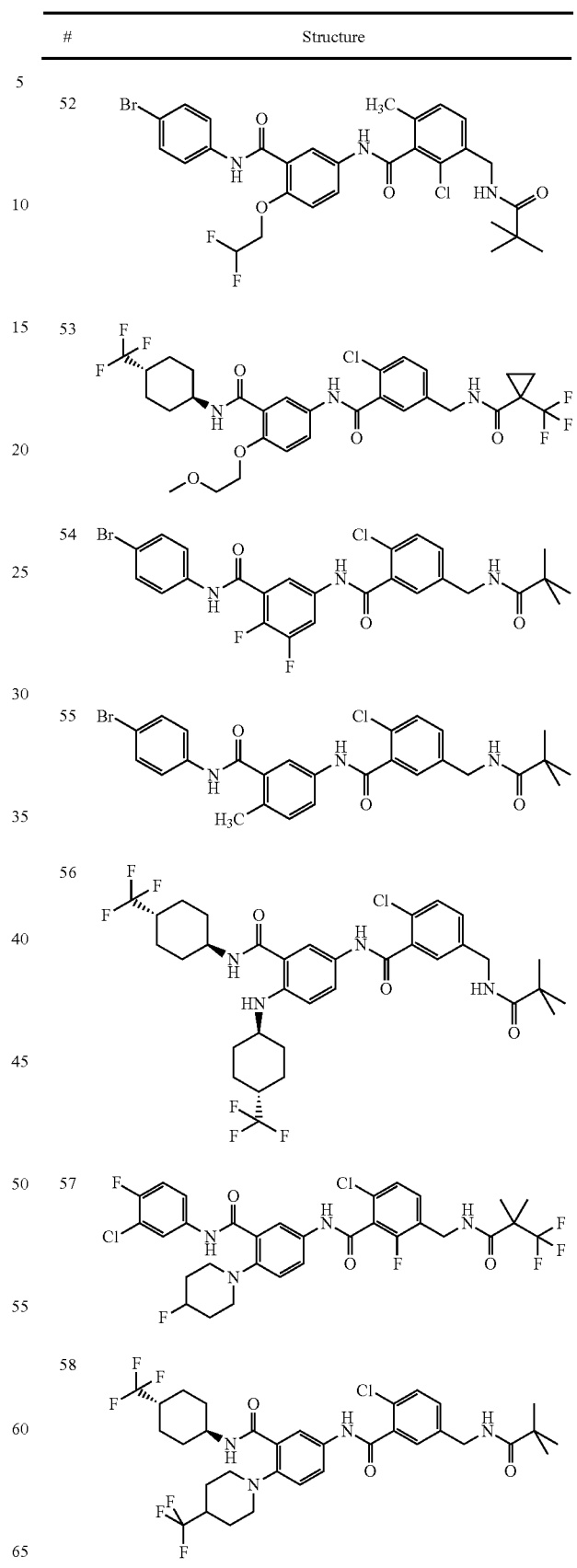 |
| 53 | |
| 54 | |
| 55 | |
| 56 | |
| 57 | |
| 58 | |

-continued
| # | Structure |
|---|---|
| 59 | 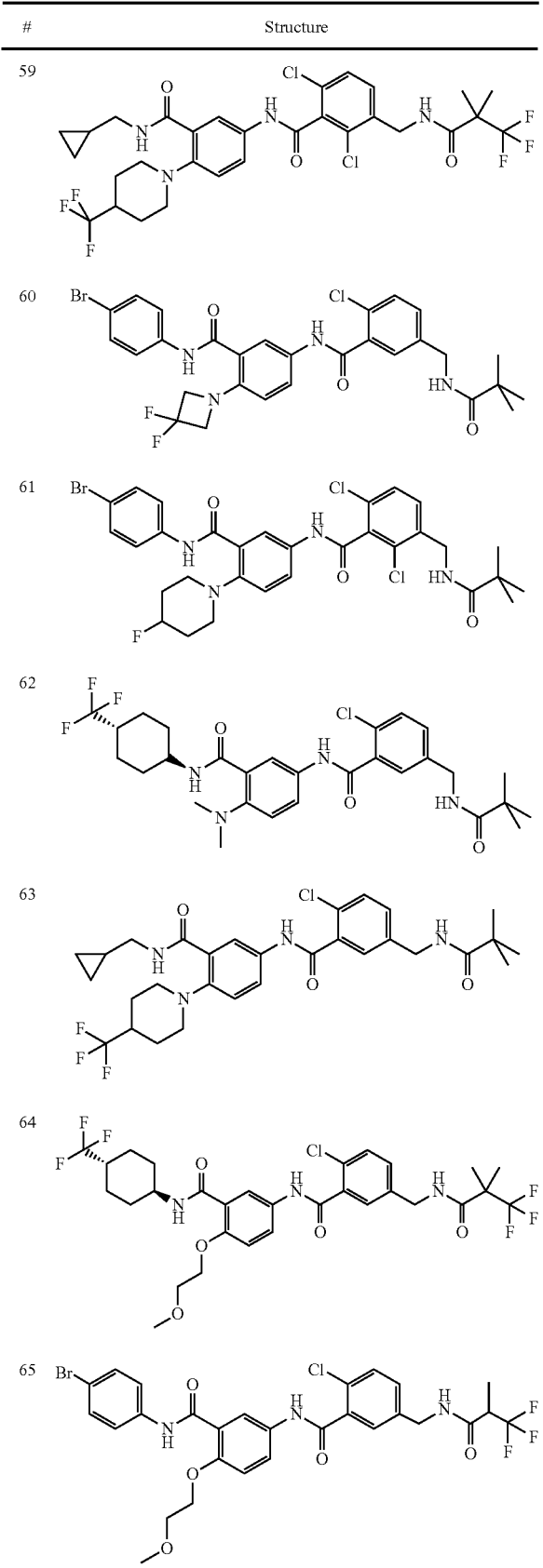 |
| 60 | 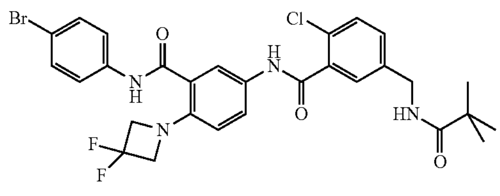 [SMILES: CC(C)(C)C(=O)NCc1ccc(Cl)c(C(=O)Nc2ccc(N3CC(F)(F)C3)c(C(=O)Nc3ccc(Br)cc3)c2)c1] |
| 61 | 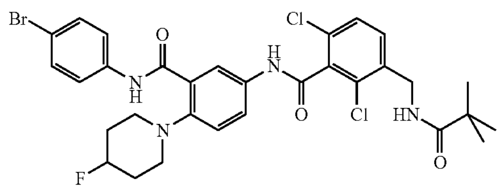 [SMILES: CC(C)(C)C(=O)NCc1ccc(Cl)c(C(=O)Nc2ccc(N3CCC(F)CC3)c(C(=O)Nc3ccc(Br)cc3)c2)c1Cl] |
| 62 | 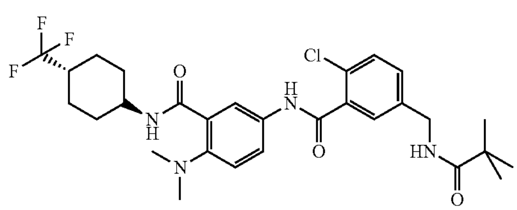 |
| 63 | 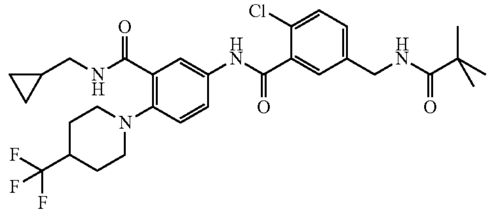 [SMILES: CC(C)(C)C(=O)NCc1ccc(Cl)c(C(=O)Nc2ccc(N3CCC(C(F)(F)F)CC3)c(C(=O)NCC3CC3)c2)c1] |
| 64 | 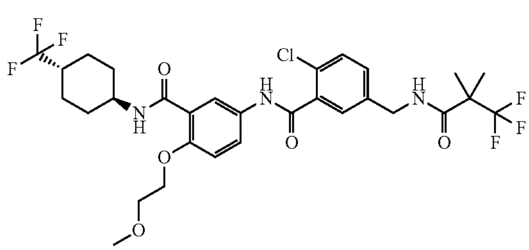 [SMILES: COCCOc1ccc(NC(=O)c2cc(CNC(=O)C(C)(C)C(F)(F)F)ccc2Cl)cc1C(=O)N[C@H]1CC[C@H](C(F)(F)F)CC1] |
| 65 | 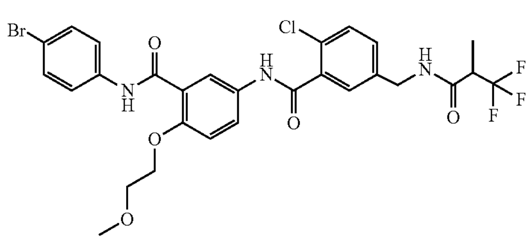 [SMILES: COCCOc1ccc(NC(=O)c2cc(CNC(=O)C(C)C(F)(F)F)ccc2Cl)cc1C(=O)Nc1ccc(Br)cc1] |
-continued
| # | Structure |
|---|---|
| 66 | 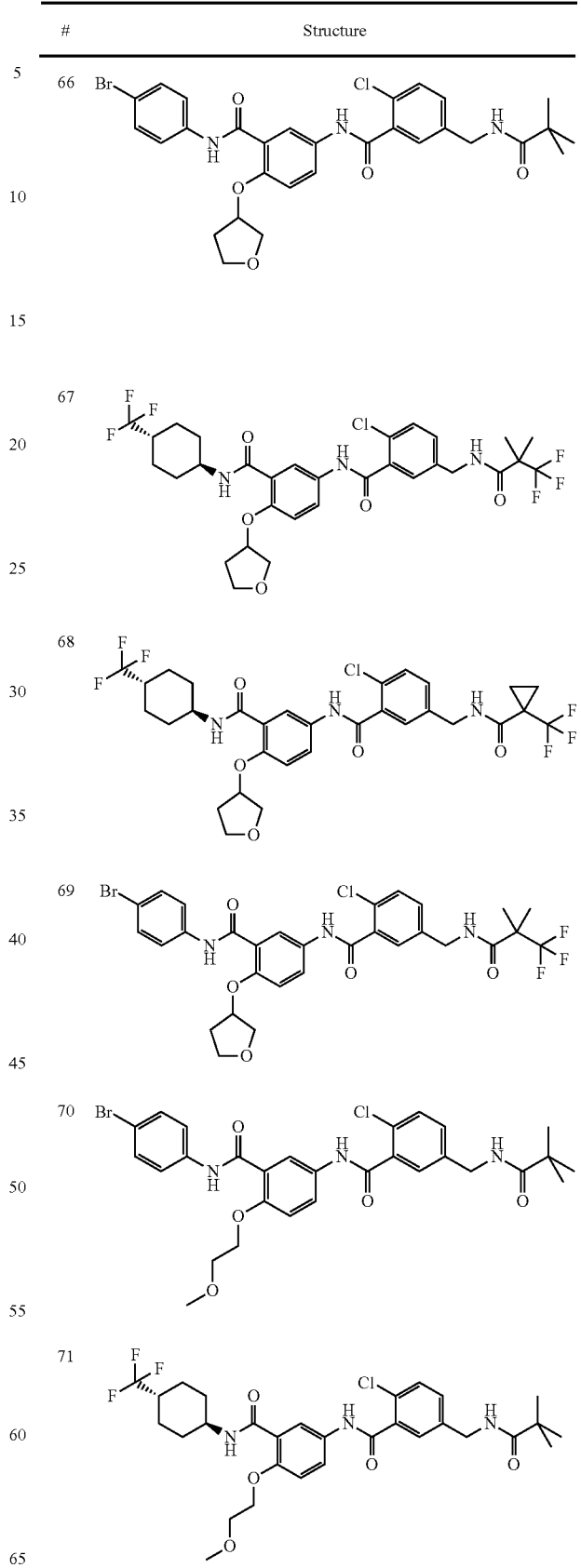 |
| 67 | 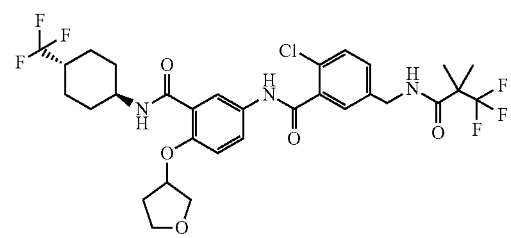 [SMILES: CC(C)(C(=O)NCc1ccc(Cl)c(C(=O)Nc2ccc(OC3CCOC3)c(C(=O)N[C@H]3CC[C@H](C(F)(F)F)CC3)c2)c1)C(F)(F)F] |
| 68 | 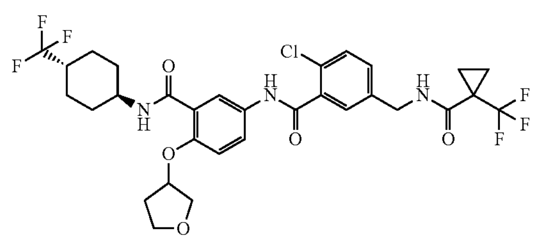 [SMILES: O=C(Nc1ccc(OC2CCOC2)c(C(=O)N[C@H]2CC[C@H](C(F)(F)F)CC2)c1)c1cc(CNC(=O)C2(C(F)(F)F)CC2)ccc1Cl] |
| 69 | 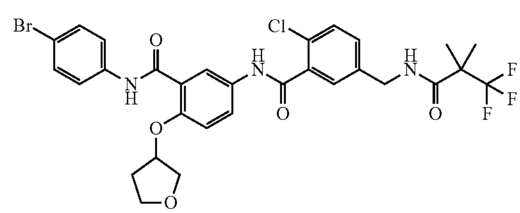 [SMILES: CC(C)(C(=O)NCc1ccc(Cl)c(C(=O)Nc2ccc(OC3CCOC3)c(C(=O)Nc3ccc(Br)cc3)c2)c1)C(F)(F)F] |
| 70 | 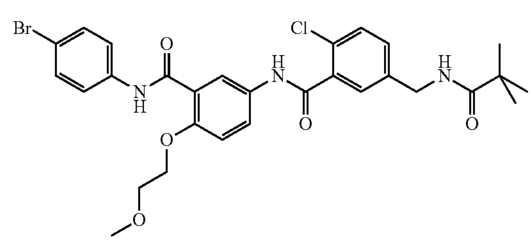 [SMILES: COCCOc1ccc(NC(=O)c2cc(CNC(=O)C(C)(C)C)ccc2Cl)cc1C(=O)Nc1ccc(Br)cc1] |
| 71 | 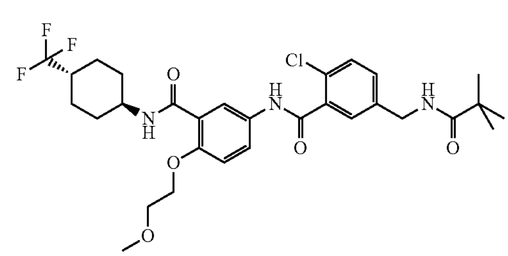 [SMILES: COCCOc1ccc(NC(=O)c2cc(CNC(=O)C(C)(C)C)ccc2Cl)cc1C(=O)N[C@H]1CC[C@H](C(F)(F)F)CC1] |

| # | Structure |
|---|---|
| 72 | 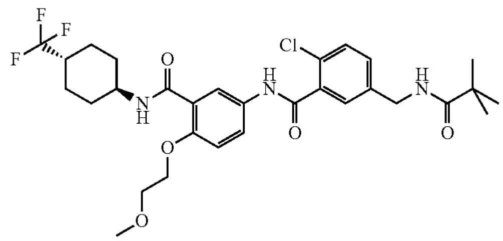 [SMILES: COCCOc1ccc(NC(=O)c2cc(CNC(=O)C(C)(C)C)ccc2Cl)cc1C(=O)N[C@H]1CC[C@H](C(F)(F)F)CC1] |
| 77 | 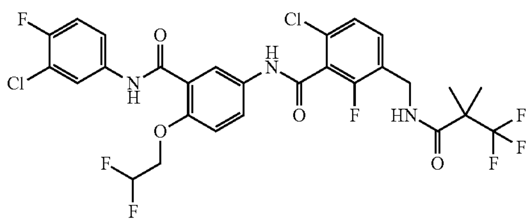 [SMILES: CC(C)(C(=O)NCc1ccc(Cl)c(C(=O)Nc2ccc(OCC(F)F)c(C(=O)Nc3ccc(F)c(Cl)c3)c2)c1F)C(F)(F)F] |
| 78 | 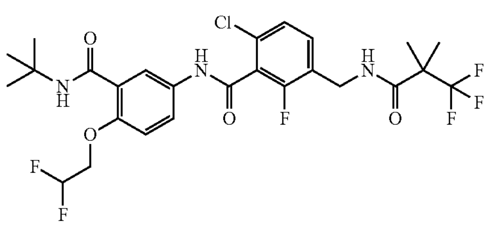 [SMILES: CC(C)(C)NC(=O)c1cc(NC(=O)c2c(Cl)ccc(CNC(=O)C(C)(C)C(F)(F)F)c2F)ccc1OCC(F)F] |
| 79 | 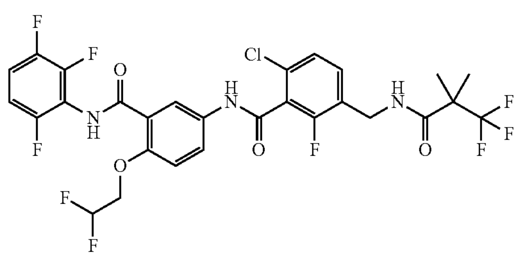 [SMILES: CC(C)(C(=O)NCc1ccc(Cl)c(C(=O)Nc2ccc(OCC(F)F)c(C(=O)Nc3c(F)ccc(F)c3F)c2)c1F)C(F)(F)F] |
| 80 | 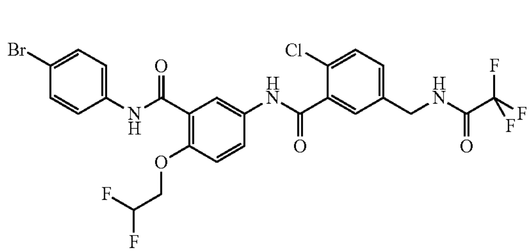 [SMILES: O=C(Nc1ccc(OCC(F)F)c(C(=O)Nc2ccc(Br)cc2)c1)c1cc(CNC(=O)C(F)(F)F)ccc1Cl] |
| 81 | 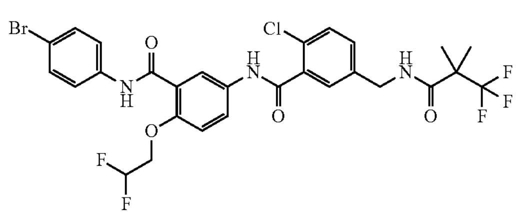 |

| # | Structure |
|---|---|
| 82 | 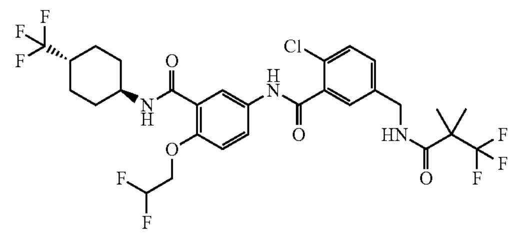 [SMILES: CC(C)(C(=O)NCc1ccc(Cl)c(C(=O)Nc2ccc(OCC(F)F)c(C(=O)N[C@H]3CC[C@H](C(F)(F)F)CC3)c2)c1)C(F)(F)F] |
| 83 | 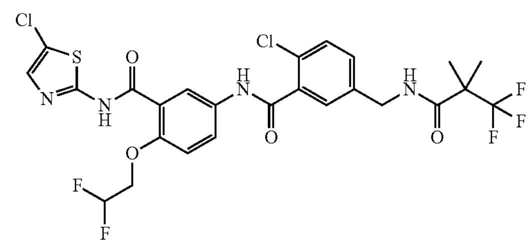 [SMILES: CC(C)(C(=O)NCc1ccc(Cl)c(C(=O)Nc2ccc(OCC(F)F)c(C(=O)Nc3ncc(Cl)s3)c2)c1)C(F)(F)F] |
| 84 | 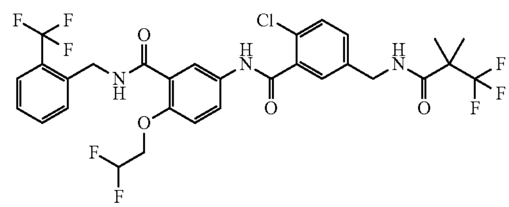 [SMILES: CC(C)(C(=O)NCc1ccc(Cl)c(C(=O)Nc2ccc(OCC(F)F)c(C(=O)NCc3ccccc3C(F)(F)F)c2)c1)C(F)(F)F] |
| 85 | 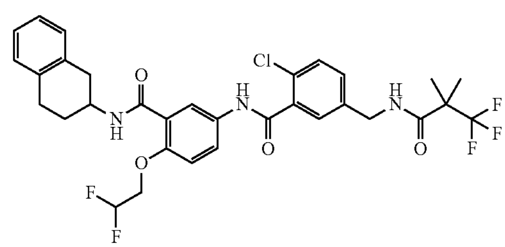 [SMILES: CC(C)(C(=O)NCc1ccc(Cl)c(C(=O)Nc2ccc(OCC(F)F)c(C(=O)NC3CCc4ccccc4C3)c2)c1)C(F)(F)F] |
| 86 | 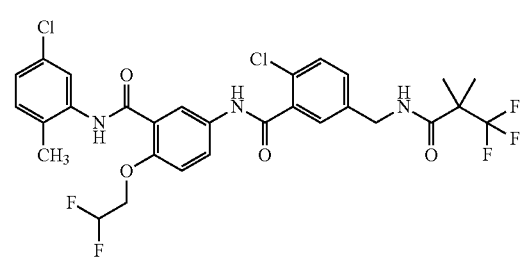 [SMILES: Cc1ccc(Cl)cc1NC(=O)c1cc(NC(=O)c2cc(CNC(=O)C(C)(C)C(F)(F)F)ccc2Cl)ccc1OCC(F)F] |
| 87 | 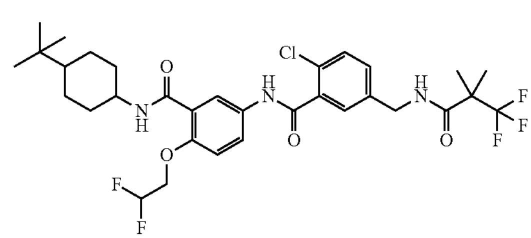 [SMILES: CC(C)(C)C1CCC(NC(=O)c2cc(NC(=O)c3cc(CNC(=O)C(C)(C)C(F)(F)F)ccc3Cl)ccc2OCC(F)F)CC1] |

-continued

| # | Structure |
|---|---|
| 88 | (structure) |
| 89 | (structure) |
| 90 | (structure) |
| 91 | (structure) |
| 92 | (structure) |
| 93 | (structure) |
| 94 | (structure) |

-continued

| # | Structure |
|---|---|
| 95 | (structure) |
| 96 | (structure) |
| 97 | (structure) |
| 98 | (structure) |
| 99 | (structure) |
| 100 | (structure) |
| 101 | (structure) |

| # | Structure |
|---|---|
| 102 | 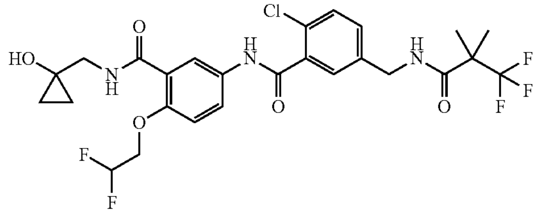 [SMILES: CC(C)(C(=O)NCc1ccc(Cl)c(C(=O)Nc2ccc(OCC(F)F)c(C(=O)NCC3(O)CC3)c2)c1)C(F)(F)F] |
| 103 | 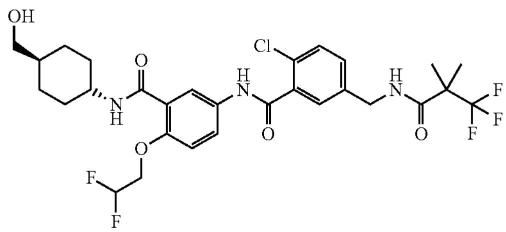 |
| 104 | 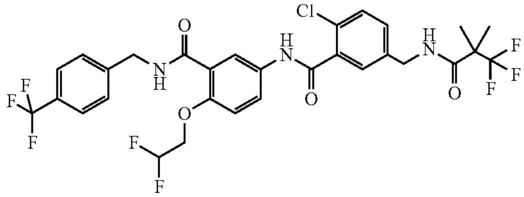 [SMILES: CC(C)(C(=O)NCc1ccc(Cl)c(C(=O)Nc2ccc(OCC(F)F)c(C(=O)NCc3ccc(C(F)(F)F)cc3)c2)c1)C(F)(F)F] |
| 105 | 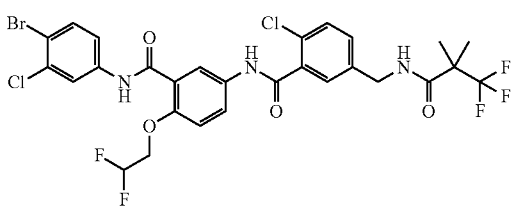 |
| 106 | 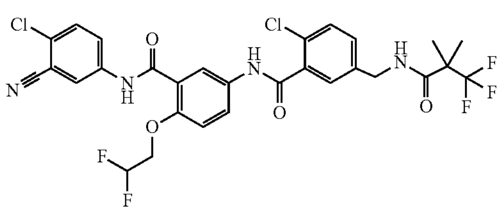 [SMILES: CC(C)(C(=O)NCc1ccc(Cl)c(C(=O)Nc2ccc(OCC(F)F)c(C(=O)Nc3ccc(Cl)c(C#N)c3)c2)c1)C(F)(F)F] |
| 107 | 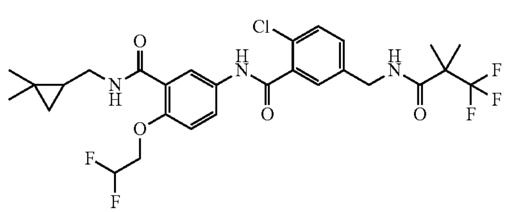 [SMILES: CC1(C)CC1CNC(=O)c1cc(NC(=O)c2cc(CNC(=O)C(C)(C)C(F)(F)F)ccc2Cl)ccc1OCC(F)F] |
| 108 | 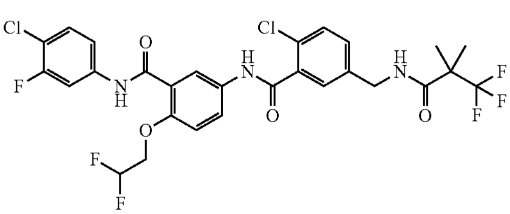 [SMILES: CC(C)(C(=O)NCc1ccc(Cl)c(C(=O)Nc2ccc(OCC(F)F)c(C(=O)Nc3ccc(Cl)c(F)c3)c2)c1)C(F)(F)F] |
| 109 | |
| 110 | |
| 111 | |
| 112 | |
| 113 | |
| 114 | |
| 115 | |

199
-continued
| # | Structure |
|---|---|
| 116 | 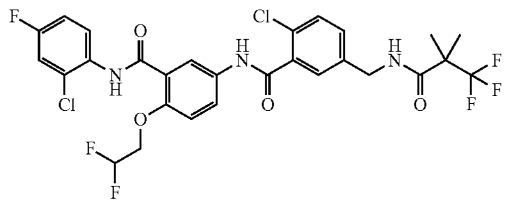 [SMILES: CC(C)(C(=O)NCc1ccc(Cl)c(C(=O)Nc2ccc(OCC(F)F)c(C(=O)Nc3ccc(F)cc3Cl)c2)c1)C(F)(F)F] |
| 117 | 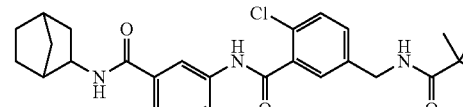 |
| 118 | 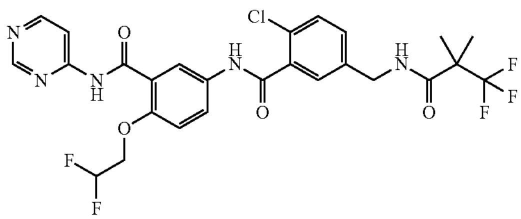 [SMILES: CC(C)(C(=O)NCc1ccc(Cl)c(C(=O)Nc2ccc(OCC(F)F)c(C(=O)Nc3ccncn3)c2)c1)C(F)(F)F] |
| 119 | 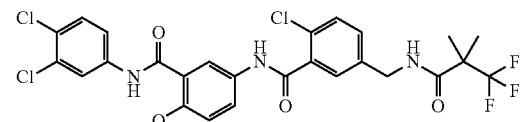 |
| 120 | 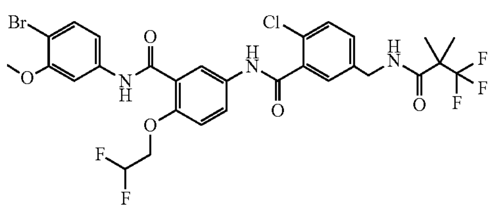 [SMILES: COc1cc(NC(=O)c2cc(NC(=O)c3cc(CNC(=O)C(C)(C)C(F)(F)F)ccc3Cl)ccc2OCC(F)F)ccc1Br] |
| 121 | 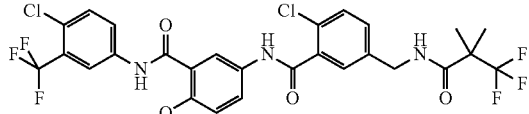 |
| 122 | 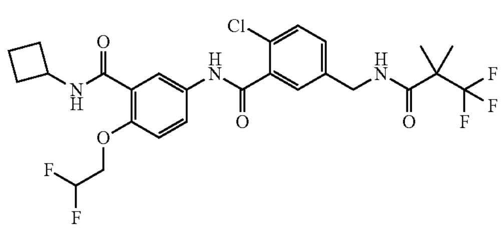 [SMILES: CC(C)(C(=O)NCc1ccc(Cl)c(C(=O)Nc2ccc(OCC(F)F)c(C(=O)NC3CCC3)c2)c1)C(F)(F)F] |
200
-continued
| # | Structure |
|---|---|
| 123 | 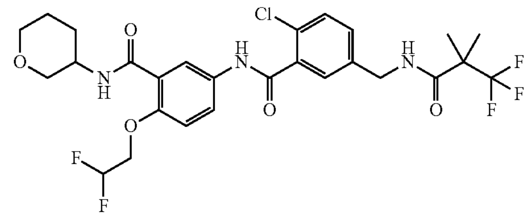 [SMILES: CC(C)(C(=O)NCc1ccc(Cl)c(C(=O)Nc2ccc(OCC(F)F)c(C(=O)NC3CCCOC3)c2)c1)C(F)(F)F] |
| 124 | 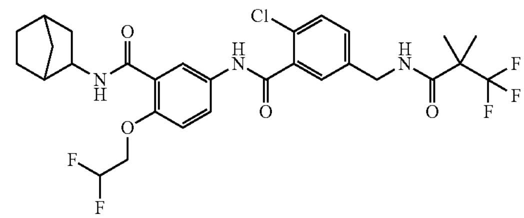 [SMILES: CC(C)(C(=O)NCc1ccc(Cl)c(C(=O)Nc2ccc(OCC(F)F)c(C(=O)NC3CC4CCC3C4)c2)c1)C(F)(F)F] |
| 125 | 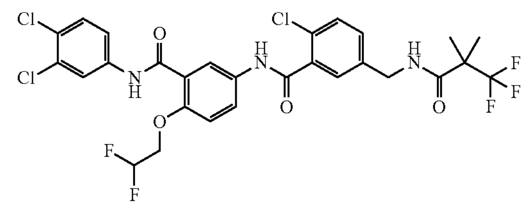 [SMILES: CC(C)(C(=O)NCc1ccc(Cl)c(C(=O)Nc2ccc(OCC(F)F)c(C(=O)Nc3ccc(Cl)c(Cl)c3)c2)c1)C(F)(F)F] |
| 126 | 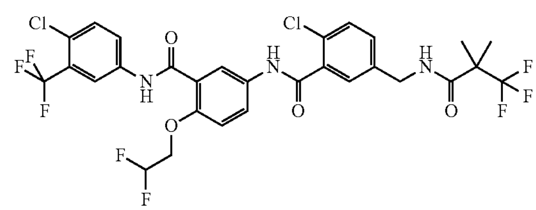 [SMILES: CC(C)(C(=O)NCc1ccc(Cl)c(C(=O)Nc2ccc(OCC(F)F)c(C(=O)Nc3ccc(Cl)c(C(F)(F)F)c3)c2)c1)C(F)(F)F] |
| 127 | 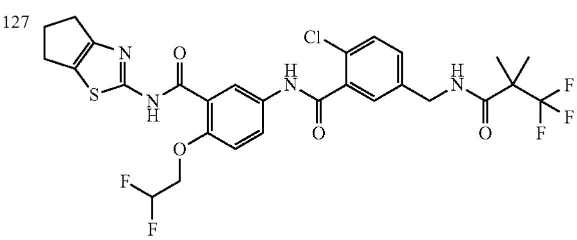 |
| 128 | 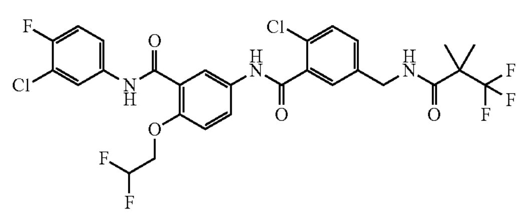 [SMILES: CC(C)(C(=O)NCc1ccc(Cl)c(C(=O)Nc2ccc(OCC(F)F)c(C(=O)Nc3ccc(F)c(Cl)c3)c2)c1)C(F)(F)F] |
| 129 | 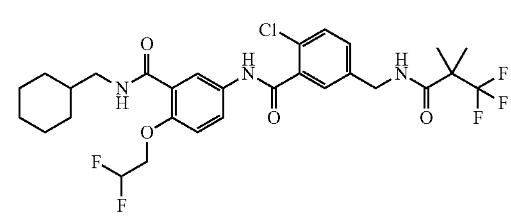 [SMILES: CC(C)(C(=O)NCc1ccc(Cl)c(C(=O)Nc2ccc(OCC(F)F)c(C(=O)NCC3CCCCC3)c2)c1)C(F)(F)F] |

| # | Structure |
|---|---|
| 130 | 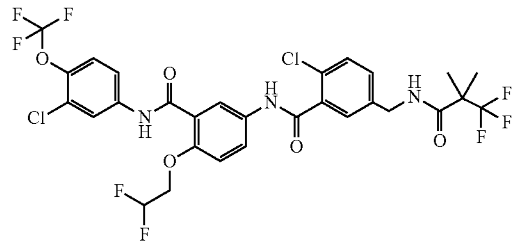 [SMILES: CC(C)(C(=O)NCc1ccc(Cl)c(C(=O)Nc2ccc(OCC(F)F)c(C(=O)Nc3ccc(OC(F)(F)F)c(Cl)c3)c2)c1)C(F)(F)F] |
| 131 | 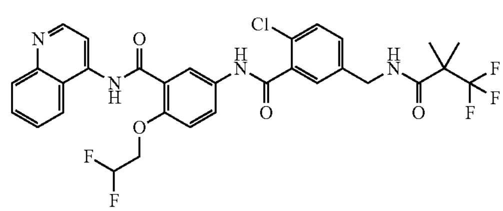 [SMILES: CC(C)(C(=O)NCc1ccc(Cl)c(C(=O)Nc2ccc(OCC(F)F)c(C(=O)Nc3ccnc4ccccc34)c2)c1)C(F)(F)F] |
| 132 | 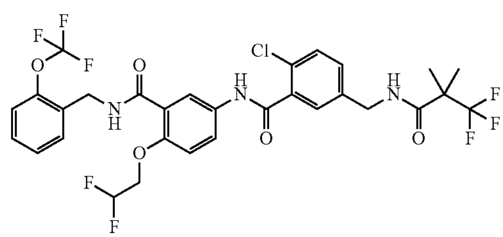 [SMILES: CC(C)(C(=O)NCc1ccc(Cl)c(C(=O)Nc2ccc(OCC(F)F)c(C(=O)NCc3ccccc3OC(F)(F)F)c2)c1)C(F)(F)F] |
| 133 | 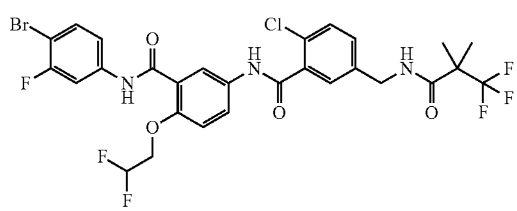 |
| 134 | 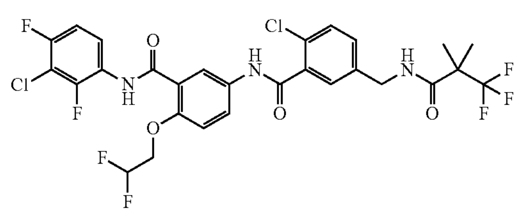 [SMILES: CC(C)(C(=O)NCc1ccc(Cl)c(C(=O)Nc2ccc(OCC(F)F)c(C(=O)Nc3ccc(F)c(Cl)c3F)c2)c1)C(F)(F)F] |
| 135 | 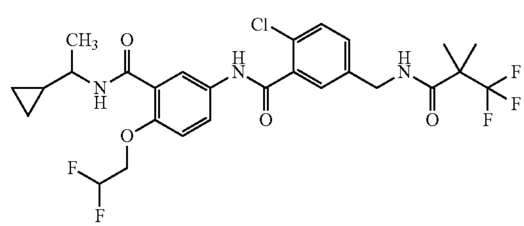 [SMILES: CC(NC(=O)c1cc(NC(=O)c2cc(CNC(=O)C(C)(C)C(F)(F)F)ccc2Cl)ccc1OCC(F)F)C1CC1] |
| 136 | 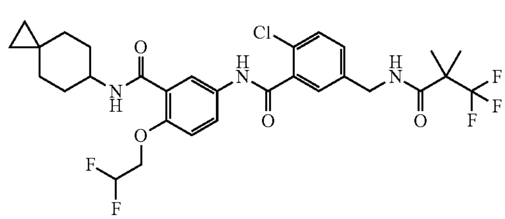 [SMILES: CC(C)(C(=O)NCc1ccc(Cl)c(C(=O)Nc2ccc(OCC(F)F)c(C(=O)NC3CCC4(CC3)CC4)c2)c1)C(F)(F)F] |
| 137 | 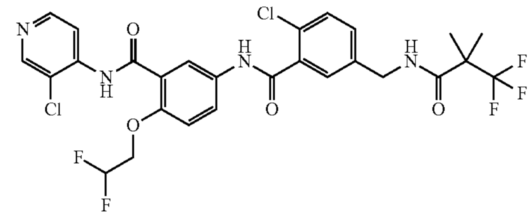 [SMILES: CC(C)(C(=O)NCc1ccc(Cl)c(C(=O)Nc2ccc(OCC(F)F)c(C(=O)Nc3ccncc3Cl)c2)c1)C(F)(F)F] |
| 138 | 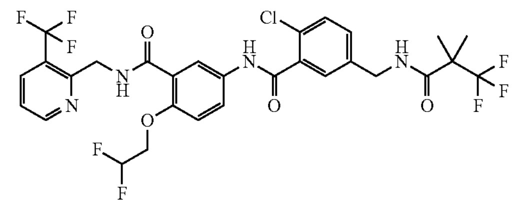 [SMILES: CC(C)(C(=O)NCc1ccc(Cl)c(C(=O)Nc2ccc(OCC(F)F)c(C(=O)NCc3ncccc3C(F)(F)F)c2)c1)C(F)(F)F] |
| 139 | 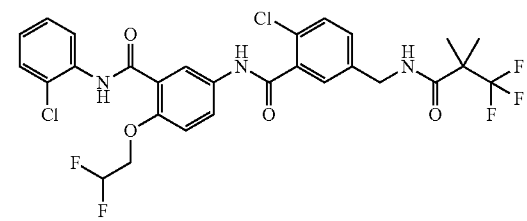 [SMILES: CC(C)(C(=O)NCc1ccc(Cl)c(C(=O)Nc2ccc(OCC(F)F)c(C(=O)Nc3ccccc3Cl)c2)c1)C(F)(F)F] |
| 140 | 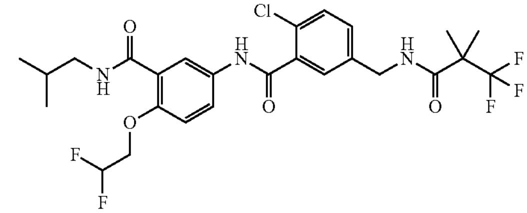 [SMILES: CC(C)CNC(=O)c1cc(NC(=O)c2cc(CNC(=O)C(C)(C)C(F)(F)F)ccc2Cl)ccc1OCC(F)F] |
| 141 | 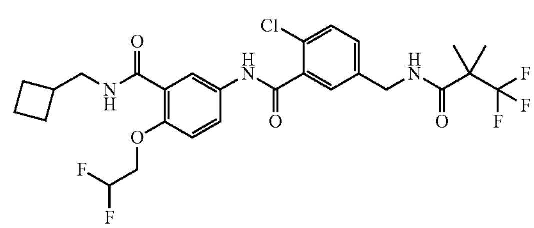 [SMILES: CC(C)(C(=O)NCc1ccc(Cl)c(C(=O)Nc2ccc(OCC(F)F)c(C(=O)NCC3CCC3)c2)c1)C(F)(F)F] |
| 142 | 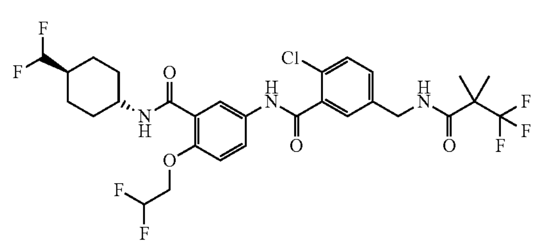 |
| 143 | 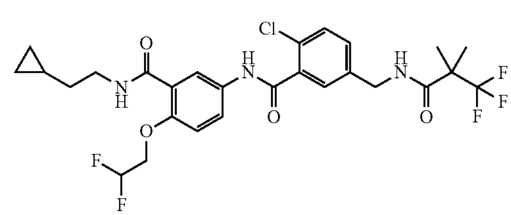 [SMILES: CC(C)(C(=O)NCc1ccc(Cl)c(C(=O)Nc2ccc(OCC(F)F)c(C(=O)NCCC3CC3)c2)c1)C(F)(F)F] |

| Structure
---|---
144 | 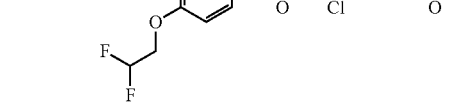
145 | 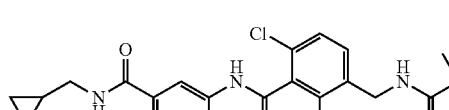
146 | 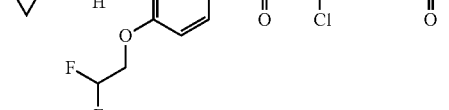
147 | 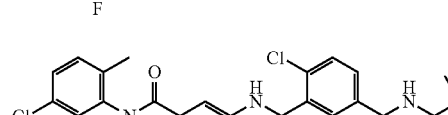
148 | 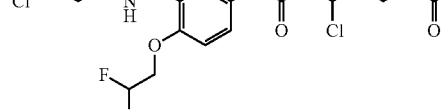
149 | 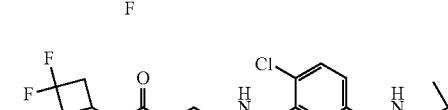
150 | 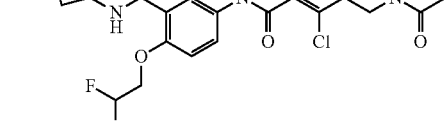
| Structure
---|---
151 |
152 |
153 |
154 |
155 |
156 |
157 |

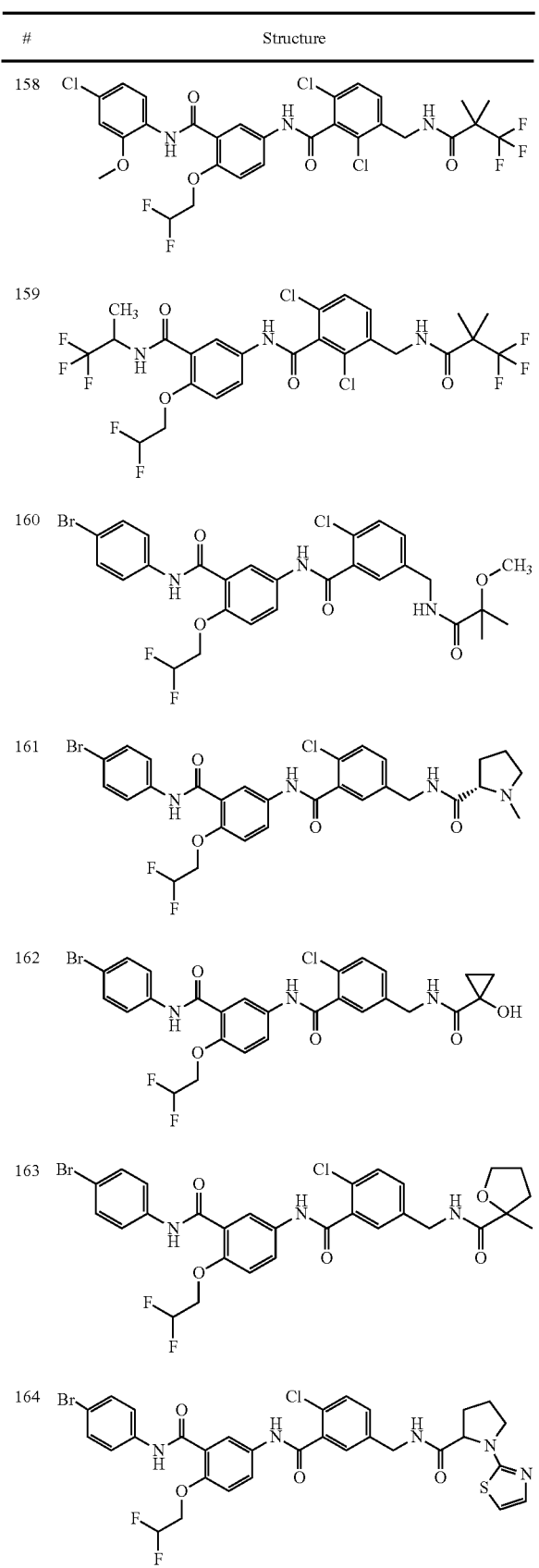
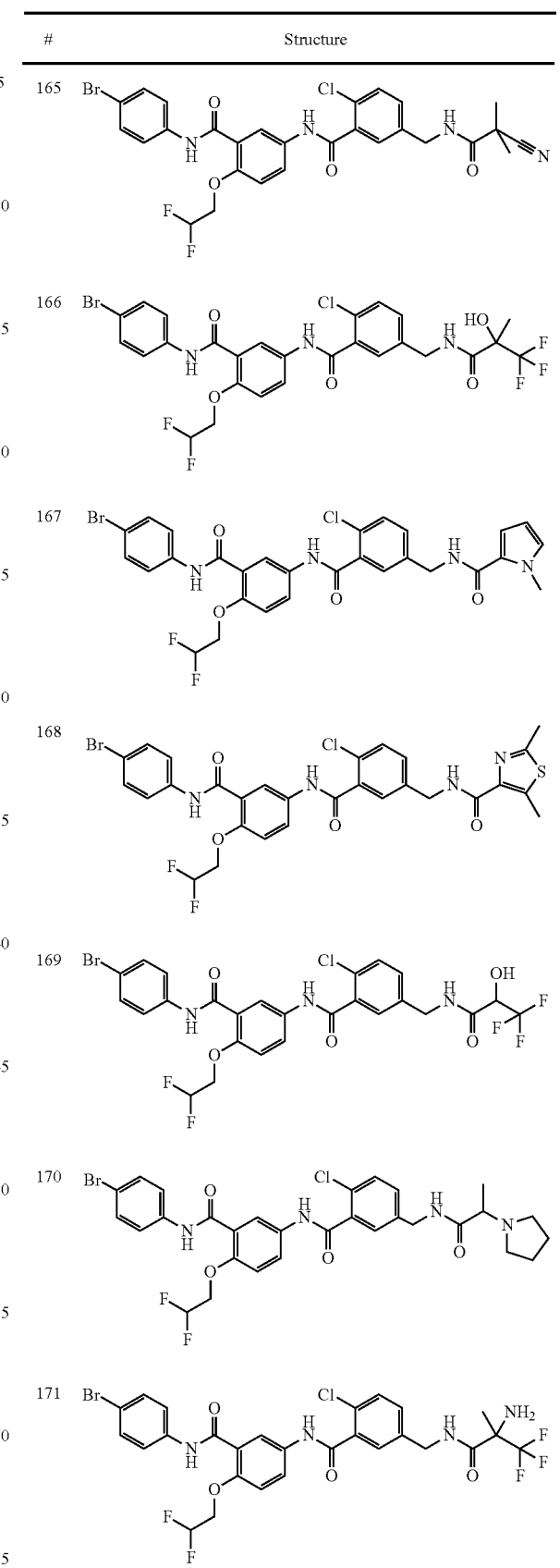

| # | Structure |
|---|---|
| 172 | 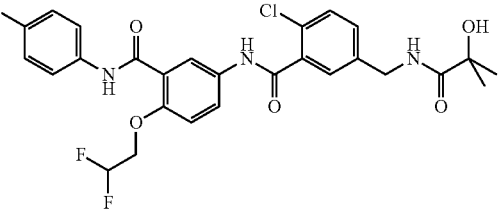 |
| 173 | 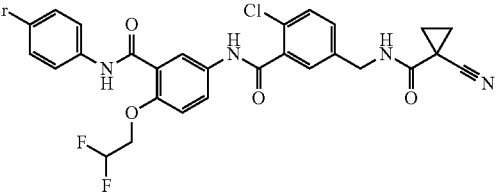 |
| 174 | 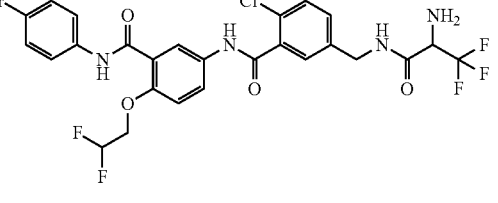 |
| 175 | 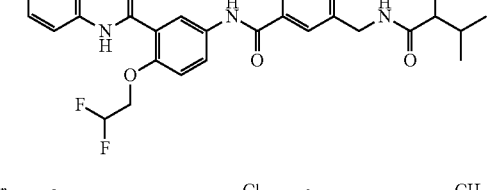 |
| 176 | 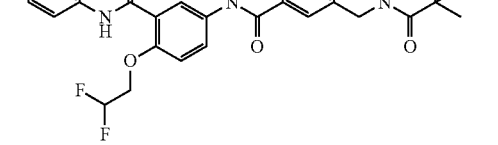 |
| 177 | 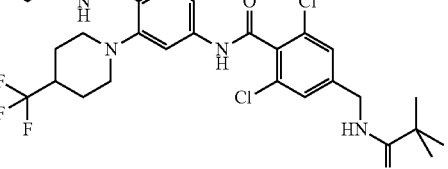 |
| 179 | 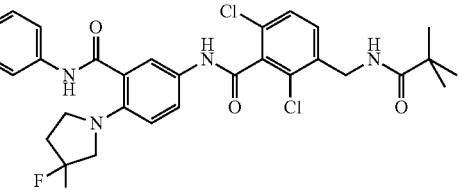 |
| 180 | 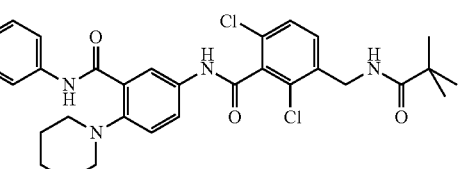 |
| 181 | 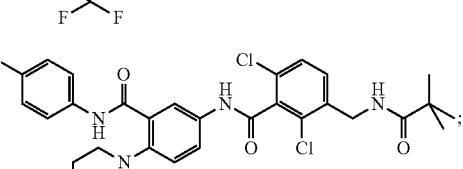 |
or a pharmaceutically acceptable salt thereof.
2. A pharmaceutical composition comprising at least one compound according to claim 1, or a pharmaceutically acceptable salt thereof, in admixture with a pharmaceutically acceptable adjuvant, diluent and/or carrier.
* * * * *